US009347088B2

(12) United States Patent
Buendia et al.

(10) Patent No.: US 9,347,088 B2
(45) Date of Patent: May 24, 2016

(54) MOLECULAR SIGNATURE OF LIVER TUMOR GRADE AND USE TO EVALUATE PROGNOSIS AND THERAPEUTIC REGIMEN

(75) Inventors: Marie-Annick Buendia, Le Perreux sur Marne (FR); Carolina Armengol Niell, Blanes (ES); Stefano Cairo, Longpont-sur-Orge (FR); Aurélien de Reynies, Paris (FR)

(73) Assignees: Institut Pasteur, Paris (FR); Institut National de la Santé et de la Recherche Médicale, Paris (FR); Centre National de la Recherche Scientifique, Paris (FR)

( * ) Notice: Subject to any disclaimer, the term of this patent is extended or adjusted under 35 U.S.C. 154(b) by 374 days.

(21) Appl. No.: 12/999,907

(22) PCT Filed: Jun. 26, 2009

(86) PCT No.: PCT/IB2009/006450
§ 371 (c)(1),
(2), (4) Date: Apr. 7, 2011

(87) PCT Pub. No.: WO2009/156858
PCT Pub. Date: Dec. 30, 2009

(65) Prior Publication Data
US 2011/0183862 A1    Jul. 28, 2011
US 2012/0040848 A2    Feb. 16, 2012

(30) Foreign Application Priority Data
Jun. 27, 2008   (EP) ..................................... 08290628
Jan. 30, 2009   (EP) ..................................... 09151808

(51) Int. Cl.
*C12Q 1/68*        (2006.01)
(52) U.S. Cl.
CPC .................................. *C12Q 1/6809* (2013.01)
(58) Field of Classification Search
None
See application file for complete search history.

(56) References Cited

U.S. PATENT DOCUMENTS

2002/0142981 A1*   10/2002   Horne et al. .................... 514/44

FOREIGN PATENT DOCUMENTS

| EP | 1 661 991 A1 | 5/2006 |
|---|---|---|
| WO | WO 03/010336 A2 | 2/2003 |
| WO | WO 2005/005601 A2 | 1/2005 |

OTHER PUBLICATIONS

International Search Report issued for application No. PCT/IB2009/006450 on Dec. 1, 2009.
Affymetrix, "Human Genome U95 Set," announcement, Apr. 1, 2000.
Out et al., "Restoration of Liver Mass after Injury Requires Proliferative and Not Embryonic Transcriptional Patterns," The Journal of Biological Chemistry, vol. 282, No. 15, pp. 11197-11204, Apr. 13, 2007.
Li et al., "Discovery and analysis of hepatocellular carcinoma genes using cDNA microarrays," J. Cancer Res. Clin. Oncol., vol. 128, pp. 369-379, 2002.
Xu et al., "Expression Profiling Suggested a Regulatory Role of Liver-enriched Transcription Factors in Human Hepatocellular Carcinoma," Cancer Research, vol. 61, pp. 3176-3181, Apr. 1, 2001.
Kurokawa et al., "Molecular-based prediction of early recurrence in hepatocellular carcinoma," Journal of Hepatology, vol. 41, pp. 284-291, 2004.
Cairo et al., "Hepatic Stem-like Phenotype and Interplay of Wnt/β-Catenin and Myc Signaling in Aggressive Childhood Liver Cancer," Cancer Cell, vol. 14, No. 6, pp. 471-484, Dec. 9, 2008.
Affymetrix, "Affymetrix GeneChip Human Genome U133 Array Set HG-U133A," GEO, Feb. 17, 2002.

\* cited by examiner

*Primary Examiner* — Anne Gussow
(74) *Attorney, Agent, or Firm* — Law Office of Salvatore Arrigo and Scott Lee, LLP

(57) ABSTRACT

The present invention concerns a method to determine the gene expression profile on a sample previously obtained from a patient diagnosed for a liver tumor, comprising assaying the expression of a set of genes in this sample and determining the gene expression profile (signature). In a particular embodiment, said method enables to determine the grade of the liver tumor, such as hepatoblastoma (HB) or a hepatocellular carcinoma (HCC). The invention is also directed to kits comprising a plurality of pairs of primers or a plurality of probes specific for a set of genes, as well as to solid support or composition comprising a set of probes specific for a set of genes. These methods are useful to determine the grade of a liver tumor in a sample obtained from a patient, to determine the risk of developing metastasis and/or to define the therapeutic regimen to apply to a patient.

12 Claims, 35 Drawing Sheets

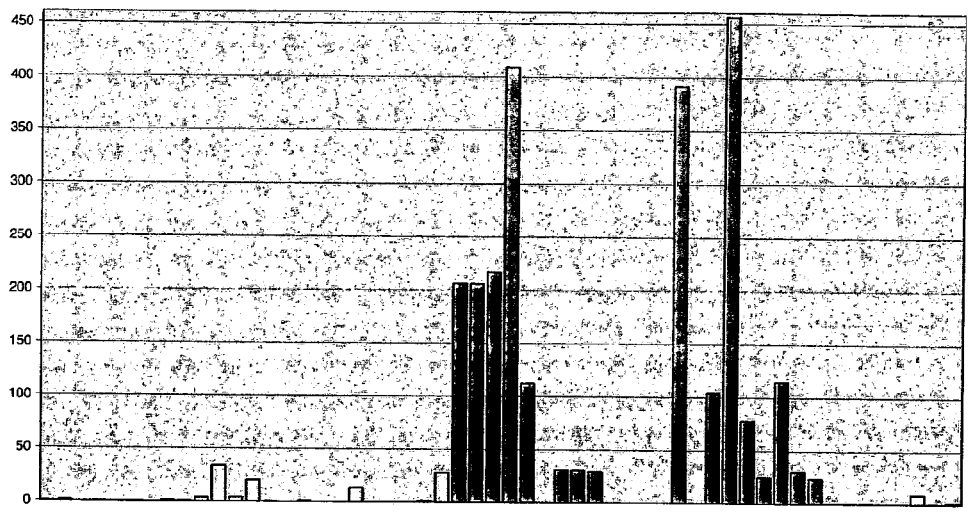
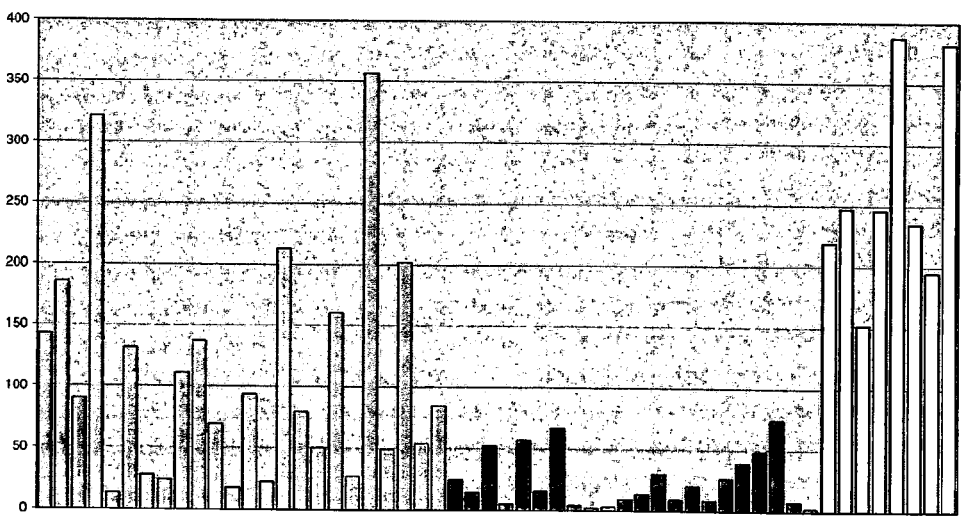
Fig. 5A

APCS
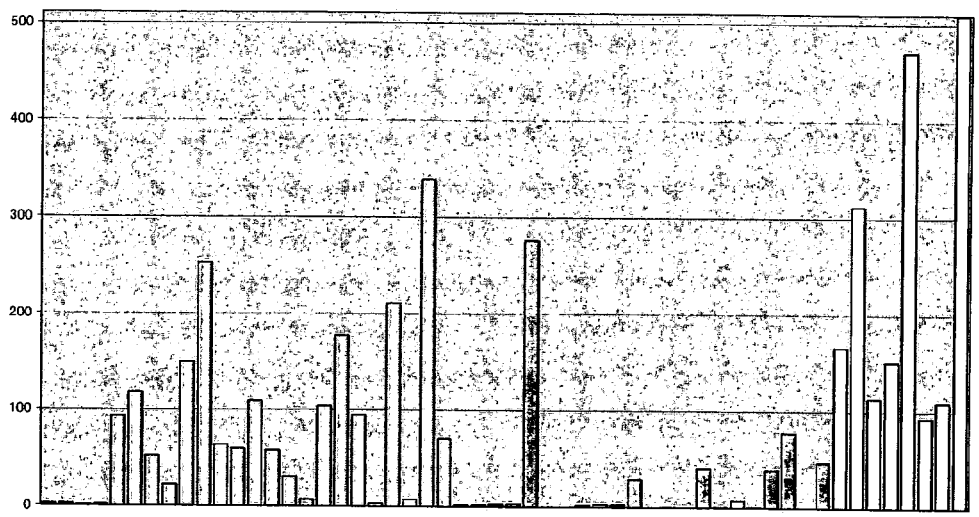
APOC4
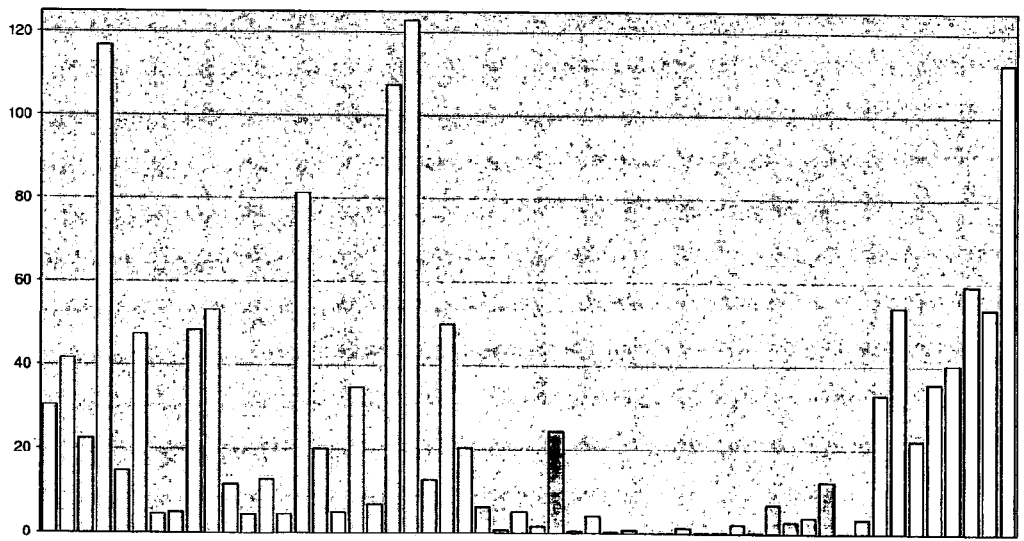
Fig. 5B

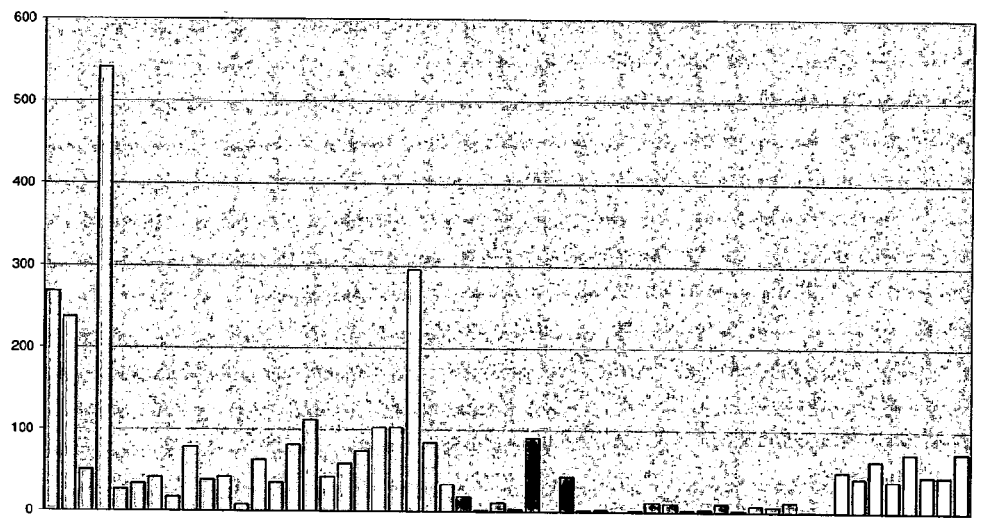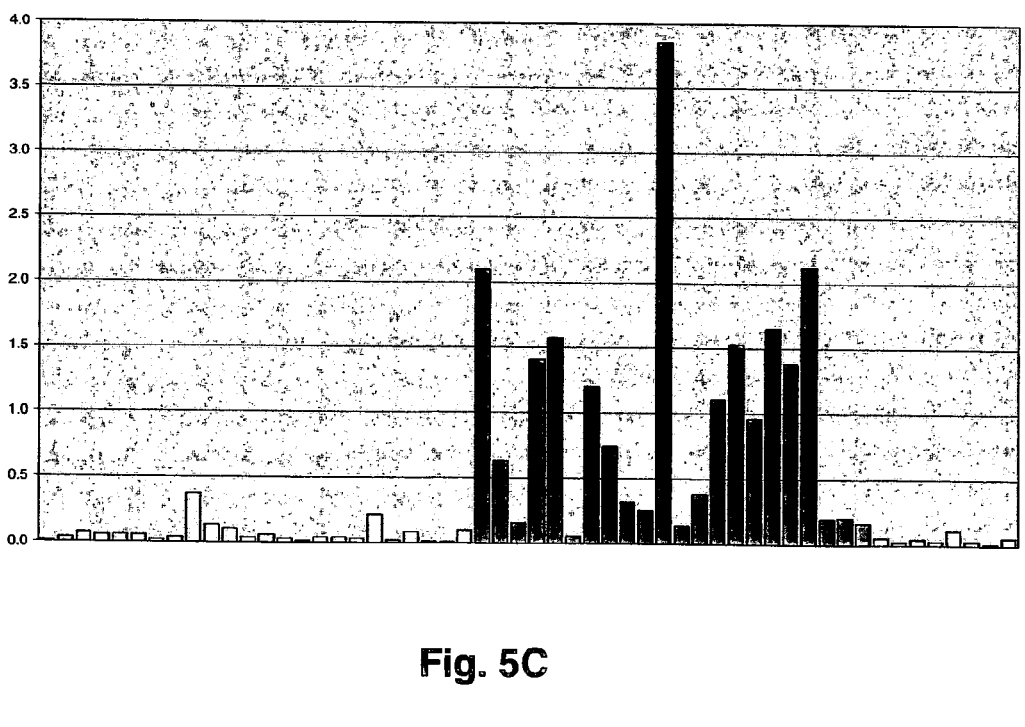
Fig. 5C

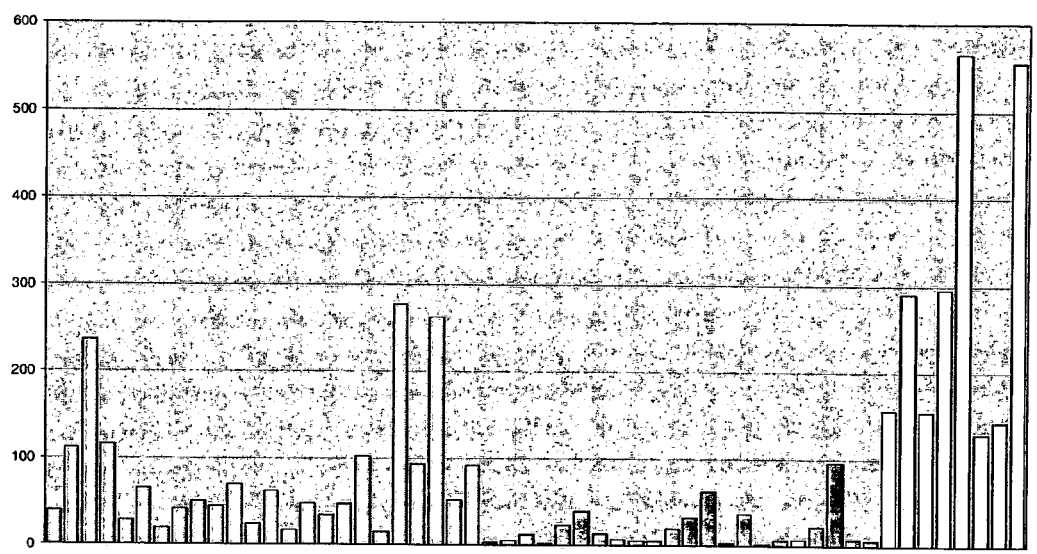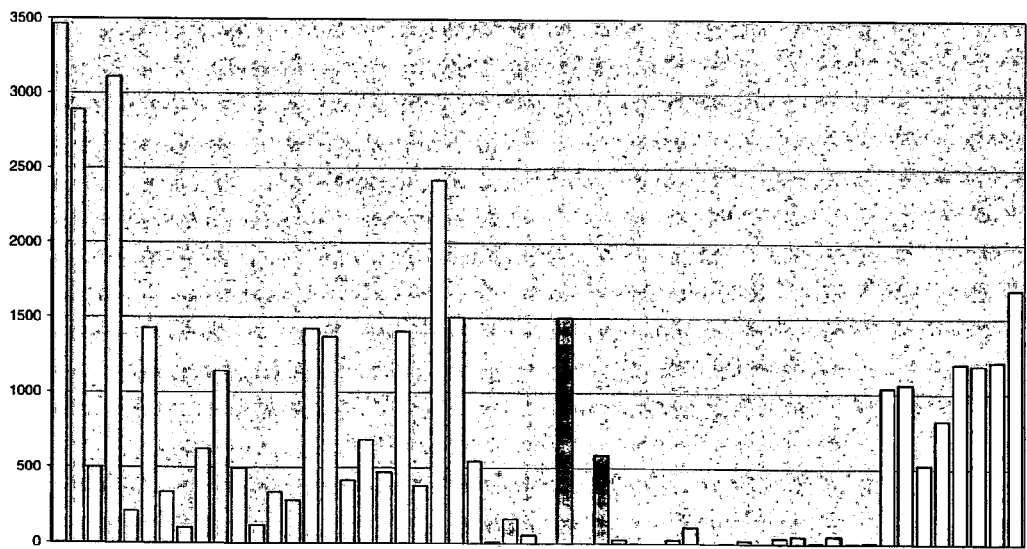
Fig. 5D

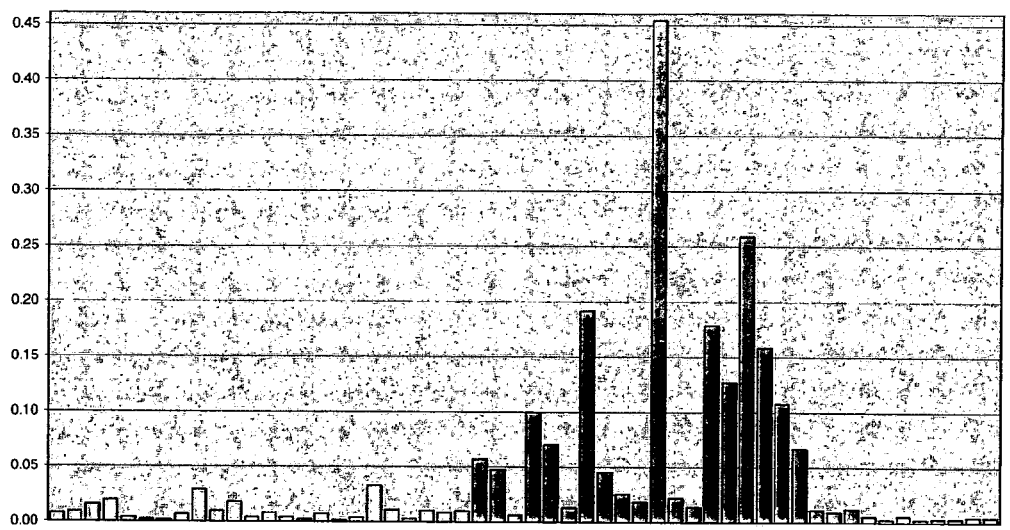
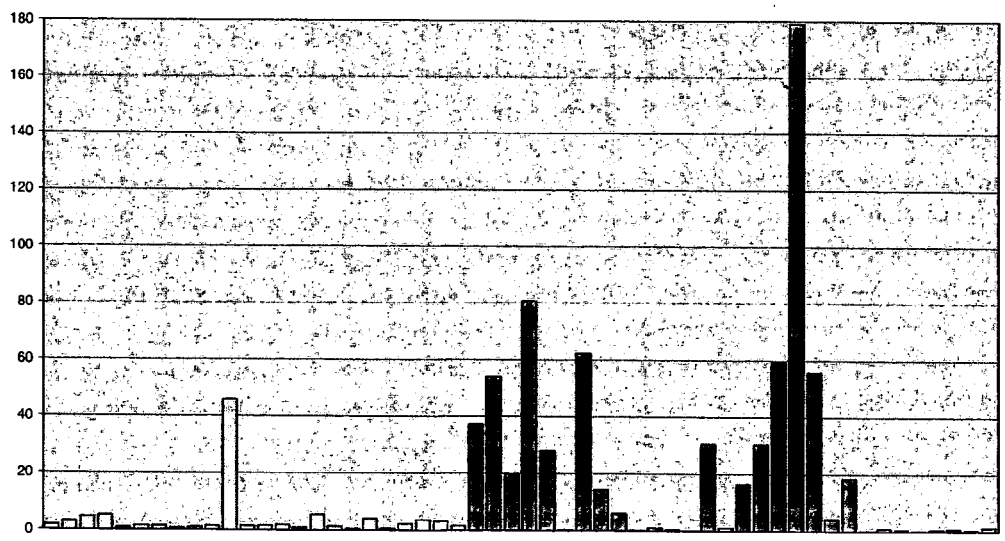
Fig. 5E

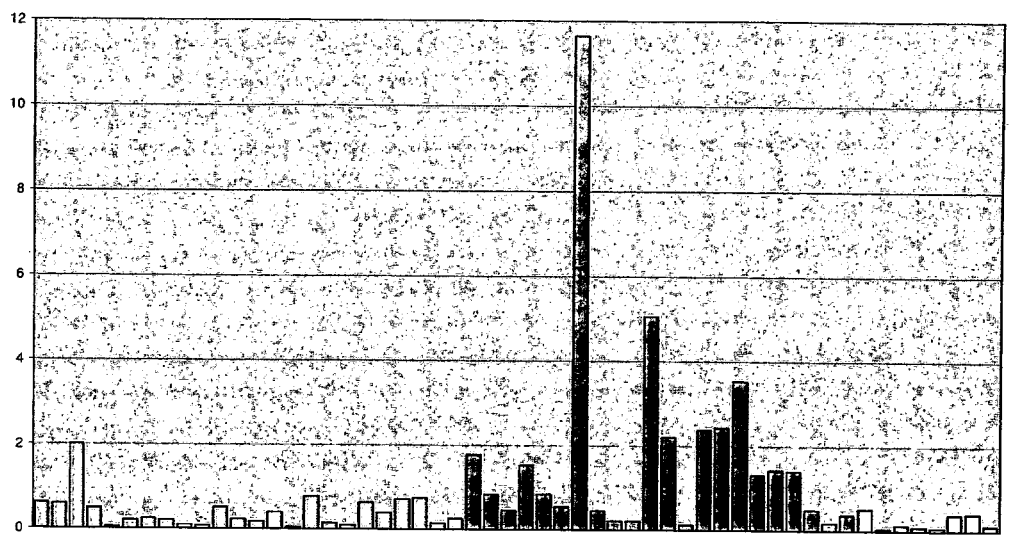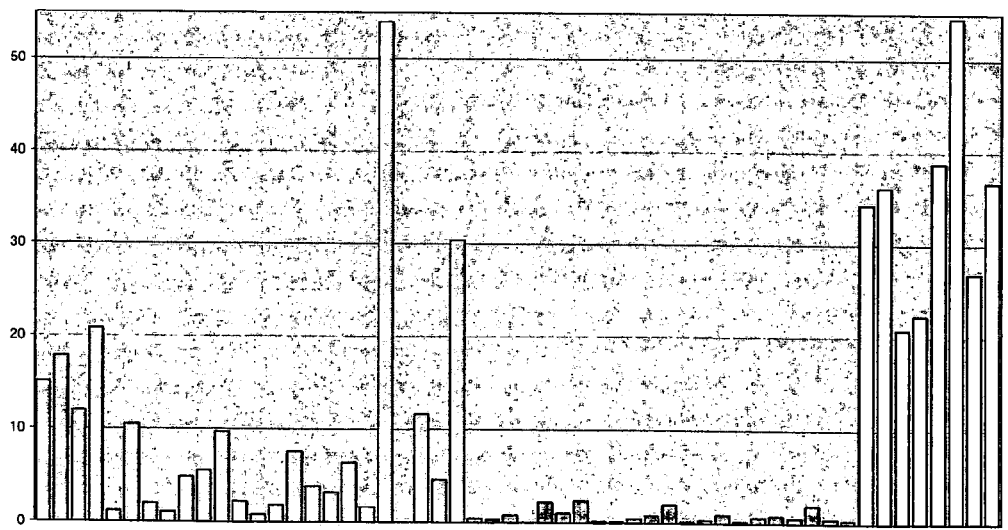
Fig. 5F

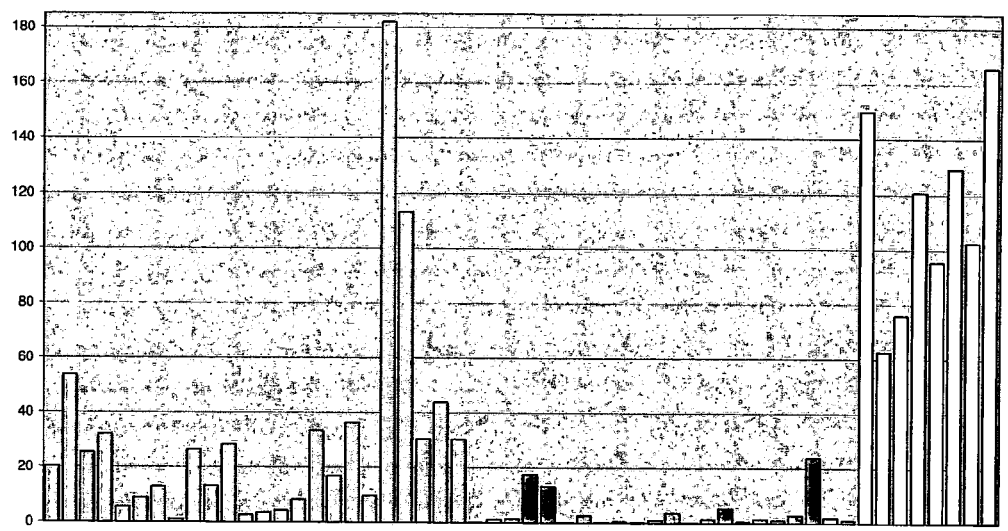
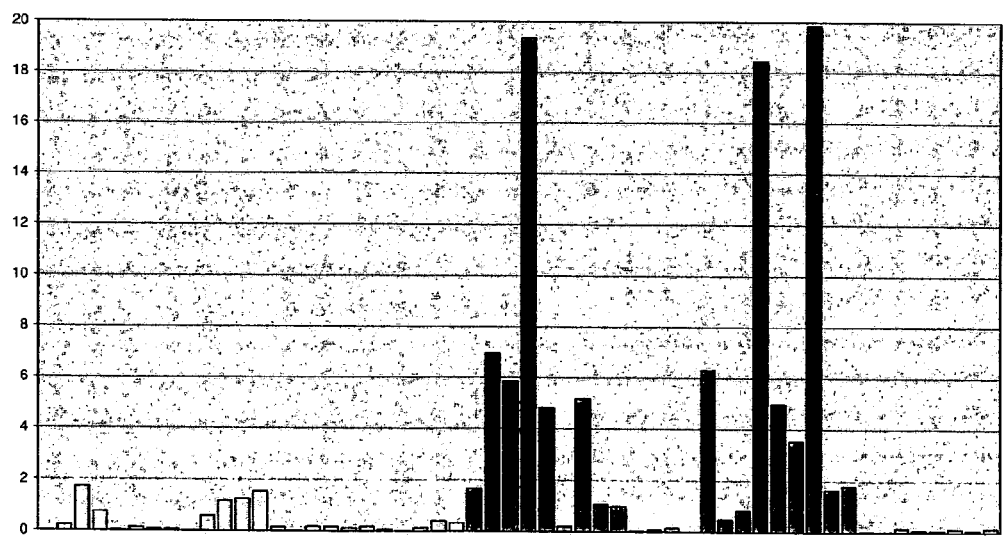
Fig. 5G

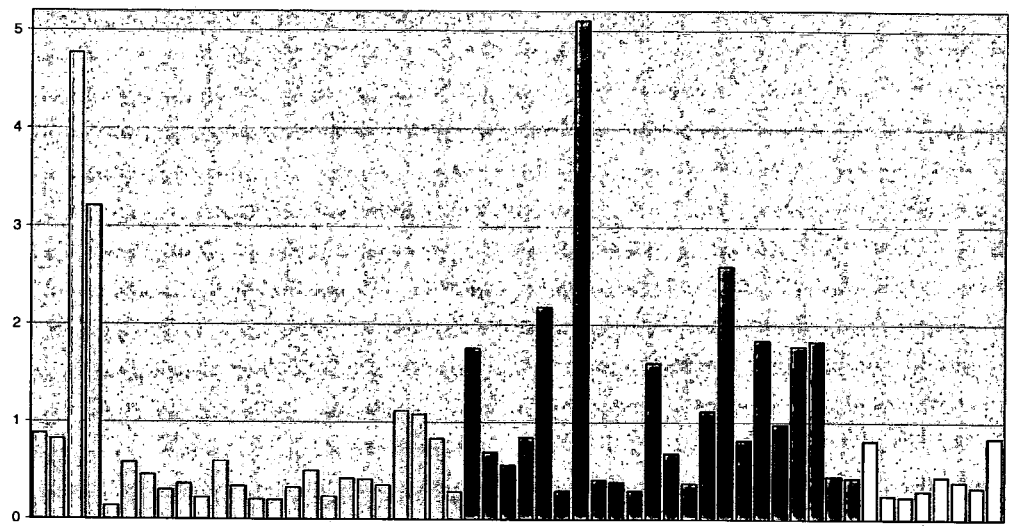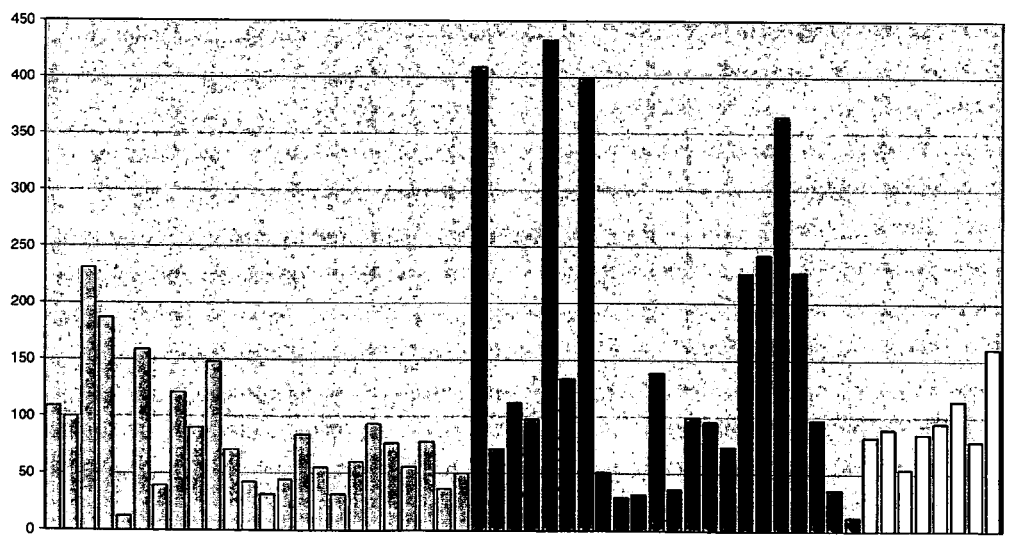
Fig. 5 H

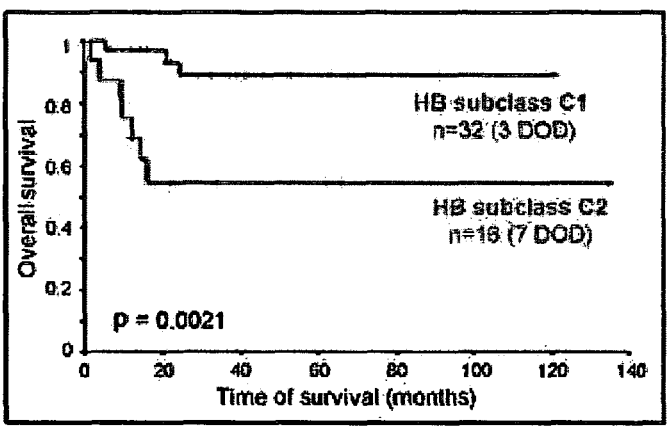
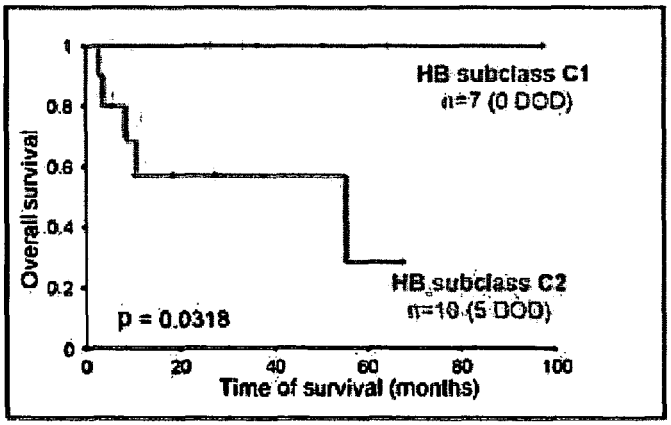
Fig. 6

|  | Microarray set n=24 | qPCR set n=37 | Complete set n=61 |
|---|---|---|---|
| - Male gender (%) | 17 (71%) | 20 (54%) | 37 (61%) |
| - Median age, years (range) | 2 (0-17) | 2 (0-10) | 2 (0-17) |
| - AFP at diagnosis (ng/mL): median | 131000 | 75873 | 84000 |
| range | 180-1990800 | 44-2265000 | 44-2265000 |
| - Preoperative chemotherapy | 19 (79%) | 29 (78%) | 48 (79%) |
| Treatment protocol (SR/HR/NA) | 9/9/1 | 16/9/4 | 25/18/5 |
| - Tumor characteristics |  |  |  |
| Tumor stage (SIOPEL): |  |  |  |
| Distant metastasis at diagnosis | 6 (25%) | 10 (27%) | 16 (26%) |
| Vascular invasion* | 14 (58%) | 15 (40%) | 29 (47%) |
| PRETEXT stage (I/II/III/IV) | 3/10/7/4 | 5/11/13/8 | 8/21/20/12 |
| Multifocality | 9 (37%) | 9 (24%) | 18 (29%) |
| Histology: |  |  |  |
| Epithelial/Mixed | 19/5 | 23/14 | 43/19 |
| Predominant Epith. histotype (Fetal/others**/NA) | 16/8/0 | 21/13/3 | 37/21/3 |
| *CTNNB1* mutation | 19 (79%) | 28 (76%) | 47 (77%) |
| *AXIN1* mutation | 1 (4%) | 0 (0%) | 1 (2%) |
| - Median follow-up, months (range) | 40 (4-120) | 22 (1-135) | 32 (1-135) |
| Alive/DOD/complication-related death | 16/7/1 | 28/8/1 | 44/15/2 |

Fig. 7

| Tumor ID | robust cluster sample | Microarray analysis | aCGH analysis | qPCR analysis | Training set | array test set | qPCR test set | 16-gene-based classification | Gender | Age (months) | Pre-operative AFP (ng/mL) | Chemotherapy treatment | Treatment protocol | PRETEXT stage | Tumor stage | Distant Metastasis | Vascular invasion | Multifocality | Histology | Main Epithelial component | β-catenin status | Follow-up (months) | Outcome |
|---|---|---|---|---|---|---|---|---|---|---|---|---|---|---|---|---|---|---|---|---|---|---|---|
| HB1 | | | | 1 | | | 1 | C2 | F | 43 | NA | Y | H | IV | A | Y | Y | M | E | E | wt (FAP) | 12 | DOD |
| HB3 | | | | 1 | | | 1 | C1 | F | 22 | 114 | Y | S | I | E | N | N | S | E | F | wt | 55 | A |
| HB5 | rC1 | 1 | 1 | | | 1 | | C1 | M | 84 | 10400 | Y | H | III | A | Y | Y | M | E | F | Δex3 | 24 | DOD |
| HB6 | | | | 1 | | | 1 | C1 | M | 24 | NA | Y | S | II | A | N | Y | S | E | F | D32N | 48 | A |
| HB7 | | | | 1 | | | 1 | C1 | M | 33 | 1300 | Y | S | I | A | N | Y | S | M | F | Δex3 | 46 | A |
| HB8 | | | | 1 | | | 1 | C2 | F | 8 | 20000 | Y | NA | II | A | N | Y | S | E | E | D32G | 135 | A |
| HB9 | | | | 1 | | | 1 | C1 | F | 16 | 64 | Y | NA | III | E | N | N | S | E | PF | G34E | 91 | A |
| HB11 | | 1 | 1 | | | 1 | | C1 | F | 18 | NA | Y | H | IV | A | Y | Y | M | M | F | Δex3 | 21 | DOD |
| HB20 | | | | 1 | | | 1 | C1 | F | 50 | 52 | Y | S | II | E | N | N | S | E | F | Δex3 | 42 | A |
| HB28 | | 1 | 1 | | | 1 | | C1 | M | 34 | 32000 | Y | NA | II | E | N | N | S | E | F | wt | 120 | A |
| HB33 | | 1 | 1 | | | 1 | | C2 | M | 12 | 60000 | Y | H | IV | A | N | Y | M | E | CF | wt (AXIN1) | 3.5 | DOD |
| HB39 | | | 1 | | | 1 | | C2 | F | 11 | 20000 | Y | S | III | A | N | Y | S | M | NA | S37Y | 66 | A |
| HB48 | | 1 | 1 | | | 1 | | C2 | M | 72 | NA | Y | H | IV | A | N | Y | M | E | CF | G34/E | 9 | DOD |
| HB49 | rC1 | 1 | 1 | | | 1 | | C1 | F | 15 | 2355 | Y | S | II | E | N | N | S | E | F | I35/S | 6 | D |
| HB54 | | 1 | | | | 1 | | C1 | M | 10 | NA | N | | I | E | N | N | S | E | PF | Δex3 | 49 | A |
| HB59 | rC1 | 1 | 1 | 1 | 1 | | | C1 | F | 24 | 53 | Y | S | II | E | N | N | S | E | PF | D32Y | 72 | A |
| HB60 | | 1 | 1 | | | 1 | | C1 | F | 30 | 6872 | Y | H | II | A | N | Y | S | E | F | wt | 63 | A |
| HB61 | | | | 1 | | | 1 | C1 | F | 126 | 280000 | Y | NA | IV | A | Y | Y | M | M | F | Δex3 | 5 | DOD |
| HB62 | | 1 | 1 | | | 1 | | C1 | M | 16 | 3451 | Y | H | IV | A | N | N | S | M | F | Δex3 | 69 | A |
| HB63 | | 1 | 1 | | | 1 | | C1 | M | 204 | NA | N | | III | A | N | Y | M | M | F | Δex3 | 96 | A |
| HB65 | | | | 1 | | | 1 | C2 | M | 6 | NA | N | | III | E | N | N | M | M | E | wt | 2 | DOD |
| HB66 | | | | 1 | | | 1 | C1 | M | 6 | 6900 | Y | S | III | E | N | N | S | E | F | G34V | 68 | A |
| HB68 | | | | 1 | | | 1 | C1 | F | 11 | 1230 | Y | S | III | E | N | N | S | M | E | G34V | 52 | A |
| HB69 | rC1 | 1 | 1 | 1 | 1 | | | C1 | M | 25 | 84 | Y | S | I | E | N | N | S | E | PF | wt | 55 | A |
| HB70 | | 1 | 1 | | | | 1 | C1 | F | 42 | 392 | Y | S | II | E | N | N | S | E | PF | Δex3 | 53 | R |
| HB72 | rC2 | 1 | 1 | 1 | 1 | | | C2 | F | 16 | 190000 | Y | S | III | A | Y | Y | M | M | E | Δex3 | 9.5 | DOD |
| HB73 | rC2 | 1 | 1 | 1 | 1 | | | C2 | F | 24 | 41844 | Y | H | III | A | Y | Y | S | E | E | Δex3 | 16 | DOD |
| HB74F* | rC1 | 1 | 1 | 1 | 1 | | | C1 | M | 96 | NA | N | | I | A | N | Y | S | E | F | Δex3 | 35 | A |
| HB74e | rC2 | 1 | 1 | 1 | 1 | | | C2 | M | 96 | NA | N | | I | A | N | Y | S | E | E | Δex3 | 35 | A |
| HB75 | rC1 | 1 | 1 | 1 | 1 | | | C1 | M | 21 | 6600 | Y | S | II | A | N | Y | S | M | F | Δex3 | 41 | A |
| HB77 | | | | 1 | | | 1 | C1 | F | 9 | 500 | Y | S | II | E | N | N | S | E | F | Δex3 | 37 | A |
| HB78 | | 1 | 1 | | | 1 | | C1 | M | 126 | 23000 | Y | S | II | A | N | Y | M | E | CF | wt | 32 | A |
| HB79 | | 1 | 1 | | | 1 | | C1 | M | 144 | 196 | Y | S | II | E | N | N | M | E | M | Δex3 | 39 | A |

Fig. 8A

| Tumor ID* | robust cluster sample | Microarray analysis | aCGH analysis | qPCR analysis | training set | array test set | qPCR test set | 16-gene-based classification | Gender | Age (months) | Pre-operative AFP (ng/mL) | Chemotherapy treatment | Treatment protocol | PRETEXT stage | Invasive phenotype | Distant Metastasis | Vascular invasion | Multifocality | Histology | Main Epithelial component | β-catenin status | Follow-up (months) | Outcome |
|---|---|---|---|---|---|---|---|---|---|---|---|---|---|---|---|---|---|---|---|---|---|---|---|
| HB80 | rC2 | 1 | 1 | 1 | 1 | | | C2 | M | 180 | 12500 | Y | H | III | A | Y | Y | S | E | CF | Δex3 | 14 | DOD |
| HB81 | rC1 | 1 | 1 | 1 | 1 | | | C1 | M | 22 | 229 | Y | H | III | A | Y | Y | M | E | F | I35S | 36 | A |
| HB82 | | 1 | 1 | | | 1 | | C1 | M | 120 | NA | N | | II | E | N | N | S | E | F | Δex3 | 63 | A |
| HB83 | rC1 | 1 | 1 | 1 | 1 | | | C1 | M | 15 | 73 | Y | S | II | E | N | N | S | E | PF | Δex3 | 53 | A |
| HB86 | rC2 | 1 | 1 | 1 | 1 | | | C2 | M | 0,08 | NA | N | | III | A | N | Y | S | E | E | Δex3 | 57 | A |
| HB89 | | | 1 | | | 1 | C1 | M | 13 | 180 | Y | S | I | E | N | N | S | E | F | Δex3 | 33 | A |
| HB90 | | | 1 | | | 1 | C1 | F | 74 | NA | N | | II | E | N | N | S | E | F | Δex3 | 25 | A |
| HB93 | | | 1 | | | 1 | C2 | M | 22 | 20000 | Y | S | III | A | N | Y | M | M | E | G34E | 22 | A |
| HB94* | | | 1 | | | 1 | C1 | M | 29 | 523 | Y | S | I | E | N | N | S | E | PF | wt | 21 | A |
| HB94b | | | 1 | | | 1 | C1 | M | 26 | NA | N | | I | E | N | N | S | E | PF | wt | 24 | A |
| HB95 | | | 1 | | | 1 | C1 | M | 28 | 840 | Y | H | IV | A | Y | Y | M | M | F | Δex3 | 14 | A |
| HB96 | | | 1 | | | 1 | C1 | M | 101 | 23669 | Y | H | IV | A | N | Y | M | E | F | Δex3 | 12 | A |
| HB97 | | | 1 | | | 1 | C2 | F | 42 | 50000 | Y | H | IV | A | Y | Y | M | E | F | Δex3 | 12 | A |
| HB98 | | | 1 | | | 1 | C2 | M | 60 | NA | Y | H | III | A | Y | Y | S | E | M | wt (FAP) | 18 | A |
| HB99 | | | 1 | | | 1 | C2 | M | 72 | 21000 | N | | IV | A | Y | Y | M | E | E | Δex3 | 7 | DOD |
| HB100 | | | 1 | | | 1 | C2 | M | 48 | 23010 | N | | III | E | N | N | S | E | F | Δex3 | 17 | A |
| HB101 | | | 1 | | | 1 | C1 | M | 42 | 460 | Y | S | III | E | N | N | S | E | F | Δex3 | 16 | A |
| HB102 | | | 1 | | | 1 | C2 | M | 41 | 14921 | N | | II | E | N | N | S | E | CF | G34R | 4 | D |
| HB103 | | | 1 | | | 1 | C2 | F | 51 | 1800000 | N | | IV | A | Y | Y | M | E | CF | Δex3 | 9 | DOD |
| HB106* | | | 1 | | | 1 | C1 | F | 11 | 183 | Y | H | IV | A | N | N | S | M | F | Δex3 | 6 | A |
| HB106b | | | 1 | | | 1 | C2 | F | 8 | NA | N | | IV | A | N | N | S | M | CF | Δex3 | 9 | A |
| HB112* | | | 1 | | | 1 | C1 | M | 36 | 34 | Y | S | II | E | N | N | S | E | F | wt | 29 | A |
| HB112b | | | 1 | | | 1 | C1 | M | 33 | NA | N | | II | E | N | N | S | E | F | wt | 32 | A |
| HB114* | | | 1 | | | 1 | C2 | F | 21 | 145 | Y | S | II | E | N | N | S | M | E | Δex3 | 23 | A |
| HB114b | | | 1 | | | 1 | C2 | F | 18 | NA | N | | II | E | N | N | S | M | M | Δex3 | 26 | A |
| HB129 | | | 1 | | | 1 | C2 | M | 96 | NA | N | | I | E | N | N | S | M | E | wt | 54 | DOD |
| HB130 | | | 1 | | | 1 | C2 | F | 19 | 1208 | Y | H | II | A | Y | N | S | M | NA | Δex3 | 62 | A |
| HB131 | | | 1 | | | 1 | C2 | M | 6 | NA | Y | H | II | A | Y | N | S | E | E | wt | 1 | DOD |
| HB132 | | | 1 | | | 1 | C1 | F | 23 | NA | Y | NA | III | E | N | N | S | M | F | Δex3 | 121 | A |
| HB136 | | | 1 | | | 1 | C2 | M | 6 | 52 | Y | S | III | E | N | N | S | M | F | wt | 34 | A |
| HB137 | | | 1 | | | 1 | C2 | M | 5 | NA | N | | III | A | Y | Y | S | E | S | Δex3 | 1 | DOD |
| HB140 | | | 1 | | | 1 | C1 | M | 3 | 148 | Y | S | II | E | N | N | S | M | F | Δex3 | 22 | A |
| HB142 | | | 1 | | | 1 | C2 | F | 48 | 8248 | Y | H | III | A | Y | Y | S | E | NA | Δex3 | 15 | A |

Fig. 8B

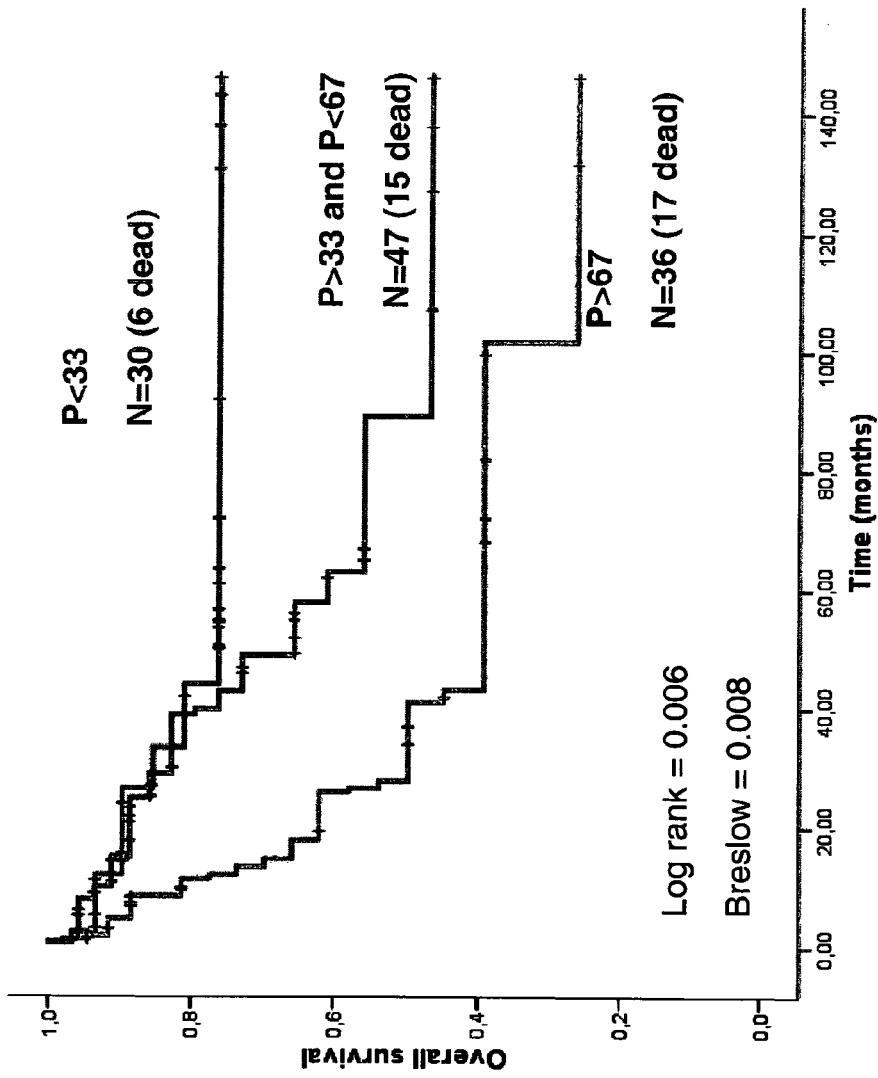
Fig 12A  Kaplan-Meier curves of overall survival (OS) for 3 HCC subclasses including OLT and PH cases

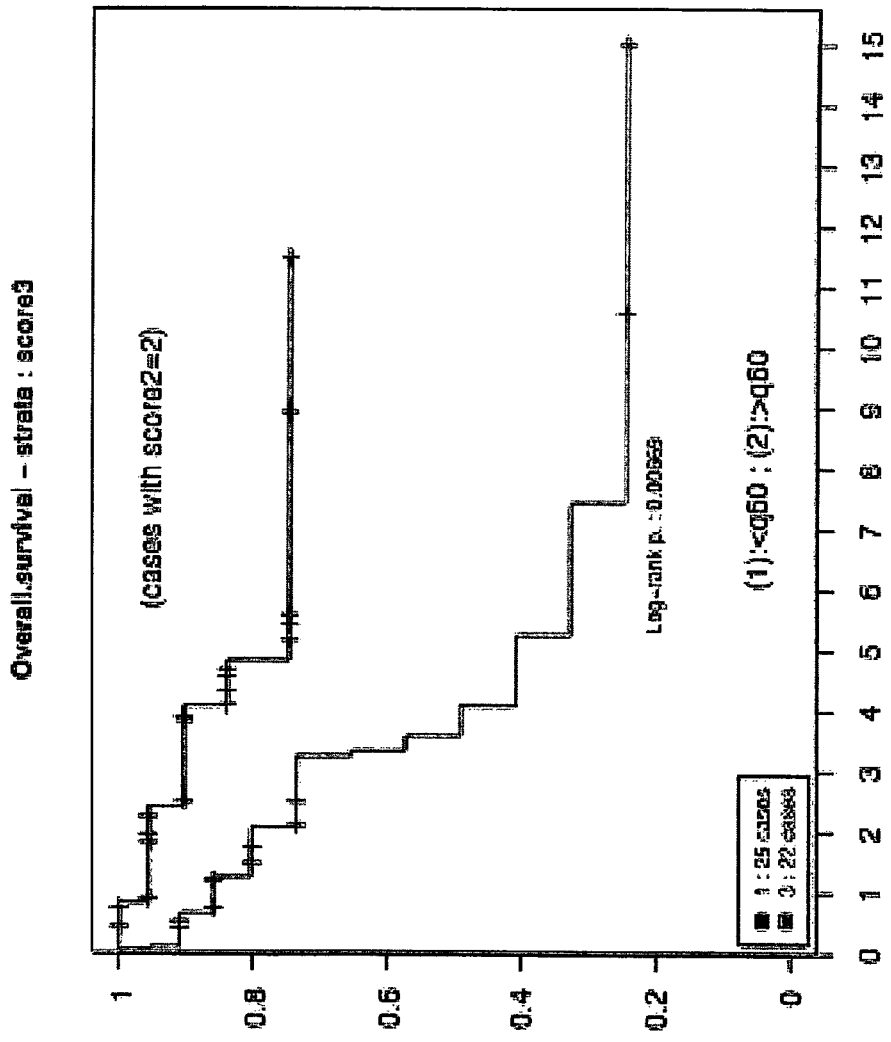
Fig 12B  Subdivision of HCC cases of the intermediate class into 2 new subclasses. Kaplan-Meier curves of OS

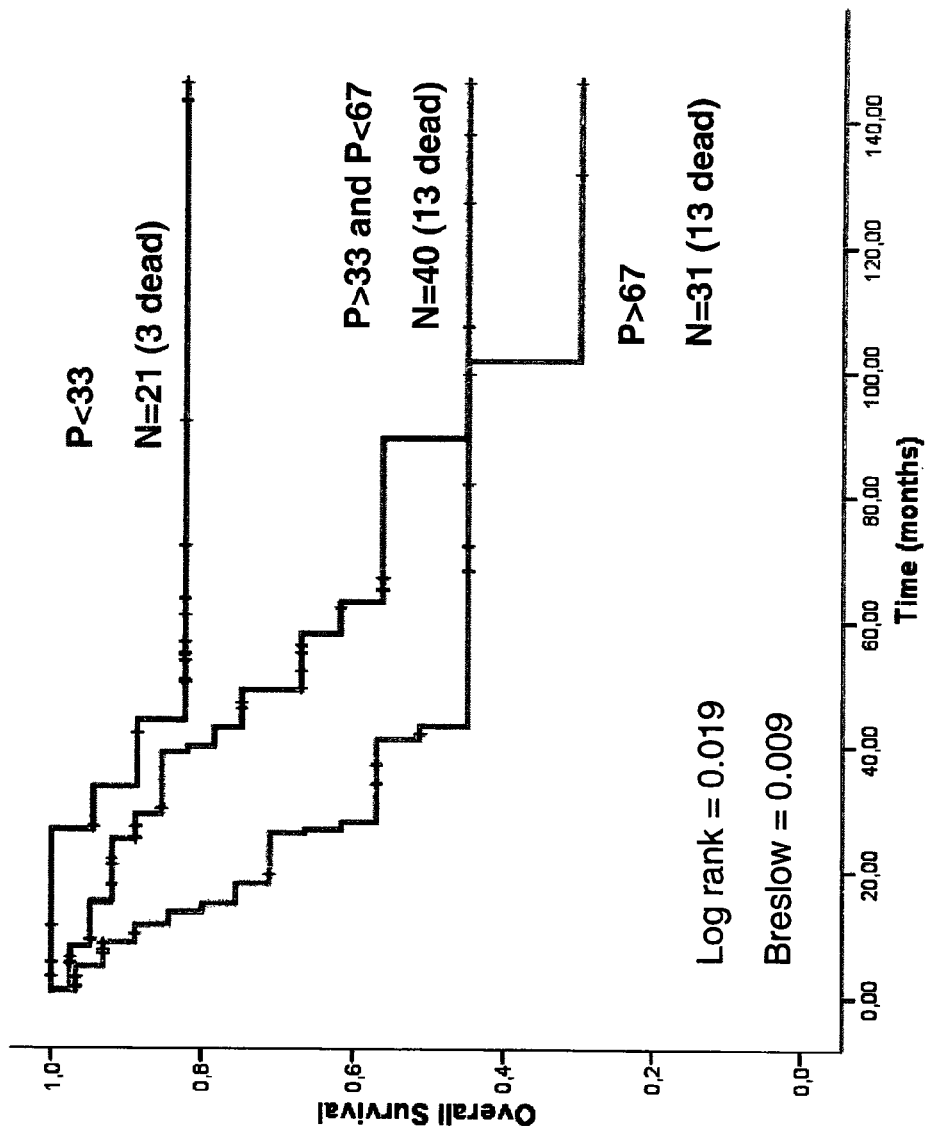
Fig 12C  Kaplan-Meier curves of OS for 3 HCC subclasses including PH cases only

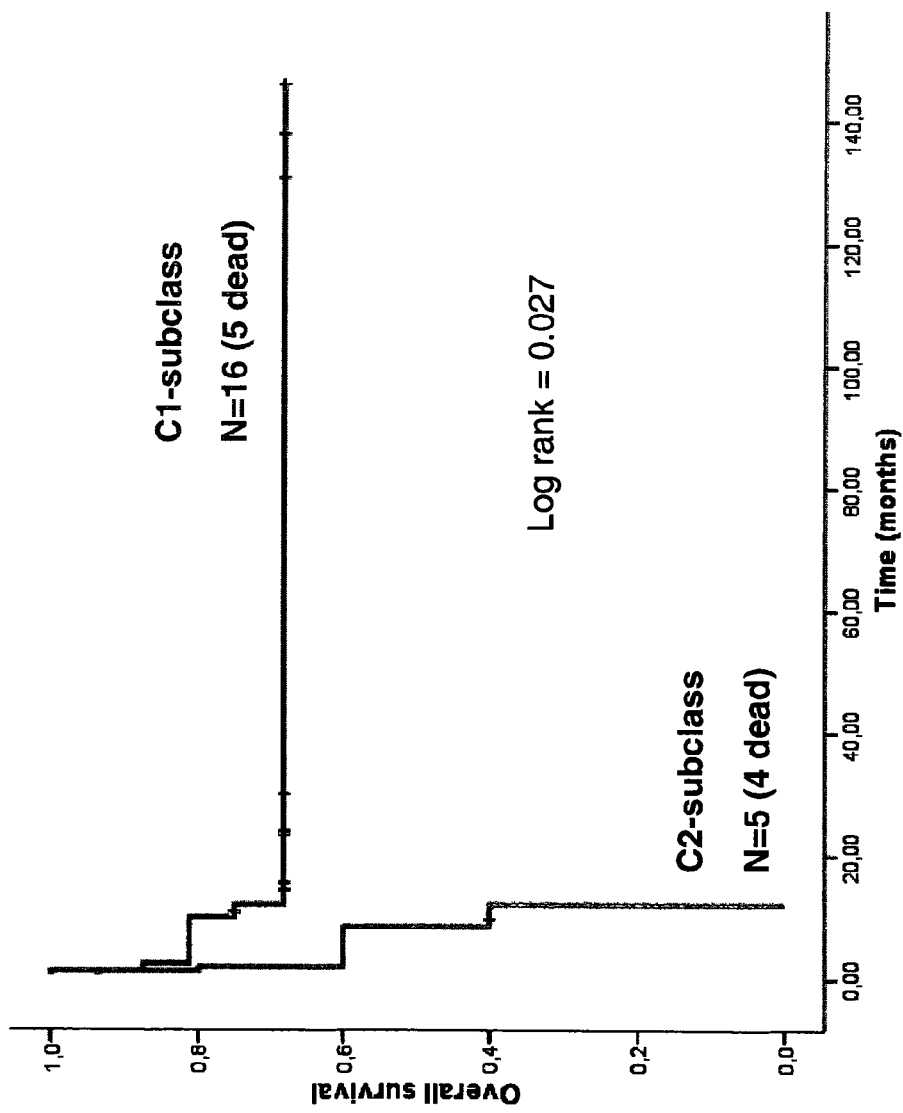

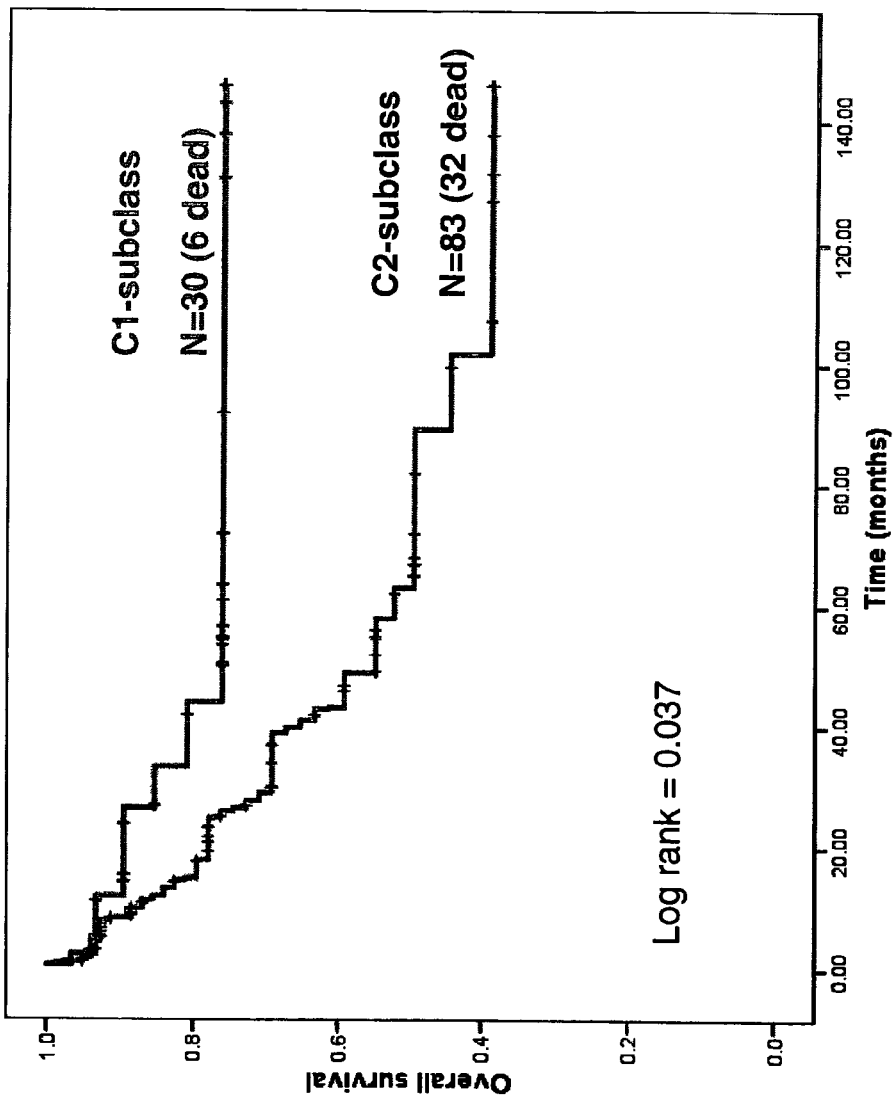
Fig 12 F  Kaplan-Meier curves of Overall Survival for 2 HCC subclasses using the 33rd percentile

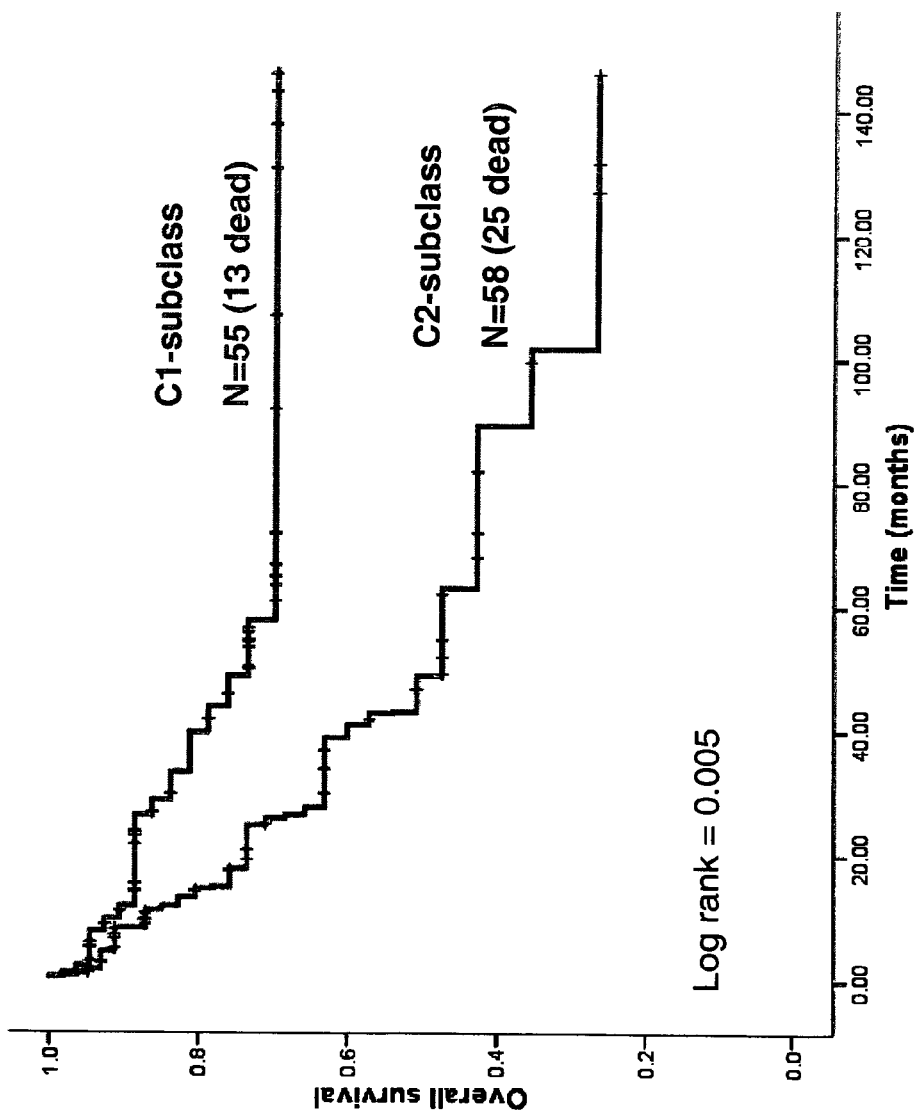
Fig 12 G  Kaplan-Meier curves of OS using the 50th percentile

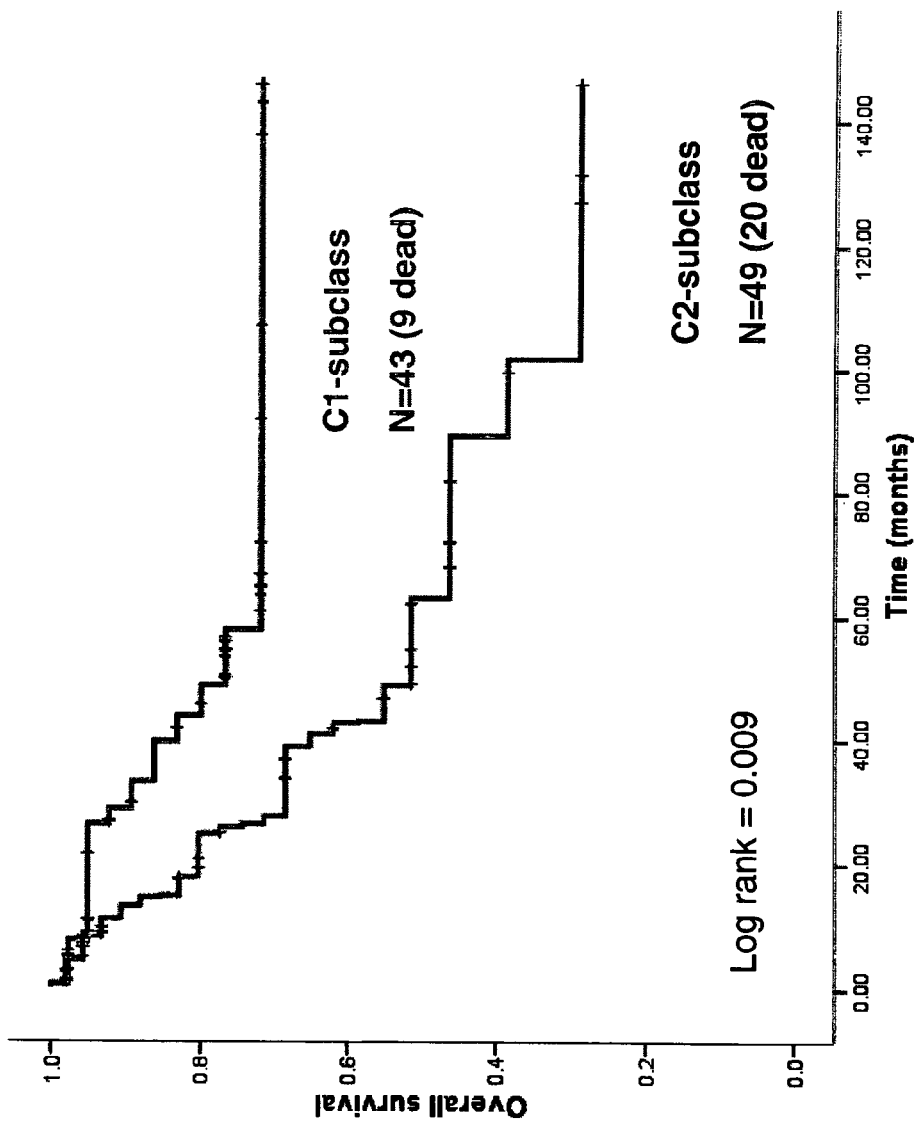
Fig 12J  Kaplan-Meier curves of OS using the 50th percentile: PH cases only

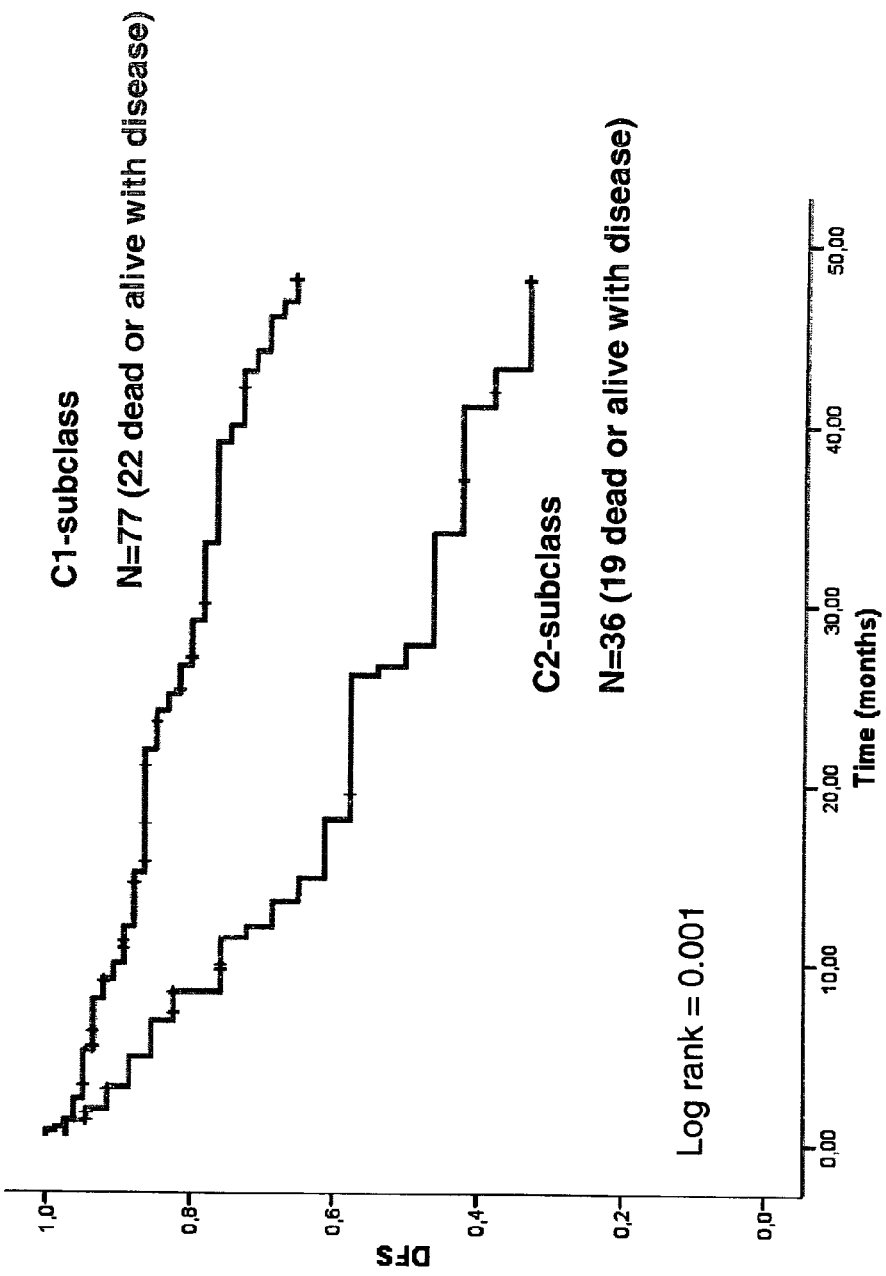

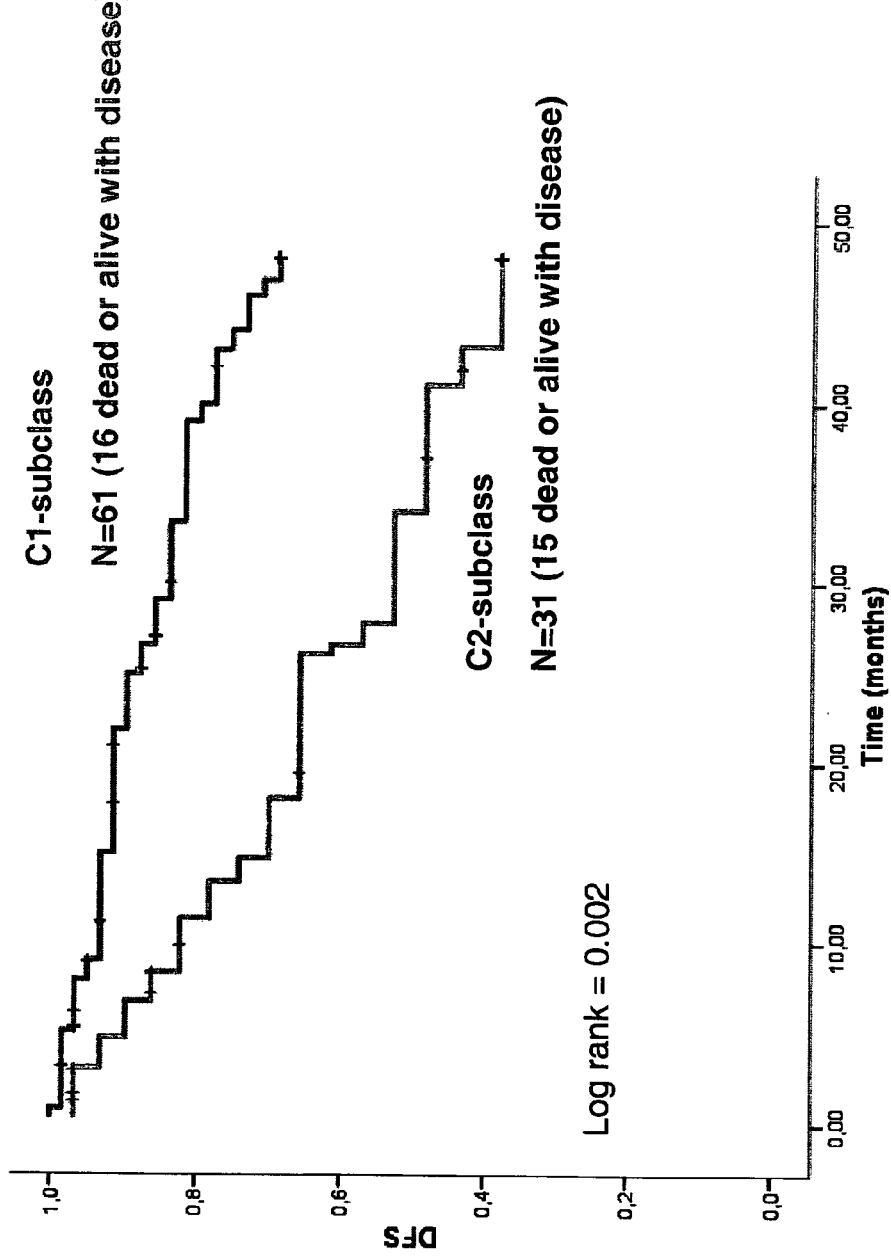
Fig 12M Kaplan-Meier curves of DFS, using the 67th percentile, PH cases only (follow-up closed at 4-years)

SEQUENCE LISTING

```
<160> NUMBER OF SEQ ID NOS: 140

<210> SEQ ID NO 1
<211> LENGTH: 2014
<212> TYPE: DNA
<213> ORGANISM: Homo sapiens
<220> FEATURE:
<223> OTHER INFORMATION: AFP mRNA
<220> FEATURE:
<221> NAME/KEY: CDS
<222> LOCATION: (31)..(1854)

<400> SEQUENCE: 1
ccactgccaa taacaaaata actagcaacc atg aag tgg gtg gaa tca att ttt         54
                                 Met Lys Trp Val Glu Ser Ile Phe
                                  1               5 tta att ttc cta cta aat ttt act gaa tcc aga aca ctg cat aga aat        102
Leu Ile Phe Leu Leu Asn Phe Thr Glu Ser Arg Thr Leu His Arg Asn
         10                  15                  20 gaa tat gga ata gct tcc ata ttg gat tct tac caa tgt act gca gag        150
Glu Tyr Gly Ile Ala Ser Ile Leu Asp Ser Tyr Gln Cys Thr Ala Glu
 25                  30                  35                  40 ata agt tta gct gac ctg gct acc ata ttt ttt gcc cag ttt gtt caa        198
Ile Ser Leu Ala Asp Leu Ala Thr Ile Phe Phe Ala Gln Phe Val Gln
                 45                  50                  55 gaa gcc act tac aag gaa gta agc aaa atg gtg aaa gat gca ttg act        246
Glu Ala Thr Tyr Lys Glu Val Ser Lys Met Val Lys Asp Ala Leu Thr
             60                  65                  70 gca att gag aaa ccc act gga gat gaa cag tct tca ggg tgt tta gaa        294
Ala Ile Glu Lys Pro Thr Gly Asp Glu Gln Ser Ser Gly Cys Leu Glu
         75                  80                  85
```

| | | | | | | | | | | | | | | | |
|---|---|---|---|---|---|---|---|---|---|---|---|---|---|---|---|
| aac | cag | cta | cct | gcc | ttt | ctg | gaa | gaa | ctt | tgc | cat | gag | aaa | gaa | att | 342 |
| Asn | Gln | Leu | Pro | Ala | Phe | Leu | Glu | Glu | Leu | Cys | His | Glu | Lys | Glu | Ile | |
| | 90 | | | | 95 | | | | | 100 | | | | | | |

| ttg | gag | aag | tac | gga | cat | tca | gac | tgc | tgc | agc | caa | agt | gaa | gag | gga | 390 |
| Leu | Glu | Lys | Tyr | Gly | His | Ser | Asp | Cys | Cys | Ser | Gln | Ser | Glu | Glu | Gly | |
| 105 | | | | | 110 | | | | | 115 | | | | | 120 | |

| aga | cat | aac | tgt | ttt | ctt | gca | cac | aaa | aag | ccc | act | cca | gca | tcg | atc | 438 |
| Arg | His | Asn | Cys | Phe | Leu | Ala | His | Lys | Lys | Pro | Thr | Pro | Ala | Ser | Ile | |
| | | | | 125 | | | | | 130 | | | | | 135 | | |

| cca | ctt | ttc | caa | gtt | cca | gaa | cct | gtc | aca | agc | tgt | gaa | gca | tat | gaa | 486 |
| Pro | Leu | Phe | Gln | Val | Pro | Glu | Pro | Val | Thr | Ser | Cys | Glu | Ala | Tyr | Glu | |
| | | | 140 | | | | | 145 | | | | | 150 | | | |

| gaa | gac | agg | gag | aca | ttc | atg | aac | aaa | ttc | att | tat | gag | ata | gca | aga | 534 |
| Glu | Asp | Arg | Glu | Thr | Phe | Met | Asn | Lys | Phe | Ile | Tyr | Glu | Ile | Ala | Arg | |
| | | | 155 | | | | | 160 | | | | | 165 | | | |

| agg | cat | ccc | ttc | ctg | tat | gca | cct | aca | att | ctt | ctt | tgg | gct | gct | cgc | 582 |
| Arg | His | Pro | Phe | Leu | Tyr | Ala | Pro | Thr | Ile | Leu | Leu | Trp | Ala | Ala | Arg | |
| | 170 | | | | | 175 | | | | | 180 | | | | | |

| tat | gac | aaa | ata | att | cca | tct | tgc | tgc | aaa | gct | gaa | aat | gca | gtt | gaa | 630 |
| Tyr | Asp | Lys | Ile | Ile | Pro | Ser | Cys | Cys | Lys | Ala | Glu | Asn | Ala | Val | Glu | |
| 185 | | | | | 190 | | | | | 195 | | | | | 200 | |

| tgc | ttc | caa | aca | aag | gca | gca | aca | gtt | aca | aaa | gaa | tta | aga | gaa | agc | 678 |
| Cys | Phe | Gln | Thr | Lys | Ala | Ala | Thr | Val | Thr | Lys | Glu | Leu | Arg | Glu | Ser | |
| | | | | 205 | | | | | 210 | | | | | 215 | | |

| agc | ttg | tta | aat | caa | cat | gca | tgt | gca | gta | atg | aaa | aat | ttt | ggg | acc | 726 |
| Ser | Leu | Leu | Asn | Gln | His | Ala | Cys | Ala | Val | Met | Lys | Asn | Phe | Gly | Thr | |
| | | | 220 | | | | | 225 | | | | | 230 | | | |

| cga | act | ttc | caa | gcc | ata | act | gtt | act | aaa | ctg | agt | cag | aag | ttt | acc | 774 |
| Arg | Thr | Phe | Gln | Ala | Ile | Thr | Val | Thr | Lys | Leu | Ser | Gln | Lys | Phe | Thr | |
| | | 235 | | | | | 240 | | | | | 245 | | | | |

| aaa | gtt | aat | ttt | act | gaa | atc | cag | aaa | cta | gtc | ctg | gat | gtg | gcc | cat | 822 |
| Lys | Val | Asn | Phe | Thr | Glu | Ile | Gln | Lys | Leu | Val | Leu | Asp | Val | Ala | His | |
| | 250 | | | | | 255 | | | | | 260 | | | | | |

| gta | cat | gag | cac | tgt | tgc | aga | gga | gat | gtg | ctg | gat | tgt | ctg | cag | gat | 870 |
| Val | His | Glu | His | Cys | Cys | Arg | Gly | Asp | Val | Leu | Asp | Cys | Leu | Gln | Asp | |
| 265 | | | | | 270 | | | | | 275 | | | | | 280 | |

| ggg | gaa | aaa | atc | atg | tcc | tac | ata | tgt | tct | caa | caa | gac | act | ctg | tca | 918 |
| Gly | Glu | Lys | Ile | Met | Ser | Tyr | Ile | Cys | Ser | Gln | Gln | Asp | Thr | Leu | Ser | |
| | | | | 285 | | | | | 290 | | | | | 295 | | |

| aac | aaa | ata | aca | gaa | tgc | tgc | aaa | ctg | acc | acg | ctg | gaa | cgt | ggt | caa | 966 |
| Asn | Lys | Ile | Thr | Glu | Cys | Cys | Lys | Leu | Thr | Thr | Leu | Glu | Arg | Gly | Gln | |
| | | | 300 | | | | | 305 | | | | | 310 | | | |

| tgt | ata | att | cat | gca | gaa | aat | gat | gaa | aaa | cct | gaa | ggt | cta | tct | cca | 1014 |
| Cys | Ile | Ile | His | Ala | Glu | Asn | Asp | Glu | Lys | Pro | Glu | Gly | Leu | Ser | Pro | |
| | | 315 | | | | | 320 | | | | | 325 | | | | |

| aat | cta | aac | agg | ttt | tta | gga | gat | aga | gat | ttt | aac | caa | ttt | tct | tca | 1062 |
| Asn | Leu | Asn | Arg | Phe | Leu | Gly | Asp | Arg | Asp | Phe | Asn | Gln | Phe | Ser | Ser | |
| | 330 | | | | | 335 | | | | | 340 | | | | | |

| ggg | gaa | aaa | aat | atc | ttc | ttg | gca | agt | ttt | gtt | cat | gaa | tat | tca | aga | 1110 |
| Gly | Glu | Lys | Asn | Ile | Phe | Leu | Ala | Ser | Phe | Val | His | Glu | Tyr | Ser | Arg | |
| 345 | | | | | 350 | | | | | 355 | | | | | 360 | |

| aga | cat | cct | cag | ctt | gct | gtc | tca | gta | att | cta | aga | gtt | gct | aaa | gga | 1158 |
| Arg | His | Pro | Gln | Leu | Ala | Val | Ser | Val | Ile | Leu | Arg | Val | Ala | Lys | Gly | |
| | | | | 365 | | | | | 370 | | | | | 375 | | |

| tac | cag | gag | tta | ttg | gag | aag | tgt | ttc | cag | act | gaa | aac | cct | ctt | gaa | 1206 |
| Tyr | Gln | Glu | Leu | Leu | Glu | Lys | Cys | Phe | Gln | Thr | Glu | Asn | Pro | Leu | Glu | |
| | | | 380 | | | | | 385 | | | | | 390 | | | |

| tgc | caa | gat | aaa | gga | gaa | gaa | gaa | tta | cag | aaa | tac | atc | cag | gag | agc | 1254 |
| Cys | Gln | Asp | Lys | Gly | Glu | Glu | Glu | Leu | Gln | Lys | Tyr | Ile | Gln | Glu | Ser | |
| | 395 | | | | | 400 | | | | | 405 | | | | | |

```
caa gca ttg gca aag cga agc tgc ggc ctc ttc cag aaa cta gga gaa    1302
Gln Ala Leu Ala Lys Arg Ser Cys Gly Leu Phe Gln Lys Leu Gly Glu
    410                 415                 420 tat tac tta caa aat gcg ttt ctc gtt gct tac aca aag aaa gcc ccc    1350
Tyr Tyr Leu Gln Asn Ala Phe Leu Val Ala Tyr Thr Lys Lys Ala Pro
425                 430                 435                 440 cag ctg acc tcg tcg gag ctg atg gcc atc acc aga aaa atg gca gcc    1398
Gln Leu Thr Ser Ser Glu Leu Met Ala Ile Thr Arg Lys Met Ala Ala
    445                 450                 455 aca gca gcc act tgt tgc caa ctc agt gag gac aaa cta ttg gcc tgt    1446
Thr Ala Ala Thr Cys Cys Gln Leu Ser Glu Asp Lys Leu Leu Ala Cys
    460                 465                 470 ggc gag gga gcg gac att att atc gga cac tta tgt atc aga cat gaa    1494
Gly Glu Gly Ala Asp Ile Ile Ile Gly His Leu Cys Ile Arg His Glu
    475                 480                 485 atg act cca gta aac cct ggt gtt ggc cag tgc tgc act tct tca tat    1542
Met Thr Pro Val Asn Pro Gly Val Gly Gln Cys Cys Thr Ser Ser Tyr
    490                 495                 500 gcc aac agg agg cca tgc ttc agc agc ttg gtg gtg gat gaa aca tat    1590
Ala Asn Arg Arg Pro Cys Phe Ser Ser Leu Val Val Asp Glu Thr Tyr
505                 510                 515                 520 gtc cct cct gca ttc tct gat gac aag ttc att ttc cat aag gat ctg    1638
Val Pro Pro Ala Phe Ser Asp Asp Lys Phe Ile Phe His Lys Asp Leu
                525                 530                 535 tgc caa gct cag ggt gta gcg ctg caa aca atg aag caa gag ttt ctc    1686
Cys Gln Ala Gln Gly Val Ala Leu Gln Thr Met Lys Gln Glu Phe Leu
            540                 545                 550 att aac ctt gtg aag caa aag cca caa ata aca gag gaa caa ctt gag    1734
Ile Asn Leu Val Lys Gln Lys Pro Gln Ile Thr Glu Glu Gln Leu Glu
        555                 560                 565 gct gtc att gca gat ttc tca ggc ctg ttg gag aaa tgc tgc caa ggc    1782
Ala Val Ile Ala Asp Phe Ser Gly Leu Leu Glu Lys Cys Cys Gln Gly
    570                 575                 580 cag gaa cag gaa gtc tgc ttt gct gaa gag gga caa aaa ctg att tca    1830
Gln Glu Gln Glu Val Cys Phe Ala Glu Glu Gly Gln Lys Leu Ile Ser
585                 590                 595                 600 aaa act cgt gct gct ttg gga gtt taaattactt caggggaaga gaagacaaaa  1884
Lys Thr Arg Ala Ala Leu Gly Val
                605 cgagtctttc attcggtgtg aactttctc tttaatttta actgatttaa cacttttgt    1944 gaattaatga aatgataaag acttttatgt gagatttcct tatcacagaa ataaaatatc  2004 tccaaatgtt                                                         2014

<210> SEQ ID NO 2
<211> LENGTH: 608
<212> TYPE: PRT
<213> ORGANISM: Homo sapiens
<220> FEATURE:
<223> OTHER INFORMATION: AFP

<400> SEQUENCE: 2

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
```

-continued

```
            50                  55                  60
Lys Met Val Lys Asp Ala Leu Thr Ala Ile Glu Lys Pro Thr Gly Asp
 65                  70                  75                  80

Glu Gln Ser Ser Gly Cys Leu Glu Asn Gln Leu Pro Ala Phe Leu Glu
                 85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
            115                 120                 125

Lys Lys Pro Thr Pro Ala Ser Ile Pro Leu Phe Gln Val Pro Glu Pro
130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
                180                 185                 190

Cys Lys Ala Glu Asn Ala Val Glu Cys Phe Gln Thr Lys Ala Ala Thr
                195                 200                 205

Val Thr Lys Glu Leu Arg Glu Ser Ser Leu Leu Asn Gln His Ala Cys
                210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
                260                 265                 270

Asp Val Leu Asp Cys Leu Gln Asp Gly Glu Lys Ile Met Ser Tyr Ile
                275                 280                 285

Cys Ser Gln Gln Asp Thr Leu Ser Asn Lys Ile Thr Glu Cys Cys Lys
                290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
                340                 345                 350

Ser Phe Val His Glu Tyr Ser Arg Arg His Pro Gln Leu Ala Val Ser
                355                 360                 365

Val Ile Leu Arg Val Ala Lys Gly Tyr Gln Glu Leu Leu Glu Lys Cys
                370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
                420                 425                 430

Val Ala Tyr Thr Lys Lys Ala Pro Gln Leu Thr Ser Ser Glu Leu Met
                435                 440                 445

Ala Ile Thr Arg Lys Met Ala Ala Thr Ala Thr Cys Cys Gln Leu
                450                 455                 460

Ser Glu Asp Lys Leu Leu Ala Cys Gly Glu Gly Ala Asp Ile Ile Ile
465                 470                 475                 480
```

```
Gly His Leu Cys Ile Arg His Glu Met Thr Pro Val Asn Pro Gly Val
            485                 490                 495

Gly Gln Cys Cys Thr Ser Ser Tyr Ala Asn Arg Arg Pro Cys Phe Ser
            500                 505                 510

Ser Leu Val Val Asp Glu Thr Tyr Val Pro Pro Ala Phe Ser Asp Asp
            515                 520                 525

Lys Phe Ile Phe His Lys Asp Leu Cys Gln Ala Gln Gly Val Ala Leu
            530                 535                 540

Gln Thr Met Lys Gln Glu Phe Leu Ile Asn Leu Val Lys Gln Lys Pro
545                 550                 555                 560

Gln Ile Thr Glu Glu Gln Leu Glu Ala Val Ile Ala Asp Phe Ser Gly
            565                 570                 575

Leu Leu Glu Lys Cys Cys Gln Gly Gln Glu Gln Glu Val Cys Phe Ala
            580                 585                 590

Glu Glu Gly Gln Lys Leu Ile Ser Lys Thr Arg Ala Ala Leu Gly Val
            595                 600                 605

<210> SEQ ID NO 3
<211> LENGTH: 2001
<212> TYPE: DNA
<213> ORGANISM: Homo sapiens
<220> FEATURE:
<223> OTHER INFORMATION: ALDH2 mRNA
<220> FEATURE:
<221> NAME/KEY: CDS
<222> LOCATION: (45)..(1595)

<400> SEQUENCE: 3
ctagctctgc tctcggtccg ctcgctgtcc gctagcccgc tgcg atg ttg cgc gct         56
                                                 Met Leu Arg Ala
                                                   1 gcc gcc cgc ttc ggg ccc cgc ctg ggc cgc cgc ctc ttg tca gcc gcc        104
Ala Ala Arg Phe Gly Pro Arg Leu Gly Arg Arg Leu Leu Ser Ala Ala
  5                  10                  15                  20 gcc acc cag gcc gtg cct gcc ccc aac cag cag ccc gag gtc ttc tgc        152
Ala Thr Gln Ala Val Pro Ala Pro Asn Gln Gln Pro Glu Val Phe Cys
                 25                  30                  35 aac cag att ttc ata aac aat gaa tgg cac gat gcc gtc agc agg aaa        200
Asn Gln Ile Phe Ile Asn Asn Glu Trp His Asp Ala Val Ser Arg Lys
             40                  45                  50 aca ttc ccc acc gtc aat ccg tcc act gga gag gtc atc tgt cag gta        248
Thr Phe Pro Thr Val Asn Pro Ser Thr Gly Glu Val Ile Cys Gln Val
         55                  60                  65 gct gaa ggg gac aag gaa gat gtg gac aag gca gtg aag gcc gcc cgg        296
Ala Glu Gly Asp Lys Glu Asp Val Asp Lys Ala Val Lys Ala Ala Arg
     70                  75                  80 gcc gcc ttc cag ctg ggc tca cct tgg cgc cgc atg gac gca tca cac        344
Ala Ala Phe Gln Leu Gly Ser Pro Trp Arg Arg Met Asp Ala Ser His
 85                  90                  95                 100 agg ggc cgg ctg ctg aac cgc ctg gcc gat ctg atc gag cgg gac cgg        392
Arg Gly Arg Leu Leu Asn Arg Leu Ala Asp Leu Ile Glu Arg Asp Arg
                105                 110                 115 acc tac ctg gcg gcc ttg gag acc ctg gac aat ggc aag ccc tat gtc        440
Thr Tyr Leu Ala Ala Leu Glu Thr Leu Asp Asn Gly Lys Pro Tyr Val
            120                 125                 130 atc tcc tac ctg gtg gat ttg gac atg gtc ctc aaa tgt ctc cgg tat        488
Ile Ser Tyr Leu Val Asp Leu Asp Met Val Leu Lys Cys Leu Arg Tyr
        135                 140                 145 tat gcc ggc tgg gct gat aag tac cac ggg aaa acc atc ccc att gac        536
```

```
Tyr Ala Gly Trp Ala Asp Lys Tyr His Gly Lys Thr Ile Pro Ile Asp
    150                 155                 160 gga gac ttc ttc agc tac aca cgc cat gaa cct gtg ggg gtg tgc ggg      584
Gly Asp Phe Phe Ser Tyr Thr Arg His Glu Pro Val Gly Val Cys Gly
165                 170                 175                 180 cag atc att ccg tgg aat ttc ccg ctc ctg atg caa gca tgg aag ctg      632
Gln Ile Ile Pro Trp Asn Phe Pro Leu Leu Met Gln Ala Trp Lys Leu
                185                 190                 195 ggc cca gcc ttg gca act gga aac gtg gtt gtg atg aag gta gct gag      680
Gly Pro Ala Leu Ala Thr Gly Asn Val Val Val Met Lys Val Ala Glu
            200                 205                 210 cag aca ccc ctc acc gcc ctc tat gtg gcc aac ctg atc aag gag gct      728
Gln Thr Pro Leu Thr Ala Leu Tyr Val Ala Asn Leu Ile Lys Glu Ala
        215                 220                 225 ggc ttt ccc cct ggt gtg gtc aac att gtg cct gga ttt ggc ccc acg      776
Gly Phe Pro Pro Gly Val Val Asn Ile Val Pro Gly Phe Gly Pro Thr
    230                 235                 240 gct ggg gcc gcc att gcc tcc cat gag gat gtg gac aaa gtg gca ttc      824
Ala Gly Ala Ala Ile Ala Ser His Glu Asp Val Asp Lys Val Ala Phe
245                 250                 255                 260 aca ggc tcc act gag att ggc cgc gta atc cag gtt gct gct ggg agc      872
Thr Gly Ser Thr Glu Ile Gly Arg Val Ile Gln Val Ala Ala Gly Ser
                265                 270                 275 agc aac ctc aag aga gtg acc ttg gag ctg ggg ggg aag agc ccc aac      920
Ser Asn Leu Lys Arg Val Thr Leu Glu Leu Gly Gly Lys Ser Pro Asn
            280                 285                 290 atc atc atg tca gat gcc gat atg gat tgg gcc gtg gaa cag gcc cac      968
Ile Ile Met Ser Asp Ala Asp Met Asp Trp Ala Val Glu Gln Ala His
        295                 300                 305 ttc gcc ctg ttc ttc aac cag ggc cag tgc tgc tgt gcc ggc tcc cgg     1016
Phe Ala Leu Phe Phe Asn Gln Gly Gln Cys Cys Cys Ala Gly Ser Arg
    310                 315                 320 acc ttc gtg cag gag gac atc tat gat gag ttt gtg gag cgg agc gtt     1064
Thr Phe Val Gln Glu Asp Ile Tyr Asp Glu Phe Val Glu Arg Ser Val
325                 330                 335                 340 gcc cgg gcc aag tct cgg gtg gtc ggg aac ccc ttt gat agc aag acc     1112
Ala Arg Ala Lys Ser Arg Val Val Gly Asn Pro Phe Asp Ser Lys Thr
                345                 350                 355 gag cag ggg ccg cag gtg gat gaa act cag ttt aag aag atc ctc ggc     1160
Glu Gln Gly Pro Gln Val Asp Glu Thr Gln Phe Lys Lys Ile Leu Gly
            360                 365                 370 tac atc aac acg ggg aag caa gag ggg gcg aag ctg ctg tgt ggt ggg     1208
Tyr Ile Asn Thr Gly Lys Gln Glu Gly Ala Lys Leu Leu Cys Gly Gly
        375                 380                 385 ggc att gct gct gac cgt ggt tac ttc atc cag ccc act gtg ttt gga     1256
Gly Ile Ala Ala Asp Arg Gly Tyr Phe Ile Gln Pro Thr Val Phe Gly
    390                 395                 400 gat gtg cag gat ggc atg acc atc gcc aag gag gag atc ttc ggg cca     1304
Asp Val Gln Asp Gly Met Thr Ile Ala Lys Glu Glu Ile Phe Gly Pro
405                 410                 415                 420 gtg atg cag atc ctg aag ttc aag acc ata gag gag gtt gtt ggg aga     1352
Val Met Gln Ile Leu Lys Phe Lys Thr Ile Glu Glu Val Val Gly Arg
                425                 430                 435 gcc aac aat tcc acg tac ggg ctg gca gca gct gtc ttc aca aag gat     1400
Ala Asn Asn Ser Thr Tyr Gly Leu Ala Ala Ala Val Phe Thr Lys Asp
            440                 445                 450 ttg gac aag gcc aat tac ctg tcc cag gcc ctc cag gcg ggc act gtg     1448
Leu Asp Lys Ala Asn Tyr Leu Ser Gln Ala Leu Gln Ala Gly Thr Val
        455                 460                 465
```

-continued

| | | | | | | | | | | | | | | | | |
|---|---|---|---|---|---|---|---|---|---|---|---|---|---|---|---|---|
| tgg | gtc | aac | tgc | tat | gat | gtg | ttt | gga | gcc | cag | tca | ccc | ttt | ggt | ggc | 1496 |
| Trp | Val | Asn | Cys | Tyr | Asp | Val | Phe | Gly | Ala | Gln | Ser | Pro | Phe | Gly | Gly | |
| 470 | | | | 475 | | | | | 480 | | | | | | | |

| | | | | | | | | | | | | | | | | |
|---|---|---|---|---|---|---|---|---|---|---|---|---|---|---|---|---|
| tac | aag | atg | tcg | ggg | agt | ggc | cgg | gag | ttg | ggc | gag | tac | ggg | ctg | cag | 1544 |
| Tyr | Lys | Met | Ser | Gly | Ser | Gly | Arg | Glu | Leu | Gly | Glu | Tyr | Gly | Leu | Gln | |
| 485 | | | | | 490 | | | | | 495 | | | | | 500 | |

| | | | | | | | | | | | | | | | | |
|---|---|---|---|---|---|---|---|---|---|---|---|---|---|---|---|---|
| gca | tac | act | gaa | gtg | aaa | act | gtc | aca | gtc | aaa | gtg | cct | cag | aag | aac | 1592 |
| Ala | Tyr | Thr | Glu | Val | Lys | Thr | Val | Thr | Val | Lys | Val | Pro | Gln | Lys | Asn | |
| | | | | 505 | | | | | 510 | | | | | 515 | | | tca taagaatcat gcaagcttcc tccctcagcc attgatggaa agttcagcaa    1645
Ser gatcagcaac aaaaccaaga aaatgatccc ttgcgtgctg aatatctgaa aagagaaatt    1705
tttcctacaa aatctcttgg gtcaagaaag ttctagaatt tgaattgata aacatggtgg    1765
gttggctgag ggtaagagta tatgaggaac cttttaaacg acaacaatac tgctagcttt    1825
caggatgatt tttaaaaaat agattcaaat gtgttatcct ctctctgaaa cgcttcctat    1885
aactcgagtt tataggggaa gaaaaagcta ttgtttacaa ttatatcacc attaaggcaa    1945
ctgctacacc ctgctttgta ttctgggcta agattcatta aaaactagct gctctt    2001

<210> SEQ ID NO 4
<211> LENGTH: 517
<212> TYPE: PRT
<213> ORGANISM: Homo sapiens
<220> FEATURE:
<223> OTHER INFORMATION: ALDH2

<400> SEQUENCE: 4

Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
                20                  25                  30

Glu Val Phe Cys Asn Gln Ile Phe Ile Asn Asn Glu Trp His Asp Ala
            35                  40                  45

Val Ser Arg Lys Thr Phe Pro Thr Val Asn Pro Ser Thr Gly Glu Val
    50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

```
Ile Lys Glu Ala Gly Phe Pro Pro Gly Val Val Asn Ile Val Pro Gly
225                 230                 235                 240

Phe Gly Pro Thr Ala Gly Ala Ile Ala Ser His Glu Asp Val Asp
            245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
            275                 280                 285

Lys Ser Pro Asn Ile Ile Met Ser Asp Ala Asp Met Asp Trp Ala Val
290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
            325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
            355                 360                 365

Lys Ile Leu Gly Tyr Ile Asn Thr Gly Lys Gln Glu Gly Ala Lys Leu
370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
                420                 425                 430

Val Val Gly Arg Ala Asn Asn Ser Thr Tyr Gly Leu Ala Ala Ala Val
            435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
            500                 505                 510

Pro Gln Lys Asn Ser
        515

<210> SEQ ID NO 5
<211> LENGTH: 928
<212> TYPE: DNA
<213> ORGANISM: Homo sapiens
<220> FEATURE:
<223> OTHER INFORMATION: APCS mRNA
<220> FEATURE:
<221> NAME/KEY: CDS
<222> LOCATION: (97)..(765)

<400> SEQUENCE: 5
gggcatgaat atcagacgct aggggggacag ccactgtgtt gtctgctacc ctcatcctgg      60
tcactgcttc tgctataaca gccctaggcc aggaat atg aac aag ccg ctg ctt     114
                                       Met Asn Lys Pro Leu Leu
                                         1               5 tgg atc tct gtc ctc acc agc ctc ctg gaa gcc ttt gct cac aca gac     162
Trp Ile Ser Val Leu Thr Ser Leu Leu Glu Ala Phe Ala His Thr Asp
         10                  15                  20
```

```
ctc agt ggg aag gtg ttt gta ttt cct aga gaa tct gtt act gat cat    210
Leu Ser Gly Lys Val Phe Val Phe Pro Arg Glu Ser Val Thr Asp His
        25                  30                  35 gta aac ttg atc aca ccg ctg gag aag cct cta cag aac ttt acc ttg    258
Val Asn Leu Ile Thr Pro Leu Glu Lys Pro Leu Gln Asn Phe Thr Leu
40                  45                  50 tgt ttt cga gcc tat agt gat ctc tct cgt gcc tac agc ctc ttc tcc    306
Cys Phe Arg Ala Tyr Ser Asp Leu Ser Arg Ala Tyr Ser Leu Phe Ser
55                  60                  65                  70 tac aat acc caa ggc agg gat aat gag cta cta gtt tat aaa gaa aga    354
Tyr Asn Thr Gln Gly Arg Asp Asn Glu Leu Leu Val Tyr Lys Glu Arg
                75                  80                  85 gtt gga gag tat agt cta tac att gga aga cac aaa gtt aca tcc aaa    402
Val Gly Glu Tyr Ser Leu Tyr Ile Gly Arg His Lys Val Thr Ser Lys
                90                  95                  100 gtt atc gaa aag ttc ccg gct cca gtg cac atc tgt gtg agc tgg gag    450
Val Ile Glu Lys Phe Pro Ala Pro Val His Ile Cys Val Ser Trp Glu
                105                 110                 115 tcc tca tca ggt att gct gaa ttt tgg atc aat ggg aca cct ttg gtg    498
Ser Ser Ser Gly Ile Ala Glu Phe Trp Ile Asn Gly Thr Pro Leu Val
        120                 125                 130 aaa aag ggt ctg cga cag ggt tac ttt gta gaa gct cag ccc aag att    546
Lys Lys Gly Leu Arg Gln Gly Tyr Phe Val Glu Ala Gln Pro Lys Ile
135                 140                 145                 150 gtc ctg ggg cag gaa cag gat tcc tat ggg ggc aag ttt gat agg agc    594
Val Leu Gly Gln Glu Gln Asp Ser Tyr Gly Gly Lys Phe Asp Arg Ser
                155                 160                 165 cag tcc ttt gtg gga gag att ggg gat ttg tac atg tgg gac tct gtg    642
Gln Ser Phe Val Gly Glu Ile Gly Asp Leu Tyr Met Trp Asp Ser Val
                170                 175                 180 ctg ccc cca gaa aat atc ctg tct gcc tat cag ggt acc cct ctc cct    690
Leu Pro Pro Glu Asn Ile Leu Ser Ala Tyr Gln Gly Thr Pro Leu Pro
                185                 190                 195 gcc aat atc ctg gac tgg cag gct ctg aac tat gaa atc aga gga tat    738
Ala Asn Ile Leu Asp Trp Gln Ala Leu Asn Tyr Glu Ile Arg Gly Tyr
200                 205                 210 gtc atc atc aaa ccc ttg gtg tgg gtc tgaggtcttg actcaacgag          785
Val Ile Ile Lys Pro Leu Val Trp Val
215                 220 agcacttgaa aatgaaatga ctgtctaaga gatctggtca aagcaactgg atactagatc  845
ttacatctgc agctctttct tctttgaatt tcctatctgt atgtctgcct aattaaaaaa  905
atatatattg tattatgcta cct                                         928

<210> SEQ ID NO 6
<211> LENGTH: 223
<212> TYPE: PRT
<213> ORGANISM: Homo sapiens
<220> FEATURE:
<223> OTHER INFORMATION: APCS

<400> SEQUENCE: 6

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
                20                  25                  30

Glu Ser Val Thr Asp His Val Asn Leu Ile Thr Pro Leu Glu Lys Pro
            35                  40                  45

Leu Gln Asn Phe Thr Leu Cys Phe Arg Ala Tyr Ser Asp Leu Ser Arg
```

```
                  50                  55                  60
Ala Tyr Ser Leu Phe Ser Tyr Asn Thr Gln Gly Arg Asp Asn Glu Leu
 65                  70                  75                  80

Leu Val Tyr Lys Glu Arg Val Gly Glu Tyr Ser Leu Tyr Ile Gly Arg
                 85                  90                  95

His Lys Val Thr Ser Lys Val Ile Glu Lys Phe Pro Ala Pro Val His
                100                 105                 110

Ile Cys Val Ser Trp Glu Ser Ser Gly Ile Ala Glu Phe Trp Ile
                115                 120                 125

Asn Gly Thr Pro Leu Val Lys Lys Gly Leu Arg Gln Gly Tyr Phe Val
                130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
                180                 185                 190

Gln Gly Thr Pro Leu Pro Ala Asn Ile Leu Asp Trp Gln Ala Leu Asn
                195                 200                 205

Tyr Glu Ile Arg Gly Tyr Val Ile Ile Lys Pro Leu Val Trp Val
                210                 215                 220

<210> SEQ ID NO 7
<211> LENGTH: 577
<212> TYPE: DNA
<213> ORGANISM: Homo sapiens
<220> FEATURE:
<223> OTHER INFORMATION: APOC4 mRNA
<220> FEATURE:
<221> NAME/KEY: CDS
<222> LOCATION: (5)..(385)

<400> SEQUENCE: 7 agaa atg tcc ctc ctc aga aac agg ctc cag gcc ctg cct gcc ctg tgc        49
     Met Ser Leu Leu Arg Asn Arg Leu Gln Ala Leu Pro Ala Leu Cys
      1               5                  10                  15 ctc tgc gtg ctg gtc ctg gcc tgc att ggg gca tgc cag cca gag gcc        97
Leu Cys Val Leu Val Leu Ala Cys Ile Gly Ala Cys Gln Pro Glu Ala
                 20                  25                  30 cag gaa gga acc ctg agc ccc cca cca aag cta aag atg agt cgc tgg       145
Gln Glu Gly Thr Leu Ser Pro Pro Pro Lys Leu Lys Met Ser Arg Trp
                 35                  40                  45 agc ctg gtg agg ggc agg atg aag gag ctg ctg gag aca gtg gtg aac       193
Ser Leu Val Arg Gly Arg Met Lys Glu Leu Leu Glu Thr Val Val Asn
             50                  55                  60 agg acc aga gac ggg tgg caa tgg ttc tgg agc ccg agc acc ttc cgg       241
Arg Thr Arg Asp Gly Trp Gln Trp Phe Trp Ser Pro Ser Thr Phe Arg
 65                  70                  75 ggc ttc atg cag acc tac tat gac gac cac ctg agg gac ctg ggt ccg       289
Gly Phe Met Gln Thr Tyr Tyr Asp Asp His Leu Arg Asp Leu Gly Pro
 80                  85                  90                  95 ctc acc aag gcc tgg ttc ctc gaa tcc aaa gac agc ctc ttg aag aag       337
Leu Thr Lys Ala Trp Phe Leu Glu Ser Lys Asp Ser Leu Leu Lys Lys
                100                 105                 110 acc cac agc ctg tgc ccc agg ctt gtc tgt ggg gac aag gac cag ggt       385
Thr His Ser Leu Cys Pro Arg Leu Val Cys Gly Asp Lys Asp Gln Gly
                115                 120                 125 taaaatgttc ataaaagcca ggtgtggttg tggcgggtgc ctgtagtccc agctactcag     445
```

```
gaggctgagg taggatgatg gcttgagccc aggagttcga gaccagcctg ggcaacacag      505
cgagatctct tggggtaaa acaaaaagaa aaaaaaagt tcatacttct ccaataaata       565
aagtctcacc tg                                                          577
```

<210> SEQ ID NO 8
<211> LENGTH: 127
<212> TYPE: PRT
<213> ORGANISM: Homo sapiens
<220> FEATURE:
<223> OTHER INFORMATION: APOC4

<400> SEQUENCE: 8

```
Met Ser Leu Leu Arg Asn Arg Leu Gln Ala Leu Pro Ala Leu Cys Leu
1               5                   10                  15

Cys Val Leu Val Leu Ala Cys Ile Gly Ala Cys Gln Pro Glu Ala Gln
            20                  25                  30

Glu Gly Thr Leu Ser Pro Pro Lys Leu Lys Met Ser Arg Trp Ser
        35                  40                  45

Leu Val Arg Gly Arg Met Lys Glu Leu Leu Glu Thr Val Val Asn Arg
    50                  55                  60

Thr Arg Asp Gly Trp Gln Trp Phe Trp Ser Pro Ser Thr Phe Arg Gly
65                  70                  75                  80

Phe Met Gln Thr Tyr Tyr Asp Asp His Leu Arg Asp Leu Gly Pro Leu
                85                  90                  95

Thr Lys Ala Trp Phe Leu Glu Ser Lys Asp Ser Leu Leu Lys Lys Thr
            100                 105                 110

His Ser Leu Cys Pro Arg Leu Val Cys Gly Asp Lys Asp Gln Gly
        115                 120                 125
```

<210> SEQ ID NO 9
<211> LENGTH: 2801
<212> TYPE: DNA
<213> ORGANISM: Homo sapiens
<220> FEATURE:
<223> OTHER INFORMATION: AQP9 mRNA
<220> FEATURE:
<221> NAME/KEY: CDS
<222> LOCATION: (186)..(1070)

<400> SEQUENCE: 9

```
ccaccagaag acgattaagc cacagcctct aattggaacg gcatttgtac agtcagagac       60
tcttaccaga catctccagg aatctgtgag ccattgtcaa acgtccatt ttcatctggc      120 tgtgaaagtg aggaccacaa caggtaggta ttggtagaaa caggagtcct cagagaagcc     180 ccaag atg cag cct gag gga gca gaa aag gga aaa agc ttc aag cag aga     230
      Met Gln Pro Glu Gly Ala Glu Lys Gly Lys Ser Phe Lys Gln Arg
      1               5                   10                  15 ctg gtc ttg aag agc agc tta gcg aaa gaa acc ctc tct gag ttc ttg       278
Leu Val Leu Lys Ser Ser Leu Ala Lys Glu Thr Leu Ser Glu Phe Leu
            20                  25                  30 ggc acg ttc atc ttg att gtc ctt gga tgt ggc tgt gtt gcc caa gct       326
Gly Thr Phe Ile Leu Ile Val Leu Gly Cys Gly Cys Val Ala Gln Ala
        35                  40                  45 att ctc agt cga gga cgt ttt gga ggg gtc atc act atc aat gtt gga       374
Ile Leu Ser Arg Gly Arg Phe Gly Gly Val Ile Thr Ile Asn Val Gly
    50                  55                  60 ttt tca atg gca gtt gca atg gcc att tat gtg gct ggc ggt gtc tct       422
Phe Ser Met Ala Val Ala Met Ala Ile Tyr Val Ala Gly Gly Val Ser
65                  70                  75
```

| | | |
|---|---|---|
| ggt ggt cac atc aac cca gct gtg tct tta gca atg tgt ctc ttt gga<br>Gly Gly His Ile Asn Pro Ala Val Ser Leu Ala Met Cys Leu Phe Gly<br>80                              85                             90                          95 | 470 |
| cgg atg aaa tgg ttc aaa ttg cca ttt tat gtg gga gcc cag ttc ttg<br>Arg Met Lys Trp Phe Lys Leu Pro Phe Tyr Val Gly Ala Gln Phe Leu<br>                    100                             105                            110 | 518 |
| gga gcc ttt gtg ggg gct gca acc gtc ttt ggc att tac tat gat gga<br>Gly Ala Phe Val Gly Ala Ala Thr Val Phe Gly Ile Tyr Tyr Asp Gly<br>               115                            120                           125 | 566 |
| ctt atg tcc ttt gct ggt gga aaa ctg ctc atc gtg gga gaa aat gca<br>Leu Met Ser Phe Ala Gly Gly Lys Leu Leu Ile Val Gly Glu Asn Ala<br>        130                            135                           140 | 614 |
| aca gca cac att ttt gca aca tac cca gct ccg tat cta tct ctg gcg<br>Thr Ala His Ile Phe Ala Thr Tyr Pro Ala Pro Tyr Leu Ser Leu Ala<br>145                             150                           155 | 662 |
| aac gca ttt gca gat caa gtg gtg gcc acc atg ata ctc ctc ata atc<br>Asn Ala Phe Ala Asp Gln Val Val Ala Thr Met Ile Leu Leu Ile Ile<br>160                             165                         170                       175 | 710 |
| gtc ttt gcc atc ttt gac tcc aga aac ttg gga gcc ccc aga ggc cta<br>Val Phe Ala Ile Phe Asp Ser Arg Asn Leu Gly Ala Pro Arg Gly Leu<br>               180                            185                           190 | 758 |
| gag ccc att gcc atc ggc ctc ctg att att gtc att gct tcc tcc ctg<br>Glu Pro Ile Ala Ile Gly Leu Leu Ile Ile Val Ile Ala Ser Ser Leu<br>             195                           200                           205 | 806 |
| gga ctg aac agt ggc tgt gcc atg aac cca gct cga gac ctg agt ccc<br>Gly Leu Asn Ser Gly Cys Ala Met Asn Pro Ala Arg Asp Leu Ser Pro<br>210                             215                           220 | 854 |
| aga ctt ttc act gcc ttg gca ggc tgg ggg ttt gaa gtc ttc aga gct<br>Arg Leu Phe Thr Ala Leu Ala Gly Trp Gly Phe Glu Val Phe Arg Ala<br>225                             230                           235 | 902 |
| gga aac aac ttc tgg tgg att cct gta gtg ggc cct ttg gtt ggt gct<br>Gly Asn Asn Phe Trp Trp Ile Pro Val Val Gly Pro Leu Val Gly Ala<br>240                             245                           250                       255 | 950 |
| gtc att gga ggc ctc atc tat gtt ctt gtc att gaa atc cac cat cca<br>Val Ile Gly Gly Leu Ile Tyr Val Leu Val Ile Glu Ile His His Pro<br>                    260                             265                           270 | 998 |
| gag cct gac tca gtc ttt aag aca gaa caa tct gag gac aaa cca gag<br>Glu Pro Asp Ser Val Phe Lys Thr Glu Gln Ser Glu Asp Lys Pro Glu<br>275                             280                           285 | 1046 |
| aaa tat gaa ctc agt gtc atc atg tagtggcatg ctcagctctg gatttgcagt<br>Lys Tyr Glu Leu Ser Val Ile Met<br>        290                       295 | 1100 |
| cagtttggga ttctcttcag aaagatggca tctaagtgtc tgtgttcttg taagcctgag | 1160 |
| gtggaatcca cccagttttg tctgctagcc atatgggaca tctaattgga aaagcatctg | 1220 |
| cataaaagtt tggaaacaat gaccacttct ctaccattgt cccccacccc caccccccag | 1280 |
| aataacgctg actgtcccct gaaacagcct tctctcctgc cctgtttatt tcatcctcga | 1340 |
| tgggaattct tgctaggtaa gcactaataa ctcggcatga aatggtgtca ccaaaaccct | 1400 |
| tttcttcagt atcgacaaag attacattct gagtaccaac caaaccctaa attgaaagac | 1460 |
| aaaactatgg tttcagtcaa catattcatg aattagggag ctaatgggtt aagcttccag | 1520 |
| ttcccgctat gctactggat ttgtataaat actgatattc tccaaaccta gtggtgtagg | 1580 |
| gagcaagaga atgcagctgg aaggcacaag gggaggacat tgtggcattc agaaactgca | 1640 |
| ggagacaaga tgaatttgag aagccaaatg gaatttttaa tggaaaccat ttatcagatt | 1700 |
| aatctcttgc tctcctgcat tttagaggac accaattaat ttcctggtct ttagtatata | 1760 |
| ataacctaaa ataccattgt aacctcagtc atgaaaaata catcactctg tctttttagc | 1820 |

```
tcaaatgtat tttcctaatt gcccacttga gaacagacat ttgacaagtt atatcaacga  1880
ctgtgcttgt ccattatttt acacatgccc tagaagccaa aactgaaagc cactggatcc  1940
tggtctagct gaatcttcag agtgggaggt ctccaaaaag atattacctt attgggctta  2000
acaattcaca aggcactttc acacccatta tctaatttaa tcctcataat gactatgtga  2060
ggcaaatgcc acattgccca tttttcagat aaagaaacaa aatcttaggg aagataagtt  2120
gagttgtcca agagcacact gaaagttgaa tgttatctaa tgcattcctc tacctttcag  2180
aagatcagta gctggctgac aatctttgcc aaatcttcct tgctagccag aagtggaatt  2240
ggcagcttct agaatatgta cacctctgga caaaatgttc ctcaatctta agatacaaag  2300
accctcattg tctgggtcta ttcccacact tactgagtac agatgaagga aagtggtagc  2360
aatttaatca taactttcat ttgctgaaaa acattatgag aaggcctccc ttcctaagcc  2420
acctctggtc ttgctaagtc ttgatcttgc ttcctgccag caccaaacat tacattcagg  2480
ggatttcctc tggctcagtc ttttccccctt gaagttctct aatagatgtt acttttgaca  2540
aaagatcgcc tatgagttac aagcaccagg ggatgctcta catcaaggga tgcaccttca  2600
gtcaaactgt caaaaagccc agaattccca aaggcattag gtttcccaac tgctttgtgc  2660
tgatatcaga acagcagaaa ttaaatgtga aatgtttctg atgacttatg ttctacaatc  2720
tatggacata cgggattttt ttttcttgct ttgaagctac ctggatattt cctatttgaa  2780
ataaaattgt tcggtcattg t                                            2801
```

<210> SEQ ID NO 10
<211> LENGTH: 295
<212> TYPE: PRT
<213> ORGANISM: Homo sapiens
<220> FEATURE:
<223> OTHER INFORMATION: AQP9

<400> SEQUENCE: 10

```
Met Gln Pro Glu Gly Ala Glu Lys Gly Lys Ser Phe Lys Gln Arg Leu
1               5                   10                  15

Val Leu Lys Ser Ser Leu Ala Lys Glu Thr Leu Ser Glu Phe Leu Gly
            20                  25                  30

Thr Phe Ile Leu Ile Val Leu Gly Cys Gly Cys Val Ala Gln Ala Ile
        35                  40                  45

Leu Ser Arg Gly Arg Phe Gly Gly Val Ile Thr Ile Asn Val Gly Phe
    50                  55                  60

Ser Met Ala Val Ala Met Ala Ile Tyr Val Ala Gly Gly Val Ser Gly
65                  70                  75                  80

Gly His Ile Asn Pro Ala Val Ser Leu Ala Met Cys Leu Phe Gly Arg
                85                  90                  95

Met Lys Trp Phe Lys Leu Pro Phe Tyr Val Gly Ala Gln Phe Leu Gly
            100                 105                 110

Ala Phe Val Gly Ala Ala Thr Val Phe Gly Ile Tyr Tyr Asp Gly Leu
        115                 120                 125

Met Ser Phe Ala Gly Gly Lys Leu Leu Ile Val Gly Glu Asn Ala Thr
    130                 135                 140

Ala His Ile Phe Ala Thr Tyr Pro Ala Pro Tyr Leu Ser Leu Ala Asn
145                 150                 155                 160

Ala Phe Ala Asp Gln Val Val Ala Thr Met Ile Leu Leu Ile Ile Val
                165                 170                 175

Phe Ala Ile Phe Asp Ser Arg Asn Leu Gly Ala Pro Arg Gly Leu Glu
```

```
                180              185              190
Pro Ile Ala Ile Gly Leu Leu Ile Ile Val Ile Ala Ser Ser Leu Gly
            195              200              205

Leu Asn Ser Gly Cys Ala Met Asn Pro Ala Arg Asp Leu Ser Pro Arg
    210              215              220

Leu Phe Thr Ala Leu Ala Gly Trp Gly Phe Glu Val Phe Arg Ala Gly
225              230              235              240

Asn Asn Phe Trp Trp Ile Pro Val Val Gly Pro Leu Val Gly Ala Val
            245              250              255

Ile Gly Gly Leu Ile Tyr Val Leu Val Ile Glu Ile His His Pro Glu
        260              265              270

Pro Asp Ser Val Phe Lys Thr Glu Gln Ser Glu Asp Lys Pro Glu Lys
    275              280              285

Tyr Glu Leu Ser Val Ile Met
    290              295

<210> SEQ ID NO 11
<211> LENGTH: 3445
<212> TYPE: DNA
<213> ORGANISM: Homo sapiens
<220> FEATURE:
<223> OTHER INFORMATION: BUB1 mRNA
<220> FEATURE:
<221> NAME/KEY: CDS
<222> LOCATION: (58)..(3312)

<400> SEQUENCE: 11
cggcggcttc tagtttgcgg ttcaggtttg gccgctgccg gccagcgtcc tctggcc       57 atg gac acc ccg gaa aat gtc ctt cag atg ctt gaa gcc cac atg cag     105
Met Asp Thr Pro Glu Asn Val Leu Gln Met Leu Glu Ala His Met Gln
1               5                   10                  15 agc tac aag ggc aat gac cct ctt ggt gaa tgg gaa aga tac ata cag     153
Ser Tyr Lys Gly Asn Asp Pro Leu Gly Glu Trp Glu Arg Tyr Ile Gln
            20                  25                  30 tgg gta gaa gag aat ttt cct gag aat aaa gaa tac ttg ata act tta     201
Trp Val Glu Glu Asn Phe Pro Glu Asn Lys Glu Tyr Leu Ile Thr Leu
        35                  40                  45 cta gaa cat tta atg aag gaa ttt tta gat aag aag aaa tac cac aat     249
Leu Glu His Leu Met Lys Glu Phe Leu Asp Lys Lys Lys Tyr His Asn
    50                  55                  60 gac cca aga ttc atc agt tat tgt tta aaa ttt gct gag tac aac agt     297
Asp Pro Arg Phe Ile Ser Tyr Cys Leu Lys Phe Ala Glu Tyr Asn Ser
65                  70                  75                  80 gac ctc cat caa ttt ttt gag ttt ctg tac aac cat ggg att gga acc     345
Asp Leu His Gln Phe Phe Glu Phe Leu Tyr Asn His Gly Ile Gly Thr
                85                  90                  95 ctg tca tcc cct ctg tac att gcc tgg gcg ggg cat ctg gaa gcc caa     393
Leu Ser Ser Pro Leu Tyr Ile Ala Trp Ala Gly His Leu Glu Ala Gln
            100                 105                 110 gga gag ctg cag cat gcc agt gct gtc ctt cag aga gga att caa aac     441
Gly Glu Leu Gln His Ala Ser Ala Val Leu Gln Arg Gly Ile Gln Asn
        115                 120                 125 cag gct gaa ccc aga gag ttc ctg caa caa caa tac agg tta ttt cag     489
Gln Ala Glu Pro Arg Glu Phe Leu Gln Gln Gln Tyr Arg Leu Phe Gln
    130                 135                 140 aca cgc ctc act gaa acc cat ttg cca gct caa gct aga acc tca gaa     537
Thr Arg Leu Thr Glu Thr His Leu Pro Ala Gln Ala Arg Thr Ser Glu
145                 150                 155                 160 cct ctg cat aat gtt cag gtt tta aat caa atg ata aca tca aaa tca     585
```

```
            Pro Leu His Asn Val Gln Val Leu Asn Gln Met Ile Thr Ser Lys Ser
                        165                 170                 175 aat cca gga aat aac atg gcc tgc att tct aag aat cag ggt tca gag        633
Asn Pro Gly Asn Asn Met Ala Cys Ile Ser Lys Asn Gln Gly Ser Glu
            180                 185                 190 ctt tct gga gtg ata tct tca gct tgt gat aaa gag tca aat atg gaa        681
Leu Ser Gly Val Ile Ser Ser Ala Cys Asp Lys Glu Ser Asn Met Glu
            195                 200                 205 cga aga gtg atc acg att tct aaa tca gaa tat tct gtg cac tca tct        729
Arg Arg Val Ile Thr Ile Ser Lys Ser Glu Tyr Ser Val His Ser Ser
    210                 215                 220 ttg gca tcc aaa gtt gat gtt gag cag gtt gtt atg tat tgc aag gag        777
Leu Ala Ser Lys Val Asp Val Glu Gln Val Val Met Tyr Cys Lys Glu
225                 230                 235                 240 aag ctt att cgt ggg gaa tca gaa ttt tcc ttt gaa gaa ttg aga gcc        825
Lys Leu Ile Arg Gly Glu Ser Glu Phe Ser Phe Glu Glu Leu Arg Ala
                245                 250                 255 cag aaa tac aat caa cgg aga aag cat gag caa tgg gta aat gaa gac        873
Gln Lys Tyr Asn Gln Arg Arg Lys His Glu Gln Trp Val Asn Glu Asp
            260                 265                 270 aga cat tat atg aaa agg aaa gaa gca aat gct ttt gaa gaa cag cta        921
Arg His Tyr Met Lys Arg Lys Glu Ala Asn Ala Phe Glu Glu Gln Leu
        275                 280                 285 tta aaa cag aaa atg gat gaa ctt cat aag aag ttg cat cag gtg gtg        969
Leu Lys Gln Lys Met Asp Glu Leu His Lys Lys Leu His Gln Val Val
    290                 295                 300 gag aca tcc cat gag gat ctg ccc gct tcc cag gaa agg tcc gag gtt       1017
Glu Thr Ser His Glu Asp Leu Pro Ala Ser Gln Glu Arg Ser Glu Val
305                 310                 315                 320 aat cca gca cgt atg ggg cca agt gta ggc tcc cag cag gaa ctg aga       1065
Asn Pro Ala Arg Met Gly Pro Ser Val Gly Ser Gln Gln Glu Leu Arg
                325                 330                 335 gcg cca tgt ctt cca gta acc tat cag cag aca cca gtg aac atg gaa       1113
Ala Pro Cys Leu Pro Val Thr Tyr Gln Gln Thr Pro Val Asn Met Glu
            340                 345                 350 aag aac cca aga gag gca cct cct gtt gtt cct cct ttg gca aat gct       1161
Lys Asn Pro Arg Glu Ala Pro Pro Val Val Pro Pro Leu Ala Asn Ala
        355                 360                 365 att tct gca gct ttg gtg tcc cca gcc acc agc cag agc att gct cct       1209
Ile Ser Ala Ala Leu Val Ser Pro Ala Thr Ser Gln Ser Ile Ala Pro
    370                 375                 380 cct gtt cct ttg aaa gcc cag aca gta aca gac tcc atg ttt gca gtg       1257
Pro Val Pro Leu Lys Ala Gln Thr Val Thr Asp Ser Met Phe Ala Val
385                 390                 395                 400 gcc agc aaa gat gct gga tgt gtg aat aag agt act cat gaa ttc aag       1305
Ala Ser Lys Asp Ala Gly Cys Val Asn Lys Ser Thr His Glu Phe Lys
                405                 410                 415 cca cag agt gga gca gag atc aaa gaa ggg tgt gaa aca cat aag gtt       1353
Pro Gln Ser Gly Ala Glu Ile Lys Glu Gly Cys Glu Thr His Lys Val
            420                 425                 430 gcc aac aca agt tct ttt cac aca act cca aac aca tca ctg gga atg       1401
Ala Asn Thr Ser Ser Phe His Thr Thr Pro Asn Thr Ser Leu Gly Met
        435                 440                 445 gtt cag gca acg cca tcc aaa gtg cag cca tca ccc acc gtg cac aca       1449
Val Gln Ala Thr Pro Ser Lys Val Gln Pro Ser Pro Thr Val His Thr
    450                 455                 460 aaa gaa gca tta ggt ttc atc atg aat atg ttt cag gct cct aca ctt       1497
Lys Glu Ala Leu Gly Phe Ile Met Asn Met Phe Gln Ala Pro Thr Leu
465                 470                 475                 480
```

```
cct gat att tct gat gac aaa gat gaa tgg caa tct cta gat caa aat    1545
Pro Asp Ile Ser Asp Asp Lys Asp Glu Trp Gln Ser Leu Asp Gln Asn
                485                 490                 495 gaa gat gca ttt gaa gcc cag ttt caa aaa aat gta agg tca tct ggg    1593
Glu Asp Ala Phe Glu Ala Gln Phe Gln Lys Asn Val Arg Ser Ser Gly
            500                 505                 510 gct tgg gga gtc aat aag atc atc tct tct ttg tca tct gct ttt cat    1641
Ala Trp Gly Val Asn Lys Ile Ile Ser Ser Leu Ser Ser Ala Phe His
                515                 520                 525 gtg ttt gaa gat gga aac aaa gaa aat tat gga tta cca cag cct aaa    1689
Val Phe Glu Asp Gly Asn Lys Glu Asn Tyr Gly Leu Pro Gln Pro Lys
            530                 535                 540 aat aaa ccc aca gga gcc agg acc ttt gga gaa cgc tct gtc agc aga    1737
Asn Lys Pro Thr Gly Ala Arg Thr Phe Gly Glu Arg Ser Val Ser Arg
545                 550                 555                 560 ctt cct tca aaa cca aag gag gaa gtg cct cat gct gaa gag ttt ttg    1785
Leu Pro Ser Lys Pro Lys Glu Glu Val Pro His Ala Glu Glu Phe Leu
                565                 570                 575 gat gac tca act gta tgg ggt att cgc tgc aac aaa acc ctg gca ccc    1833
Asp Asp Ser Thr Val Trp Gly Ile Arg Cys Asn Lys Thr Leu Ala Pro
            580                 585                 590 agt cct aag agc cca gga gac ttc aca tct gct gca caa ctt gcg tct    1881
Ser Pro Lys Ser Pro Gly Asp Phe Thr Ser Ala Ala Gln Leu Ala Ser
                595                 600                 605 aca cca ttc cac aag ctt cca gtg gag tca gtg cac att tta gaa gat    1929
Thr Pro Phe His Lys Leu Pro Val Glu Ser Val His Ile Leu Glu Asp
            610                 615                 620 aaa gaa aat gtg gta gca aaa cag tgt acc cag gcg act ttg gat tct    1977
Lys Glu Asn Val Val Ala Lys Gln Cys Thr Gln Ala Thr Leu Asp Ser
625                 630                 635                 640 tgt gag gaa aac atg gtg gtg cct tca agg gat gga aaa ttc agt cca    2025
Cys Glu Glu Asn Met Val Val Pro Ser Arg Asp Gly Lys Phe Ser Pro
                645                 650                 655 att caa gag aaa agc cca aaa cag gcc ttg tcg tct cac atg tat tca    2073
Ile Gln Glu Lys Ser Pro Lys Gln Ala Leu Ser Ser His Met Tyr Ser
            660                 665                 670 gca tcc tta ctt cgt ctg agc cag cct gct gca ggt ggg gta ctt acc    2121
Ala Ser Leu Leu Arg Leu Ser Gln Pro Ala Ala Gly Gly Val Leu Thr
                675                 680                 685 tgt gag gca gag ttg ggc gtt gag gct tgc aga ctc aca gac act gac    2169
Cys Glu Ala Glu Leu Gly Val Glu Ala Cys Arg Leu Thr Asp Thr Asp
            690                 695                 700 gct gcc att gca gaa gat cca cca gat gct att gct ggg ctc caa gca    2217
Ala Ala Ile Ala Glu Asp Pro Pro Asp Ala Ile Ala Gly Leu Gln Ala
705                 710                 715                 720 gaa tgg atg cag atg agt tca ctt ggg act gtt gat gct cca aac ttc    2265
Glu Trp Met Gln Met Ser Ser Leu Gly Thr Val Asp Ala Pro Asn Phe
                725                 730                 735 att gtt ggg aac cca tgg gat gat aag ctg att ttc aaa ctt tta tct    2313
Ile Val Gly Asn Pro Trp Asp Asp Lys Leu Ile Phe Lys Leu Leu Ser
            740                 745                 750 ggg ctt tct aaa cca gtg agt tcc tat cca aat act ttt gaa tgg caa    2361
Gly Leu Ser Lys Pro Val Ser Ser Tyr Pro Asn Thr Phe Glu Trp Gln
                755                 760                 765 tgt aaa ctt cca gcc atc aag ccc aag act gaa ttt caa ttg ggt tct    2409
Cys Lys Leu Pro Ala Ile Lys Pro Lys Thr Glu Phe Gln Leu Gly Ser
            770                 775                 780 aag ctg gtc tat gtc cat cac ctt ctt gga gaa gga gcc ttt gcc cag    2457
Lys Leu Val Tyr Val His His Leu Leu Gly Glu Gly Ala Phe Ala Gln
785                 790                 795                 800
```

```
gtg tac gaa gct acc cag gga gat ctg aat gat gct aaa aat aaa cag    2505
Val Tyr Glu Ala Thr Gln Gly Asp Leu Asn Asp Ala Lys Asn Lys Gln
            805                 810                 815 aaa ttt gtt tta aag gtc caa aag cct gcc aac ccc tgg gaa ttc tac    2553
Lys Phe Val Leu Lys Val Gln Lys Pro Ala Asn Pro Trp Glu Phe Tyr
        820                 825                 830 att ggg acc cag ttg atg gaa aga cta aag cca tct atg cag cac atg    2601
Ile Gly Thr Gln Leu Met Glu Arg Leu Lys Pro Ser Met Gln His Met
            835                 840                 845 ttt atg aag ttc tat tct gcc cac tta ttc cag aat ggc agt gta tta    2649
Phe Met Lys Phe Tyr Ser Ala His Leu Phe Gln Asn Gly Ser Val Leu
        850                 855                 860 gta gga gag ctc tac agc tat gga aca tta tta aat gcc att aac ctc    2697
Val Gly Glu Leu Tyr Ser Tyr Gly Thr Leu Leu Asn Ala Ile Asn Leu
865                 870                 875                 880 tat aaa aat acc cct gaa aaa gtg atg cct caa ggt ctt gtc atc tct    2745
Tyr Lys Asn Thr Pro Glu Lys Val Met Pro Gln Gly Leu Val Ile Ser
                885                 890                 895 ttt gct atg aga atg ctt tac atg att gag caa gtg cat gac tgt gaa    2793
Phe Ala Met Arg Met Leu Tyr Met Ile Glu Gln Val His Asp Cys Glu
        900                 905                 910 atc att cat gga gac att aaa cca gac aat ttc ata ctt gga aac gga    2841
Ile Ile His Gly Asp Ile Lys Pro Asp Asn Phe Ile Leu Gly Asn Gly
            915                 920                 925 ttt ttg gaa cag gat gat gaa gat gat tta tct gct ggc ttg gca ctg    2889
Phe Leu Glu Gln Asp Asp Glu Asp Asp Leu Ser Ala Gly Leu Ala Leu
        930                 935                 940 att gac ctg ggt cag agt ata gat atg aaa ctt ttt cca aaa gga act    2937
Ile Asp Leu Gly Gln Ser Ile Asp Met Lys Leu Phe Pro Lys Gly Thr
945                 950                 955                 960 ata ttc aca gca aag tgt gaa aca tct ggt ttt cag tgt gtt gag atg    2985
Ile Phe Thr Ala Lys Cys Glu Thr Ser Gly Phe Gln Cys Val Glu Met
                965                 970                 975 ctc agc aac aaa cca tgg aac tac cag atc gat tac ttt ggg gtt gct    3033
Leu Ser Asn Lys Pro Trp Asn Tyr Gln Ile Asp Tyr Phe Gly Val Ala
        980                 985                 990 gca aca gta tat tgc atg ctc ttt ggc act tac atg aaa  gtg aaa aat   3081
Ala Thr Val Tyr Cys Met Leu Phe Gly Thr Tyr Met Lys  Val Lys Asn
            995                 1000                1005 gaa gga gga gag tgt aag cct gaa ggt ctt ttt aga agg ctt cct        3126
Glu Gly Gly Glu Cys Lys Pro Glu Gly Leu Phe Arg Arg Leu Pro
        1010                1015                1020 cat ttg gat atg tgg aat gaa ttt ttt cat gtt atg ttg aat att        3171
His Leu Asp Met Trp Asn Glu Phe Phe His Val Met Leu Asn Ile
    1025                1030                1035 cca gat tgt cat cat ctt cca tct ttg gat ttg tta agg caa aag        3216
Pro Asp Cys His His Leu Pro Ser Leu Asp Leu Leu Arg Gln Lys
    1040                1045                1050 ctg aag aaa gta ttt caa caa cac tat act aac aag att agg gcc        3261
Leu Lys Lys Val Phe Gln Gln His Tyr Thr Asn Lys Ile Arg Ala
    1055                1060                1065 cta cgt aat agg cta att gta ctg ctc tta gaa tgt aag cgt tca        3306
Leu Arg Asn Arg Leu Ile Val Leu Leu Leu Glu Cys Lys Arg Ser
    1070                1075                1080 cga aaa    taaaatttgg atatagacag tccttaaaaa tcacactgta aatatgaatc  3362
Arg Lys
    1085 tgctcacttt aaacctgttt ttttttcatt tattgtttat gtaaatgttt gttaaaaata  3422
```
aatcccatgg aatatttcca tgt                                                      3445

<210> SEQ ID NO 12
<211> LENGTH: 1085
<212> TYPE: PRT
<213> ORGANISM: Homo sapiens
<220> FEATURE:
<223> OTHER INFORMATION: BUB1

<400> SEQUENCE: 12

Met Asp Thr Pro Glu Asn Val Leu Gln Met Leu Glu Ala His Met Gln
1               5                   10                  15

Ser Tyr Lys Gly Asn Asp Pro Leu Gly Glu Trp Glu Arg Tyr Ile Gln
            20                  25                  30

Trp Val Glu Glu Asn Phe Pro Glu Asn Lys Glu Tyr Leu Ile Thr Leu
        35                  40                  45

Leu Glu His Leu Met Lys Glu Phe Leu Asp Lys Lys Lys Tyr His Asn
    50                  55                  60

Asp Pro Arg Phe Ile Ser Tyr Cys Leu Lys Phe Ala Glu Tyr Asn Ser
65                  70                  75                  80

Asp Leu His Gln Phe Phe Glu Phe Leu Tyr Asn His Gly Ile Gly Thr
                85                  90                  95

Leu Ser Ser Pro Leu Tyr Ile Ala Trp Ala Gly His Leu Glu Ala Gln
            100                 105                 110

Gly Glu Leu Gln His Ala Ser Ala Val Leu Gln Arg Gly Ile Gln Asn
        115                 120                 125

Gln Ala Glu Pro Arg Glu Phe Leu Gln Gln Tyr Arg Leu Phe Gln
    130                 135                 140

Thr Arg Leu Thr Glu Thr His Leu Pro Ala Gln Ala Arg Thr Ser Glu
145                 150                 155                 160

Pro Leu His Asn Val Gln Val Leu Asn Gln Met Ile Thr Ser Lys Ser
                165                 170                 175

Asn Pro Gly Asn Asn Met Ala Cys Ile Ser Lys Asn Gln Gly Ser Glu
            180                 185                 190

Leu Ser Gly Val Ile Ser Ser Ala Cys Asp Lys Glu Ser Asn Met Glu
        195                 200                 205

Arg Arg Val Ile Thr Ile Ser Lys Ser Glu Tyr Ser Val His Ser Ser
    210                 215                 220

Leu Ala Ser Lys Val Asp Val Glu Gln Val Val Met Tyr Cys Lys Glu
225                 230                 235                 240

Lys Leu Ile Arg Gly Glu Ser Glu Phe Ser Phe Glu Glu Leu Arg Ala
                245                 250                 255

Gln Lys Tyr Asn Gln Arg Arg Lys His Glu Gln Trp Val Asn Glu Asp
            260                 265                 270

Arg His Tyr Met Lys Arg Lys Glu Ala Asn Ala Phe Glu Glu Gln Leu
        275                 280                 285

Leu Lys Gln Lys Met Asp Glu Leu His Lys Leu His Gln Val Val
    290                 295                 300

Glu Thr Ser His Glu Asp Leu Pro Ala Ser Gln Glu Arg Ser Glu Val
305                 310                 315                 320

Asn Pro Ala Arg Met Gly Pro Ser Val Gly Ser Gln Gln Glu Leu Arg
                325                 330                 335

Ala Pro Cys Leu Pro Val Thr Tyr Gln Gln Thr Pro Val Asn Met Glu
            340                 345                 350

Lys Asn Pro Arg Glu Ala Pro Pro Val Val Pro Pro Leu Ala Asn Ala

-continued

```
            355                 360                 365
Ile Ser Ala Ala Leu Val Ser Pro Ala Thr Ser Gln Ser Ile Ala Pro
370                 375                 380

Pro Val Pro Leu Lys Ala Gln Thr Val Thr Asp Ser Met Phe Ala Val
385                 390                 395                 400

Ala Ser Lys Asp Ala Gly Cys Val Asn Lys Ser Thr His Glu Phe Lys
                405                 410                 415

Pro Gln Ser Gly Ala Glu Ile Lys Glu Gly Cys Glu Thr His Lys Val
                420                 425                 430

Ala Asn Thr Ser Ser Phe His Thr Thr Pro Asn Thr Ser Leu Gly Met
                435                 440                 445

Val Gln Ala Thr Pro Ser Lys Val Gln Pro Ser Pro Thr Val His Thr
            450                 455                 460

Lys Glu Ala Leu Gly Phe Ile Met Asn Met Phe Gln Ala Pro Thr Leu
465                 470                 475                 480

Pro Asp Ile Ser Asp Asp Lys Asp Glu Trp Gln Ser Leu Asp Gln Asn
                485                 490                 495

Glu Asp Ala Phe Glu Ala Gln Phe Gln Lys Asn Val Arg Ser Ser Gly
                500                 505                 510

Ala Trp Gly Val Asn Lys Ile Ile Ser Ser Leu Ser Ser Ala Phe His
                515                 520                 525

Val Phe Glu Asp Gly Asn Lys Glu Asn Tyr Gly Leu Pro Gln Pro Lys
530                 535                 540

Asn Lys Pro Thr Gly Ala Arg Thr Phe Gly Glu Arg Ser Val Ser Arg
545                 550                 555                 560

Leu Pro Ser Lys Pro Lys Glu Val Pro His Ala Glu Glu Phe Leu
                565                 570                 575

Asp Asp Ser Thr Val Trp Gly Ile Arg Cys Asn Lys Thr Leu Ala Pro
                580                 585                 590

Ser Pro Lys Ser Pro Gly Asp Phe Thr Ser Ala Ala Gln Leu Ala Ser
                595                 600                 605

Thr Pro Phe His Lys Leu Pro Val Glu Ser Val His Ile Leu Glu Asp
            610                 615                 620

Lys Glu Asn Val Val Ala Lys Gln Cys Thr Gln Ala Thr Leu Asp Ser
625                 630                 635                 640

Cys Glu Glu Asn Met Val Val Pro Ser Arg Asp Gly Lys Phe Ser Pro
                645                 650                 655

Ile Gln Glu Lys Ser Pro Lys Gln Ala Leu Ser Ser His Met Tyr Ser
                660                 665                 670

Ala Ser Leu Leu Arg Leu Ser Gln Pro Ala Ala Gly Val Leu Thr
                675                 680                 685

Cys Glu Ala Glu Leu Gly Val Glu Ala Cys Arg Leu Thr Asp Thr Asp
            690                 695                 700

Ala Ala Ile Ala Glu Asp Pro Asp Ala Ile Ala Gly Leu Gln Ala
705                 710                 715                 720

Glu Trp Met Gln Met Ser Ser Leu Gly Thr Val Asp Ala Pro Asn Phe
                725                 730                 735

Ile Val Gly Asn Pro Trp Asp Asp Lys Leu Ile Phe Lys Leu Leu Ser
                740                 745                 750

Gly Leu Ser Lys Pro Val Ser Ser Tyr Pro Asn Thr Phe Glu Trp Gln
                755                 760                 765

Cys Lys Leu Pro Ala Ile Lys Pro Lys Thr Glu Phe Gln Leu Gly Ser
                770                 775                 780
```

```
Lys Leu Val Tyr Val His His Leu Gly Glu Gly Ala Phe Ala Gln
785                 790                 795                 800

Val Tyr Glu Ala Thr Gln Gly Asp Leu Asn Asp Ala Lys Asn Lys Gln
            805                 810                 815

Lys Phe Val Leu Lys Val Gln Lys Pro Ala Asn Pro Trp Glu Phe Tyr
        820                 825                 830

Ile Gly Thr Gln Leu Met Glu Arg Leu Lys Pro Ser Met Gln His Met
            835                 840                 845

Phe Met Lys Phe Tyr Ser Ala His Leu Phe Gln Asn Gly Ser Val Leu
        850                 855                 860

Val Gly Glu Leu Tyr Ser Tyr Gly Thr Leu Leu Asn Ala Ile Asn Leu
865                 870                 875                 880

Tyr Lys Asn Thr Pro Glu Lys Val Met Pro Gln Gly Leu Val Ile Ser
            885                 890                 895

Phe Ala Met Arg Met Leu Tyr Met Ile Glu Gln Val His Asp Cys Glu
        900                 905                 910

Ile Ile His Gly Asp Ile Lys Pro Asp Asn Phe Ile Leu Gly Asn Gly
        915                 920                 925

Phe Leu Glu Gln Asp Asp Glu Asp Asp Leu Ser Ala Gly Leu Ala Leu
    930                 935                 940

Ile Asp Leu Gly Gln Ser Ile Asp Met Lys Leu Phe Pro Lys Gly Thr
945                 950                 955                 960

Ile Phe Thr Ala Lys Cys Glu Thr Ser Gly Phe Gln Cys Val Glu Met
            965                 970                 975

Leu Ser Asn Lys Pro Trp Asn Tyr Gln Ile Asp Tyr Phe Gly Val Ala
        980                 985                 990

Ala Thr Val Tyr Cys Met Leu Phe  Gly Thr Tyr Met Lys  Val Lys Asn
            995                 1000                1005

Glu Gly  Gly Glu Cys Lys Pro  Glu Gly Leu Phe Arg  Arg Leu Pro
    1010                1015                 1020

His Leu  Asp Met Trp Asn Glu  Phe Phe His Val Met  Leu Asn Ile
    1025                1030                 1035

Pro Asp  Cys His His Leu Pro  Ser Leu Asp Leu Leu  Arg Gln Lys
    1040                1045                 1050

Leu Lys  Lys Val Phe Gln Gln  His Tyr Thr Asn Lys  Ile Arg Ala
    1055                1060                 1065

Leu Arg  Asn Arg Leu Ile Val  Leu Leu Leu Glu Cys  Lys Arg Ser
    1070                1075                 1080

Arg Lys
    1085

<210> SEQ ID NO 13
<211> LENGTH: 2748
<212> TYPE: DNA
<213> ORGANISM: Homo sapiens
<220> FEATURE:
<223> OTHER INFORMATION: C1S mRNA
<220> FEATURE:
<221> NAME/KEY: CDS
<222> LOCATION: (304)..(2367)

<400> SEQUENCE: 13
ggacagggag gctggccgga ggttcctgca gagggagcgt caaggccctg tgctgctgtc    60
cctgggggcc agaggggttg cccagcatgc ccactggcag agagaggga actgaccccac    120 ttgctcctac cagcttctga aggtgacact gagccccagg tgacgccgca ccaccaaaga    180
```

```
aggtgcttgt gtttgtcaga caaatacagc caggcctgcc accccttagg ctccaaagtc      240
cggaggtgca gaaagccagg accaagagac aggcagctca ccagggtgga caaatcgcca      300 gag atg tgg tgc att gtc ctg ttt tca ctt ttg gca tgg gtt tat gct        348
    Met Trp Cys Ile Val Leu Phe Ser Leu Leu Ala Trp Val Tyr Ala
    1               5                   10                  15 gag cct acc atg tat ggg gag atc ctg tcc cct aac tat cct cag gca        396
Glu Pro Thr Met Tyr Gly Glu Ile Leu Ser Pro Asn Tyr Pro Gln Ala
                20                  25                  30 tat ccc agt gag gta gag aaa tct tgg gac ata gaa gtt cct gaa ggg        444
Tyr Pro Ser Glu Val Glu Lys Ser Trp Asp Ile Glu Val Pro Glu Gly
            35                  40                  45 tat ggg att cac ctc tac ttc acc cat ctg gac att gag ctg tca gag        492
Tyr Gly Ile His Leu Tyr Phe Thr His Leu Asp Ile Glu Leu Ser Glu
        50                  55                  60 aac tgt gcg tat gac tca gtg cag ata atc tca gga gac act gaa gaa        540
Asn Cys Ala Tyr Asp Ser Val Gln Ile Ile Ser Gly Asp Thr Glu Glu
65                  70                  75 ggg agg ctc tgt gga cag agg agc agt aac aat ccc cac tct cca att        588
Gly Arg Leu Cys Gly Gln Arg Ser Ser Asn Asn Pro His Ser Pro Ile
80                  85                  90                  95 gtg gaa gag ttc caa gtc cca tac aac aaa ctc cag gtg atc ttt aag        636
Val Glu Glu Phe Gln Val Pro Tyr Asn Lys Leu Gln Val Ile Phe Lys
                100                 105                 110 tca gac ttt tcc aat gaa gag cgt ttt acg ggg ttt gct gca tac tat        684
Ser Asp Phe Ser Asn Glu Glu Arg Phe Thr Gly Phe Ala Ala Tyr Tyr
            115                 120                 125 gtt gcc aca gac ata aat gaa tgc aca gat ttt gta gat gtc cct tgt        732
Val Ala Thr Asp Ile Asn Glu Cys Thr Asp Phe Val Asp Val Pro Cys
        130                 135                 140 agc cac ttc tgc aac aat ttc att ggt ggt tac ttc tgc tcc tgc ccc        780
Ser His Phe Cys Asn Asn Phe Ile Gly Gly Tyr Phe Cys Ser Cys Pro
145                 150                 155 ccg gaa tat ttc ctc cat gat gac atg aag aat tgc gga gtt aat tgc        828
Pro Glu Tyr Phe Leu His Asp Asp Met Lys Asn Cys Gly Val Asn Cys
160                 165                 170                 175 agt ggg gat gta ttc act gca ctg att ggg gag att gca agt ccc aat        876
Ser Gly Asp Val Phe Thr Ala Leu Ile Gly Glu Ile Ala Ser Pro Asn
                180                 185                 190 tat ccc aaa cca tat cca gag aac tca agg tgt gaa tac cag atc cgg        924
Tyr Pro Lys Pro Tyr Pro Glu Asn Ser Arg Cys Glu Tyr Gln Ile Arg
            195                 200                 205 ttg gag aaa ggg ttc caa gtg gtg gtg acc ttg cgg aga gaa gat ttt        972
Leu Glu Lys Gly Phe Gln Val Val Val Thr Leu Arg Arg Glu Asp Phe
        210                 215                 220 gat gtg gaa gca gct gac tca gcg gga aac tgc ctt gac agt tta gtt       1020
Asp Val Glu Ala Ala Asp Ser Ala Gly Asn Cys Leu Asp Ser Leu Val
225                 230                 235 ttt gtt gca gga gat cgg caa ttt ggt cct tac tgt ggt cat gga ttc       1068
Phe Val Ala Gly Asp Arg Gln Phe Gly Pro Tyr Cys Gly His Gly Phe
240                 245                 250                 255 cct ggg cct cta aat att gaa acc aag agt aat gct ctt gat atc atc       1116
Pro Gly Pro Leu Asn Ile Glu Thr Lys Ser Asn Ala Leu Asp Ile Ile
                260                 265                 270 ttc caa act gat cta aca ggg caa aaa aag ggc tgg aaa ctt cgc tat       1164
Phe Gln Thr Asp Leu Thr Gly Gln Lys Lys Gly Trp Lys Leu Arg Tyr
            275                 280                 285 cat gga gat cca atg ccc tgc cct aag gaa gac act ccc aat tct gtt       1212
His Gly Asp Pro Met Pro Cys Pro Lys Glu Asp Thr Pro Asn Ser Val
```

```
              290                 295                 300
tgg gag cct gcg aag gca aaa tat gtc ttt aga gat gtg gtg cag ata    1260
Trp Glu Pro Ala Lys Ala Lys Tyr Val Phe Arg Asp Val Val Gln Ile
    305                 310                 315 acc tgt ctg gat ggg ttt gaa gtt gtg gag gga cgt gtt ggt gca aca    1308
Thr Cys Leu Asp Gly Phe Glu Val Val Glu Gly Arg Val Gly Ala Thr
320                 325                 330                 335 tct ttc tat tcg act tgt caa agc aat gga aag tgg agt aat tcc aaa    1356
Ser Phe Tyr Ser Thr Cys Gln Ser Asn Gly Lys Trp Ser Asn Ser Lys
                340                 345                 350 ctg aaa tgt caa cct gtg gac tgt ggc att cct gaa tcc att gag aat    1404
Leu Lys Cys Gln Pro Val Asp Cys Gly Ile Pro Glu Ser Ile Glu Asn
            355                 360                 365 ggt aaa gtt gaa gac cca gag agc act ttg ttt ggt tct gtc atc cgc    1452
Gly Lys Val Glu Asp Pro Glu Ser Thr Leu Phe Gly Ser Val Ile Arg
        370                 375                 380 tac act tgt gag gag cca tat tac tac atg gaa aat gga gga ggt ggg    1500
Tyr Thr Cys Glu Glu Pro Tyr Tyr Tyr Met Glu Asn Gly Gly Gly Gly
    385                 390                 395 gag tat cac tgt gct ggt aac ggg agc tgg gtg aat gag gtg ctg ggc    1548
Glu Tyr His Cys Ala Gly Asn Gly Ser Trp Val Asn Glu Val Leu Gly
400                 405                 410                 415 ccg gag ctg ccg aaa tgt gtt cca gtc tgt gga gtc ccc aga gaa ccc    1596
Pro Glu Leu Pro Lys Cys Val Pro Val Cys Gly Val Pro Arg Glu Pro
                420                 425                 430 ttt gaa gaa aaa cag agg ata att gga gga tcc gat gca gat att aaa    1644
Phe Glu Glu Lys Gln Arg Ile Ile Gly Gly Ser Asp Ala Asp Ile Lys
            435                 440                 445 aac ttc ccc tgg caa gtc ttc ttt gac aac cca tgg gct ggt gga gcg    1692
Asn Phe Pro Trp Gln Val Phe Phe Asp Asn Pro Trp Ala Gly Gly Ala
        450                 455                 460 ctc att aat gag tac tgg gtg ctg acg gct gct cat gtt gtg gag gga    1740
Leu Ile Asn Glu Tyr Trp Val Leu Thr Ala Ala His Val Val Glu Gly
    465                 470                 475 aac agg gag cca aca atg tat gtt ggg tcc acc tca gtg cag acc tca    1788
Asn Arg Glu Pro Thr Met Tyr Val Gly Ser Thr Ser Val Gln Thr Ser
480                 485                 490                 495 cgg ctg gca aaa tcc aag atg ctc act cct gag cat gtg ttt att cat    1836
Arg Leu Ala Lys Ser Lys Met Leu Thr Pro Glu His Val Phe Ile His
                500                 505                 510 ccg gga tgg aag ctg ctg gaa gtc cca gaa gga cga acc aat ttt gat    1884
Pro Gly Trp Lys Leu Leu Glu Val Pro Glu Gly Arg Thr Asn Phe Asp
            515                 520                 525 aat gac att gca ctg gtg cgg ctg aaa gac cca gtg aaa atg gga ccc    1932
Asn Asp Ile Ala Leu Val Arg Leu Lys Asp Pro Val Lys Met Gly Pro
        530                 535                 540 acc gtc tct ccc atc tgc cta cca ggc acc tct tcc gac tac aac ctc    1980
Thr Val Ser Pro Ile Cys Leu Pro Gly Thr Ser Ser Asp Tyr Asn Leu
    545                 550                 555 atg gat ggg gac ctg gga ctg atc tca ggc tgg ggc cga aca gag aag    2028
Met Asp Gly Asp Leu Gly Leu Ile Ser Gly Trp Gly Arg Thr Glu Lys
560                 565                 570                 575 aga gat cgt gct gtt cgc ctc aag gcg gca agg tta cct gta gct cct    2076
Arg Asp Arg Ala Val Arg Leu Lys Ala Ala Arg Leu Pro Val Ala Pro
                580                 585                 590 tta aga aaa tgc aaa gaa gtg aaa gtg gag aaa ccc aca gca gat gca    2124
Leu Arg Lys Cys Lys Glu Val Lys Val Glu Lys Pro Thr Ala Asp Ala
            595                 600                 605 gag gcc tat gtt ttc act cct aac atg atc tgt gct gga gga gag aag    2172
```

```
            Glu Ala Tyr Val Phe Thr Pro Asn Met Ile Cys Ala Gly Gly Glu Lys
                610                 615                 620 ggc atg gat agc tgt aaa ggg gac agt ggt ggg gcc ttt gct gta cag              2220
Gly Met Asp Ser Cys Lys Gly Asp Ser Gly Gly Ala Phe Ala Val Gln
            625                 630                 635 gat ccc aat gac aag acc aaa ttc tac gca gct ggc ctg gtg tcc tgg              2268
Asp Pro Asn Asp Lys Thr Lys Phe Tyr Ala Ala Gly Leu Val Ser Trp
640                 645                 650                 655 ggg ccc cag tgt ggg acc tat ggg ctc tac aca cgg gta aag aac tat              2316
Gly Pro Gln Cys Gly Thr Tyr Gly Leu Tyr Thr Arg Val Lys Asn Tyr
                660                 665                 670 gtt gac tgg ata atg aag act atg cag gaa aat agc acc ccc cgt gag              2364
Val Asp Trp Ile Met Lys Thr Met Gln Glu Asn Ser Thr Pro Arg Glu
            675                 680                 685 gac taatccagat acatcccacc agcctctcca agggtggtga ccaatgcatt                   2417
Asp accttctgtt ccttatgata ttctcattat ttcatcatga ctgaaagaag acacgagcga            2477
atgatttaaa tagaacttga ttgttgagac gccttgctag aggtagagtt tgatcataga            2537
attgtgctgg tcatacattt gtggtctgac tccttgggt ccttcccg gagtacctat               2597 tgtagataac actatgggtg gggcactcct ttcttgcact attccacagg gatacccttaa           2657 ttctttgttt cctctttacc tgttcaaaat tccatttact tgatcattct cagtatccac            2717
tgtctatgta caataaagga tgtttataag c                                          2748
```

<210> SEQ ID NO 14
<211> LENGTH: 688
<212> TYPE: PRT
<213> ORGANISM: Homo sapiens
<220> FEATURE:
<223> OTHER INFORMATION: C1S

<400> SEQUENCE: 14

```
Met Trp Cys Ile Val Leu Phe Ser Leu Leu Ala Trp Val Tyr Ala Glu
1               5                   10                  15

Pro Thr Met Tyr Gly Glu Ile Leu Ser Pro Asn Tyr Pro Gln Ala Tyr
                20                  25                  30

Pro Ser Glu Val Glu Lys Ser Trp Asp Ile Glu Val Pro Glu Gly Tyr
            35                  40                  45

Gly Ile His Leu Tyr Phe Thr His Leu Asp Ile Glu Leu Ser Glu Asn
        50                  55                  60

Cys Ala Tyr Asp Ser Val Gln Ile Ile Ser Gly Asp Thr Glu Gly Gly
65                  70                  75                  80

Arg Leu Cys Gly Gln Arg Ser Ser Asn Asn Pro His Ser Pro Ile Val
                85                  90                  95

Glu Glu Phe Gln Val Pro Tyr Asn Lys Leu Gln Val Ile Phe Lys Ser
                100                 105                 110

Asp Phe Ser Asn Glu Glu Arg Phe Thr Gly Phe Ala Ala Tyr Tyr Val
            115                 120                 125

Ala Thr Asp Ile Asn Glu Cys Thr Asp Phe Val Asp Val Pro Cys Ser
        130                 135                 140

His Phe Cys Asn Asn Phe Ile Gly Gly Tyr Phe Cys Ser Cys Pro Pro
145                 150                 155                 160

Glu Tyr Phe Leu His Asp Asp Met Lys Asn Cys Gly Val Asn Cys Ser
                165                 170                 175

Gly Asp Val Phe Thr Ala Leu Ile Gly Glu Ile Ala Ser Pro Asn Tyr
            180                 185                 190
```

```
Pro Lys Pro Tyr Pro Glu Asn Ser Arg Cys Glu Tyr Gln Ile Arg Leu
        195                 200                 205

Glu Lys Gly Phe Gln Val Val Thr Leu Arg Arg Glu Asp Phe Asp
    210                 215                 220

Val Glu Ala Ala Asp Ser Ala Gly Asn Cys Leu Asp Ser Leu Val Phe
225                 230                 235                 240

Val Ala Gly Asp Arg Gln Phe Gly Pro Tyr Cys Gly His Gly Phe Pro
                245                 250                 255

Gly Pro Leu Asn Ile Glu Thr Lys Ser Asn Ala Leu Asp Ile Ile Phe
            260                 265                 270

Gln Thr Asp Leu Thr Gly Gln Lys Lys Gly Trp Lys Leu Arg Tyr His
        275                 280                 285

Gly Asp Pro Met Pro Cys Pro Lys Glu Asp Thr Pro Asn Ser Val Trp
    290                 295                 300

Glu Pro Ala Lys Ala Lys Tyr Val Phe Arg Asp Val Val Gln Ile Thr
305                 310                 315                 320

Cys Leu Asp Gly Phe Glu Val Val Glu Gly Arg Val Gly Ala Thr Ser
                325                 330                 335

Phe Tyr Ser Thr Cys Gln Ser Asn Gly Lys Trp Ser Asn Ser Lys Leu
            340                 345                 350

Lys Cys Gln Pro Val Asp Cys Gly Ile Pro Glu Ser Ile Glu Asn Gly
        355                 360                 365

Lys Val Glu Asp Pro Glu Ser Thr Leu Phe Gly Ser Val Ile Arg Tyr
    370                 375                 380

Thr Cys Glu Glu Pro Tyr Tyr Tyr Met Glu Asn Gly Gly Gly Gly Glu
385                 390                 395                 400

Tyr His Cys Ala Gly Asn Gly Ser Trp Val Asn Glu Val Leu Gly Pro
                405                 410                 415

Glu Leu Pro Lys Cys Val Pro Val Cys Gly Val Pro Arg Glu Pro Phe
            420                 425                 430

Glu Glu Lys Gln Arg Ile Ile Gly Gly Ser Asp Ala Asp Ile Lys Asn
        435                 440                 445

Phe Pro Trp Gln Val Phe Phe Asp Asn Pro Trp Ala Gly Gly Ala Leu
    450                 455                 460

Ile Asn Glu Tyr Trp Val Leu Thr Ala Ala His Val Val Glu Gly Asn
465                 470                 475                 480

Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
        515                 520                 525

Asp Ile Ala Leu Val Arg Leu Lys Asp Pro Val Lys Met Gly Pro Thr
    530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Ala Arg Leu Pro Val Ala Pro Leu
            580                 585                 590

Arg Lys Cys Lys Glu Val Lys Val Glu Lys Pro Thr Ala Asp Ala Glu
        595                 600                 605
```

```
Ala Tyr Val Phe Thr Pro Asn Met Ile Cys Ala Gly Gly Glu Lys Gly
            610                 615                 620

Met Asp Ser Cys Lys Gly Asp Ser Gly Gly Ala Phe Ala Val Gln Asp
625                 630                 635                 640

Pro Asn Asp Lys Thr Lys Phe Tyr Ala Ala Gly Leu Val Ser Trp Gly
                    645                 650                 655

Pro Gln Cys Gly Thr Tyr Gly Leu Tyr Thr Arg Val Lys Asn Tyr Val
                660                 665                 670

Asp Trp Ile Met Lys Thr Met Gln Glu Asn Ser Thr Pro Arg Glu Asp
                675                 680                 685

<210> SEQ ID NO 15
<211> LENGTH: 1543
<212> TYPE: DNA
<213> ORGANISM: Homo sapiens
<220> FEATURE:
<223> OTHER INFORMATION: CYP2E1 mRNA
<220> FEATURE:
<221> NAME/KEY: CDS
<222> LOCATION: (10)..(1488)

<400> SEQUENCE: 15 agcggcacc atg tct gcc ctc gga gtc acc gtg gcc ctg ctg gtg tgg gcg         51
          Met Ser Ala Leu Gly Val Thr Val Ala Leu Leu Val Trp Ala
          1               5                   10 gcc ttc ctc ctg ctg gtg tcc atg tgg agg cag gtg cac agc agc tgg           99
Ala Phe Leu Leu Leu Val Ser Met Trp Arg Gln Val His Ser Ser Trp
15                  20                  25                  30 aat ctg ccc cca ggc cct ttc ccg ctt ccc atc atc ggg aac ctc ttc          147
Asn Leu Pro Pro Gly Pro Phe Pro Leu Pro Ile Ile Gly Asn Leu Phe
                35                  40                  45 cag ttg gaa ttg aag aat att ccc aag tcc ttc acc cgg ttg gcc cag          195
Gln Leu Glu Leu Lys Asn Ile Pro Lys Ser Phe Thr Arg Leu Ala Gln
            50                  55                  60 cgc ttc ggg ccg gtg ttc acg ctg tac gtg ggc tcg cag cgc atg gtg          243
Arg Phe Gly Pro Val Phe Thr Leu Tyr Val Gly Ser Gln Arg Met Val
65                  70                  75 gtg atg cac ggc tac aag gcg gtg aag gaa gcg ctg ctg gac tac aag          291
Val Met His Gly Tyr Lys Ala Val Lys Glu Ala Leu Leu Asp Tyr Lys
            80                  85                  90 gac gag ttc tcg ggc aga ggc gac ctc ccc gcg ttc cat gcg cac agg          339
Asp Glu Phe Ser Gly Arg Gly Asp Leu Pro Ala Phe His Ala His Arg
95                  100                 105                 110 gac agg gga atc att ttt aat aat gga cct acc tgg aag gac atc cgg          387
Asp Arg Gly Ile Ile Phe Asn Asn Gly Pro Thr Trp Lys Asp Ile Arg
                115                 120                 125 cgg ttt tcc ctg acc acc ctc cgg aac tat ggg atg ggg aaa cag ggc          435
Arg Phe Ser Leu Thr Thr Leu Arg Asn Tyr Gly Met Gly Lys Gln Gly
            130                 135                 140 aat gag agc cgg atc cag agg gag gcc cac ttc ctg ctg gaa gca ctc          483
Asn Glu Ser Arg Ile Gln Arg Glu Ala His Phe Leu Leu Glu Ala Leu
145                 150                 155 agg aag acc caa ggc cag cct ttc gac ccc acc ttc ctc atc ggc tgc          531
Arg Lys Thr Gln Gly Gln Pro Phe Asp Pro Thr Phe Leu Ile Gly Cys
            160                 165                 170 gcg ccc tgc aac gtc ata gcc gac atc ctc ttc cgc aag cat ttt gac          579
Ala Pro Cys Asn Val Ile Ala Asp Ile Leu Phe Arg Lys His Phe Asp
175                 180                 185                 190 tac aat gat gag aag ttt cta agg ctg atg tat ttg ttt aat gag aac          627
Tyr Asn Asp Glu Lys Phe Leu Arg Leu Met Tyr Leu Phe Asn Glu Asn
                195                 200                 205
```

```
ttc cac cta ctc agc act ccc tgg ctc cag ctt tac aat aat ttt ccc        675
Phe His Leu Leu Ser Thr Pro Trp Leu Gln Leu Tyr Asn Asn Phe Pro
            210                 215                 220 agc ttt cta cac tac ttg cct gga agc cac aga aaa gtc ata aaa aat        723
Ser Phe Leu His Tyr Leu Pro Gly Ser His Arg Lys Val Ile Lys Asn
            225                 230                 235 gtg gct gaa gta aaa gag tat gtg tct gaa agg gtg aag gag cac cat        771
Val Ala Glu Val Lys Glu Tyr Val Ser Glu Arg Val Lys Glu His His
240                 245                 250 caa tct ctg gac ccc aac tgt ccc cgg gac ctc acc gac tgc ctg ctc        819
Gln Ser Leu Asp Pro Asn Cys Pro Arg Asp Leu Thr Asp Cys Leu Leu
255                 260                 265                 270 gtg gaa atg gag aag gaa aag cac agt gca gag cgc ttg tac aca atg        867
Val Glu Met Glu Lys Glu Lys His Ser Ala Glu Arg Leu Tyr Thr Met
                275                 280                 285 gac ggt atc acc gtg act gtg gcc gac ctg ttc ttt gcg ggg aca gag        915
Asp Gly Ile Thr Val Thr Val Ala Asp Leu Phe Phe Ala Gly Thr Glu
                290                 295                 300 acc acc agc aca act ctg aga tat ggg ctc ctg att ctc atg aaa tac        963
Thr Thr Ser Thr Thr Leu Arg Tyr Gly Leu Leu Ile Leu Met Lys Tyr
            305                 310                 315 cct gag att gaa gag aag ctc cat gaa gaa att gac agg gtg att ggg       1011
Pro Glu Ile Glu Glu Lys Leu His Glu Glu Ile Asp Arg Val Ile Gly
            320                 325                 330 cca agc cga atc cct gcc atc aag gat agg caa gag atg ccc tac atg       1059
Pro Ser Arg Ile Pro Ala Ile Lys Asp Arg Gln Glu Met Pro Tyr Met
335                 340                 345                 350 gat gct gtg gtg cat gag att cag cgg ttc atc acc ctc gtg ccc tcc       1107
Asp Ala Val Val His Glu Ile Gln Arg Phe Ile Thr Leu Val Pro Ser
                355                 360                 365 aac ctg ccc cat gaa gca acc cga gac acc att ttc aga gga tac ctc       1155
Asn Leu Pro His Glu Ala Thr Arg Asp Thr Ile Phe Arg Gly Tyr Leu
            370                 375                 380 atc ccc aag ggc aca gtc gta gtg cca act ctg gac tct gtt ttg tat       1203
Ile Pro Lys Gly Thr Val Val Val Pro Thr Leu Asp Ser Val Leu Tyr
            385                 390                 395 gac aac caa gaa ttt cct gat cca gaa aag ttt aag cca gaa cac ttc       1251
Asp Asn Gln Glu Phe Pro Asp Pro Glu Lys Phe Lys Pro Glu His Phe
400                 405                 410 ctg aat gaa aat gga aag ttt aag tac agt gac tat ttc aag cca ttt       1299
Leu Asn Glu Asn Gly Lys Phe Lys Tyr Ser Asp Tyr Phe Lys Pro Phe
415                 420                 425                 430 tcc aca gga aaa cga gtg tgt gct gga gaa ggc ctg gct cgc atg gag       1347
Ser Thr Gly Lys Arg Val Cys Ala Gly Glu Gly Leu Ala Arg Met Glu
                435                 440                 445 ttg ttt ctt ttg ttg tgt gcc att ttg cag cat ttt aat ttg aag cct       1395
Leu Phe Leu Leu Leu Cys Ala Ile Leu Gln His Phe Asn Leu Lys Pro
            450                 455                 460 ctc gtt gac cca aag gat atc gac ctc agc cct ata cat att ggg ttt       1443
Leu Val Asp Pro Lys Asp Ile Asp Leu Ser Pro Ile His Ile Gly Phe
            465                 470                 475 ggc tgt atc cca cca cgt tac aaa ctc tgt gtc att ccc cgc tca           1488
Gly Cys Ile Pro Pro Arg Tyr Lys Leu Cys Val Ile Pro Arg Ser
            480                 485                 490 tgagtgtgtg gaggacaccc tgaaccccccc gctttcaaac aagttttcaa attgt         1543

<210> SEQ ID NO 16
<211> LENGTH: 493
<212> TYPE: PRT
```

<213> ORGANISM: Homo sapiens
<220> FEATURE:
<223> OTHER INFORMATION: CYP2E1

<400> SEQUENCE: 16

```
Met Ser Ala Leu Gly Val Thr Val Ala Leu Leu Val Trp Ala Ala Phe
1               5                   10                  15

Leu Leu Leu Val Ser Met Trp Arg Gln Val His Ser Ser Trp Asn Leu
            20                  25                  30

Pro Pro Gly Pro Phe Pro Leu Pro Ile Ile Gly Asn Leu Phe Gln Leu
        35                  40                  45

Glu Leu Lys Asn Ile Pro Lys Ser Phe Thr Arg Leu Ala Gln Arg Phe
50                  55                  60

Gly Pro Val Phe Thr Leu Tyr Val Gly Ser Gln Arg Met Val Val Met
65                  70                  75                  80

His Gly Tyr Lys Ala Val Lys Glu Ala Leu Leu Asp Tyr Lys Asp Glu
                85                  90                  95

Phe Ser Gly Arg Gly Asp Leu Pro Ala Phe His Ala His Arg Asp Arg
            100                 105                 110

Gly Ile Ile Phe Asn Asn Gly Pro Thr Trp Lys Asp Ile Arg Arg Phe
        115                 120                 125

Ser Leu Thr Thr Leu Arg Asn Tyr Gly Met Gly Lys Gln Gly Asn Glu
130                 135                 140

Ser Arg Ile Gln Arg Glu Ala His Phe Leu Leu Glu Ala Leu Arg Lys
145                 150                 155                 160

Thr Gln Gly Gln Pro Phe Asp Pro Thr Phe Leu Ile Gly Cys Ala Pro
                165                 170                 175

Cys Asn Val Ile Ala Asp Ile Leu Phe Arg Lys His Phe Asp Tyr Asn
            180                 185                 190

Asp Glu Lys Phe Leu Arg Leu Met Tyr Leu Phe Asn Glu Asn Phe His
        195                 200                 205

Leu Leu Ser Thr Pro Trp Leu Gln Leu Tyr Asn Asn Phe Pro Ser Phe
210                 215                 220

Leu His Tyr Leu Pro Gly Ser His Arg Lys Val Ile Lys Asn Val Ala
225                 230                 235                 240

Glu Val Lys Glu Tyr Val Ser Glu Arg Val Lys Glu His His Gln Ser
                245                 250                 255

Leu Asp Pro Asn Cys Pro Arg Asp Leu Thr Asp Cys Leu Leu Val Glu
            260                 265                 270

Met Glu Lys Glu Lys His Ser Ala Glu Arg Leu Tyr Thr Met Asp Gly
        275                 280                 285

Ile Thr Val Thr Val Ala Asp Leu Phe Phe Ala Gly Thr Glu Thr Thr
290                 295                 300

Ser Thr Thr Leu Arg Tyr Gly Leu Leu Ile Leu Met Lys Tyr Pro Glu
305                 310                 315                 320

Ile Glu Glu Lys Leu His Glu Glu Ile Asp Arg Val Ile Gly Pro Ser
                325                 330                 335

Arg Ile Pro Ala Ile Lys Asp Arg Gln Glu Met Pro Tyr Met Asp Ala
            340                 345                 350

Val Val His Glu Ile Gln Arg Phe Ile Thr Leu Val Pro Ser Asn Leu
        355                 360                 365

Pro His Glu Ala Thr Arg Asp Thr Ile Phe Arg Gly Tyr Leu Ile Pro
370                 375                 380

Lys Gly Thr Val Val Val Pro Thr Leu Asp Ser Val Leu Tyr Asp Asn
```

```
                385                 390                 395                 400
Gln Glu Phe Pro Asp Pro Glu Lys Phe Lys Pro Glu His Phe Leu Asn
                    405                 410                 415

Glu Asn Gly Lys Phe Lys Tyr Ser Asp Tyr Phe Lys Pro Phe Ser Thr
                420                 425                 430

Gly Lys Arg Val Cys Ala Gly Glu Gly Leu Ala Arg Met Glu Leu Phe
            435                 440                 445

Leu Leu Leu Cys Ala Ile Leu Gln His Phe Asn Leu Lys Pro Leu Val
        450                 455                 460

Asp Pro Lys Asp Ile Asp Leu Ser Pro Ile His Ile Gly Phe Gly Cys
465                 470                 475                 480

Ile Pro Pro Arg Tyr Lys Leu Cys Val Ile Pro Arg Ser
                    485                 490

<210> SEQ ID NO 17
<211> LENGTH: 2871
<212> TYPE: DNA
<213> ORGANISM: Homo sapiens
<220> FEATURE:
<223> OTHER INFORMATION: DLG7 mRNA
<220> FEATURE:
<221> NAME/KEY: CDS
<222> LOCATION: (110)..(2647)

<400> SEQUENCE: 17
ggaggctcgg gttgtgaggg ttcctgcttc ggagtcggcg gtggtcgtcc agaccgagtg     60
ttctttactt tttgtttggt tgaggtttca cgctagaagg tggctcagg atg tct tca    118
                                                    Met Ser Ser
                                                      1 tca cat ttt gcc agt cga cac agg aag gat ata agt act gaa atg att     166
Ser His Phe Ala Ser Arg His Arg Lys Asp Ile Ser Thr Glu Met Ile
  5                  10                  15 aga act aaa att gct cat agg aaa tca ctg tct cag aaa gaa aat aga     214
Arg Thr Lys Ile Ala His Arg Lys Ser Leu Ser Gln Lys Glu Asn Arg
 20                  25                  30                  35 cat aag gaa tac gaa cga aat aga cac ttt ggt ttg aaa gat gta aac     262
His Lys Glu Tyr Glu Arg Asn Arg His Phe Gly Leu Lys Asp Val Asn
                 40                  45                  50 att cca acc ttg gaa ggt aga att ctt gtt gaa tta gat gag aca tct     310
Ile Pro Thr Leu Glu Gly Arg Ile Leu Val Glu Leu Asp Glu Thr Ser
             55                  60                  65 caa ggg ctt gtt cca gaa aag acc aat gtt aag cca agg gca atg aaa     358
Gln Gly Leu Val Pro Glu Lys Thr Asn Val Lys Pro Arg Ala Met Lys
         70                  75                  80 act att cta ggt gat caa cga aaa cag atg ctc caa aaa tac aaa gaa     406
Thr Ile Leu Gly Asp Gln Arg Lys Gln Met Leu Gln Lys Tyr Lys Glu
     85                  90                  95 gaa aag caa ctt caa aaa ttg aaa gag cag aga gag aaa gct aaa cga     454
Glu Lys Gln Leu Gln Lys Leu Lys Glu Gln Arg Glu Lys Ala Lys Arg
100                 105                 110                 115 gga ata ttt aaa gtg ggt cgt tat aga cct gat atg cct tgt ttt ctt     502
Gly Ile Phe Lys Val Gly Arg Tyr Arg Pro Asp Met Pro Cys Phe Leu
                 120                 125                 130 tta tca aac cag aat gct gtg aaa gct gag cca aaa aag gct att cca     550
Leu Ser Asn Gln Asn Ala Val Lys Ala Glu Pro Lys Lys Ala Ile Pro
             135                 140                 145 tct tct gta cgg att aca agg tca aag gcc aaa gac caa atg gag cag     598
Ser Ser Val Arg Ile Thr Arg Ser Lys Ala Lys Asp Gln Met Glu Gln
         150                 155                 160
```

| | | |
|---|---|---|
| act aag att gat aac gag agt gat gtt cga gca atc cga cct ggt cca<br>Thr Lys Ile Asp Asn Glu Ser Asp Val Arg Ala Ile Arg Pro Gly Pro<br>165                       170                    175 | | 646 |
| aga caa act tct gaa aag aaa gtg tca gac aaa gag aaa aaa gtt gtg<br>Arg Gln Thr Ser Glu Lys Lys Val Ser Asp Lys Glu Lys Lys Val Val<br>180                       185                   190                 195 | | 694 |
| cag cct gta atg ccc acg tcg ttg aga atg act cga tca gct act caa<br>Gln Pro Val Met Pro Thr Ser Leu Arg Met Thr Arg Ser Ala Thr Gln<br>                    200                   205                   210 | | 742 |
| gca gca aag cag gtt ccc aga aca gtc tca tct acc aca gca aga aag<br>Ala Ala Lys Gln Val Pro Arg Thr Val Ser Ser Thr Thr Ala Arg Lys<br>               215                   220                   225 | | 790 |
| cca gtc aca aga gct gct aat gaa aac gaa cca gaa gga aag gtg cca<br>Pro Val Thr Arg Ala Ala Asn Glu Asn Glu Pro Glu Gly Lys Val Pro<br>230                       235                   240 | | 838 |
| agt aaa gga aga cct gcc aaa aat gta gaa aca aaa ccc gac aag ggt<br>Ser Lys Gly Arg Pro Ala Lys Asn Val Glu Thr Lys Pro Asp Lys Gly<br>245                       250                   255 | | 886 |
| att tct tgt aaa gtc gat agt gaa gaa aat act ttg aat tca caa act<br>Ile Ser Cys Lys Val Asp Ser Glu Glu Asn Thr Leu Asn Ser Gln Thr<br>260                       265                   270                 275 | | 934 |
| aat gca aca agt gga atg aat cca gat gga gtc tta tca aaa atg gaa<br>Asn Ala Thr Ser Gly Met Asn Pro Asp Gly Val Leu Ser Lys Met Glu<br>                    280                   285                   290 | | 982 |
| aac tta cct gag ata aat act gca aaa ata aaa ggg aag aat tcc ttt<br>Asn Leu Pro Glu Ile Asn Thr Ala Lys Ile Lys Gly Lys Asn Ser Phe<br>                    295                   300                   305 | | 1030 |
| gca cct aag gat ttt atg ttt cag cca ctg gat ggt ctg aag acc tat<br>Ala Pro Lys Asp Phe Met Phe Gln Pro Leu Asp Gly Leu Lys Thr Tyr<br>310                       315                   320 | | 1078 |
| caa gta aca cct atg act ccc aga agt gcc aat gct ttt ttg aca ccc<br>Gln Val Thr Pro Met Thr Pro Arg Ser Ala Asn Ala Phe Leu Thr Pro<br>325                       330                   335 | | 1126 |
| agt tac acc tgg act cct tta aaa aca gaa gtt gat gag tct caa gca<br>Ser Tyr Thr Trp Thr Pro Leu Lys Thr Glu Val Asp Glu Ser Gln Ala<br>340                       345                   350                 355 | | 1174 |
| aca aaa gaa att ttg gca caa aaa tgt aaa act tac tct acc aag aca<br>Thr Lys Glu Ile Leu Ala Gln Lys Cys Lys Thr Tyr Ser Thr Lys Thr<br>                    360                   365                   370 | | 1222 |
| ata cag caa gat tca aat aaa ttg cca tgt cct ttg ggt cct cta act<br>Ile Gln Gln Asp Ser Asn Lys Leu Pro Cys Pro Leu Gly Pro Leu Thr<br>                    375                   380                   385 | | 1270 |
| gtt tgg cat gaa gaa cat gtt tta aat aaa aat gaa gct act act aaa<br>Val Trp His Glu Glu His Val Leu Asn Lys Asn Glu Ala Thr Thr Lys<br>390                       395                   400 | | 1318 |
| aat tta aat ggc ctt cca ata aaa gaa gtc cca tca ctt gaa aga aat<br>Asn Leu Asn Gly Leu Pro Ile Lys Glu Val Pro Ser Leu Glu Arg Asn<br>405                       410                   415 | | 1366 |
| gaa ggt cga att gct cag ccc cac cat ggt gtg cca tat ttc aga aat<br>Glu Gly Arg Ile Ala Gln Pro His His Gly Val Pro Tyr Phe Arg Asn<br>420                       425                   430                 435 | | 1414 |
| atc ctc cag tca gaa act gag aaa tta act tca cat tgc ttc gag tgg<br>Ile Leu Gln Ser Glu Thr Glu Lys Leu Thr Ser His Cys Phe Glu Trp<br>                    440                   445                   450 | | 1462 |
| gac agg aaa ctt gaa ttg gac att cca gat gat gct aaa gat ctt att<br>Asp Arg Lys Leu Glu Leu Asp Ile Pro Asp Asp Ala Lys Asp Leu Ile<br>                    455                   460                   465 | | 1510 |
| cgc aca gca gtt ggt caa aca aga ctc ctt atg aag gaa agg ttt aaa<br>Arg Thr Ala Val Gly Gln Thr Arg Leu Leu Met Lys Glu Arg Phe Lys<br>470                       475                   480 | | 1558 |

```
cag ttt gaa gga ctg gtt gat gat tgt gaa tat aaa cga ggt ata aag    1606
Gln Phe Glu Gly Leu Val Asp Asp Cys Glu Tyr Lys Arg Gly Ile Lys
    485                 490                 495 gag act acc tgt aca gat ctg gat gga ttt tgg gat atg gtt agt ttt    1654
Glu Thr Thr Cys Thr Asp Leu Asp Gly Phe Trp Asp Met Val Ser Phe
500                 505                 510                 515 cag ata gaa gat gta atc cac aaa ttc aac aat ctg atc aaa ctt gag    1702
Gln Ile Glu Asp Val Ile His Lys Phe Asn Asn Leu Ile Lys Leu Glu
            520                 525                 530 gaa tct ggg tgg caa gtc aat aat aat atg aat cat aat atg aac aaa    1750
Glu Ser Gly Trp Gln Val Asn Asn Asn Met Asn His Asn Met Asn Lys
        535                 540                 545 aat gtc ttt agg aaa aaa gtt gtc tca ggt ata gca agt aaa cca aaa    1798
Asn Val Phe Arg Lys Lys Val Val Ser Gly Ile Ala Ser Lys Pro Lys
    550                 555                 560 cag gat gat gct gga aga att gca gcg aga aat cgc cta gct gcc ata    1846
Gln Asp Asp Ala Gly Arg Ile Ala Ala Arg Asn Arg Leu Ala Ala Ile
565                 570                 575 aaa aat gca atg aga gag aga att agg cag gaa gaa tgt gct gaa aca    1894
Lys Asn Ala Met Arg Glu Arg Ile Arg Gln Glu Glu Cys Ala Glu Thr
580                 585                 590                 595 gca gtt tct gtg ata cca aag gaa gtt gat aaa ata gtg ttc gat gct    1942
Ala Val Ser Val Ile Pro Lys Glu Val Asp Lys Ile Val Phe Asp Ala
            600                 605                 610 gga ttt ttc aga gtt gaa agt cct gtt aaa tta ttc tca gga ctt tct    1990
Gly Phe Phe Arg Val Glu Ser Pro Val Lys Leu Phe Ser Gly Leu Ser
        615                 620                 625 gtc tct tct gaa ggc cct tct caa aga ctt gga aca cct aag tct gtc    2038
Val Ser Ser Glu Gly Pro Ser Gln Arg Leu Gly Thr Pro Lys Ser Val
    630                 635                 640 aac aaa gct gta tct cag agt aga aat gag atg ggc att cca caa caa    2086
Asn Lys Ala Val Ser Gln Ser Arg Asn Glu Met Gly Ile Pro Gln Gln
645                 650                 655 act aca tca cca gaa aat gcc ggt cct cag aat acg aaa agt gaa cat    2134
Thr Thr Ser Pro Glu Asn Ala Gly Pro Gln Asn Thr Lys Ser Glu His
660                 665                 670                 675 gtg aag aag act ttg ttt ttg agt att cct gaa agc agg agc agc ata    2182
Val Lys Lys Thr Leu Phe Leu Ser Ile Pro Glu Ser Arg Ser Ser Ile
            680                 685                 690 gaa gat gct cag tgt cct gga tta cca gat tta att gaa gaa aat cat    2230
Glu Asp Ala Gln Cys Pro Gly Leu Pro Asp Leu Ile Glu Glu Asn His
        695                 700                 705 gtt gta aat aag aca gac ttg aag gtg gat tgt tta tcc agt gag aga    2278
Val Val Asn Lys Thr Asp Leu Lys Val Asp Cys Leu Ser Ser Glu Arg
    710                 715                 720 atg agt ttg cct ctt ctt gct ggt gga gta gca gat gat att aat act    2326
Met Ser Leu Pro Leu Leu Ala Gly Gly Val Ala Asp Asp Ile Asn Thr
725                 730                 735 aac aaa aaa gaa gga att tca gat gtt gtg gaa gga atg gaa ctg aat    2374
Asn Lys Lys Glu Gly Ile Ser Asp Val Val Glu Gly Met Glu Leu Asn
740                 745                 750                 755 tct tca att aca tca cag gat gtt ttg atg agt agc cct gaa aaa aat    2422
Ser Ser Ile Thr Ser Gln Asp Val Leu Met Ser Ser Pro Glu Lys Asn
            760                 765                 770 aca gct tca caa aat agc atc tta gaa gaa ggg gaa act aaa att tct    2470
Thr Ala Ser Gln Asn Ser Ile Leu Glu Glu Gly Glu Thr Lys Ile Ser
        775                 780                 785 cag tca gaa cta ttt gat aat aaa agt ctc act act gaa tgc cac ctt    2518
Gln Ser Glu Leu Phe Asp Asn Lys Ser Leu Thr Thr Glu Cys His Leu
```

```
                790                795                800
ctt gat tca cca ggt cta aac tgc agt aat cca ttt act cag ctg gag    2566
Leu Asp Ser Pro Gly Leu Asn Cys Ser Asn Pro Phe Thr Gln Leu Glu
805                810                815 agg aga cat caa gaa cat gcc aga cac att tct ttt ggt ggt aac ctg    2614
Arg Arg His Gln Glu His Ala Arg His Ile Ser Phe Gly Gly Asn Leu
820                825                830                835 att act ttt tca cct cta caa cca gga gaa ttt tgaatttaaa aataaatcca  2667
Ile Thr Phe Ser Pro Leu Gln Pro Gly Glu Phe
                840                845 aacattttcc ttcatattat caatgcttat atattcctta gactattgaa attttggaga  2727
aaatgtattt gtgttcactt ctatagcata taatgtttta atattctgtg ttcatcaaag  2787
tgtattttag atatactctt tctcaaggga agtggggata ttttgtacat tttcaacaca  2847
gaataaaaaa tgtactgtgc cttg                                         2871
```

<210> SEQ ID NO 18
<211> LENGTH: 846
<212> TYPE: PRT
<213> ORGANISM: Homo sapiens
<220> FEATURE:
<223> OTHER INFORMATION: DLG7

<400> SEQUENCE: 18

```
Met Ser Ser His Phe Ala Ser Arg His Arg Lys Asp Ile Ser Thr
1               5                   10                  15

Glu Met Ile Arg Thr Lys Ile Ala His Arg Lys Ser Leu Ser Gln Lys
                20                  25                  30

Glu Asn Arg His Lys Glu Tyr Glu Arg Asn Arg His Phe Gly Leu Lys
            35                  40                  45

Asp Val Asn Ile Pro Thr Leu Glu Gly Arg Ile Leu Val Glu Leu Asp
        50                  55                  60

Glu Thr Ser Gln Gly Leu Val Pro Glu Lys Thr Asn Val Lys Pro Arg
65                  70                  75                  80

Ala Met Lys Thr Ile Leu Gly Asp Gln Arg Lys Gln Met Leu Gln Lys
                85                  90                  95

Tyr Lys Glu Glu Lys Gln Leu Gln Lys Leu Lys Glu Gln Arg Glu Lys
            100                 105                 110

Ala Lys Arg Gly Ile Phe Lys Val Gly Arg Tyr Arg Pro Asp Met Pro
        115                 120                 125

Cys Phe Leu Leu Ser Asn Gln Asn Ala Val Lys Ala Glu Pro Lys Lys
    130                 135                 140

Ala Ile Pro Ser Ser Val Arg Ile Thr Arg Ser Lys Ala Lys Asp Gln
145                 150                 155                 160

Met Glu Gln Thr Lys Ile Asp Asn Glu Ser Asp Val Arg Ala Ile Arg
                165                 170                 175

Pro Gly Pro Arg Gln Thr Ser Glu Lys Lys Val Ser Asp Lys Glu Lys
            180                 185                 190

Lys Val Val Gln Pro Val Met Pro Thr Ser Leu Arg Met Thr Arg Ser
        195                 200                 205

Ala Thr Gln Ala Ala Lys Gln Val Pro Arg Thr Val Ser Ser Thr Thr
    210                 215                 220

Ala Arg Lys Pro Val Thr Arg Ala Ala Asn Glu Asn Glu Pro Glu Gly
225                 230                 235                 240

Lys Val Pro Ser Lys Gly Arg Pro Ala Lys Asn Val Glu Thr Lys Pro
                245                 250                 255
```

-continued

```
Asp Lys Gly Ile Ser Cys Lys Val Asp Ser Glu Asn Thr Leu Asn
            260                 265                 270

Ser Gln Thr Asn Ala Thr Ser Gly Met Asn Pro Asp Gly Val Leu Ser
            275                 280                 285

Lys Met Glu Asn Leu Pro Glu Ile Asn Thr Ala Lys Ile Lys Gly Lys
        290                 295                 300

Asn Ser Phe Ala Pro Lys Asp Phe Met Phe Gln Pro Leu Asp Gly Leu
305                 310                 315                 320

Lys Thr Tyr Gln Val Thr Pro Met Thr Pro Arg Ser Ala Asn Ala Phe
                325                 330                 335

Leu Thr Pro Ser Tyr Thr Trp Thr Pro Leu Lys Thr Glu Val Asp Glu
            340                 345                 350

Ser Gln Ala Thr Lys Glu Ile Leu Ala Gln Lys Cys Lys Thr Tyr Ser
            355                 360                 365

Thr Lys Thr Ile Gln Gln Asp Ser Asn Lys Leu Pro Cys Pro Leu Gly
        370                 375                 380

Pro Leu Thr Val Trp His Glu His Val Leu Asn Lys Asn Glu Ala
385                 390                 395                 400

Thr Thr Lys Asn Leu Asn Gly Leu Pro Ile Lys Glu Val Pro Ser Leu
                405                 410                 415

Glu Arg Asn Glu Gly Arg Ile Ala Gln Pro His His Gly Val Pro Tyr
            420                 425                 430

Phe Arg Asn Ile Leu Gln Ser Glu Thr Glu Lys Leu Thr Ser His Cys
            435                 440                 445

Phe Glu Trp Asp Arg Lys Leu Glu Leu Asp Ile Pro Asp Asp Ala Lys
        450                 455                 460

Asp Leu Ile Arg Thr Ala Val Gly Gln Thr Arg Leu Leu Met Lys Glu
465                 470                 475                 480

Arg Phe Lys Gln Phe Glu Gly Leu Val Asp Asp Cys Glu Tyr Lys Arg
                485                 490                 495

Gly Ile Lys Glu Thr Thr Cys Thr Asp Leu Asp Gly Phe Trp Asp Met
            500                 505                 510

Val Ser Phe Gln Ile Glu Asp Val Ile His Lys Phe Asn Asn Leu Ile
            515                 520                 525

Lys Leu Glu Glu Ser Gly Trp Gln Val Asn Asn Met Asn His Asn
        530                 535                 540

Met Asn Lys Asn Val Phe Arg Lys Lys Val Val Ser Gly Ile Ala Ser
545                 550                 555                 560

Lys Pro Lys Gln Asp Asp Ala Gly Arg Ile Ala Ala Arg Asn Arg Leu
                565                 570                 575

Ala Ala Ile Lys Asn Ala Met Arg Glu Arg Ile Arg Gln Glu Glu Cys
            580                 585                 590

Ala Glu Thr Ala Val Ser Val Ile Pro Lys Glu Val Asp Lys Ile Val
            595                 600                 605

Phe Asp Ala Gly Phe Phe Arg Val Glu Ser Pro Val Lys Leu Phe Ser
        610                 615                 620

Gly Leu Ser Val Ser Ser Glu Gly Pro Ser Gln Arg Leu Gly Thr Pro
625                 630                 635                 640

Lys Ser Val Asn Lys Ala Val Ser Gln Ser Arg Asn Glu Met Gly Ile
                645                 650                 655

Pro Gln Gln Thr Thr Ser Pro Glu Asn Ala Gly Pro Asn Thr Lys
            660                 665                 670
```

```
Ser Glu His Val Lys Lys Thr Leu Phe Leu Ser Ile Pro Glu Ser Arg
            675                 680                 685

Ser Ser Ile Glu Asp Ala Gln Cys Pro Gly Leu Pro Asp Leu Ile Glu
        690                 695                 700

Glu Asn His Val Asn Lys Thr Asp Leu Lys Val Asp Cys Leu Ser
705                 710                 715                 720

Ser Glu Arg Met Ser Leu Pro Leu Leu Ala Gly Val Ala Asp Asp
                725                 730                 735

Ile Asn Thr Asn Lys Lys Glu Gly Ile Ser Asp Val Val Glu Gly Met
            740                 745                 750

Glu Leu Asn Ser Ser Ile Thr Ser Gln Asp Val Leu Met Ser Ser Pro
            755                 760                 765

Glu Lys Asn Thr Ala Ser Gln Asn Ser Ile Leu Glu Glu Gly Glu Thr
            770                 775                 780

Lys Ile Ser Gln Ser Glu Leu Phe Asp Asn Lys Ser Leu Thr Thr Glu
785                 790                 795                 800

Cys His Leu Leu Asp Ser Pro Gly Leu Asn Cys Ser Asn Pro Phe Thr
                805                 810                 815

Gln Leu Glu Arg Arg His Gln Glu His Ala Arg His Ile Ser Phe Gly
            820                 825                 830

Gly Asn Leu Ile Thr Phe Ser Pro Leu Gln Pro Gly Glu Phe
            835                 840                 845

<210> SEQ ID NO 19
<211> LENGTH: 2284
<212> TYPE: DNA
<213> ORGANISM: Homo sapiens
<220> FEATURE:
<223> OTHER INFORMATION: DUSP9 mRNA
<220> FEATURE:
<221> NAME/KEY: CDS
<222> LOCATION: (114)..(1265)

<400> SEQUENCE: 19
cgcttcccgc cgcccgagct tcggaaactt cccggccgcg acgcagggaa ccggcgcgga      60
gaaccgagca gagcggagcg cccgtggtcc agcgtgtagg agccgatcg ccc atg         116
                                                           Met
                                                            1 gag ggt ctg ggc cgc tcg tgc ctg tgg ctg cgt cgg gag ctg tcg ccc       164
Glu Gly Leu Gly Arg Ser Cys Leu Trp Leu Arg Arg Glu Leu Ser Pro
        5                   10                  15 ccg cgg ccg cgg ctc ctg ctc ctg gac tgc cgc agc cgc gag ctg tac       212
Pro Arg Pro Arg Leu Leu Leu Leu Asp Cys Arg Ser Arg Glu Leu Tyr
            20                  25                  30 gag tcg gcg cgc atc ggt ggg gcg ctg agc gtg gcc ctg ccg gcg ctc       260
Glu Ser Ala Arg Ile Gly Gly Ala Leu Ser Val Ala Leu Pro Ala Leu
    35                  40                  45 ctg ctg cgc cgc ctg cgg agg ggc agc ctg tcg gtg cgc gcg ctc ctg       308
Leu Leu Arg Arg Leu Arg Arg Gly Ser Leu Ser Val Arg Ala Leu Leu
50                  55                  60                  65 cct ggg ccg ccg ctg cag ccg ccc ccg cct gcc ccc gtg ctc ctg tac       356
Pro Gly Pro Pro Leu Gln Pro Pro Pro Ala Pro Val Leu Leu Tyr
                70                  75                  80 gac cag ggc ggg ggc cgg cgc cgg cgc ggg gag gcc gag gcc gag gcc       404
Asp Gln Gly Gly Gly Arg Arg Arg Arg Gly Glu Ala Glu Ala Glu Ala
            85                  90                  95 gag gag tgg gag gcc gag tcg gtg ctg ggc acc ctg ctg cag aag ctg       452
Glu Glu Trp Glu Ala Glu Ser Val Leu Gly Thr Leu Leu Gln Lys Leu
        100                 105                 110
```

```
cga gag gaa ggc tac ctg gcc tac tac ctc cag gga ggc ttc agc aga      500
Arg Glu Glu Gly Tyr Leu Ala Tyr Tyr Leu Gln Gly Gly Phe Ser Arg
    115                 120                 125 ttc cag gcc gag tgc cct cac ctg tgt gag acc agc ctt gct ggc cgt      548
Phe Gln Ala Glu Cys Pro His Leu Cys Glu Thr Ser Leu Ala Gly Arg
130                 135                 140                 145 gcc ggc tcc agc atg gcg ccg gtg ccc ggt cca gtg ccc gtg gtg ggg      596
Ala Gly Ser Ser Met Ala Pro Val Pro Gly Pro Val Pro Val Val Gly
                150                 155                 160 ttg ggc agc ctg tgc ctg ggc tcc gac tgc tct gat gcg gaa tcc gag      644
Leu Gly Ser Leu Cys Leu Gly Ser Asp Cys Ser Asp Ala Glu Ser Glu
            165                 170                 175 gct gac cgc gac tcc atg agc tgt ggc ctg gat tcg gag ggt gcc aca      692
Ala Asp Arg Asp Ser Met Ser Cys Gly Leu Asp Ser Glu Gly Ala Thr
        180                 185                 190 ccc cca cca gtg ggg ctg cgg gca tcc ttc cct gtc cag atc ctg ccc      740
Pro Pro Pro Val Gly Leu Arg Ala Ser Phe Pro Val Gln Ile Leu Pro
    195                 200                 205 aac ctc tat ctg ggc agt gcc cgg gat tcc gcc aat ttg gag agc ctg      788
Asn Leu Tyr Leu Gly Ser Ala Arg Asp Ser Ala Asn Leu Glu Ser Leu
210                 215                 220                 225 gcc aaa ctg ggc atc cgc tac atc ctc aat gtc acc ccc aac ctc cca      836
Ala Lys Leu Gly Ile Arg Tyr Ile Leu Asn Val Thr Pro Asn Leu Pro
                230                 235                 240 aac ttc ttc gag aag aat ggt gac ttt cac tac aag cag atc ccc atc      884
Asn Phe Phe Glu Lys Asn Gly Asp Phe His Tyr Lys Gln Ile Pro Ile
            245                 250                 255 tcc gac cac tgg agc cag aac ctg tcg cgg ttc ttt ccg gag gcc att      932
Ser Asp His Trp Ser Gln Asn Leu Ser Arg Phe Phe Pro Glu Ala Ile
        260                 265                 270 gag ttc att gat gag gcc ttg tcc cag aac tgc ggg gtg ctc gtc cac      980
Glu Phe Ile Asp Glu Ala Leu Ser Gln Asn Cys Gly Val Leu Val His
    275                 280                 285 tgc ttg gcg ggg gtc agc cgt tct gtc acc gtc act gtg gcc tac ctc     1028
Cys Leu Ala Gly Val Ser Arg Ser Val Thr Val Thr Val Ala Tyr Leu
290                 295                 300                 305 atg cag aag ctc cac ctc tct ctc aac gat gcc tat gac ctg gtc aag     1076
Met Gln Lys Leu His Leu Ser Leu Asn Asp Ala Tyr Asp Leu Val Lys
                310                 315                 320 agg aag aag tct aac atc tcc ccc aac ttc aac ttc atg ggg cag ttg     1124
Arg Lys Lys Ser Asn Ile Ser Pro Asn Phe Asn Phe Met Gly Gln Leu
            325                 330                 335 ctg gac ttt gag cgc agc ttg cgg ctg gag gag cgc cac tcg cag gag     1172
Leu Asp Phe Glu Arg Ser Leu Arg Leu Glu Glu Arg His Ser Gln Glu
        340                 345                 350 cag ggc agt ggg ggg cag gca tct gcg gcc tcc aac ccg ccc tcc ttc     1220
Gln Gly Ser Gly Gly Gln Ala Ser Ala Ala Ser Asn Pro Pro Ser Phe
    355                 360                 365 ttc acc acc ccc acc agt gat ggc gcc ttc gag ctg gcc ccc acc         1265
Phe Thr Thr Pro Thr Ser Asp Gly Ala Phe Glu Leu Ala Pro Thr
370                 375                 380 tagggccccg tggccggcag gccggcccct gccccacccc cacccacggg tgtccctgcc   1325
cactcgtgtg gcaagggagg ggagggcagg agggctcggc ctgagcaggg tgctgggggg   1385
agagcgcaat acctcacgcg ggctgccgtc ctaatcaacg tgcctatggc gggaccacgc   1445
tcggagcctg cctcttctgc gactgttact ttttctttgc gggatggggg tggggttcc    1505 ctctccaggt ggttgtccag gcccatgtcc cggccctggg tgctcagcca gctcggctag   1565
```

```
gccctgcgcc tccctgcgct tcccccttca ggaagggtgt gtgccacctc gttgcactgg    1625
atcccagtgg ctgcttgggg gagaggcgtt tgccatcact ggtgttgtca cctccctgtt    1685
tctccaccaa gggcttgggc ctctcggggc tggggcctcc caggggatgg ggacccagag    1745
tgcagtggcc gcccacatcc atggcctagg agctactggg caggttcccg gccacacatc    1805
tggtgggctg ttttgttttt ttttttttcct cttcccccag atgtcttgac gggatcactg    1865
gggctctttg tgagtgaggg tggccaaact accgccggag gagatggggt ctcagagcga    1925
gagctgcgga gggggagggg aagaagaagg cctcactttt gctgctgcgg ggcccacaca    1985
gccgctgcta ctttgggggg tggggaaggg gccaagctgc agacacacac agtcattcat    2045
ttctgtccac accctgtgg gtggcgggtg tgcgtgtgtg tgcttgtgtg tgcgcacgtg    2105
tcggcgctca cacacacatg ctagcccact gatgcaccca gcccagggct ggcagtcttt    2165
gcagcgtggg gccgtctcac cctggagcct ggagaggatc tatgcttgtt tgttttttgta   2225 atccatatca tagttgcttt ctttaattgt tccttctgaa taaacagttt atttaagat     2284
```

<210> SEQ ID NO 20
<211> LENGTH: 384
<212> TYPE: PRT
<213> ORGANISM: Homo sapiens
<220> FEATURE:
<223> OTHER INFORMATION: DUSP9

<400> SEQUENCE: 20

```
Met Glu Gly Leu Gly Arg Ser Cys Leu Trp Leu Arg Arg Glu Leu Ser
1               5                   10                  15

Pro Pro Arg Pro Arg Leu Leu Leu Asp Cys Arg Ser Arg Glu Leu
            20                  25                  30

Tyr Glu Ser Ala Arg Ile Gly Gly Ala Leu Ser Val Ala Leu Pro Ala
        35                  40                  45

Leu Leu Leu Arg Arg Leu Arg Arg Gly Ser Leu Ser Val Arg Ala Leu
    50                  55                  60

Leu Pro Gly Pro Pro Leu Gln Pro Pro Pro Ala Pro Val Leu Leu
65                  70                  75                  80

Tyr Asp Gln Gly Gly Gly Arg Arg Arg Gly Glu Ala Glu Ala Glu
                85                  90                  95

Ala Glu Glu Trp Glu Ala Glu Ser Val Leu Gly Thr Leu Leu Gln Lys
            100                 105                 110

Leu Arg Glu Glu Gly Tyr Leu Ala Tyr Tyr Leu Gln Gly Gly Phe Ser
        115                 120                 125

Arg Phe Gln Ala Glu Cys Pro His Leu Cys Glu Thr Ser Leu Ala Gly
    130                 135                 140

Arg Ala Gly Ser Ser Met Ala Pro Val Pro Gly Pro Val Pro Val Val
145                 150                 155                 160

Gly Leu Gly Ser Leu Cys Leu Gly Ser Asp Cys Ser Asp Ala Glu Ser
                165                 170                 175

Glu Ala Asp Arg Asp Ser Met Ser Cys Gly Leu Asp Ser Glu Gly Ala
            180                 185                 190

Thr Pro Pro Pro Val Gly Leu Arg Ala Ser Phe Pro Val Gln Ile Leu
        195                 200                 205

Pro Asn Leu Tyr Leu Gly Ser Ala Arg Asp Ser Ala Asn Leu Glu Ser
    210                 215                 220

Leu Ala Lys Leu Gly Ile Arg Tyr Ile Leu Asn Val Thr Pro Asn Leu
225                 230                 235                 240
```

```
Pro Asn Phe Phe Glu Lys Asn Gly Asp Phe His Tyr Lys Gln Ile Pro
                245                 250                 255

Ile Ser Asp His Trp Ser Gln Asn Leu Ser Arg Phe Phe Pro Glu Ala
        260                 265                 270

Ile Glu Phe Ile Asp Glu Ala Leu Ser Gln Asn Cys Gly Val Leu Val
    275                 280                 285

His Cys Leu Ala Gly Val Ser Arg Ser Val Thr Val Thr Val Ala Tyr
290                 295                 300

Leu Met Gln Lys Leu His Leu Ser Leu Asn Asp Ala Tyr Asp Leu Val
305                 310                 315                 320

Lys Arg Lys Lys Ser Asn Ile Ser Pro Asn Phe Asn Phe Met Gly Gln
                325                 330                 335

Leu Leu Asp Phe Glu Arg Ser Leu Arg Leu Glu Glu Arg His Ser Gln
            340                 345                 350

Glu Gln Gly Ser Gly Gly Gln Ala Ser Ala Ala Ser Asn Pro Pro Ser
        355                 360                 365

Phe Phe Thr Thr Pro Thr Ser Asp Gly Ala Phe Glu Leu Ala Pro Thr
    370                 375                 380

<210> SEQ ID NO 21
<211> LENGTH: 1724
<212> TYPE: DNA
<213> ORGANISM: Homo sapiens
<220> FEATURE:
<223> OTHER INFORMATION: E2F5 mRNA
<220> FEATURE:
<221> NAME/KEY: CDS
<222> LOCATION: (31)..(1068)

<400> SEQUENCE: 21
ggggcccgac caccgcgggg ccgggacgcg atg gcg gcg gca gag ccc gcg agc      54
                                    Met Ala Ala Ala Glu Pro Ala Ser
                                    1               5 tcg ggc cag cag gcg ccg gca ggg cag ggg cag ggc cag cgg ccg ccg     102
Ser Gly Gln Gln Ala Pro Ala Gly Gln Gly Gln Gly Gln Arg Pro Pro
        10                  15                  20 ccg cag cct ccg cag gcg caa gcc ccg cag ccg ccc ccg ccg ccg cag     150
Pro Gln Pro Pro Gln Ala Gln Ala Pro Gln Pro Pro Pro Pro Pro Gln
25                  30                  35                  40 ctc ggg ggc gcc ggg ggc ggc agc agc agg cac gag aag agc ctg ggg     198
Leu Gly Gly Ala Gly Gly Gly Ser Ser Arg His Glu Lys Ser Leu Gly
                45                  50                  55 ctg ctc act acc aag ttc gtg tcg ctg ctg cag gag gcc aag gac ggc     246
Leu Leu Thr Thr Lys Phe Val Ser Leu Leu Gln Glu Ala Lys Asp Gly
            60                  65                  70 gtt ctg gat ctc aaa gcg gct gct gat act ttg gct gtg agg caa aaa     294
Val Leu Asp Leu Lys Ala Ala Ala Asp Thr Leu Ala Val Arg Gln Lys
        75                  80                  85 agg aga att tat gat atc acc aat gtc tta gag gga att gac ttg att     342
Arg Arg Ile Tyr Asp Ile Thr Asn Val Leu Glu Gly Ile Asp Leu Ile
    90                  95                  100 gaa aaa aag tca aaa aac agt atc cag tgg aaa ggt gta ggt gct ggc     390
Glu Lys Lys Ser Lys Asn Ser Ile Gln Trp Lys Gly Val Gly Ala Gly
105                 110                 115                 120 tgt aat act aaa gaa gtc ata gat aga tta aga tat ctt aaa gct gaa     438
Cys Asn Thr Lys Glu Val Ile Asp Arg Leu Arg Tyr Leu Lys Ala Glu
                125                 130                 135 att gaa gat cta gaa ctg aag gaa aga gaa ctt gat cag cag aag ttg     486
Ile Glu Asp Leu Glu Leu Lys Glu Arg Glu Leu Asp Gln Gln Lys Leu
            140                 145                 150
```

| | | | | | | | | | | | | | | |
|---|---|---|---|---|---|---|---|---|---|---|---|---|---|---|
| tgg | cta | cag | caa | agc | atc | aaa | aat | gtg | atg | gac | gat | tcc | att | aat aat |
| Trp | Leu | Gln | Gln | Ser | Ile | Lys | Asn | Val | Met | Asp | Asp | Ser | Ile | Asn Asn |
| | | | 155 | | | | 160 | | | | | 165 | | |

```
tgg cta cag caa agc atc aaa aat gtg atg gac gat tcc att aat aat      534
Trp Leu Gln Gln Ser Ile Lys Asn Val Met Asp Asp Ser Ile Asn Asn
            155                 160                 165 aga ttt tcc tat gta act cat gaa gac atc tgt aat tgc ttt aat ggt      582
Arg Phe Ser Tyr Val Thr His Glu Asp Ile Cys Asn Cys Phe Asn Gly
    170                 175                 180 gat aca ctt ttg gcc att cag gca cct tct ggt aca caa ctg gag gta      630
Asp Thr Leu Leu Ala Ile Gln Ala Pro Ser Gly Thr Gln Leu Glu Val
185                 190                 195                 200 ccc att cca gaa atg ggt cag aat gga caa aag aaa tac cag atc aat      678
Pro Ile Pro Glu Met Gly Gln Asn Gly Gln Lys Lys Tyr Gln Ile Asn
                205                 210                 215 cta aag agt cat tca gga cct atc cat gtg ctg ctt ata aat aaa gag      726
Leu Lys Ser His Ser Gly Pro Ile His Val Leu Leu Ile Asn Lys Glu
        220                 225                 230 tcg agt tca tct aag ccc gtg gtt ttt cct gtt ccc cca cct gat gac      774
Ser Ser Ser Ser Lys Pro Val Val Phe Pro Val Pro Pro Pro Asp Asp
    235                 240                 245 ctc aca cag cct tcc tcc cag tcc ttg act cca gtg act cca cag aaa      822
Leu Thr Gln Pro Ser Ser Gln Ser Leu Thr Pro Val Thr Pro Gln Lys
250                 255                 260 tcc agc atg gca act caa aat ctg cct gag caa cat gtc tct gaa aga      870
Ser Ser Met Ala Thr Gln Asn Leu Pro Glu Gln His Val Ser Glu Arg
265                 270                 275                 280 agc cag gct ctg cag cag aca tca gct aca gat ata tct tca gca gga      918
Ser Gln Ala Leu Gln Gln Thr Ser Ala Thr Asp Ile Ser Ser Ala Gly
                285                 290                 295 tct att agt gga gat atc att gat gag tta atg tct tct gac gtg ttt      966
Ser Ile Ser Gly Asp Ile Ile Asp Glu Leu Met Ser Ser Asp Val Phe
            300                 305                 310 cct ctc tta agg ctt tct cct acc ccg gca gat gac tac aac ttt aat     1014
Pro Leu Leu Arg Leu Ser Pro Thr Pro Ala Asp Asp Tyr Asn Phe Asn
        315                 320                 325 tta gat gat aac gaa gga gtt tgt gat ctg ttt gat gtc cag ata cta     1062
Leu Asp Asp Asn Glu Gly Val Cys Asp Leu Phe Asp Val Gln Ile Leu
330                 335                 340 aat tat tagattccat ggaaacttgg gactgttatc tacctctaac tgtgtaacat     1118
Asn Tyr
345 tttagacttc ttaataacct aaatatttaa aataatgaat gtaacacctt ttttagttca   1178 ctgattctga agtgttcttc cctaatactt tctttacttc acaaaacttc aaccataaaa   1238 acaaagggct ctgattgctt taggggataa gtgatttaat atccacaaac gtccccactc   1298 ccaaaagtaa ctatattctg gatttcaact tttcttctaa ttgtgaatcc ttctgttttt   1358 tcttcttaag gaggaaagtt aaaggacact acaggtcatc aaaaacaagt tggccaagga   1418 ctcattactt gtcttatatt tttactgcca ctaaactgcc tgtatttctg tatgtccttc   1478 tatccaaaca gacgttcact gccacttgta aagtgaagga tgtaaacgag gatatataac   1538 tgtttcagtg aacagatttt gtgaagtgcc ttctgtttta gcactttaag tttatcacat   1598 tttgttgact tctgacattc cactttccta ggttatagga aagatctgtt tatgtagttt   1658 gtttttaaaa tgtgccaatg cctgtacatt aacaagattt ttaaaaataa aattgtataa   1718 aacatt                                                              1724
```

<210> SEQ ID NO 22
<211> LENGTH: 346
<212> TYPE: PRT

```
<213> ORGANISM: Homo sapiens
<220> FEATURE:
<223> OTHER INFORMATION: E2F5

<400> SEQUENCE: 22

Met Ala Ala Ala Glu Pro Ala Ser Ser Gly Gln Gln Ala Pro Ala Gly
1               5                   10                  15

Gln Gly Gln Gly Gln Arg Pro Pro Gln Pro Gln Ala Gln Ala
            20                  25                  30

Pro Gln Pro Pro Pro Pro Gln Leu Gly Gly Ala Gly Gly Ser
        35                  40                  45

Ser Arg His Glu Lys Ser Leu Gly Leu Thr Thr Lys Phe Val Ser
    50                  55                  60

Leu Leu Gln Glu Ala Lys Asp Gly Val Leu Asp Leu Lys Ala Ala Ala
65                  70                  75                  80

Asp Thr Leu Ala Val Arg Gln Lys Arg Arg Ile Tyr Asp Ile Thr Asn
                85                  90                  95

Val Leu Glu Gly Ile Asp Leu Ile Glu Lys Lys Ser Lys Asn Ser Ile
            100                 105                 110

Gln Trp Lys Gly Val Gly Ala Gly Cys Asn Thr Lys Glu Val Ile Asp
        115                 120                 125

Arg Leu Arg Tyr Leu Lys Ala Glu Ile Glu Asp Leu Glu Leu Lys Glu
130                 135                 140

Arg Glu Leu Asp Gln Gln Lys Leu Trp Leu Gln Gln Ser Ile Lys Asn
145                 150                 155                 160

Val Met Asp Asp Ser Ile Asn Asn Arg Phe Ser Tyr Val Thr His Glu
                165                 170                 175

Asp Ile Cys Asn Cys Phe Asn Gly Asp Thr Leu Leu Ala Ile Gln Ala
            180                 185                 190

Pro Ser Gly Thr Gln Leu Glu Val Pro Ile Pro Glu Met Gly Gln Asn
        195                 200                 205

Gly Gln Lys Lys Tyr Gln Ile Asn Leu Lys Ser His Ser Gly Pro Ile
210                 215                 220

His Val Leu Leu Ile Asn Lys Glu Ser Ser Ser Lys Pro Val Val
225                 230                 235                 240

Phe Pro Val Pro Pro Asp Asp Leu Thr Gln Pro Ser Ser Gln Ser
                245                 250                 255

Leu Thr Pro Val Thr Pro Gln Lys Ser Ser Met Ala Thr Gln Asn Leu
            260                 265                 270

Pro Glu Gln His Val Ser Glu Arg Ser Gln Ala Leu Gln Gln Thr Ser
        275                 280                 285

Ala Thr Asp Ile Ser Ser Ala Gly Ser Ile Ser Gly Asp Ile Ile Asp
290                 295                 300

Glu Leu Met Ser Ser Asp Val Phe Pro Leu Leu Arg Leu Ser Pro Thr
305                 310                 315                 320

Pro Ala Asp Asp Tyr Asn Phe Asn Leu Asp Asn Glu Gly Val Cys
                325                 330                 335

Asp Leu Phe Asp Val Gln Ile Leu Asn Tyr
            340                 345

<210> SEQ ID NO 23
<211> LENGTH: 4413
<212> TYPE: DNA
<213> ORGANISM: Homo sapiens
<220> FEATURE:
<223> OTHER INFORMATION: GHR mRNA
```

```
<220> FEATURE:
<221> NAME/KEY: CDS
<222> LOCATION: (44)..(1957)

<400> SEQUENCE: 23
```

| | | | | | | | | | | | | | |
|---|---|---|---|---|---|---|---|---|---|---|---|---|---|
| ccgcgctctc tgatcagagg cgaagctcgg aggtcctaca ggt atg gat ctc tgg | | | | | | | | | | | | | 55 |
| | | | | | | | | | | Met | Asp | Leu | Trp |
| | | | | | | | | | | 1 | | | |

| cag | ctg | ctg | ttg | acc | ttg | gca | ctg | gca | gga | tca | agt | gat | gct | ttt | tct | 103 |
|---|---|---|---|---|---|---|---|---|---|---|---|---|---|---|---|---|
| Gln | Leu | Leu | Leu | Thr | Leu | Ala | Leu | Ala | Gly | Ser | Ser | Asp | Ala | Phe | Ser | |
| 5 | | | | 10 | | | | | 15 | | | | | | 20 | |

| gga | agt | gag | gcc | aca | gca | gct | atc | ctt | agc | aga | gca | ccc | tgg | agt | ctg | 151 |
|---|---|---|---|---|---|---|---|---|---|---|---|---|---|---|---|---|
| Gly | Ser | Glu | Ala | Thr | Ala | Ala | Ile | Leu | Ser | Arg | Ala | Pro | Trp | Ser | Leu | |
| | | | | 25 | | | | | 30 | | | | | 35 | | |

| caa | agt | gtt | aat | cca | ggc | cta | aag | aca | aat | tct | tct | aag | gag | cct | aaa | 199 |
|---|---|---|---|---|---|---|---|---|---|---|---|---|---|---|---|---|
| Gln | Ser | Val | Asn | Pro | Gly | Leu | Lys | Thr | Asn | Ser | Ser | Lys | Glu | Pro | Lys | |
| | | | 40 | | | | | 45 | | | | | 50 | | | |

| ttc | acc | aag | tgc | cgt | tca | cct | gag | cga | gag | act | ttt | tca | tgc | cac | tgg | 247 |
|---|---|---|---|---|---|---|---|---|---|---|---|---|---|---|---|---|
| Phe | Thr | Lys | Cys | Arg | Ser | Pro | Glu | Arg | Glu | Thr | Phe | Ser | Cys | His | Trp | |
| | | 55 | | | | | 60 | | | | | 65 | | | | |

| aca | gat | gag | gtt | cat | cat | ggt | aca | aag | aac | cta | gga | ccc | ata | cag | ctg | 295 |
|---|---|---|---|---|---|---|---|---|---|---|---|---|---|---|---|---|
| Thr | Asp | Glu | Val | His | His | Gly | Thr | Lys | Asn | Leu | Gly | Pro | Ile | Gln | Leu | |
| 70 | | | | | 75 | | | | | 80 | | | | | | |

| ttc | tat | acc | aga | agg | aac | act | caa | gaa | tgg | act | caa | gaa | tgg | aaa | gaa | 343 |
|---|---|---|---|---|---|---|---|---|---|---|---|---|---|---|---|---|
| Phe | Tyr | Thr | Arg | Arg | Asn | Thr | Gln | Glu | Trp | Thr | Gln | Glu | Trp | Lys | Glu | |
| 85 | | | | | 90 | | | | | 95 | | | | | 100 | |

| tgc | cct | gat | tat | gtt | tct | gct | ggg | gaa | aac | agc | tgt | tac | ttt | aat | tca | 391 |
|---|---|---|---|---|---|---|---|---|---|---|---|---|---|---|---|---|
| Cys | Pro | Asp | Tyr | Val | Ser | Ala | Gly | Glu | Asn | Ser | Cys | Tyr | Phe | Asn | Ser | |
| | | | | 105 | | | | | 110 | | | | | 115 | | |

| tcg | ttt | acc | tcc | atc | tgg | ata | cct | tat | tgt | atc | aag | cta | act | agc | aat | 439 |
|---|---|---|---|---|---|---|---|---|---|---|---|---|---|---|---|---|
| Ser | Phe | Thr | Ser | Ile | Trp | Ile | Pro | Tyr | Cys | Ile | Lys | Leu | Thr | Ser | Asn | |
| | | | 120 | | | | | 125 | | | | | 130 | | | |

| ggt | ggt | aca | gtg | gat | gaa | aag | tgt | ttc | tct | gtt | gat | gaa | ata | gtg | caa | 487 |
|---|---|---|---|---|---|---|---|---|---|---|---|---|---|---|---|---|
| Gly | Gly | Thr | Val | Asp | Glu | Lys | Cys | Phe | Ser | Val | Asp | Glu | Ile | Val | Gln | |
| | | 135 | | | | | 140 | | | | | 145 | | | | |

| cca | gat | cca | ccc | att | gcc | ctc | aac | tgg | act | tta | ctg | aac | gtc | agt | tta | 535 |
|---|---|---|---|---|---|---|---|---|---|---|---|---|---|---|---|---|
| Pro | Asp | Pro | Pro | Ile | Ala | Leu | Asn | Trp | Thr | Leu | Leu | Asn | Val | Ser | Leu | |
| | 150 | | | | | 155 | | | | | 160 | | | | | |

| act | ggg | att | cat | gca | gat | atc | caa | gtg | aga | tgg | gaa | gca | cca | cgc | aat | 583 |
|---|---|---|---|---|---|---|---|---|---|---|---|---|---|---|---|---|
| Thr | Gly | Ile | His | Ala | Asp | Ile | Gln | Val | Arg | Trp | Glu | Ala | Pro | Arg | Asn | |
| 165 | | | | 170 | | | | | 175 | | | | | 180 | | |

| gca | gat | att | cag | aaa | gga | tgg | atg | gtt | ctg | gag | tat | gaa | ctt | caa | tac | 631 |
|---|---|---|---|---|---|---|---|---|---|---|---|---|---|---|---|---|
| Ala | Asp | Ile | Gln | Lys | Gly | Trp | Met | Val | Leu | Glu | Tyr | Glu | Leu | Gln | Tyr | |
| | | | 185 | | | | | 190 | | | | | 195 | | | |

| aaa | gaa | gta | aat | gaa | act | aaa | tgg | aaa | atg | atg | gac | cct | ata | ttg | aca | 679 |
|---|---|---|---|---|---|---|---|---|---|---|---|---|---|---|---|---|
| Lys | Glu | Val | Asn | Glu | Thr | Lys | Trp | Lys | Met | Met | Asp | Pro | Ile | Leu | Thr | |
| | | | 200 | | | | | 205 | | | | | 210 | | | |

| aca | tca | gtt | cca | gtg | tac | tca | ttg | aaa | gtg | gat | aag | gaa | tat | gaa | gtg | 727 |
|---|---|---|---|---|---|---|---|---|---|---|---|---|---|---|---|---|
| Thr | Ser | Val | Pro | Val | Tyr | Ser | Leu | Lys | Val | Asp | Lys | Glu | Tyr | Glu | Val | |
| | | 215 | | | | | 220 | | | | | 225 | | | | |

| cgt | gtg | aga | tcc | aaa | caa | cga | aac | tct | gga | aat | tat | ggc | gag | ttc | agt | 775 |
|---|---|---|---|---|---|---|---|---|---|---|---|---|---|---|---|---|
| Arg | Val | Arg | Ser | Lys | Gln | Arg | Asn | Ser | Gly | Asn | Tyr | Gly | Glu | Phe | Ser | |
| | 230 | | | | | 235 | | | | | 240 | | | | | |

| gag | gtg | ctc | tat | gta | aca | ctt | cct | cag | atg | agc | caa | ttt | aca | tgt | gaa | 823 |
|---|---|---|---|---|---|---|---|---|---|---|---|---|---|---|---|---|
| Glu | Val | Leu | Tyr | Val | Thr | Leu | Pro | Gln | Met | Ser | Gln | Phe | Thr | Cys | Glu | |
| 245 | | | | | 250 | | | | | 255 | | | | | 260 | |

| gaa | gat | ttc | tac | ttt | cca | tgg | ctc | tta | att | att | atc | ttt | gga | ata | ttt | 871 |
|---|---|---|---|---|---|---|---|---|---|---|---|---|---|---|---|---|
| Glu | Asp | Phe | Tyr | Phe | Pro | Trp | Leu | Leu | Ile | Ile | Ile | Phe | Gly | Ile | Phe | |
| | | | | 265 | | | | | 270 | | | | | 275 | | |

| ggg | cta | aca | gtg | atg | cta | ttt | gta | ttc | tta | ttt | tct | aaa | cag | caa | agg | 919 |
|---|---|---|---|---|---|---|---|---|---|---|---|---|---|---|---|---|

-continued

```
            Gly Leu Thr Val Met Leu Phe Val Phe Leu Phe Ser Lys Gln Gln Arg
                        280                 285                 290 att aaa atg ctg att ctg ccc cca gtt cca gtt cca aag att aaa gga       967
Ile Lys Met Leu Ile Leu Pro Pro Val Pro Val Pro Lys Ile Lys Gly
            295                 300                 305 atc gat cca gat ctc ctc aag gaa gga aaa tta gag gag gtg aac aca      1015
Ile Asp Pro Asp Leu Leu Lys Glu Gly Lys Leu Glu Glu Val Asn Thr
310                 315                 320 atc tta gcc att cat gat agc tat aaa ccc gaa ttc cac agt gat gac      1063
Ile Leu Ala Ile His Asp Ser Tyr Lys Pro Glu Phe His Ser Asp Asp
325                 330                 335                 340 tct tgg gtt gaa ttt att gag cta gat att gat gag cca gat gaa aag      1111
Ser Trp Val Glu Phe Ile Glu Leu Asp Ile Asp Glu Pro Asp Glu Lys
                345                 350                 355 act gag gaa tca gac aca gac aga ctt cta agc agt gac cat gag aaa      1159
Thr Glu Glu Ser Asp Thr Asp Arg Leu Leu Ser Ser Asp His Glu Lys
            360                 365                 370 tca cat agt aac cta ggg gtg aag gat ggc gac tct gga cgt acc agc      1207
Ser His Ser Asn Leu Gly Val Lys Asp Gly Asp Ser Gly Arg Thr Ser
            375                 380                 385 tgt tgt gaa cct gac att ctg gag act gat ttc aat gcc aat gac ata      1255
Cys Cys Glu Pro Asp Ile Leu Glu Thr Asp Phe Asn Ala Asn Asp Ile
390                 395                 400 cat gag ggt acc tca gag gtt gct cag cca cag agg tta aaa ggg gaa      1303
His Glu Gly Thr Ser Glu Val Ala Gln Pro Gln Arg Leu Lys Gly Glu
405                 410                 415                 420 gca gat ctc tta tgc ctt gac cag aag aat caa aat aac tca cct tat      1351
Ala Asp Leu Leu Cys Leu Asp Gln Lys Asn Gln Asn Asn Ser Pro Tyr
                425                 430                 435 cat gat gct tgc cct gct act cag cag ccc agt gtt atc caa gca gag      1399
His Asp Ala Cys Pro Ala Thr Gln Gln Pro Ser Val Ile Gln Ala Glu
            440                 445                 450 aaa aac aaa cca caa cca ctt cct act gaa gga gct gag tca act cac      1447
Lys Asn Lys Pro Gln Pro Leu Pro Thr Glu Gly Ala Glu Ser Thr His
            455                 460                 465 caa gct gcc cat att cag cta agc aat cca agt tca ctg tca aac atc      1495
Gln Ala Ala His Ile Gln Leu Ser Asn Pro Ser Ser Leu Ser Asn Ile
470                 475                 480 gac ttt tat gcc cag gtg agc gac att aca cca gca ggt agt gtg gtc      1543
Asp Phe Tyr Ala Gln Val Ser Asp Ile Thr Pro Ala Gly Ser Val Val
485                 490                 495                 500 ctt tcc ccg ggc caa aag aat aag gca ggg atg tcc caa tgt gac atg      1591
Leu Ser Pro Gly Gln Lys Asn Lys Ala Gly Met Ser Gln Cys Asp Met
                505                 510                 515 cac ccg gaa atg gtc tca ctc tgc caa gaa aac ttc ctt atg gac aat      1639
His Pro Glu Met Val Ser Leu Cys Gln Glu Asn Phe Leu Met Asp Asn
            520                 525                 530 gcc tac ttc tgt gag gca gat gcc aaa aag tgc atc cct gtg gct cct      1687
Ala Tyr Phe Cys Glu Ala Asp Ala Lys Lys Cys Ile Pro Val Ala Pro
            535                 540                 545 cac atc aag gtt gaa tca cac ata cag cca agc tta aac caa gag gac      1735
His Ile Lys Val Glu Ser His Ile Gln Pro Ser Leu Asn Gln Glu Asp
550                 555                 560 att tac atc acc aca gaa agc ctt acc act gct gct ggg agg cct ggg      1783
Ile Tyr Ile Thr Thr Glu Ser Leu Thr Thr Ala Ala Gly Arg Pro Gly
565                 570                 575                 580 aca gga gaa cat gtt cca ggt tct gag atg cct gtc cca gac tat acc      1831
Thr Gly Glu His Val Pro Gly Ser Glu Met Pro Val Pro Asp Tyr Thr
                585                 590                 595
```

| | | |
|---|---|---|
| tcc att cat ata gta cag tcc cca cag ggc ctc ata ctc aat gcg act<br>Ser Ile His Ile Val Gln Ser Pro Gln Gly Leu Ile Leu Asn Ala Thr<br>600 605 610 | 1879 | |
| gcc ttg ccc ttg cct gac aaa gag ttt ctc tca tca tgt ggc tat gtg<br>Ala Leu Pro Leu Pro Asp Lys Glu Phe Leu Ser Ser Cys Gly Tyr Val<br>615 620 625 | 1927 | |
| agc aca gac caa ctg aac aaa atc atg cct tagcctttct ttggtttccc<br>Ser Thr Asp Gln Leu Asn Lys Ile Met Pro<br>630 635 | 1977 | |
| aagagctacg tatttaatag caaagaattg actggggcaa taacgtttaa gccaaaacaa | 2037 | |
| tgtttaaacc ttttttgggg gagtgacagg atggggtatg gattctaaaa tgccttttcc | 2097 | |
| caaaatgttg aaatatgatg ttaaaaaaat aagaagaatg cttaatcaga tagatattcc | 2157 | |
| tattgtgcaa tgtaaatatt ttaaagaatt gtgtcagact gtttagtagc agtgattgtc | 2217 | |
| ttaatattgt gggtgttaat ttttgatact aagcattgaa tggctatgtt tttaatgtat | 2277 | |
| agtaaatcac gcttttttgaa aaagcgaaaa atcaggtgg cttttgcggt tcaggaaaat | 2337 | |
| tgaatgcaaa ccatagcaca ggctaatttt ttgttgtttc ttaaataaga aactttttta | 2397 | |
| tttaaaaaac taaaaactag aggtgagaaa tttaaactat aagcaagaag caaaaatag | 2457 | |
| tttggatatg taaaacattt atttttgacat aaagttgata aagattttt aataatttag | 2517 | |
| acttcaagca tggctatttt atattacact acacactgtg tactgcagtt ggtatgaccc | 2577 | |
| ctctaaggag tgtagcaact acagtctaaa gctggtttaa tgttttggcc aatgcaccta | 2637 | |
| aagaaaaaca aactcgtttt ttacaaagcc cttttatacc tccccagact ccttcaacaa | 2697 | |
| ttctaaaatg attgtagtaa tctgcattat tggaatataa ttgttttatc tgaatttta | 2757 | |
| aacaagtatt tgttaattta gaaaactta aagcgtttgc acagatcaac ttaccaggca | 2817 | |
| ccaaaagaag taaagcaaa aagaaaaacc tttcttcacc aaatcttggt tgatgccaaa | 2877 | |
| aaaaaataca tgctaagaga agtagaaatc atagctggtt cacactgacc aagatactta | 2937 | |
| agtgctgcaa ttgcacgcgg agtgagtttt ttagtgcgtg cagatggtga gagataagat | 2997 | |
| ctatagcctc tgcagcggaa tctgttcaca cccaacttgg ttttgctaca taattatcca | 3057 | |
| ggaagggaat aaggtacaag aagcattttg taagttgaag caaatcgaat gaaattaact | 3117 | |
| gggtaatgaa acaaagagtt caagaaataa gttttgtttt cacagcctat aaccagacac | 3177 | |
| atactcattt tcatgataa tgaacagaac atagacagaa gaaacaaggt tttcagtccc | 3237 | |
| cacagataac tgaaaattat ttaaaccgct aaaagaaact ttctttctca ctaaatcttt | 3297 | |
| tataggattt atttaaaata gcaaagaag aagtttcatc attttttact tcctctctga | 3357 | |
| gtggactggc ctcaaagcaa gcattcagaa gaaaagaag caacctcagt aatttagaaa | 3417 | |
| tcattttgca atcccttaat atcctaaaca tcattcattt tgttgttgt tgttgttgtt | 3477 | |
| gagacagagt ctcgctctgt cgccaggcta gagtgcggtg gcgcgatctt gactcactgc | 3537 | |
| aatctccacc tcccacaggt tcaggcgatt cccgtgcctc agcctcctga gtagctggga | 3597 | |
| ctacaggcac gcaccaccat gccaggctaa ttttttttgta ttttagcaga acggggtttt | 3657 | |
| caccatgttg gccaggatgg tctcgatctc ctgacctcgt gatccacccg actcggcctc | 3717 | |
| ccaaagtgct gggattacag gtgtaagcca ccgtgcccag ccctaaacat cattcttgag | 3777 | |
| agcattggga tatctcctga aaaggtttat gaaaagaag aatctcatct cagtgaagaa | 3837 | |
| tacttctcat ttttaaaaa agcttaaaac tttgaagtta gctttaactt aaatagtatt | 3897 | |
| tcccatttat cgcagacctt ttttaggaag caagcttaat ggctgataat tttaaattct | 3957 | |
| ctctcttgca ggaaggacta tgaaaagcta gaattgagtg tttaaagttc aacatgttat | 4017 | |

```
ttgtaataga tgtttgatag attttctgct actttgctgc tatggttttc tccaagagct    4077 acataaattta gtttcatata aagtatcatc agtgtagaac ctaattcaat tcaaagctgt    4137
gtgtttggaa gactatctta ctatttcaca acagcctgac aacatttcta tagccaaaaa    4197
tagctaaata cctcaatcag tctcagaatg tcattttggt actttggtgg ccacataagc    4257
cattattcac tagtatgact agttgtgtct ggcagtttat atttaactct ctttatgtct    4317
gtggattttt tccttcaaag tttaataaat ttattttctt ggattcctga tagtgtgctt    4377
ctgttatcaa acaccaacat aaaaatgatc taaacc                              4413
```

<210> SEQ ID NO 24
<211> LENGTH: 638
<212> TYPE: PRT
<213> ORGANISM: Homo sapiens
<220> FEATURE:
<223> OTHER INFORMATION: GHR

<400> SEQUENCE: 24

```
Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
            20                  25                  30

Pro Trp Ser Leu Gln Ser Val Asn Pro Gly Leu Lys Thr Asn Ser Ser
        35                  40                  45

Lys Glu Pro Lys Phe Thr Lys Cys Arg Ser Pro Glu Arg Glu Thr Phe
    50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
        115                 120                 125

Leu Thr Ser Asn Gly Gly Thr Val Asp Glu Lys Cys Phe Ser Val Asp
    130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
    210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
                245                 250                 255

Phe Thr Cys Glu Glu Asp Phe Tyr Phe Pro Trp Leu Leu Ile Ile Ile
            260                 265                 270

Phe Gly Ile Phe Gly Leu Thr Val Met Leu Phe Val Phe Leu Phe Ser
        275                 280                 285
```

-continued

```
Lys Gln Gln Arg Ile Lys Met Leu Ile Leu Pro Pro Val Pro Val Pro
    290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Ser Asp Thr Asp Arg Leu Leu Ser Ser
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635
```

<210> SEQ ID NO 25
<211> LENGTH: 1403
<212> TYPE: DNA
<213> ORGANISM: Homo sapiens
<220> FEATURE:
<223> OTHER INFORMATION: HPD mRNA
<220> FEATURE:
<221> NAME/KEY: CDS
<222> LOCATION: (23)..(1201)

<400> SEQUENCE: 25

```
ggaggtttga ctaagatcaa tc atg acg act tac agt gac aaa ggg gca aag        52
                         Met Thr Thr Tyr Ser Asp Lys Gly Ala Lys
                         1               5                   10 cct gag aga ggc cga ttc ctc cac ttc cac tct gtg acc ttc tgg gtt         100
Pro Glu Arg Gly Arg Phe Leu His Phe His Ser Val Thr Phe Trp Val
            15                  20                  25 ggc aac gcc aag cag gcc acg tca ttc tac tgc agc aag atg ggc ttt         148
Gly Asn Ala Lys Gln Ala Thr Ser Phe Tyr Cys Ser Lys Met Gly Phe
        30                  35                  40 gaa cct cta gcc tac agg ggc ctg gag acc ggt tcc cgg gag gtg gtc         196
Glu Pro Leu Ala Tyr Arg Gly Leu Glu Thr Gly Ser Arg Glu Val Val
            45                  50                  55 agc cat gta atc aaa caa ggg aag att gtg ttt gtc ctc tcc tca gcg         244
Ser His Val Ile Lys Gln Gly Lys Ile Val Phe Val Leu Ser Ser Ala
    60                  65                  70 ctc aac ccc tgg aac aaa gag atg ggc gat cac ctg gtg aaa cac ggt         292
Leu Asn Pro Trp Asn Lys Glu Met Gly Asp His Leu Val Lys His Gly
75                  80                  85                  90 gac gga gtg aag gac att gcg ttc gag gtg gaa gat tgt gac tac atc         340
Asp Gly Val Lys Asp Ile Ala Phe Glu Val Glu Asp Cys Asp Tyr Ile
                95                  100                 105 gtg cag aaa gca cgg gaa cgg ggc gcc aaa atc atg cgg gag ccc tgg         388
Val Gln Lys Ala Arg Glu Arg Gly Ala Lys Ile Met Arg Glu Pro Trp
            110                 115                 120 gta gag caa gac aag ttt ggg aag gtg aag ttt gct gtg ctg cag acg         436
Val Glu Gln Asp Lys Phe Gly Lys Val Lys Phe Ala Val Leu Gln Thr
        125                 130                 135 tat ggg gac acc aca cac acc ctg gtg gag aag atg aac tac atc ggc         484
Tyr Gly Asp Thr Thr His Thr Leu Val Glu Lys Met Asn Tyr Ile Gly
    140                 145                 150 caa ttc ttg cct gga tat gag gcc cca gcg ttc atg gac ccc cta ctt         532
Gln Phe Leu Pro Gly Tyr Glu Ala Pro Ala Phe Met Asp Pro Leu Leu
155                 160                 165                 170 cct aaa ctg ccc aaa tgc agt ctg gag atg atc gac cac att gtg gga         580
Pro Lys Leu Pro Lys Cys Ser Leu Glu Met Ile Asp His Ile Val Gly
                175                 180                 185 aac cag cct gat cag gag atg gtg tcc gcc tcc gaa tgg tac ctg aaa         628
Asn Gln Pro Asp Gln Glu Met Val Ser Ala Ser Glu Trp Tyr Leu Lys
            190                 195                 200 aac ctg cag ttc cac cgc ttc tgg tcc gtg gat gac acg cag gtg cac         676
Asn Leu Gln Phe His Arg Phe Trp Ser Val Asp Asp Thr Gln Val His
        205                 210                 215 acg gaa tat agc tct ctg cga tcc att gtg gtg gcc aac tat gaa gag         724
Thr Glu Tyr Ser Ser Leu Arg Ser Ile Val Val Ala Asn Tyr Glu Glu
    220                 225                 230 tcc atc aag atg ccc atc aat gag cca gcg cct ggc aag aag aag tcc         772
Ser Ile Lys Met Pro Ile Asn Glu Pro Ala Pro Gly Lys Lys Lys Ser
235                 240                 245                 250 cag atc cag gaa tat gtg gac tat aac ggg ggc gct ggg gtc cag cac         820
Gln Ile Gln Glu Tyr Val Asp Tyr Asn Gly Gly Ala Gly Val Gln His
                255                 260                 265 atc gct ctc aag acc gaa gac atc atc aca gcg att cgc cac ttg aga         868
Ile Ala Leu Lys Thr Glu Asp Ile Ile Thr Ala Ile Arg His Leu Arg
            270                 275                 280 gag aga ggc ctg gag ttc tta tct gtt ccc tcc acg tac tac aaa caa         916
Glu Arg Gly Leu Glu Phe Leu Ser Val Pro Ser Thr Tyr Tyr Lys Gln
        285                 290                 295 ctg cgg gag aag ctg aag acg gcc aag atc aag gtg aag gag aac att         964
Leu Arg Glu Lys Leu Lys Thr Ala Lys Ile Lys Val Lys Glu Asn Ile
    300                 305                 310
```

-continued

```
gat gcc ctg gag gag ctg aaa atc ctg gtg gac tac gac gag aaa ggc    1012
Asp Ala Leu Glu Glu Leu Lys Ile Leu Val Asp Tyr Asp Glu Lys Gly
315                 320                 325                 330 tac ctc ctg cag atc ttc acc aaa ccg gtg cag gac cgg ccc acg ctc    1060
Tyr Leu Leu Gln Ile Phe Thr Lys Pro Val Gln Asp Arg Pro Thr Leu
                335                 340                 345 ttc ctg gaa gtc atc cag cgc cac aac cac cag ggt ttt gga gcc ggc    1108
Phe Leu Glu Val Ile Gln Arg His Asn His Gln Gly Phe Gly Ala Gly
            350                 355                 360 aac ttc aac tca ctg ttc aag gct ttc gag gag gag cag aac ctg cgg    1156
Asn Phe Asn Ser Leu Phe Lys Ala Phe Glu Glu Glu Gln Asn Leu Arg
        365                 370                 375 ggt aac ctc acc aac atg gag acc aat ggg gtg gtg ccc ggc atg        1201
Gly Asn Leu Thr Asn Met Glu Thr Asn Gly Val Val Pro Gly Met
    380                 385                 390 taagcccgc ccaccccacg gaggccacag ccacacagcc acgcccctg attctggaac    1261 tcgcccaact tccctactgg ctgctcccct tgggtcccgc ccaccagcgg actcggcccc   1321
caaggctccg cccacactga ccacgcccct cggcggggcc gccctctgct ccagccctcc   1381
cgattaaagc gtgccccggt cc                                            1403
```

<210> SEQ ID NO 26
<211> LENGTH: 393
<212> TYPE: PRT
<213> ORGANISM: Homo sapiens
<220> FEATURE:
<223> OTHER INFORMATION: HPD

<400> SEQUENCE: 26

```
Met Thr Thr Tyr Ser Asp Lys Gly Ala Lys Pro Glu Arg Gly Arg Phe
1               5                   10                  15

Leu His Phe His Ser Val Thr Phe Trp Val Gly Asn Ala Lys Gln Ala
                20                  25                  30

Thr Ser Phe Tyr Cys Ser Lys Met Gly Phe Glu Pro Leu Ala Tyr Arg
            35                  40                  45

Gly Leu Glu Thr Gly Ser Arg Glu Val Val Ser His Val Ile Lys Gln
        50                  55                  60

Gly Lys Ile Val Phe Val Leu Ser Ser Ala Leu Asn Pro Trp Asn Lys
65                  70                  75                  80

Glu Met Gly Asp His Leu Val Lys His Gly Asp Gly Val Lys Asp Ile
                85                  90                  95

Ala Phe Glu Val Glu Asp Cys Asp Tyr Ile Val Gln Lys Ala Arg Glu
            100                 105                 110

Arg Gly Ala Lys Ile Met Arg Glu Pro Trp Val Glu Gln Asp Lys Phe
        115                 120                 125

Gly Lys Val Lys Phe Ala Val Leu Gln Thr Tyr Gly Asp Thr Thr His
    130                 135                 140

Thr Leu Val Glu Lys Met Asn Tyr Ile Gly Gln Phe Leu Pro Gly Tyr
145                 150                 155                 160

Glu Ala Pro Ala Phe Met Asp Pro Leu Leu Pro Lys Leu Pro Lys Cys
                165                 170                 175

Ser Leu Glu Met Ile Asp His Ile Val Gly Asn Gln Pro Asp Gln Glu
            180                 185                 190

Met Val Ser Ala Ser Glu Trp Tyr Leu Lys Asn Leu Gln Phe His Arg
        195                 200                 205

Phe Trp Ser Val Asp Asp Thr Gln Val His Thr Glu Tyr Ser Ser Leu
```

```
                    210                 215                 220
Arg Ser Ile Val Val Ala Asn Tyr Glu Glu Ser Ile Lys Met Pro Ile
225                 230                 235                 240

Asn Glu Pro Ala Pro Gly Lys Lys Ser Gln Ile Gln Glu Tyr Val
                245                 250                 255

Asp Tyr Asn Gly Gly Ala Gly Val Gln His Ile Ala Leu Lys Thr Glu
                260                 265                 270

Asp Ile Ile Thr Ala Ile Arg His Leu Arg Glu Arg Gly Leu Glu Phe
            275                 280                 285

Leu Ser Val Pro Ser Thr Tyr Tyr Lys Gln Leu Arg Glu Lys Leu Lys
        290                 295                 300

Thr Ala Lys Ile Lys Val Lys Glu Asn Ile Asp Ala Leu Glu Glu Leu
305                 310                 315                 320

Lys Ile Leu Val Asp Tyr Asp Glu Lys Gly Tyr Leu Leu Gln Ile Phe
                325                 330                 335

Thr Lys Pro Val Gln Asp Arg Pro Thr Leu Phe Leu Glu Val Ile Gln
                340                 345                 350

Arg His Asn His Gln Gly Phe Gly Ala Gly Asn Phe Asn Ser Leu Phe
            355                 360                 365

Lys Ala Phe Glu Glu Glu Gln Asn Leu Arg Gly Asn Leu Thr Asn Met
        370                 375                 380

Glu Thr Asn Gly Val Val Pro Gly Met
385                 390
```

<210> SEQ ID NO 27
<211> LENGTH: 5413
<212> TYPE: DNA
<213> ORGANISM: Homo sapiens
<220> FEATURE:
<223> OTHER INFORMATION: IGSF1 mRNA
<220> FEATURE:
<221> NAME/KEY: CDS
<222> LOCATION: (1145)..(5125)

<400> SEQUENCE: 27

```
ctccctgacc ccttgcgctt cccgagtgag gcaatgcctc gccctgcttc ggctcgcgga    60
cggtgcgcgc acccactgac ctgcgcccac tgtctggcac tccctagtga gatgaacccg   120
gtacctcaga tggaaatgca gaaatcaccc gtcttctgcg tcgctcacgc tgggagctgt   180
agatcgcagc tgttcctatt cggccatctt ggctcctcca ttctgctttt aagatacaag   240
tgatgccttc aaatttgagc tcagtttctt atggtcgttt aggagcatga gggtttctgc   300
aataatctac cagtgaaatg atgatcaaga tcttggaaag cactctactg gtcaagcaga   360
atagttcctg tcatctccat taagaatcag cttattggcc gggcgcagtg gctcatgcct   420
gtaatcccag cactttggga ggctgaggcg ggtggatcac gaggtcagga gatcgagacc   480
atcctgtcta acaaggaatc ctttctggca ctcaagagtt tcaattcaa tcctgatgaa    540
tgaatcatta tttgatacca gcctaagtga agactctgcc tggtgacttt tgcaaggtgg   600
tttctggctg caacatggga agatttggga tcagtgagat ggaagagatt tttctggcta   660
ctagcgttcc taagaaagag ctttagtgtt tatccagcta ttggtatgca gacaactata   720
cccttatgag aaacactagc agagaagaag agttcttgac tgggtctggg ccatgaaact   780
gaccggataa agtgggaga agagagatg ttgaaggagg agtttgctgt tttctcagtc    840
tcctgagaaa ttccagatat cttctttcta cacacatcct ggagagggga aagaaagcct   900
ctctctgtca cccaggctgg aatgcactgg tgccatctcc actcactgca gcttcaacct   960
```

```
cctgggttca agtgatcctc ctgcctctca gccttccgag tagctgggac tacagtttgc    1020
tgcatctgga ggagctcact ggagaatctc aacatcggag gcgggccttc aactaccatc    1080
ccaccacctg ctgaggagaa aaattcttca agactcagag cacacagcca gcaccagagg    1140 cccc atg acc ctg gac aga cca ggg gag ggg gcc acc atg ctg aag aca    1189
     Met Thr Leu Asp Arg Pro Gly Glu Gly Ala Thr Met Leu Lys Thr
      1               5                  10                  15 ttc act gtt ttg ctc ttt tgc att ctg atg gac cct caa cca gag ttg    1237
Phe Thr Val Leu Leu Phe Cys Ile Leu Met Asp Pro Gln Pro Glu Leu
             20                  25                  30 tgg ata gag tcc aac tac ccc cag gcc cct tgg gag aac atc acg ctt    1285
Trp Ile Glu Ser Asn Tyr Pro Gln Ala Pro Trp Glu Asn Ile Thr Leu
                 35                  40                  45 tgg tgc cga agc ccc tct cgg ata tca agc aag ttc ctg ctg ctg aag    1333
Trp Cys Arg Ser Pro Ser Arg Ile Ser Ser Lys Phe Leu Leu Leu Lys
             50                  55                  60 gat aag aca cag atg acc tgg atc cgc cct tcc cac aag acc ttc caa    1381
Asp Lys Thr Gln Met Thr Trp Ile Arg Pro Ser His Lys Thr Phe Gln
 65                  70                  75 gtt tca ttc ctt ata ggt gcc ctt act gag tcc aat gca ggt ctt tac    1429
Val Ser Phe Leu Ile Gly Ala Leu Thr Glu Ser Asn Ala Gly Leu Tyr
 80                  85                  90                  95 cgg tgc tgc tac tgg aag gag aca ggc tgg tca aag ccc agt aaa gtt    1477
Arg Cys Cys Tyr Trp Lys Glu Thr Gly Trp Ser Lys Pro Ser Lys Val
                100                 105                 110 cta gag ttg gag gca cca ggc caa ctg ccc aag ccc atc ttc tgg att    1525
Leu Glu Leu Glu Ala Pro Gly Gln Leu Pro Lys Pro Ile Phe Trp Ile
            115                 120                 125 cag gct gag acc ccc gct ctt cct ggg tgt aat gtt aac atc ctc tgc    1573
Gln Ala Glu Thr Pro Ala Leu Pro Gly Cys Asn Val Asn Ile Leu Cys
            130                 135                 140 cat ggc tgg ctg cag gat ttg gta ttc atg ctg ttt aaa gag gga tat    1621
His Gly Trp Leu Gln Asp Leu Val Phe Met Leu Phe Lys Glu Gly Tyr
145                 150                 155 gca gag cct gtg gat tac caa gtc cca act ggg aca atg gcc ata ttc    1669
Ala Glu Pro Val Asp Tyr Gln Val Pro Thr Gly Thr Met Ala Ile Phe
160                 165                 170                 175 tcc att gac aac ctg aca cct gag gat gaa ggg gtt tac atc tgc cgc    1717
Ser Ile Asp Asn Leu Thr Pro Glu Asp Glu Gly Val Tyr Ile Cys Arg
                180                 185                 190 act cat atc cag atg ctc ccc acc ctg tgg tca gag ccc agc aac ccc    1765
Thr His Ile Gln Met Leu Pro Thr Leu Trp Ser Glu Pro Ser Asn Pro
            195                 200                 205 ctg aag ctg gtt gta gca gga ctc tac ccc aaa cca act ttg aca gcc    1813
Leu Lys Leu Val Val Ala Gly Leu Tyr Pro Lys Pro Thr Leu Thr Ala
            210                 215                 220 cat cct ggg ccc atc atg gca cct gga gaa agc ctg aat ctc agg tgc    1861
His Pro Gly Pro Ile Met Ala Pro Gly Glu Ser Leu Asn Leu Arg Cys
            225                 230                 235 caa ggg cca atc tat gga atg acc ttt gct cta atg agg gtt gaa gac    1909
Gln Gly Pro Ile Tyr Gly Met Thr Phe Ala Leu Met Arg Val Glu Asp
240                 245                 250                 255 ttg gag aag tcc ttt tac cac aag aag aca ata aaa aat gag gca aat    1957
Leu Glu Lys Ser Phe Tyr His Lys Lys Thr Ile Lys Asn Glu Ala Asn
                260                 265                 270 ttc ttc ttc cag tct ttg aag atc caa gat act gga cat tac ctc tgt    2005
Phe Phe Phe Gln Ser Leu Lys Ile Gln Asp Thr Gly His Tyr Leu Cys
            275                 280                 285
```

```
                                                   -continued ttt tac tat gac gca tca tat aga ggt tca ctc ctt agt gat gtc ctg    2053
Phe Tyr Tyr Asp Ala Ser Tyr Arg Gly Ser Leu Leu Ser Asp Val Leu
        290                 295                 300 aaa atc tgg gtg act gac act ttc ccc aag acc tgg cta ctt gct cgg    2101
Lys Ile Trp Val Thr Asp Thr Phe Pro Lys Thr Trp Leu Leu Ala Arg
305                 310                 315 ccc agt gct gtg gtc caa atg ggt cag aat gtg agc cta cgg tgt cga    2149
Pro Ser Ala Val Val Gln Met Gly Gln Asn Val Ser Leu Arg Cys Arg
320                 325                 330                 335 gga cca gtg gat gga gtg ggt ctt gca ctc tat aag aaa gga gaa gac    2197
Gly Pro Val Asp Gly Val Gly Leu Ala Leu Tyr Lys Lys Gly Glu Asp
                340                 345                 350 aaa cca ctt caa ttt ttg gat gcc acc agc atc gat gac aac aca tca    2245
Lys Pro Leu Gln Phe Leu Asp Ala Thr Ser Ile Asp Asp Asn Thr Ser
            355                 360                 365 ttc ttc ctc aac aat gta acc tac agt gat act ggc atc tat agc tgc    2293
Phe Phe Leu Asn Asn Val Thr Tyr Ser Asp Thr Gly Ile Tyr Ser Cys
        370                 375                 380 cac tat ctt ctc acc tgg aag acc tcc att agg atg cca tca cac aac    2341
His Tyr Leu Leu Thr Trp Lys Thr Ser Ile Arg Met Pro Ser His Asn
385                 390                 395 act gtg gag ctt atg gtt gta gat aag ccc ccc aaa ccc tcc ctg tca    2389
Thr Val Glu Leu Met Val Val Asp Lys Pro Pro Lys Pro Ser Leu Ser
400                 405                 410                 415 gct tgg cca agc act gtg ttc aag cta gga aag gcc atc acc ctt cag    2437
Ala Trp Pro Ser Thr Val Phe Lys Leu Gly Lys Ala Ile Thr Leu Gln
                420                 425                 430 tgc cga gta tct cat cca gta ctg gaa ttt tct ctg gaa tgg gaa gaa    2485
Cys Arg Val Ser His Pro Val Leu Glu Phe Ser Leu Glu Trp Glu Glu
            435                 440                 445 aga gaa aca ttc caa aaa ttc tca gta aac gga gac ttc atc atc agt    2533
Arg Glu Thr Phe Gln Lys Phe Ser Val Asn Gly Asp Phe Ile Ile Ser
        450                 455                 460 aat gtt gac ggg aaa ggc aca ggg acc tac agt tgc agc tat cgc gta    2581
Asn Val Asp Gly Lys Gly Thr Gly Thr Tyr Ser Cys Ser Tyr Arg Val
465                 470                 475 gag aca cat cct aac atc tgg tca cat cgc agt gag ccc ctg aag ctg    2629
Glu Thr His Pro Asn Ile Trp Ser His Arg Ser Glu Pro Leu Lys Leu
480                 485                 490                 495 atg ggg cca gca ggc tat ctc acc tgg aat tac gtt ctg aat gaa gct    2677
Met Gly Pro Ala Gly Tyr Leu Thr Trp Asn Tyr Val Leu Asn Glu Ala
                500                 505                 510 atc agg ttg tct cta atc atg cag ctt gtt gcc ttg ctg ttg gta gtg    2725
Ile Arg Leu Ser Leu Ile Met Gln Leu Val Ala Leu Leu Leu Val Val
            515                 520                 525 ctg tgg ata agg tgg aag tgt cgg aga ctc aga atc aga gaa gcc tgg    2773
Leu Trp Ile Arg Trp Lys Cys Arg Arg Leu Arg Ile Arg Glu Ala Trp
        530                 535                 540 ttg ctg gga aca gct caa ggg gtc acc atg ctc ttc ata gtc acg gcc    2821
Leu Leu Gly Thr Ala Gln Gly Val Thr Met Leu Phe Ile Val Thr Ala
545                 550                 555 ctt ctc tgc tgt gga ctg tgc aat ggg gta ttg ata gaa gag act gaa    2869
Leu Leu Cys Cys Gly Leu Cys Asn Gly Val Leu Ile Glu Glu Thr Glu
560                 565                 570                 575 ata gtc atg cca acc cct aag cct gag ctg tgg gca gag acc aac ttt    2917
Ile Val Met Pro Thr Pro Lys Pro Glu Leu Trp Ala Glu Thr Asn Phe
                580                 585                 590 cct ctg gcc ccg tgg aag aac tta acc ctc tgg tgc aga agc cct tct    2965
Pro Leu Ala Pro Trp Lys Asn Leu Thr Leu Trp Cys Arg Ser Pro Ser
            595                 600                 605
```

| | |
|---|---|
| ggc tca act aag gag ttt gtg ttg ctg aag gat ggg acc ggg tgg atc<br>Gly Ser Thr Lys Glu Phe Val Leu Leu Lys Asp Gly Thr Gly Trp Ile<br>610                       615                   620 | 3013 |
| gcc act cgc ccg gcc tca gag cag gtc cgg gct gcc ttc ccc ctt ggc<br>Ala Thr Arg Pro Ala Ser Glu Gln Val Arg Ala Ala Phe Pro Leu Gly<br>625                       630                   635 | 3061 |
| gcc ctg acc cag agc cac acc ggg agc tac cac tgc cat tca tgg gag<br>Ala Leu Thr Gln Ser His Thr Gly Ser Tyr His Cys His Ser Trp Glu<br>640                       645                   650                   655 | 3109 |
| gag atg gct gta tcg gag ccc agt gag gca ctt gag ctg gtg ggg aca<br>Glu Met Ala Val Ser Glu Pro Ser Glu Ala Leu Glu Leu Val Gly Thr<br>                   660                   665                   670 | 3157 |
| gac atc ctc ccc aaa cct gtc att tct gct tcc ccc aca atc cgg ggc<br>Asp Ile Leu Pro Lys Pro Val Ile Ser Ala Ser Pro Thr Ile Arg Gly<br>               675                   680                   685 | 3205 |
| cag gaa cta caa ctc cgg tgc aaa gga tgg ctg gca ggc atg ggg ttt<br>Gln Glu Leu Gln Leu Arg Cys Lys Gly Trp Leu Ala Gly Met Gly Phe<br>690                       695                   700 | 3253 |
| gct ctg tat aag gag gga gag caa gaa cct gtc cag caa ctt ggt gct<br>Ala Leu Tyr Lys Glu Gly Glu Gln Glu Pro Val Gln Gln Leu Gly Ala<br>705                       710                   715 | 3301 |
| gtt gga aga gaa gcc ttc ttt aca atc cag aga atg gag gat aaa gac<br>Val Gly Arg Glu Ala Phe Phe Thr Ile Gln Arg Met Glu Asp Lys Asp<br>720                       725                   730                   735 | 3349 |
| gaa ggc aat tac agc tgc cgc act cac act gaa aaa cgc ccc ttc aag<br>Glu Gly Asn Tyr Ser Cys Arg Thr His Thr Glu Lys Arg Pro Phe Lys<br>                   740                   745                   750 | 3397 |
| tgg tct gag ccc agt gag ccg ctg gag ctt gtc ata aaa gaa atg tac<br>Trp Ser Glu Pro Ser Glu Pro Leu Glu Leu Val Ile Lys Glu Met Tyr<br>               755                   760                   765 | 3445 |
| cct aag ccc ttc ttc aag aca tgg gcc agc cct gtg gtc acc cct ggt<br>Pro Lys Pro Phe Phe Lys Thr Trp Ala Ser Pro Val Val Thr Pro Gly<br>770                       775                   780 | 3493 |
| gcc cga gtg act ttc aat tgc tcc acc ccc cac cag cat atg agc ttt<br>Ala Arg Val Thr Phe Asn Cys Ser Thr Pro His Gln His Met Ser Phe<br>785                       790                   795 | 3541 |
| att ctt tac aaa gat gga agt gaa ata gca tcc agt gac agg tcc tgg<br>Ile Leu Tyr Lys Asp Gly Ser Glu Ile Ala Ser Ser Asp Arg Ser Trp<br>800                       805                   810                   815 | 3589 |
| gca agt ccg ggg gcc agt gca gct cac ttt cta atc att tcg gtg ggc<br>Ala Ser Pro Gly Ala Ser Ala Ala His Phe Leu Ile Ile Ser Val Gly<br>                   820                   825                   830 | 3637 |
| att ggt gat gga ggg aat tac agc tgc cga tat tat gac ttt tct atc<br>Ile Gly Asp Gly Gly Asn Tyr Ser Cys Arg Tyr Tyr Asp Phe Ser Ile<br>               835                   840                   845 | 3685 |
| tgg tct gag ccc agc gac cct gtg gag ctc gtg gtg aca gaa ttc tac<br>Trp Ser Glu Pro Ser Asp Pro Val Glu Leu Val Val Thr Glu Phe Tyr<br>850                       855                   860 | 3733 |
| ccc aaa ccc act ctc ctg gca cag cca ggt cct gtg gtg ttt cct ggg<br>Pro Lys Pro Thr Leu Leu Ala Gln Pro Gly Pro Val Val Phe Pro Gly<br>865                       870                   875 | 3781 |
| aag agt gtg atc ctg cgc tgc caa ggg act ttc cag ggc atg agg ttc<br>Lys Ser Val Ile Leu Arg Cys Gln Gly Thr Phe Gln Gly Met Arg Phe<br>880                       885                   890                   895 | 3829 |
| gcc ctc ttg cag gag gga gcc cat gtt ccc tta cag ttt cgg agt gtc<br>Ala Leu Leu Gln Glu Gly Ala His Val Pro Leu Gln Phe Arg Ser Val<br>                   900                   905                   910 | 3877 |
| tca ggg aac tca gct gac ttc ctt ctc cac act gtt gga gca gag gac<br>Ser Gly Asn Ser Ala Asp Phe Leu Leu His Thr Val Gly Ala Glu Asp | 3925 |

-continued

```
                915                 920                 925
tct ggg aac tat agc tgt atc tac tat gag aca acc atg tca aac agg      3973
Ser Gly Asn Tyr Ser Cys Ile Tyr Tyr Glu Thr Thr Met Ser Asn Arg
            930                 935                 940 ggg tca tat ctc agt atg ccc ctt atg atc tgg gtg act gac aca ttc      4021
Gly Ser Tyr Leu Ser Met Pro Leu Met Ile Trp Val Thr Asp Thr Phe
        945                 950                 955 cct aag cca tgg ttg ttt gct gag ccc agt tct gtg gtt ccc atg ggg      4069
Pro Lys Pro Trp Leu Phe Ala Glu Pro Ser Ser Val Val Pro Met Gly
960                 965                 970                 975 cag aat gtt act ctc tgg tgc cga ggg ccg gtc cat gga gta gga tac      4117
Gln Asn Val Thr Leu Trp Cys Arg Gly Pro Val His Gly Val Gly Tyr
                980                 985                 990 att ctg cac aaa gaa gga gaa gcc act tca atg cag ctc tgg gga tcc      4165
Ile Leu His Lys Glu Gly Glu Ala Thr Ser Met Gln Leu Trp Gly Ser
            995                 1000                1005 acc agt aat gac ggg gca ttc ccc atc acc aat ata tct ggt act          4210
Thr Ser Asn Asp Gly Ala Phe Pro Ile Thr Asn Ile Ser Gly Thr
        1010                1015                1020 agc atg ggg cgt tac agc tgc tgc tac cac cct gac tgg acc agt          4255
Ser Met Gly Arg Tyr Ser Cys Cys Tyr His Pro Asp Trp Thr Ser
    1025                1030                1035 tct atc aag ata caa cct agc aac acc ctg gaa ctc cta gtc aca          4300
Ser Ile Lys Ile Gln Pro Ser Asn Thr Leu Glu Leu Leu Val Thr
    1040                1045                1050 ggc tta ctc ccc aaa ccc agc cta tta gcc cag cct ggt ccc atg          4345
Gly Leu Leu Pro Lys Pro Ser Leu Leu Ala Gln Pro Gly Pro Met
    1055                1060                1065 gtg gcc cct ggc gaa aat atg act ctt cag tgt caa ggg gaa ctg          4390
Val Ala Pro Gly Glu Asn Met Thr Leu Gln Cys Gln Gly Glu Leu
    1070                1075                1080 cca gac tca aca ttt gtc ctg ttg aag gag ggg gct cag gag cct          4435
Pro Asp Ser Thr Phe Val Leu Leu Lys Glu Gly Ala Gln Glu Pro
        1085                1090                1095 tta gag caa cag agg cca agt ggg tac agg gct gac ttc tgg atg          4480
Leu Glu Gln Gln Arg Pro Ser Gly Tyr Arg Ala Asp Phe Trp Met
    1100                1105                1110 cca gca gtg aga ggt gaa gac tct ggg atc tat agc tgt gtt tat          4525
Pro Ala Val Arg Gly Glu Asp Ser Gly Ile Tyr Ser Cys Val Tyr
    1115                1120                1125 tat ttg gac tct act ccc ttt gca gct tca aat cac agt gac tcc          4570
Tyr Leu Asp Ser Thr Pro Phe Ala Ala Ser Asn His Ser Asp Ser
    1130                1135                1140 ctg gag atc tgg gtg act gat aag ccc cct aaa ccc tct ctg tca          4615
Leu Glu Ile Trp Val Thr Asp Lys Pro Pro Lys Pro Ser Leu Ser
    1145                1150                1155 gcc tgg ccc agc acc atg ttc aag tta ggg aag gac atc acc ctt          4660
Ala Trp Pro Ser Thr Met Phe Lys Leu Gly Lys Asp Ile Thr Leu
    1160                1165                1170 cag tgc cga gga ccc ctg cca ggt gtt gaa ttt gtc cta gaa cat          4705
Gln Cys Arg Gly Pro Leu Pro Gly Val Glu Phe Val Leu Glu His
    1175                1180                1185 gat gga gaa gaa gca cct cag cag ttt tca gag gat gga gac ttt          4750
Asp Gly Glu Glu Ala Pro Gln Gln Phe Ser Glu Asp Gly Asp Phe
    1190                1195                1200 gtc atc aac aac gta gaa gga aaa ggc att gga aac tac agc tgc          4795
Val Ile Asn Asn Val Glu Gly Lys Gly Ile Gly Asn Tyr Ser Cys
    1205                1210                1215 agc tac cgc ctc cag gcc tac cct gat atc tgg tca gag cct agt          4840
```

```
                                                         -continued
Ser Tyr Arg Leu Gln Ala Tyr Pro Asp Ile Trp Ser Glu Pro Ser
        1220                1225                1230 gat ccc ctg gag ctg gtg ggg gca gca ggg cct gtt gct cag gag              4885
Asp Pro Leu Glu Leu Val Gly Ala Ala Gly Pro Val Ala Gln Glu
1235                    1240                1245 tgc act gta ggg aac att gtc cga agt agc cta atc gtg gtg gtt              4930
Cys Thr Val Gly Asn Ile Val Arg Ser Ser Leu Ile Val Val Val
        1250                1255                1260 gtt gta gcc ttg ggg gta gtg cta gcc ata gag tgg aag aag tgg              4975
Val Val Ala Leu Gly Val Val Leu Ala Ile Glu Trp Lys Lys Trp
        1265                1270                1275 cct cga ctg cga acc aga ggc tca gag aca gac gga aga gac cag              5020
Pro Arg Leu Arg Thr Arg Gly Ser Glu Thr Asp Gly Arg Asp Gln
        1280                1285                1290 acc att gcc ctt gaa gag tgt aac caa gaa gga gaa cca ggc acc              5065
Thr Ile Ala Leu Glu Glu Cys Asn Gln Glu Gly Glu Pro Gly Thr
1295                    1300                1305 cct gcc aat tct cct tca tca acc tct cag aga atc tct gtg gaa              5110
Pro Ala Asn Ser Pro Ser Ser Thr Ser Gln Arg Ile Ser Val Glu
        1310                1315                1320 ctg ccc gtt cca ata taataatctc ctcctttaca agagctttcc tctcctctct          5165
Leu Pro Val Pro Ile
        1325 cttgctctca gagacctata aatccaacca gttaccctgc aagtcagccc catctgctgt        5225 tccttggtct ctaatcacct gagctgggta aaggggattc tgggagttga gagctctgcc        5285 agggtgagat gtttcctgaa gagaggttcc ccacccctgt aactcctcac tgtactgatt        5345 tactggcgca tgaaattcta ttaaaaatgc attcttctga ataaaagag tattcactat         5405 ttaacttc                                                                 5413

<210> SEQ ID NO 28
<211> LENGTH: 1327
<212> TYPE: PRT
<213> ORGANISM: Homo sapiens
<220> FEATURE:
<223> OTHER INFORMATION: IGSF1

<400> SEQUENCE: 28

Met Thr Leu Asp Arg Pro Gly Glu Gly Ala Thr Met Leu Lys Thr Phe
1               5                   10                  15

Thr Val Leu Leu Phe Cys Ile Leu Met Asp Pro Gln Pro Glu Leu Trp
                20                  25                  30

Ile Glu Ser Asn Tyr Pro Gln Ala Pro Trp Glu Asn Ile Thr Leu Trp
            35                  40                  45

Cys Arg Ser Pro Ser Arg Ile Ser Ser Lys Phe Leu Leu Leu Lys Asp
        50                  55                  60

Lys Thr Gln Met Thr Trp Ile Arg Pro Ser His Lys Thr Phe Gln Val
65                  70                  75                  80

Ser Phe Leu Ile Gly Ala Leu Thr Glu Ser Asn Ala Gly Leu Tyr Arg
                85                  90                  95

Cys Cys Tyr Trp Lys Glu Thr Gly Trp Ser Lys Pro Ser Lys Val Leu
            100                 105                 110

Glu Leu Glu Ala Pro Gly Gln Leu Pro Lys Pro Ile Phe Trp Ile Gln
        115                 120                 125

Ala Glu Thr Pro Ala Leu Pro Gly Cys Asn Val Asn Ile Leu Cys His
    130                 135                 140

Gly Trp Leu Gln Asp Leu Val Phe Met Leu Phe Lys Glu Gly Tyr Ala
```

```
            145                 150                 155                 160
        Glu Pro Val Asp Tyr Gln Val Pro Thr Gly Thr Met Ala Ile Phe Ser
                        165                 170                 175

Ile Asp Asn Leu Thr Pro Glu Asp Glu Gly Val Tyr Ile Cys Arg Thr
                        180                 185                 190

His Ile Gln Met Leu Pro Thr Leu Trp Ser Glu Pro Ser Asn Pro Leu
                        195                 200                 205

Lys Leu Val Val Ala Gly Leu Tyr Pro Lys Pro Thr Leu Thr Ala His
        210                 215                 220

Pro Gly Pro Ile Met Ala Pro Gly Glu Ser Leu Asn Leu Arg Cys Gln
        225                 230                 235                 240

Gly Pro Ile Tyr Gly Met Thr Phe Ala Leu Met Arg Val Glu Asp Leu
                        245                 250                 255

Glu Lys Ser Phe Tyr His Lys Lys Thr Ile Lys Asn Glu Ala Asn Phe
                        260                 265                 270

Phe Phe Gln Ser Leu Lys Ile Gln Asp Thr Gly His Tyr Leu Cys Phe
                        275                 280                 285

Tyr Tyr Asp Ala Ser Tyr Arg Gly Ser Leu Leu Ser Asp Val Leu Lys
                        290                 295                 300

Ile Trp Val Thr Asp Thr Phe Pro Lys Thr Trp Leu Leu Ala Arg Pro
        305                 310                 315                 320

Ser Ala Val Val Gln Met Gly Gln Asn Val Ser Leu Arg Cys Arg Gly
                        325                 330                 335

Pro Val Asp Gly Val Gly Leu Ala Leu Tyr Lys Lys Gly Glu Asp Lys
                        340                 345                 350

Pro Leu Gln Phe Leu Asp Ala Thr Ser Ile Asp Asp Asn Thr Ser Phe
                        355                 360                 365

Phe Leu Asn Asn Val Thr Tyr Ser Asp Thr Gly Ile Tyr Ser Cys His
                        370                 375                 380

Tyr Leu Leu Thr Trp Lys Thr Ser Ile Arg Met Pro Ser His Asn Thr
        385                 390                 395                 400

Val Glu Leu Met Val Val Asp Lys Pro Pro Lys Pro Ser Leu Ser Ala
                        405                 410                 415

Trp Pro Ser Thr Val Phe Lys Leu Gly Lys Ala Ile Thr Leu Gln Cys
                        420                 425                 430

Arg Val Ser His Pro Val Leu Glu Phe Ser Leu Glu Trp Glu Glu Arg
                        435                 440                 445

Glu Thr Phe Gln Lys Phe Ser Val Asn Gly Asp Phe Ile Ile Ser Asn
        450                 455                 460

Val Asp Gly Lys Gly Thr Gly Thr Tyr Ser Cys Ser Tyr Arg Val Glu
        465                 470                 475                 480

Thr His Pro Asn Ile Trp Ser His Arg Ser Glu Pro Leu Lys Leu Met
                        485                 490                 495

Gly Pro Ala Gly Tyr Leu Thr Trp Asn Tyr Val Leu Asn Glu Ala Ile
                        500                 505                 510

Arg Leu Ser Leu Ile Met Gln Leu Val Ala Leu Leu Val Val Leu
                        515                 520                 525

Trp Ile Arg Trp Lys Cys Arg Arg Leu Arg Ile Arg Glu Ala Trp Leu
        530                 535                 540

Leu Gly Thr Ala Gln Gly Val Thr Met Leu Phe Ile Val Thr Ala Leu
        545                 550                 555                 560

Leu Cys Cys Gly Leu Cys Asn Gly Val Leu Ile Glu Glu Thr Glu Ile
                        565                 570                 575
```

```
Val Met Pro Thr Pro Lys Pro Glu Leu Trp Ala Glu Thr Asn Phe Pro
        580                 585                 590

Leu Ala Pro Trp Lys Asn Leu Thr Leu Trp Cys Arg Ser Pro Ser Gly
        595                 600                 605

Ser Thr Lys Glu Phe Val Leu Leu Lys Asp Gly Thr Gly Trp Ile Ala
    610                 615                 620

Thr Arg Pro Ala Ser Glu Gln Val Arg Ala Ala Phe Pro Leu Gly Ala
625                 630                 635                 640

Leu Thr Gln Ser His Thr Gly Ser Tyr His Cys His Ser Trp Glu Glu
                645                 650                 655

Met Ala Val Ser Glu Pro Ser Glu Ala Leu Glu Leu Val Gly Thr Asp
                660                 665                 670

Ile Leu Pro Lys Pro Val Ile Ser Ala Ser Pro Thr Ile Arg Gly Gln
        675                 680                 685

Glu Leu Gln Leu Arg Cys Lys Gly Trp Leu Ala Gly Met Gly Phe Ala
    690                 695                 700

Leu Tyr Lys Glu Gly Glu Gln Glu Pro Val Gln Gln Leu Gly Ala Val
705                 710                 715                 720

Gly Arg Glu Ala Phe Phe Thr Ile Gln Arg Met Glu Asp Lys Asp Glu
                725                 730                 735

Gly Asn Tyr Ser Cys Arg Thr His Thr Glu Lys Arg Pro Phe Lys Trp
                740                 745                 750

Ser Glu Pro Ser Glu Pro Leu Glu Leu Val Ile Lys Glu Met Tyr Pro
        755                 760                 765

Lys Pro Phe Phe Lys Thr Trp Ala Ser Pro Val Val Thr Pro Gly Ala
        770                 775                 780

Arg Val Thr Phe Asn Cys Ser Thr Pro His Gln His Met Ser Phe Ile
785                 790                 795                 800

Leu Tyr Lys Asp Gly Ser Glu Ile Ala Ser Ser Asp Arg Ser Trp Ala
                805                 810                 815

Ser Pro Gly Ala Ser Ala Ala His Phe Leu Ile Ile Ser Val Gly Ile
                820                 825                 830

Gly Asp Gly Gly Asn Tyr Ser Cys Arg Tyr Tyr Asp Phe Ser Ile Trp
        835                 840                 845

Ser Glu Pro Ser Asp Pro Val Glu Leu Val Val Thr Glu Phe Tyr Pro
    850                 855                 860

Lys Pro Thr Leu Leu Ala Gln Pro Gly Pro Val Val Phe Pro Gly Lys
865                 870                 875                 880

Ser Val Ile Leu Arg Cys Gln Gly Thr Phe Gln Gly Met Arg Phe Ala
                885                 890                 895

Leu Leu Gln Glu Gly Ala His Val Pro Leu Gln Phe Arg Ser Val Ser
                900                 905                 910

Gly Asn Ser Ala Asp Phe Leu Leu His Thr Val Gly Ala Glu Asp Ser
        915                 920                 925

Gly Asn Tyr Ser Cys Ile Tyr Tyr Glu Thr Thr Met Ser Asn Arg Gly
        930                 935                 940

Ser Tyr Leu Ser Met Pro Leu Met Ile Trp Val Thr Asp Thr Phe Pro
945                 950                 955                 960

Lys Pro Trp Leu Phe Ala Glu Pro Ser Ser Val Val Pro Met Gly Gln
                965                 970                 975

Asn Val Thr Leu Trp Cys Arg Gly Pro Val His Gly Val Gly Tyr Ile
                980                 985                 990
```

Leu His Lys Glu Gly Glu Ala Thr Ser Met Gln Leu Trp Gly Ser Thr
            995                 1000                1005

Ser Asn Asp Gly Ala Phe Pro Ile Thr Asn Ile Ser Gly Thr Ser
    1010                1015                1020

Met Gly Arg Tyr Ser Cys Cys Tyr His Pro Asp Trp Thr Ser Ser
    1025                1030                1035

Ile Lys Ile Gln Pro Ser Asn Thr Leu Glu Leu Leu Val Thr Gly
    1040                1045                1050

Leu Leu Pro Lys Pro Ser Leu Leu Ala Gln Pro Gly Pro Met Val
    1055                1060                1065

Ala Pro Gly Glu Asn Met Thr Leu Gln Cys Gln Gly Glu Leu Pro
    1070                1075                1080

Asp Ser Thr Phe Val Leu Leu Lys Glu Gly Ala Gln Glu Pro Leu
    1085                1090                1095

Glu Gln Gln Arg Pro Ser Gly Tyr Arg Ala Asp Phe Trp Met Pro
    1100                1105                1110

Ala Val Arg Gly Glu Asp Ser Gly Ile Tyr Ser Cys Val Tyr Tyr
    1115                1120                1125

Leu Asp Ser Thr Pro Phe Ala Ala Ser Asn His Ser Asp Ser Leu
    1130                1135                1140

Glu Ile Trp Val Thr Asp Lys Pro Pro Lys Pro Ser Leu Ser Ala
    1145                1150                1155

Trp Pro Ser Thr Met Phe Lys Leu Gly Lys Asp Ile Thr Leu Gln
    1160                1165                1170

Cys Arg Gly Pro Leu Pro Gly Val Glu Phe Val Leu Glu His Asp
    1175                1180                1185

Gly Glu Glu Ala Pro Gln Gln Phe Ser Glu Asp Gly Asp Phe Val
    1190                1195                1200

Ile Asn Asn Val Glu Gly Lys Gly Ile Gly Asn Tyr Ser Cys Ser
    1205                1210                1215

Tyr Arg Leu Gln Ala Tyr Pro Asp Ile Trp Ser Glu Pro Ser Asp
    1220                1225                1230

Pro Leu Glu Leu Val Gly Ala Ala Gly Pro Val Ala Gln Glu Cys
    1235                1240                1245

Thr Val Gly Asn Ile Val Arg Ser Ser Leu Ile Val Val Val Val
    1250                1255                1260

Val Ala Leu Gly Val Val Leu Ala Ile Glu Trp Lys Lys Trp Pro
    1265                1270                1275

Arg Leu Arg Thr Arg Gly Ser Glu Thr Asp Gly Arg Asp Gln Thr
    1280                1285                1290

Ile Ala Leu Glu Glu Cys Asn Gln Glu Gly Glu Pro Gly Thr Pro
    1295                1300                1305

Ala Asn Ser Pro Ser Ser Thr Ser Gln Arg Ile Ser Val Glu Leu
    1310                1315                1320

Pro Val Pro Ile
    1325

<210> SEQ ID NO 29
<211> LENGTH: 2557
<212> TYPE: DNA
<213> ORGANISM: Homo sapiens
<220> FEATURE:
<223> OTHER INFORMATION: NLE1 mRNA
<220> FEATURE:
<221> NAME/KEY: CDS
<222> LOCATION: (14)..(1468)

<400> SEQUENCE: 29

```
gtggggacgc agg atg gcg gca gca gtg ccg gac gag gcg gtg gcg cgc         49
            Met Ala Ala Ala Val Pro Asp Glu Ala Val Ala Arg
            1               5                   10 gat gtg cag cgg ttg cta gtg cag ttc cag gat gag ggc ggg cag ctg        97
Asp Val Gln Arg Leu Leu Val Gln Phe Gln Asp Glu Gly Gly Gln Leu
            15                  20                  25 ctg ggt tcc ccg ttc gac gtg ccc gtg gac atc acc ccg gac agg ctg       145
Leu Gly Ser Pro Phe Asp Val Pro Val Asp Ile Thr Pro Asp Arg Leu
 30                  35                  40 cag ctc gtg tgc aac gcg cta ctg gcc cag gag gat ccc ctg cca ctg       193
Gln Leu Val Cys Asn Ala Leu Leu Ala Gln Glu Asp Pro Leu Pro Leu
45                  50                  55                  60 gct ttc ttt gtc cac gat gct gag atc gtc tcc tca ctg ggg aag acg       241
Ala Phe Phe Val His Asp Ala Glu Ile Val Ser Ser Leu Gly Lys Thr
                65                  70                  75 ttg gag tcc cag gca gtg gag aca gag aag gtc cta gac atc atc tac       289
Leu Glu Ser Gln Ala Val Glu Thr Glu Lys Val Leu Asp Ile Ile Tyr
             80                  85                  90 cag cca cag gct atc ttc aga gtc cgg gct gtg act cgc tgc acc agc       337
Gln Pro Gln Ala Ile Phe Arg Val Arg Ala Val Thr Arg Cys Thr Ser
         95                 100                 105 tcc ttg gag ggt cac agt gag gca gtc att tct gtg gcc ttc agc cct       385
Ser Leu Glu Gly His Ser Glu Ala Val Ile Ser Val Ala Phe Ser Pro
    110                 115                 120 acg gga aag tac ctg gcc agt ggc tct gga gac acc acc gtg cgc ttc       433
Thr Gly Lys Tyr Leu Ala Ser Gly Ser Gly Asp Thr Thr Val Arg Phe
125                 130                 135                 140 tgg gat ctc agc aca gag aca cca cat ttc aca tgc aag gga cac aga       481
Trp Asp Leu Ser Thr Glu Thr Pro His Phe Thr Cys Lys Gly His Arg
                145                 150                 155 cac tgg gtc ctt agt ata tcc tgg tct cca gat ggc agg aag ctg gcc       529
His Trp Val Leu Ser Ile Ser Trp Ser Pro Asp Gly Arg Lys Leu Ala
            160                 165                 170 tca ggc tgc aag aat ggc cag att ctc ctc tgg gac cca agc aca ggg       577
Ser Gly Cys Lys Asn Gly Gln Ile Leu Leu Trp Asp Pro Ser Thr Gly
        175                 180                 185 aag cag gtg ggc agg acc ctc gct ggc cac agc aag tgg atc aca ggc       625
Lys Gln Val Gly Arg Thr Leu Ala Gly His Ser Lys Trp Ile Thr Gly
    190                 195                 200 ctg agc tgg gag ccc ctc cat gcg aac cct gag tgc cgc tat gtg gcc       673
Leu Ser Trp Glu Pro Leu His Ala Asn Pro Glu Cys Arg Tyr Val Ala
205                 210                 215                 220 agc agc tcc aag gat ggc agt gtg cgg atc tgg gac aca act gca ggc       721
Ser Ser Ser Lys Asp Gly Ser Val Arg Ile Trp Asp Thr Thr Ala Gly
                225                 230                 235 cgc tgt gag cgc atc ctc acc ggg cac acc cag tcg gtc acc tgt ctc       769
Arg Cys Glu Arg Ile Leu Thr Gly His Thr Gln Ser Val Thr Cys Leu
            240                 245                 250 cgg tgg gga ggg gac ggg ctt ctc tac tct gcc tcc cag gac cgc acc       817
Arg Trp Gly Gly Asp Gly Leu Leu Tyr Ser Ala Ser Gln Asp Arg Thr
        255                 260                 265 atc aaa gtc tgg aga gct cat gac ggt gtg ctg tgc cgg act ctg caa       865
Ile Lys Val Trp Arg Ala His Asp Gly Val Leu Cys Arg Thr Leu Gln
    270                 275                 280 ggc cac ggc cac tgg gtg aac acc atg gcc ctc agc act gac tat gcc       913
Gly His Gly His Trp Val Asn Thr Met Ala Leu Ser Thr Asp Tyr Ala
285                 290                 295                 300
```

| | | |
|---|---|---|
| ctg cgc act ggg gcc ttt gaa cct gct gag gcc tca gtt aat ccc caa<br>Leu Arg Thr Gly Ala Phe Glu Pro Ala Glu Ala Ser Val Asn Pro Gln<br>305 310 315 | | 961 |
| gac ctc caa gga tcc ttg cag gag ttg aag gag agg gct ctg agc cga<br>Asp Leu Gln Gly Ser Leu Gln Glu Leu Lys Glu Arg Ala Leu Ser Arg<br>320 325 330 | | 1009 |
| tac aac ctc gtg cgg ggc cag ggt cca gag agg ctg gtg tct ggc tcc<br>Tyr Asn Leu Val Arg Gly Gln Gly Pro Glu Arg Leu Val Ser Gly Ser<br>335 340 345 | | 1057 |
| gac gac ttc acc tta ttc ctg tgg tcc cca gca gag gac aaa aag cct<br>Asp Asp Phe Thr Leu Phe Leu Trp Ser Pro Ala Glu Asp Lys Lys Pro<br>350 355 360 | | 1105 |
| ctc act cgg atg aca gga cac caa gct ctc atc aac cag gtg ctc ttc<br>Leu Thr Arg Met Thr Gly His Gln Ala Leu Ile Asn Gln Val Leu Phe<br>365 370 375 380 | | 1153 |
| tct cct gac tcc cgc atc gtg gct agt gcc tcc ttt gac aag tcc atc<br>Ser Pro Asp Ser Arg Ile Val Ala Ser Ala Ser Phe Asp Lys Ser Ile<br>385 390 395 | | 1201 |
| aag ctg tgg gat ggc agg acg ggc aag tac ctg gct tcc cta cgc ggc<br>Lys Leu Trp Asp Gly Arg Thr Gly Lys Tyr Leu Ala Ser Leu Arg Gly<br>400 405 410 | | 1249 |
| cac gtg gct gcc gtg tac cag att gcg tgg tca gct gac agt cgg ctc<br>His Val Ala Ala Val Tyr Gln Ile Ala Trp Ser Ala Asp Ser Arg Leu<br>415 420 425 | | 1297 |
| ctg gtc agc ggc agt agt gac agc aca ctg aag gtg tgg gat gtg aag<br>Leu Val Ser Gly Ser Ser Asp Ser Thr Leu Lys Val Trp Asp Val Lys<br>430 435 440 | | 1345 |
| gcc cag aag ctg gcc atg gac ctg ccc ggc cac gcg gat gag gta tat<br>Ala Gln Lys Leu Ala Met Asp Leu Pro Gly His Ala Asp Glu Val Tyr<br>445 450 455 460 | | 1393 |
| gct gtt gac tgg agt cca gat ggc cag aga gtg gca agt ggt ggg aag<br>Ala Val Asp Trp Ser Pro Asp Gly Gln Arg Val Ala Ser Gly Gly Lys<br>465 470 475 | | 1441 |
| gac aaa tgc ctc cgg ata tgg agg aga tgagacggcc cgaagttctc<br>Asp Lys Cys Leu Arg Ile Trp Arg Arg<br>480 485 | | 1488 |
| tctgaccccc acctcgactc ggcctctgcc agctgccttc cctgccagag aacaaaggct | | 1548 |
| gagatggcag tgcacacacc ctccccacca gtggggacct gagaatgcgt gtggcctgct | | 1608 |
| gtcctcgata daccggaatg gggttttccc acagatcccc gcctgtggca cccccagag | | 1668 |
| ccagaaatcg aaggtcacag gaagttgtca ctgaacttgg cccgtgtctg ctactctgta | | 1728 |
| ccttgctggt acagacaggg gtggtgggca gccaggctct atgagtgggc cctagtgtc | | 1788 |
| agctctgtac agggtcagat cccaggttct atgaccaaat aagtaactta agttttgtgt | | 1848 |
| gttgggttct aattccttgt cctagaatcc ccatgactca atcaaggact gtgctaaatg | | 1908 |
| agattgtcca gccccgccc ttgcactgga ctacgccaaa accacactga ccaggcactt | | 1968 |
| gccttccctc tcttccccg tgttggtaag agagaggcca gttgtgatag tggccaagga | | 2028 |
| gaatctaggg ctgtattgtt gtccactgca gtaggcaccg ccacatgtg actgctggca | | 2088 |
| tgaaatagaa gtgcagttcc tccatcgcac tgggtaaggc ctccagtatt ggacagcaca | | 2148 |
| cagaaaggtt ttcatcatca agagagttct gctggtcagc cctgctccag gggatgcctc | | 2208 |
| tgccttcgca tagcacactg cttgaggccc tgccaggcac caagcactgc cctgggccca | | 2268 |
| tgggatagag cggggaaggt gatggctctt ccagaggatt ccctcagatg ggaggcagc | | 2328 |
| agtatgagct ctgagcagaa gtgggtattg ttgatacaga ggaagttctt tgccacgaga | | 2388 |
| actttcaagc agtgaaagga attcccatca ggactcagac cccaggccga gatcttgccc | | 2448 |

```
tgaatgtacc ctgcctctgc tttctcctgc atcccatgct aagcagggtc atggtctgaa    2508
ctactcagat tggatttcca aaccatcctt gtataaactg ctcagaact                2557
```

<210> SEQ ID NO 30
<211> LENGTH: 485
<212> TYPE: PRT
<213> ORGANISM: Homo sapiens
<220> FEATURE:
<223> OTHER INFORMATION: NLE1

<400> SEQUENCE: 30

```
Met Ala Ala Val Pro Asp Glu Ala Val Ala Arg Asp Val Gln Arg
1               5                   10                  15

Leu Leu Val Gln Phe Gln Asp Glu Gly Gly Gln Leu Leu Gly Ser Pro
            20                  25                  30

Phe Asp Val Pro Val Asp Ile Thr Pro Asp Arg Leu Gln Leu Val Cys
        35                  40                  45

Asn Ala Leu Leu Ala Gln Glu Asp Pro Leu Pro Leu Ala Phe Phe Val
    50                  55                  60

His Asp Ala Glu Ile Val Ser Ser Leu Gly Lys Thr Leu Glu Ser Gln
65                  70                  75                  80

Ala Val Glu Thr Glu Lys Val Leu Asp Ile Ile Tyr Gln Pro Gln Ala
                85                  90                  95

Ile Phe Arg Val Arg Ala Val Thr Arg Cys Thr Ser Ser Leu Glu Gly
            100                 105                 110

His Ser Glu Ala Val Ile Ser Val Ala Phe Ser Pro Thr Gly Lys Tyr
        115                 120                 125

Leu Ala Ser Gly Ser Gly Asp Thr Thr Val Arg Phe Trp Asp Leu Ser
    130                 135                 140

Thr Glu Thr Pro His Phe Thr Cys Lys Gly His Arg His Trp Val Leu
145                 150                 155                 160

Ser Ile Ser Trp Ser Pro Asp Gly Arg Lys Leu Ala Ser Gly Cys Lys
                165                 170                 175

Asn Gly Gln Ile Leu Leu Trp Asp Pro Ser Thr Gly Lys Gln Val Gly
            180                 185                 190

Arg Thr Leu Ala Gly His Ser Lys Trp Ile Thr Gly Leu Ser Trp Glu
        195                 200                 205

Pro Leu His Ala Asn Pro Glu Cys Arg Tyr Val Ala Ser Ser Ser Lys
    210                 215                 220

Asp Gly Ser Val Arg Ile Trp Asp Thr Thr Ala Gly Arg Cys Glu Arg
225                 230                 235                 240

Ile Leu Thr Gly His Thr Gln Ser Val Thr Cys Leu Arg Trp Gly Gly
                245                 250                 255

Asp Gly Leu Leu Tyr Ser Ala Ser Gln Asp Arg Thr Ile Lys Val Trp
            260                 265                 270

Arg Ala His Asp Gly Val Leu Cys Arg Thr Leu Gln Gly His Gly His
        275                 280                 285

Trp Val Asn Thr Met Ala Leu Ser Thr Asp Tyr Ala Leu Arg Thr Gly
    290                 295                 300

Ala Phe Glu Pro Ala Glu Ala Ser Val Asn Pro Gln Asp Leu Gln Gly
305                 310                 315                 320

Ser Leu Gln Glu Leu Lys Glu Arg Ala Leu Ser Arg Tyr Asn Leu Val
                325                 330                 335

Arg Gly Gln Gly Pro Glu Arg Leu Val Ser Gly Ser Asp Asp Phe Thr
```

```
                    340                 345                 350
Leu Phe Leu Trp Ser Pro Ala Glu Asp Lys Pro Leu Thr Arg Met
                355                 360                 365

Thr Gly His Gln Ala Leu Ile Asn Gln Val Leu Phe Ser Pro Asp Ser
            370                 375                 380

Arg Ile Val Ala Ser Ala Ser Phe Asp Lys Ser Ile Lys Leu Trp Asp
385                 390                 395                 400

Gly Arg Thr Gly Lys Tyr Leu Ala Ser Leu Arg Gly His Val Ala Ala
                405                 410                 415

Val Tyr Gln Ile Ala Trp Ser Ala Asp Ser Arg Leu Leu Val Ser Gly
                420                 425                 430

Ser Ser Asp Ser Thr Leu Lys Val Trp Asp Val Lys Ala Gln Lys Leu
                435                 440                 445

Ala Met Asp Leu Pro Gly His Ala Asp Glu Val Tyr Ala Val Asp Trp
                450                 455                 460

Ser Pro Asp Gly Gln Arg Val Ala Ser Gly Gly Lys Asp Lys Cys Leu
465                 470                 475                 480

Arg Ile Trp Arg Arg
                485

<210> SEQ ID NO 31
<211> LENGTH: 704
<212> TYPE: DNA
<213> ORGANISM: Homo sapiens
<220> FEATURE:
<223> OTHER INFORMATION: RPL10A mRNA
<220> FEATURE:
<221> NAME/KEY: CDS
<222> LOCATION: (23)..(673)

<400> SEQUENCE: 31
ggttagcgcg gcgtgagaag cc atg agc agc aaa gtc tct cgc gac acc ctg    52
                          Met Ser Ser Lys Val Ser Arg Asp Thr Leu
                          1               5                   10 tac gag gcg gtg cgg gaa gtc ctg cac ggg aac cag cgc aag cgc cgc   100
Tyr Glu Ala Val Arg Glu Val Leu His Gly Asn Gln Arg Lys Arg Arg
                15                  20                  25 aag ttc ctg gag acg gtg gag ttg cag atc agc ttg aag aac tat gat   148
Lys Phe Leu Glu Thr Val Glu Leu Gln Ile Ser Leu Lys Asn Tyr Asp
            30                  35                  40 ccc cag aag gac aag cgc ttc tcg ggc acc gtc agg ctt aag tcc act   196
Pro Gln Lys Asp Lys Arg Phe Ser Gly Thr Val Arg Leu Lys Ser Thr
        45                  50                  55 ccc cgc cct aag ttc tct gtg tgt gtc ctg ggg gac cag cag cac tgt   244
Pro Arg Pro Lys Phe Ser Val Cys Val Leu Gly Asp Gln Gln His Cys
    60                  65                  70 gac gag gct aag gcc gtg gat atc ccc cac atg gac atc gag gcg ctg   292
Asp Glu Ala Lys Ala Val Asp Ile Pro His Met Asp Ile Glu Ala Leu
75                  80                  85                  90 aaa aaa ctc aac aag aat aaa aaa ctg gtc aag aag ctg gcc aag aag   340
Lys Lys Leu Asn Lys Asn Lys Lys Leu Val Lys Lys Leu Ala Lys Lys
                95                  100                 105 tat gat gcg ttt ttg gcc tca gag tct ctg atc aag cag att cca cga   388
Tyr Asp Ala Phe Leu Ala Ser Glu Ser Leu Ile Lys Gln Ile Pro Arg
            110                 115                 120 atc ctc ggc cca ggt tta aat aag gca gga aag ttc cct tcc ctg ctc   436
Ile Leu Gly Pro Gly Leu Asn Lys Ala Gly Lys Phe Pro Ser Leu Leu
        125                 130                 135 aca cac aac gaa aac atg gtg gcc aaa gtg gat gag gtg aag tcc aca   484
```

```
Thr His Asn Glu Asn Met Val Ala Lys Val Asp Glu Val Lys Ser Thr
    140                 145                 150 atc aag ttc caa atg aag aag gtg tta tgt ctg gct gta gct gtt ggt    532
Ile Lys Phe Gln Met Lys Lys Val Leu Cys Leu Ala Val Ala Val Gly
155                 160                 165                 170 cac gtg aag atg aca gac gat gag ctt gtg tat aac att cac ctg gct    580
His Val Lys Met Thr Asp Asp Glu Leu Val Tyr Asn Ile His Leu Ala
                175                 180                 185 gtc aac ttc ttg gtg tca ttg ctc aag aaa aac tgg cag aat gtc cgg    628
Val Asn Phe Leu Val Ser Leu Leu Lys Lys Asn Trp Gln Asn Val Arg
            190                 195                 200 gcc tta tat atc aag agc acc atg ggc aag ccc cag cgc cta tat        673
Ala Leu Tyr Ile Lys Ser Thr Met Gly Lys Pro Gln Arg Leu Tyr
        205                 210                 215 taaggcacat ttgaataaat tctattacca g                                 704
```

<210> SEQ ID NO 32
<211> LENGTH: 217
<212> TYPE: PRT
<213> ORGANISM: Homo sapiens
<220> FEATURE:
<223> OTHER INFORMATION: RPL10A

<400> SEQUENCE: 32

```
Met Ser Ser Lys Val Ser Arg Asp Thr Leu Tyr Glu Ala Val Arg Glu
1               5                   10                  15

Val Leu His Gly Asn Gln Arg Lys Arg Arg Lys Phe Leu Glu Thr Val
            20                  25                  30

Glu Leu Gln Ile Ser Leu Lys Asn Tyr Asp Pro Gln Lys Asp Lys Arg
        35                  40                  45

Phe Ser Gly Thr Val Arg Leu Lys Ser Thr Pro Arg Pro Lys Phe Ser
    50                  55                  60

Val Cys Val Leu Gly Asp Gln Gln His Cys Asp Glu Ala Lys Ala Val
65                  70                  75                  80

Asp Ile Pro His Met Asp Ile Glu Ala Leu Lys Lys Leu Asn Lys Asn
                85                  90                  95

Lys Lys Leu Val Lys Lys Leu Ala Lys Lys Tyr Asp Ala Phe Leu Ala
            100                 105                 110

Ser Glu Ser Leu Ile Lys Gln Ile Pro Arg Ile Leu Gly Pro Gly Leu
        115                 120                 125

Asn Lys Ala Gly Lys Phe Pro Ser Leu Leu Thr His Asn Glu Asn Met
    130                 135                 140

Val Ala Lys Val Asp Glu Val Lys Ser Thr Ile Lys Phe Gln Met Lys
145                 150                 155                 160

Lys Val Leu Cys Leu Ala Val Ala Val Gly His Val Lys Met Thr Asp
                165                 170                 175

Asp Glu Leu Val Tyr Asn Ile His Leu Ala Val Asn Phe Leu Val Ser
            180                 185                 190

Leu Leu Lys Lys Asn Trp Gln Asn Val Arg Ala Leu Tyr Ile Lys Ser
        195                 200                 205

Thr Met Gly Lys Pro Gln Arg Leu Tyr
    210                 215
```

<210> SEQ ID NO 33
<211> LENGTH: 1919
<212> TYPE: DNA
<213> ORGANISM: Homo sapiens
<220> FEATURE:

<223> OTHER INFORMATION: ACTG1 mRNA
<220> FEATURE:
<221> NAME/KEY: CDS
<222> LOCATION: (75)..(1199)

<400> SEQUENCE: 33

```
gtctcagtcg ccgctgccag ctctcgcact ctgttcttcc gccgctccgc cgtcgcgttt    60
ctctgccggt cgca atg gaa gaa gag atc gcc gcg ctg gtc att gac aat     110
              Met Glu Glu Glu Ile Ala Ala Leu Val Ile Asp Asn
                1               5                  10 ggc tcc ggc atg tgc aaa gct ggt ttt gct ggg gac gac gct ccc cga     158
Gly Ser Gly Met Cys Lys Ala Gly Phe Ala Gly Asp Asp Ala Pro Arg
         15                  20                  25 gcc gtg ttt cct tcc atc gtc ggg cgc ccc aga cac cag ggc gtc atg     206
Ala Val Phe Pro Ser Ile Val Gly Arg Pro Arg His Gln Gly Val Met
     30                  35                  40 gtg ggc atg ggc cag aag gac tcc tac gtg ggc gac gag gcc cag agc     254
Val Gly Met Gly Gln Lys Asp Ser Tyr Val Gly Asp Glu Ala Gln Ser
 45                  50                  55                  60 aag cgt ggc atc ctg acc ctg aag tac ccc att gag cat ggc atc gtc     302
Lys Arg Gly Ile Leu Thr Leu Lys Tyr Pro Ile Glu His Gly Ile Val
                 65                  70                  75 acc aac tgg gac gac atg gag aag atc tgg cac cac acc ttc tac aac     350
Thr Asn Trp Asp Asp Met Glu Lys Ile Trp His His Thr Phe Tyr Asn
             80                  85                  90 gag ctg cgc gtg gcc ccg gag gag cac cca gtg ctg ctg acc gag gcc     398
Glu Leu Arg Val Ala Pro Glu Glu His Pro Val Leu Leu Thr Glu Ala
         95                 100                 105 ccc ctg aac ccc aag gcc aac aga gag aag atg act cag att atg ttt     446
Pro Leu Asn Pro Lys Ala Asn Arg Glu Lys Met Thr Gln Ile Met Phe
    110                 115                 120 gag acc ttc aac acc ccg gcc atg tac gtg gcc atc cag gcc gtg ctg     494
Glu Thr Phe Asn Thr Pro Ala Met Tyr Val Ala Ile Gln Ala Val Leu
125                 130                 135                 140 tcc ctc tac gcc tct ggg cgc acc act ggc att gtc atg gac tct gga     542
Ser Leu Tyr Ala Ser Gly Arg Thr Thr Gly Ile Val Met Asp Ser Gly
                145                 150                 155 gac ggg gtc acc cac acg gtg ccc atc tac gag ggc tac gcc ctc ccc     590
Asp Gly Val Thr His Thr Val Pro Ile Tyr Glu Gly Tyr Ala Leu Pro
            160                 165                 170 cac gcc atc ctg cgt ctg gac ctg gct ggc cgg gac ctg acc gac tac     638
His Ala Ile Leu Arg Leu Asp Leu Ala Gly Arg Asp Leu Thr Asp Tyr
        175                 180                 185 ctc atg aag atc ctc act gag cga ggc tac agc ttc acc acc acg gcc     686
Leu Met Lys Ile Leu Thr Glu Arg Gly Tyr Ser Phe Thr Thr Thr Ala
    190                 195                 200 gag cgg gaa atc gtg cgc gac atc aag gag aag ctg tgc tac gtc gcc     734
Glu Arg Glu Ile Val Arg Asp Ile Lys Glu Lys Leu Cys Tyr Val Ala
205                 210                 215                 220 ctg gac ttc gag cag gag atg gcc acc gcc gca tcc tct tct ctg         782
Leu Asp Phe Glu Gln Glu Met Ala Thr Ala Ala Ser Ser Ser Leu
                225                 230                 235 gag aag agc tac gag ctg ccc gat ggc cag gtc atc acc att ggc aat     830
Glu Lys Ser Tyr Glu Leu Pro Asp Gly Gln Val Ile Thr Ile Gly Asn
            240                 245                 250 gag cgg ttc cgg tgt ccg gag gcg ctg ttc cag cct tcc ttc ctg ggt     878
Glu Arg Phe Arg Cys Pro Glu Ala Leu Phe Gln Pro Ser Phe Leu Gly
        255                 260                 265 atg gaa tct tgc ggc atc cac gag acc acc ttc aac tcc atc atg aag     926
Met Glu Ser Cys Gly Ile His Glu Thr Thr Phe Asn Ser Ile Met Lys
```

```
                    270                 275                 280
tgt gac gtg gac atc cgc aaa gac ctg tac gcc aac acg gtg ctg tcg     974
Cys Asp Val Asp Ile Arg Lys Asp Leu Tyr Ala Asn Thr Val Leu Ser
285                 290                 295                 300 ggc ggc acc acc atg tac ccg ggc att gcc gac agg atg cag aag gag    1022
Gly Gly Thr Thr Met Tyr Pro Gly Ile Ala Asp Arg Met Gln Lys Glu
                305                 310                 315 atc acc gcc ctg gcg ccc agc acc atg aag atc aag atc atc gca ccc    1070
Ile Thr Ala Leu Ala Pro Ser Thr Met Lys Ile Lys Ile Ile Ala Pro
                320                 325                 330 cca gag cgc aag tac tcg gtg tgg atc ggt ggc tcc atc ctg gcc tca    1118
Pro Glu Arg Lys Tyr Ser Val Trp Ile Gly Gly Ser Ile Leu Ala Ser
                335                 340                 345 ctg tcc acc ttc cag cag atg tgg att agc aag cag gag tac gac gag    1166
Leu Ser Thr Phe Gln Gln Met Trp Ile Ser Lys Gln Glu Tyr Asp Glu
                350                 355                 360 tcg ggc ccc tcc atc gtc cac cgc aaa tgc ttc taaacggact cagcagatgc  1219
Ser Gly Pro Ser Ile Val His Arg Lys Cys Phe
365                 370                 375 gtagcatttg ctgcatgggt taattgagaa tagaaatttg cccctggcaa atgcacacac  1279
ctcatgctag cctcacgaaa ctggaataag ccttcgaaaa gaaattgtcc ttgaagcttg  1339
tatctgatat cagcactgga ttgtagaact tgttgctgat tttgaccttg tattgaagtt  1399
aactgttccc cttggtattt gtttaatacc ctgtacatat ctttgagttc aacctttagt  1459
acgtgtggct tggtcacttc gtggctaagg taagaacgtg cttgtggaag acaagtctgt  1519
ggcttggtga gtctgtgtgg ccagcagcct ctgatctgtg cagggtatta acgtgtcagg  1579
gctgagtgtt ctgggatttc tctagaggct ggcaagaacc agttgttttg tcttgcgggt  1639
ctgtcagggt tggaaagtcc aagccgtagg acccagtttc ctttcttagc tgatgtcttt  1699
ggccagaaca ccgtgggctg ttacttgctt tgagttggaa gcggtttgca tttacgcctg  1759
taaatgtatt cattcttaat ttatgtaagg ttttttttgt acgcaattct cgattctttg  1819
aagagatgac aacaaatttt ggttttctac tgttatgtga aacattagg ccccagcaac   1879
acgtcattgt gtaaggaaaa ataaaagtgc tgccgtaacc                        1919

<210> SEQ ID NO 34
<211> LENGTH: 375
<212> TYPE: PRT
<213> ORGANISM: Homo sapiens
<220> FEATURE:
<223> OTHER INFORMATION: ACTG1

<400> SEQUENCE: 34

Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
                35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
65              70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
```

-continued

```
                100                 105                 110
        Lys Ala Asn Arg Glu Lys Met Thr Gln Ile Met Phe Glu Thr Phe Asn
            115                 120                 125

Thr Pro Ala Met Tyr Val Ala Ile Gln Ala Val Leu Ser Leu Tyr Ala
        130                 135                 140

Ser Gly Arg Thr Thr Gly Ile Val Met Asp Ser Gly Asp Gly Val Thr
        145                 150                 155                 160

His Thr Val Pro Ile Tyr Glu Gly Tyr Ala Leu Pro His Ala Ile Leu
                        165                 170                 175

Arg Leu Asp Leu Ala Gly Arg Asp Leu Thr Asp Tyr Leu Met Lys Ile
                    180                 185                 190

Leu Thr Glu Arg Gly Tyr Ser Phe Thr Thr Thr Ala Glu Arg Glu Ile
                195                 200                 205

Val Arg Asp Ile Lys Glu Lys Leu Cys Tyr Val Ala Leu Asp Phe Glu
            210                 215                 220

Gln Glu Met Ala Thr Ala Ala Ser Ser Ser Leu Glu Lys Ser Tyr
        225                 230                 235                 240

Glu Leu Pro Asp Gly Gln Val Ile Thr Ile Gly Asn Glu Arg Phe Arg
                        245                 250                 255

Cys Pro Glu Ala Leu Phe Gln Pro Ser Phe Leu Gly Met Glu Ser Cys
                    260                 265                 270

Gly Ile His Glu Thr Thr Phe Asn Ser Ile Met Lys Cys Asp Val Asp
                275                 280                 285

Ile Arg Lys Asp Leu Tyr Ala Asn Thr Val Leu Ser Gly Gly Thr Thr
            290                 295                 300

Met Tyr Pro Gly Ile Ala Asp Arg Met Gln Lys Glu Ile Thr Ala Leu
        305                 310                 315                 320

Ala Pro Ser Thr Met Lys Ile Lys Ile Ile Ala Pro Pro Glu Arg Lys
                        325                 330                 335

Tyr Ser Val Trp Ile Gly Gly Ser Ile Leu Ala Ser Leu Ser Thr Phe
                    340                 345                 350

Gln Gln Met Trp Ile Ser Lys Gln Glu Tyr Asp Glu Ser Gly Pro Ser
                355                 360                 365

Ile Val His Arg Lys Cys Phe
            370                 375

<210> SEQ ID NO 35
<211> LENGTH: 3528
<212> TYPE: DNA
<213> ORGANISM: Homo sapiens
<220> FEATURE:
<223> OTHER INFORMATION: EEF1A1 mRNA
<220> FEATURE:
<221> NAME/KEY: CDS
<222> LOCATION: (64)..(1449)

<400> SEQUENCE: 35 cttttcgca acgggtttgc cgccagaaca caggtgtcgt gaaaactacc cctaaaagcc        60 aaa atg gga aag gaa aag act cat atc aac att gtc gtc att gga cac      108
    Met Gly Lys Glu Lys Thr His Ile Asn Ile Val Val Ile Gly His
    1               5                   10                  15 gta gat tcg ggc aag tcc acc act act ggc cat ctg atc tat aaa tgc      156
Val Asp Ser Gly Lys Ser Thr Thr Thr Gly His Leu Ile Tyr Lys Cys
            20                  25                  30 ggt ggc atc gac aaa aga acc att gaa aaa ttt gag aag gag gct gct      204
Gly Gly Ile Asp Lys Arg Thr Ile Glu Lys Phe Glu Lys Glu Ala Ala
        35                  40                  45
```

```
gag atg gga aag ggc tcc ttc aag tat gcc tgg gtc ttg gat aaa ctg      252
Glu Met Gly Lys Gly Ser Phe Lys Tyr Ala Trp Val Leu Asp Lys Leu
         50                  55                  60 aaa gct gag cgt gaa cgt ggt atc acc att gat atc tcc ttg tgg aaa      300
Lys Ala Glu Arg Glu Arg Gly Ile Thr Ile Asp Ile Ser Leu Trp Lys
 65                  70                  75 ttt gag acc agc aag tac tat gtg act atc att gat gcc cca gga cac      348
Phe Glu Thr Ser Lys Tyr Tyr Val Thr Ile Ile Asp Ala Pro Gly His
 80                  85                  90                  95 aga gac ttt atc aaa aac atg att aca ggg aca tct cag gct gac tgt      396
Arg Asp Phe Ile Lys Asn Met Ile Thr Gly Thr Ser Gln Ala Asp Cys
                100                 105                 110 gct gtc ctg att gtt gct gct ggt gtt ggt gaa ttt gaa gct ggt atc      444
Ala Val Leu Ile Val Ala Ala Gly Val Gly Glu Phe Glu Ala Gly Ile
            115                 120                 125 tcc aag aat ggg cag acc cga gag cat gcc ctt ctg gct tac aca ctg      492
Ser Lys Asn Gly Gln Thr Arg Glu His Ala Leu Leu Ala Tyr Thr Leu
        130                 135                 140 ggt gtg aaa caa cta att gtc ggt gtt aac aaa atg gat tcc act gag      540
Gly Val Lys Gln Leu Ile Val Gly Val Asn Lys Met Asp Ser Thr Glu
145                 150                 155 cca ccc tac agc cag aag aga tat gag gaa att gtt aag gaa gtc agc      588
Pro Pro Tyr Ser Gln Lys Arg Tyr Glu Glu Ile Val Lys Glu Val Ser
160                 165                 170                 175 act tac att aag aaa att ggc tac aac ccc gac aca gta gca ttt gtg      636
Thr Tyr Ile Lys Lys Ile Gly Tyr Asn Pro Asp Thr Val Ala Phe Val
                180                 185                 190 cca att tct ggt tgg aat ggt gac aac atg ctg gag cca agt gct aac      684
Pro Ile Ser Gly Trp Asn Gly Asp Asn Met Leu Glu Pro Ser Ala Asn
            195                 200                 205 atg cct tgg ttc aag gga tgg aaa gtc acc cgt aag gat ggc aat gcc      732
Met Pro Trp Phe Lys Gly Trp Lys Val Thr Arg Lys Asp Gly Asn Ala
        210                 215                 220 agt gga acc acg ctg ctt gag gct ctg gac tgc atc cta cca cca act      780
Ser Gly Thr Thr Leu Leu Glu Ala Leu Asp Cys Ile Leu Pro Pro Thr
225                 230                 235 cgt cca act gac aag ccc ttg cgc ctg cct ctc cag gat gtc tac aaa      828
Arg Pro Thr Asp Lys Pro Leu Arg Leu Pro Leu Gln Asp Val Tyr Lys
240                 245                 250                 255 att ggt ggt att ggt act gtt cct gtt ggc cga gtg gag act ggt gtt      876
Ile Gly Gly Ile Gly Thr Val Pro Val Gly Arg Val Glu Thr Gly Val
                260                 265                 270 ctc aaa ccc ggt atg gtg gtc acc ttt gct cca gtc aac gtt aca acg      924
Leu Lys Pro Gly Met Val Val Thr Phe Ala Pro Val Asn Val Thr Thr
            275                 280                 285 gaa gta aaa tct gtc gaa atg cac cat gaa gct ttg agt gaa gct ctt      972
Glu Val Lys Ser Val Glu Met His His Glu Ala Leu Ser Glu Ala Leu
        290                 295                 300 cct ggg gac aat gtg ggc ttc aat gtc aag aat gtg tct gtc aag gat     1020
Pro Gly Asp Asn Val Gly Phe Asn Val Lys Asn Val Ser Val Lys Asp
305                 310                 315 gtt cgt cgt ggc aac gtt gct ggt gac agc aaa aat gac cca cca atg     1068
Val Arg Arg Gly Asn Val Ala Gly Asp Ser Lys Asn Asp Pro Pro Met
320                 325                 330                 335 gaa gca gct ggc ttc act gct cag gtg att atc ctg aac cat cca ggc     1116
Glu Ala Ala Gly Phe Thr Ala Gln Val Ile Ile Leu Asn His Pro Gly
                340                 345                 350 caa ata agc gcc ggc tat gcc cct gta ttg gat tgc cac acg gct cac     1164
Gln Ile Ser Ala Gly Tyr Ala Pro Val Leu Asp Cys His Thr Ala His
```

|  |  |  |  |  | 355 |  |  |  |  | 360 |  |  |  |  | 365 |  |  |
|---|---|---|---|---|---|---|---|---|---|---|---|---|---|---|---|---|---|
| att | gca | tgc | aag | ttt | gct | gag | ctg | aag | gaa | aag | att | gat | cgc | cgt | tct |  | 1212 |
| Ile | Ala | Cys | Lys | Phe | Ala | Glu | Leu | Lys | Glu | Lys | Ile | Asp | Arg | Arg | Ser |  |  |
|  |  | 370 |  |  |  |  | 375 |  |  |  |  | 380 |  |  |  |  |  |
| ggt | aaa | aag | ctg | gaa | gat | ggc | cct | aaa | ttc | ttg | aag | tct | ggt | gat | gct |  | 1260 |
| Gly | Lys | Lys | Leu | Glu | Asp | Gly | Pro | Lys | Phe | Leu | Lys | Ser | Gly | Asp | Ala |  |  |
|  | 385 |  |  |  |  | 390 |  |  |  |  | 395 |  |  |  |  |  |  |
| gcc | att | gtt | gat | atg | gtt | cct | ggc | aag | ccc | atg | tgt | gtt | gag | agc | ttc |  | 1308 |
| Ala | Ile | Val | Asp | Met | Val | Pro | Gly | Lys | Pro | Met | Cys | Val | Glu | Ser | Phe |  |  |
| 400 |  |  |  |  | 405 |  |  |  |  | 410 |  |  |  |  | 415 |  |  |
| tca | gac | tat | cca | cct | ttg | ggt | cgc | ttt | gct | gtt | cgt | gat | atg | aga | cag |  | 1356 |
| Ser | Asp | Tyr | Pro | Pro | Leu | Gly | Arg | Phe | Ala | Val | Arg | Asp | Met | Arg | Gln |  |  |
|  |  |  |  | 420 |  |  |  |  | 425 |  |  |  |  | 430 |  |  |  |
| aca | gtt | gcg | gtg | ggt | gtc | atc | aaa | gca | gtg | gac | aag | aag | gct | gct | gga |  | 1404 |
| Thr | Val | Ala | Val | Gly | Val | Ile | Lys | Ala | Val | Asp | Lys | Lys | Ala | Ala | Gly |  |  |
|  |  |  | 435 |  |  |  |  | 440 |  |  |  |  | 445 |  |  |  |  |
| gct | ggc | aag | gtc | acc | aag | tct | gcc | cag | aaa | gct | cag | aag | gct | aaa |  |  | 1449 |
| Ala | Gly | Lys | Val | Thr | Lys | Ser | Ala | Gln | Lys | Ala | Gln | Lys | Ala | Lys |  |  |  |
|  |  | 450 |  |  |  |  | 455 |  |  |  |  | 460 |  |  |  |  |  |

```
tgaatattat ccctaatacc tgccacccca ctcttaatca gtggtggaag aacggtctca    1509
gaactgtttg tttcaattgg ccatttaagt ttagtagtaa aagactggtt aatgataaca    1569
atgcatcgta aaaccttcag aaggaaagga gaatgttttg tggaccactt tggttttctt    1629
ttttgcgtgt ggcagtttta agttattagt ttttaaaatc agtacttttt aatggaaaca    1689
acttgaccaa aaatttgtca cagaattttg agacccatta aaaagttaa atgagaaacc     1749
tgtgtgttcc tttggtcaac accgagacat ttaggtgaaa gacatctaat tctggtttta    1809
cgaatctgga aacttcttga aaatgtaatt cttgagttaa cacttctggg tggagaatag    1869
ggttgttttc cccccacata attggaaggg gaaggaatat catttaaagc tatgggaggg    1929
ttgctttgat tacaacactg gagagaaatg cagcatgttg ctgattgcct gtcactaaaa    1989
caggccaaaa actgagtcct tgtgttgcat agaaagcttc atgttgctaa ccaatgtta    2049
agtgaatctt tggaaacaaa atgtttccaa attactggga tgtgcatgtt gaaacgtggg    2109
ttaaaatgac tgggcagtga agttgacta tttgccatga cataagaaat aagtgtagtg     2169
gctagtgtac accctatgag tggaagggtc cattttgaag tcagtggagt aagctttatg    2229
ccagtttgat ggtttcacaa gttctattga gtgctattca gaataggaac aaggttctaa    2289
tagaaaaaga tggcaatttg aagtagctat aaaattagac taatctacat tgcttttctc    2349
ctgcagagtc taatacccttt tatgctttga taattagcag tttgtctact ggtcactag    2409
gaatgaaact acatggtaat aggcttaaca ggtgtaatag cccacttact cctgaatctt    2469
taagcatttg tgcatttgaa aaatgctttt cgcgatcttc ctgctgggat tacaggcatg    2529
agccactgtg cctgacctcc catatgtaaa agtgtctaaa ggttttttt tggttataaa     2589
aggaaaattt ttgcttaagt ttgaaggata ggtaaaatta aaggacatgc tttctgtttg    2649
tgtgatggtt tttaaaaatt ttttttaaga tggagttctt gttgcccagg ctagaatgca    2709
atggcaaaat ctcactgcaa tctcctcctc ctgggttcaa gcaattctcc tacttcagcc    2769
tcccaagtag ctgggattac aggcatgtgc taatttggtg tttttaatag agatgaggtt    2829
tttccatgtt ggtcaggctg gtctcaaact cctgacctta ggtgatcgcc tcggcctcct    2889
aaagtgctgg aattacaggc atgagccacc atgcctggcc aggacatgtg ttcttaagga    2949
catgctaagc aggagttaaa gcagcccaag agataaggcc tcttaaagtg actggcaatg    3009
tgtattgctc aagattcaaa ggtacttgaa ttggccatag acaagtctgt aatgaagtgt    3069
```

```
tatcgttttc cctcatctga gtctgaatta gataaaatgc cttcccatca gccagtgctc    3129
tgaggtatca agtctaaatt gaactagaga tttttgtcct tagtttctttt gctatctaat    3189 gtttacacaa gtaaatagtc taagatttgc tggatgacag aaaaaacagg taaggccttt    3249
aatagatggc caatagatgc cctgataatg aaagttgaca cctgtaagat ttaccagtag    3309
agaattcttg acatgcaagg aagcaagatt taactgaaaa attgttccca ctggaagcag    3369
gaatgagtca gtttacttgc atatactgag attgagatta acttcctgtg aaacccagtg    3429
tcttagacaa ctgtggcttg agcaccacct gctggtattc attacaaact tgctcactac    3489
aataaatgaa ttttaagctt taaaaaaaaa aaaaaaaaa                           3528
```

<210> SEQ ID NO 36
<211> LENGTH: 462
<212> TYPE: PRT
<213> ORGANISM: Homo sapiens
<220> FEATURE:
<223> OTHER INFORMATION: EEF1A1

<400> SEQUENCE: 36

```
Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ser Leu Trp Lys Phe
65                  70                  75                  80

Glu Thr Ser Lys Tyr Tyr Val Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
        195                 200                 205

Pro Trp Phe Lys Gly Trp Lys Val Thr Arg Lys Asp Gly Asn Ala Ser
    210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
```

```
                275                 280                 285
    Val Lys Ser Val Glu Met His His Glu Ala Leu Ser Glu Ala Leu Pro
        290                 295                 300

Gly Asp Asn Val Gly Phe Asn Val Lys Asn Val Ser Lys Asp Val
    305                 310                 315                 320

Arg Arg Gly Asn Val Ala Gly Asp Ser Lys Asn Asp Pro Pro Met Glu
                    325                 330                 335

Ala Ala Gly Phe Thr Ala Gln Val Ile Ile Leu Asn His Pro Gly Gln
                340                 345                 350

Ile Ser Ala Gly Tyr Ala Pro Val Leu Asp Cys His Thr Ala His Ile
                355                 360                 365

Ala Cys Lys Phe Ala Glu Leu Lys Glu Lys Ile Asp Arg Arg Ser Gly
        370                 375                 380

Lys Lys Leu Glu Asp Gly Pro Lys Phe Leu Lys Ser Gly Asp Ala Ala
    385                 390                 395                 400

Ile Val Asp Met Val Pro Gly Lys Pro Met Cys Val Glu Ser Phe Ser
                    405                 410                 415

Asp Tyr Pro Pro Leu Gly Arg Phe Ala Val Arg Asp Met Arg Gln Thr
                420                 425                 430

Val Ala Val Gly Val Ile Lys Ala Val Asp Lys Lys Ala Ala Gly Ala
                435                 440                 445

Gly Lys Val Thr Lys Ser Ala Gln Lys Ala Gln Lys Ala Lys
        450                 455                 460

<210> SEQ ID NO 37
<211> LENGTH: 3606
<212> TYPE: DNA
<213> ORGANISM: Homo sapiens
<220> FEATURE:
<223> OTHER INFORMATION: PNN mRNA
<220> FEATURE:
<221> NAME/KEY: CDS
<222> LOCATION: (98)..(2248)

<400> SEQUENCE: 37
attggctgag cccggctgtc agtcctttcg cgcctcggcg gcgcggcata gcccggctcg      60
gcctgtaaag cagtctcaag cctgccgcag ggagaag atg gcg gtc gcc gtg aga     115
                                         Met Ala Val Ala Val Arg
                                           1               5 act ttg cag gaa cag ctg gaa aag gcc aaa gag agt ctt aag aac gtg      163
Thr Leu Gln Glu Gln Leu Glu Lys Ala Lys Glu Ser Leu Lys Asn Val
                 10                  15                  20 gat gag aac att cgc aag ctc acc ggg cgg gat ccg aat gac gtg agg      211
Asp Glu Asn Ile Arg Lys Leu Thr Gly Arg Asp Pro Asn Asp Val Arg
             25                  30                  35 ccc atc caa gcc aga ttg ctg gcc ctt tct ggt cct gga gga ggt aga      259
Pro Ile Gln Ala Arg Leu Leu Ala Leu Ser Gly Pro Gly Gly Gly Arg
         40                  45                  50 gga cgt ggt agt tta tta ctg agg cgt gga ttc tca gat agt gga gga      307
Gly Arg Gly Ser Leu Leu Leu Arg Arg Gly Phe Ser Asp Ser Gly Gly
 55                  60                  65                  70 gga ccc cca gcc aaa cag aga gac ctt gaa ggg gca gtc agt agg ctg      355
Gly Pro Pro Ala Lys Gln Arg Asp Leu Glu Gly Ala Val Ser Arg Leu
                 75                  80                  85 ggc ggg gag cgt cgg acc aga aga gaa tca cgc cag gaa agc gac ccg      403
Gly Gly Glu Arg Arg Thr Arg Arg Glu Ser Arg Gln Glu Ser Asp Pro
                 90                  95                 100 gag gat gat gat gtt aaa aag cca gca ttg cag tct tca gtt gta gct      451
```

```
                Glu Asp Asp Val Lys Lys Pro Ala Leu Gln Ser Ser Val Val Ala
                        105                 110                 115 acc tcc aaa gag cgc aca cgt aga gac ctt atc cag gat caa aat atg         499
Thr Ser Lys Glu Arg Thr Arg Arg Asp Leu Ile Gln Asp Gln Asn Met
        120                 125                 130 gat gaa aag gga aag caa agg aac cgg cga ata ttt ggc ttg ttg atg         547
Asp Glu Lys Gly Lys Gln Arg Asn Arg Arg Ile Phe Gly Leu Leu Met
135                 140                 145                 150 ggt acc ctt caa aaa ttt aaa caa gaa tcc act gtt gct act gaa agg         595
Gly Thr Leu Gln Lys Phe Lys Gln Glu Ser Thr Val Ala Thr Glu Arg
                155                 160                 165 caa aag cgg cgc cag gaa att gaa caa aaa ctt gaa gtt cag gca gaa         643
Gln Lys Arg Arg Gln Glu Ile Glu Gln Lys Leu Glu Val Gln Ala Glu
            170                 175                 180 gaa gag aga aag cag gtt gaa aat gaa agg aga gaa ctg ttt gaa gag         691
Glu Glu Arg Lys Gln Val Glu Asn Glu Arg Arg Glu Leu Phe Glu Glu
            185                 190                 195 agg cgt gct aaa cag aca gaa ctg cgg ctt ttg gaa cag aaa gtt gag         739
Arg Arg Ala Lys Gln Thr Glu Leu Arg Leu Leu Glu Gln Lys Val Glu
        200                 205                 210 ctt gcg cag ctg caa gaa gaa tgg aat gaa cat aat gcc aaa ata att         787
Leu Ala Gln Leu Gln Glu Glu Trp Asn Glu His Asn Ala Lys Ile Ile
215                 220                 225                 230 aaa tat ata aga act aag aca aag ccc cat ttg ttt tat att cct gga         835
Lys Tyr Ile Arg Thr Lys Thr Lys Pro His Leu Phe Tyr Ile Pro Gly
                235                 240                 245 aga atg tgt cca gct acc caa aaa cta ata gaa gag tca cag aga aaa        883
Arg Met Cys Pro Ala Thr Gln Lys Leu Ile Glu Glu Ser Gln Arg Lys
            250                 255                 260 atg aac gct tta ttt gaa ggt aga cgc atc gaa ttt gca gaa caa ata         931
Met Asn Ala Leu Phe Glu Gly Arg Arg Ile Glu Phe Ala Glu Gln Ile
            265                 270                 275 aat aaa atg gag gct agg cct aga aga caa tca atg aag gaa aaa gag        979
Asn Lys Met Glu Ala Arg Pro Arg Arg Gln Ser Met Lys Glu Lys Glu
        280                 285                 290 cat cag gtg gtg cgt aat gaa gaa cag aag gcg gaa caa gaa gag ggt        1027
His Gln Val Val Arg Asn Glu Glu Gln Lys Ala Glu Gln Glu Glu Gly
295                 300                 305                 310 aag gtg gct cag cga gag gaa gag ttg gag gag aca ggt aat cag cac        1075
Lys Val Ala Gln Arg Glu Glu Glu Leu Glu Glu Thr Gly Asn Gln His
                315                 320                 325 aat gat gta gaa ata gag gaa gca gga gag gaa gag gaa aag gaa ata        1123
Asn Asp Val Glu Ile Glu Glu Ala Gly Glu Glu Glu Lys Glu Ile
            330                 335                 340 gcg att gtt cat agt gat gca gag aaa gaa cag gag gag gaa gaa caa        1171
Ala Ile Val His Ser Asp Ala Glu Lys Glu Gln Glu Glu Glu Glu Gln
            345                 350                 355 aaa cag gaa atg gag gtt aag atg gag gag gaa act gag gta agg gaa        1219
Lys Gln Glu Met Glu Val Lys Met Glu Glu Glu Thr Glu Val Arg Glu
360                 365                 370 agt gag aag cag cag gat agt cag cct gaa gaa gtt atg gat gtg cta        1267
Ser Glu Lys Gln Gln Asp Ser Gln Pro Glu Glu Val Met Asp Val Leu
375                 380                 385                 390 gag atg gtt gag aat gtc aaa cat gta att gct gac cag gag gta atg        1315
Glu Met Val Glu Asn Val Lys His Val Ile Ala Asp Gln Glu Val Met
                395                 400                 405 gaa act aat cga gtt gaa agt gta gaa cct tca gaa aat gaa gct agc        1363
Glu Thr Asn Arg Val Glu Ser Val Glu Pro Ser Glu Asn Glu Ala Ser
            410                 415                 420
```

-continued

| | | |
|---|---|---|
| aaa gaa ttg gaa cca gaa atg gaa ttt gaa att gag cca gat aaa gaa<br>Lys Glu Leu Glu Pro Glu Met Glu Phe Glu Ile Glu Pro Asp Lys Glu<br>         425                    430                435 | | 1411 |
| tgt aaa tcc ctt tct cct ggg aaa gag aat gtc agt gct tta gac atg<br>Cys Lys Ser Leu Ser Pro Gly Lys Glu Asn Val Ser Ala Leu Asp Met<br>      440                    445                450 | | 1459 |
| gaa aag gag tct gag gaa aaa gaa gaa aaa gaa tct gag ccc caa cct<br>Glu Lys Glu Ser Glu Glu Lys Glu Glu Lys Glu Ser Glu Pro Gln Pro<br>455                  460                465              470 | | 1507 |
| gag cct gtg gct caa cct cag cct cag tct cag ccc cag ctt cag ctt<br>Glu Pro Val Ala Gln Pro Gln Pro Gln Ser Gln Pro Gln Leu Gln Leu<br>                475                  480              485 | | 1555 |
| caa tcc cag tcc caa cca gta ctc cag tcc cag cct ccc tct cag cct<br>Gln Ser Gln Ser Gln Pro Val Leu Gln Ser Gln Pro Pro Ser Gln Pro<br>      490                    495                500 | | 1603 |
| gag gat ttg tca tta gct gtt tta cag cca aca ccc caa gtt act cag<br>Glu Asp Leu Ser Leu Ala Val Leu Gln Pro Thr Pro Gln Val Thr Gln<br>505                  510                515 | | 1651 |
| gag caa ggg cat tta cta cct gag agg aag gat ttt cct gta gag tct<br>Glu Gln Gly His Leu Leu Pro Glu Arg Lys Asp Phe Pro Val Glu Ser<br>         520                    525              530 | | 1699 |
| gta aaa ctc act gag gta cca gta gag cca gtc ttg aca gta cat cca<br>Val Lys Leu Thr Glu Val Pro Val Glu Pro Val Leu Thr Val His Pro<br>535                  540              545              550 | | 1747 |
| gag agc aag agc aaa acc aaa act agg agc aga agt aga ggt cga gct<br>Glu Ser Lys Ser Lys Thr Lys Thr Arg Ser Arg Ser Arg Gly Arg Ala<br>                555                  560              565 | | 1795 |
| aga aat aaa aca agc aag agt aga agt cga agc agt agc agt agc agt<br>Arg Asn Lys Thr Ser Lys Ser Arg Ser Arg Ser Ser Ser Ser Ser Ser<br>      570                    575                580 | | 1843 |
| tct agt agc agt tca acc agt agc agc agt gga agt agt tcc agc agt<br>Ser Ser Ser Ser Thr Ser Ser Ser Ser Gly Ser Ser Ser Ser Ser Ser<br>         585                    590              595 | | 1891 |
| gga agt agt agc agt cgc agt agt tcc agt agc agc tcc agt aca agt<br>Gly Ser Ser Ser Ser Arg Ser Ser Ser Ser Ser Ser Ser Ser Thr Ser<br>600                  605                610 | | 1939 |
| ggc agc agc agc aga gat agt agc agt agc act agt agt agt agt gag<br>Gly Ser Ser Ser Arg Asp Ser Ser Ser Ser Thr Ser Ser Ser Ser Glu<br>615                  620              625              630 | | 1987 |
| agt aga agt cgg agt agg ggc cgg gga cat aat aga gat aga aag cac<br>Ser Arg Ser Arg Ser Arg Gly Arg Gly His Asn Arg Asp Arg Lys His<br>                635                  640              645 | | 2035 |
| aga agg agc gtg gat cgg aag aga agg gat act tca gga cta gaa aga<br>Arg Arg Ser Val Asp Arg Lys Arg Arg Asp Thr Ser Gly Leu Glu Arg<br>         650                    655              660 | | 2083 |
| agt cac aaa tct tca aaa ggt ggt agt agt aga gat aca aaa gga tca<br>Ser His Lys Ser Ser Lys Gly Gly Ser Ser Arg Asp Thr Lys Gly Ser<br>665                  670              675 | | 2131 |
| aag gat aag aat tcc cgg tcc gac aga aag agg tct ata tca gag agt<br>Lys Asp Lys Asn Ser Arg Ser Asp Arg Lys Arg Ser Ile Ser Glu Ser<br>      680                    685              690 | | 2179 |
| agt cga tca ggc aaa aga tct tca aga agt gaa aga gac cga aaa tca<br>Ser Arg Ser Gly Lys Arg Ser Ser Arg Ser Glu Arg Asp Arg Lys Ser<br>695                  700              705              710 | | 2227 |
| gac agg aaa gac aaa agg cgt taatggaaga agccaggctt tcttagccat<br>Asp Arg Lys Asp Lys Arg Arg<br>                715 | | 2278 |
| tctttgcagc agaagatttc ttgataaaaa aggattacct ttccttgtaa agaggatgct | | 2338 |
| gccttaagaa ttgcatgttg taaaaaatct ttttggaaaa tacagactgt tgtttacca | | 2398 |

```
gacattcttg tacttttgc ataattttgt aagagttatt tatcaaaatt atgtgaggtt    2458
ccaaaatatg taaaaatgat aataataaaa aaagattaac atcccttgtc atctttttta    2518
aatatcctat actcttcagt aagaatctgt atattttaat aggcaaatct ttaagtctgt    2578
tcccttctaa ttctgtatca tacattgctt ttgtagaaat aaatgtgtgt ttatttcatt    2638 attttggga tgtcctcgtt gacacttgta taataaatat cctctttatc attttcagct    2698
tttaacacta gatactgcac gtgattagaa tgttttgaa ggtttcctcg tttttatttg    2758
ccttggacag ttttagttg tcagagtcag agctttgcag ctttgaggg gaacagttct    2818 cttaaaatc atttgctatt ttctattctc ccttgttatt ttaatctaag cattttcccc    2878
cgtttctcat attttaacca tatgttcggt agataactaa acagtatgat ctggttggca    2938
ttttcttcct gatgatggga gcgtcattct tttgtcttca tggttacttg tgtgatataa    2998
catacatctg ttaaagaaaa tcacttcttt ctagggagg gaggtagaaa agtatctttc    3058
aaacttggtt tttgagtttg tgtcttgtct taactttgtg ttggctctaa cttaaacatg    3118
ctgatatgtg ttttcaagaa ttttgtttaa ggaagtattg tatggaagtc cacaaaatga    3178
aggaagttca tctaggtttt aatatgtaag caagataaca cacaagtgta ccaagtgatt    3238
attaactttg ttgttttaca aatttgtatg aacttggagt atctgttggc cattactata    3298
catgtgcaaa taatgtggc ttagacttgt gtgactgctt aagactagta cttgtattaa    3358
ctttctgatg ctttatacaa gagagcactt aaattgcatc cttctttgag tttaacactg    3418 tagcttagc cttgactttg aatattcatt ttgccttccc ttgacaagta aatggttaca    3478
gtgaaaatgt gaagaagtat ttccagttag tttttgtgtg tatataactc acttgtgtaa    3538
gtggatgtgt taaagatct cttttaaaa atccttttat tggagtaatt attaaaacag    3598
taaatgca                                                              3606
```

<210> SEQ ID NO 38
<211> LENGTH: 717
<212> TYPE: PRT
<213> ORGANISM: Homo sapiens
<220> FEATURE:
<223> OTHER INFORMATION: PNN

<400> SEQUENCE: 38

```
Met Ala Val Ala Val Arg Thr Leu Gln Glu Gln Leu Glu Lys Ala Lys
  1               5                  10                  15

Glu Ser Leu Lys Asn Val Asp Glu Asn Ile Arg Lys Leu Thr Gly Arg
             20                  25                  30

Asp Pro Asn Asp Val Arg Pro Ile Gln Ala Arg Leu Leu Ala Leu Ser
         35                  40                  45

Gly Pro Gly Gly Gly Arg Gly Arg Gly Ser Leu Leu Arg Arg Gly
     50                  55                  60

Phe Ser Asp Ser Gly Gly Gly Pro Ala Lys Gln Arg Asp Leu Glu
 65                  70                  75                  80

Gly Ala Val Ser Arg Leu Gly Gly Glu Arg Thr Arg Arg Glu Ser
             85                  90                  95

Arg Gln Glu Ser Asp Pro Glu Asp Asp Val Lys Lys Pro Ala Leu
            100                 105                 110

Gln Ser Ser Val Val Ala Thr Ser Lys Glu Arg Thr Arg Arg Asp Leu
            115                 120                 125

Ile Gln Asp Gln Asn Met Asp Glu Lys Gly Lys Gln Arg Asn Arg Arg
        130                 135                 140
```

-continued

```
Ile Phe Gly Leu Leu Met Gly Thr Leu Gln Lys Phe Lys Gln Glu Ser
145                 150                 155                 160

Thr Val Ala Thr Glu Arg Gln Lys Arg Arg Gln Glu Ile Glu Gln Lys
            165                 170                 175

Leu Glu Val Gln Ala Glu Glu Arg Lys Gln Val Glu Asn Glu Arg
        180                 185                 190

Arg Glu Leu Phe Glu Glu Arg Arg Ala Lys Gln Thr Glu Leu Arg Leu
            195                 200                 205

Leu Glu Gln Lys Val Glu Leu Ala Gln Leu Gln Glu Glu Trp Asn Glu
210                 215                 220

His Asn Ala Lys Ile Ile Lys Tyr Ile Arg Thr Lys Thr Lys Pro His
225                 230                 235                 240

Leu Phe Tyr Ile Pro Gly Arg Met Cys Pro Ala Thr Gln Lys Leu Ile
                245                 250                 255

Glu Glu Ser Gln Arg Lys Met Asn Ala Leu Phe Glu Gly Arg Arg Ile
            260                 265                 270

Glu Phe Ala Glu Gln Ile Asn Lys Met Glu Ala Arg Pro Arg Arg Gln
        275                 280                 285

Ser Met Lys Glu Lys Glu His Gln Val Val Arg Asn Glu Glu Gln Lys
290                 295                 300

Ala Glu Gln Glu Glu Gly Lys Val Ala Gln Arg Glu Glu Leu Glu
305                 310                 315                 320

Glu Thr Gly Asn Gln His Asn Asp Val Glu Ile Glu Ala Gly Glu
            325                 330                 335

Glu Glu Glu Lys Glu Ile Ala Ile Val His Ser Asp Ala Glu Lys Glu
            340                 345                 350

Gln Glu Glu Glu Gln Lys Gln Glu Met Glu Val Lys Met Glu Glu
        355                 360                 365

Glu Thr Glu Val Arg Glu Ser Glu Lys Gln Gln Asp Ser Gln Pro Glu
        370                 375                 380

Glu Val Met Asp Val Leu Glu Met Val Glu Asn Val Lys His Val Ile
385                 390                 395                 400

Ala Asp Gln Glu Val Met Glu Thr Asn Arg Val Glu Ser Val Glu Pro
                405                 410                 415

Ser Glu Asn Glu Ala Ser Lys Glu Leu Glu Pro Glu Met Glu Phe Glu
            420                 425                 430

Ile Glu Pro Asp Lys Glu Cys Lys Ser Leu Ser Pro Gly Lys Glu Asn
        435                 440                 445

Val Ser Ala Leu Asp Met Glu Lys Glu Ser Glu Lys Glu Lys
        450                 455                 460

Glu Ser Glu Pro Gln Pro Glu Pro Val Ala Gln Pro Gln Pro Gln Ser
465                 470                 475                 480

Gln Pro Gln Leu Gln Leu Gln Ser Gln Ser Gln Pro Val Leu Gln Ser
                485                 490                 495

Gln Pro Pro Ser Gln Pro Glu Asp Leu Ser Leu Ala Val Leu Gln Pro
            500                 505                 510

Thr Pro Gln Val Thr Gln Glu Gln Gly His Leu Leu Pro Glu Arg Lys
        515                 520                 525

Asp Phe Pro Val Glu Ser Val Lys Leu Thr Glu Val Pro Val Glu Pro
        530                 535                 540

Val Leu Thr Val His Pro Glu Ser Lys Ser Lys Thr Lys Thr Arg Ser
545                 550                 555                 560
```

```
Arg Ser Arg Gly Arg Ala Arg Asn Lys Thr Ser Lys Ser Arg Ser Arg
                565                 570                 575

Ser Ser Ser Ser Ser Ser Ser Ser Ser Ser Thr Ser Ser Ser
        580                 585                 590

Gly Ser Ser Ser Ser Gly Ser Ser Ser Arg Ser Ser Ser Ser
        595                 600                 605

Ser Ser Ser Ser Thr Ser Gly Ser Ser Arg Asp Ser Ser Ser
        610                 615                 620

Thr Ser Ser Ser Ser Glu Ser Arg Ser Arg Ser Arg Gly Arg Gly His
625                 630                 635                 640

Asn Arg Asp Arg Lys His Arg Arg Ser Val Asp Arg Lys Arg Arg Asp
                645                 650                 655

Thr Ser Gly Leu Glu Arg Ser His Lys Ser Ser Lys Gly Gly Ser Ser
                660                 665                 670

Arg Asp Thr Lys Gly Ser Lys Asp Lys Asn Ser Arg Ser Asp Arg Lys
                675                 680                 685

Arg Ser Ile Ser Glu Ser Ser Arg Ser Gly Lys Arg Ser Ser Arg Ser
690                 695                 700

Glu Arg Asp Arg Lys Ser Asp Arg Lys Asp Lys Arg Arg
705                 710                 715

<210> SEQ ID NO 39
<211> LENGTH: 2509
<212> TYPE: DNA
<213> ORGANISM: Homo sapiens
<220> FEATURE:
<223> OTHER INFORMATION: RHOT2 mRNA
<220> FEATURE:
<221> NAME/KEY: CDS
<222> LOCATION: (68)..(1921)

<400> SEQUENCE: 39
gagcgaaagg cttgaggacc aggtcggggc cgggttccgg gtcggggagc ggctccgggc        60 ggcagct atg agg cgg gac gtg cgc atc ctg tta ctg ggc gag gcc cag        109
        Met Arg Arg Asp Val Arg Ile Leu Leu Leu Gly Glu Ala Gln
        1               5                   10 gtg ggg aag acg tcg ctg atc ctg tcc ctg gtg ggc gag gag ttc ccc        157
Val Gly Lys Thr Ser Leu Ile Leu Ser Leu Val Gly Glu Glu Phe Pro
15                  20                  25                  30 gag gag gtc cct ccc cgc gcg gag gag atc acg atc ccc gcg gac gtc        205
Glu Glu Val Pro Pro Arg Ala Glu Glu Ile Thr Ile Pro Ala Asp Val
                35                  40                  45 acc ccg gag aag gtg ccc acc cac atc gtg gac tac tca gaa gcc gag        253
Thr Pro Glu Lys Val Pro Thr His Ile Val Asp Tyr Ser Glu Ala Glu
            50                  55                  60 cag acg gac gag gag ctg cgg gag gag atc cac aag gca aac gtg gtg        301
Gln Thr Asp Glu Glu Leu Arg Glu Glu Ile His Lys Ala Asn Val Val
        65                  70                  75 tgt gtg gtg tat gac gtc tct gag gag gcc acc att gag aag att cga        349
Cys Val Val Tyr Asp Val Ser Glu Glu Ala Thr Ile Glu Lys Ile Arg
    80                  85                  90 act aag tgg atc cca ctg gtg aat ggg ggg acc acg cag ggg ccc agg        397
Thr Lys Trp Ile Pro Leu Val Asn Gly Gly Thr Thr Gln Gly Pro Arg
95                  100                 105                 110 gtg ccc atc atc cta gtg ggc aac aag tca gac ctg cgg tcg ggg agc        445
Val Pro Ile Ile Leu Val Gly Asn Lys Ser Asp Leu Arg Ser Gly Ser
                115                 120                 125 tcc atg gag gcc gtg ctc ccc atc atg agc cag ttt ccc gag att gag        493
Ser Met Glu Ala Val Leu Pro Ile Met Ser Gln Phe Pro Glu Ile Glu
```

```
                    130                 135                 140
acc tgc gtg gag tgt tcg gcc aag aac ctg agg aac atc tca gag ctg       541
Thr Cys Val Glu Cys Ser Ala Lys Asn Leu Arg Asn Ile Ser Glu Leu
            145                 150                 155 ttc tac tac gcc cag aag gcc gtc ctg cat ccc aca gcc ccc ctc tat       589
Phe Tyr Tyr Ala Gln Lys Ala Val Leu His Pro Thr Ala Pro Leu Tyr
160                 165                 170 gac cct gag gcc aag cag ttg agg ccc gcg tgc gcc cag gcg ctg acg       637
Asp Pro Glu Ala Lys Gln Leu Arg Pro Ala Cys Ala Gln Ala Leu Thr
175                 180                 185                 190 cgc atc ttc agg ctc tca gat cag gac ctg gac cag gcg ctc agt gac       685
Arg Ile Phe Arg Leu Ser Asp Gln Asp Leu Asp Gln Ala Leu Ser Asp
                195                 200                 205 gaa gag ctc aac gct ttc cag aaa tcc tgc ttt ggg cac ccc ctg gcc       733
Glu Glu Leu Asn Ala Phe Gln Lys Ser Cys Phe Gly His Pro Leu Ala
            210                 215                 220 ccg cag gcc ctg gag gac gtg aag acg gtg gtg tgc agg aac gtg gcg       781
Pro Gln Ala Leu Glu Asp Val Lys Thr Val Val Cys Arg Asn Val Ala
        225                 230                 235 ggc ggc gtg cgg gag gac cgg ctg acc ctg gat ggt ttc ctc ttc ctg       829
Gly Gly Val Arg Glu Asp Arg Leu Thr Leu Asp Gly Phe Leu Phe Leu
240                 245                 250 aac acg ctc ttc atc cag cgc ggc cgg cac gag acc acc tgg acc atc       877
Asn Thr Leu Phe Ile Gln Arg Gly Arg His Glu Thr Thr Trp Thr Ile
255                 260                 265                 270 ctg cgg cgc ttc ggc tac agc gat gcc ctg gag ctg act gcg gac tat       925
Leu Arg Arg Phe Gly Tyr Ser Asp Ala Leu Glu Leu Thr Ala Asp Tyr
                275                 280                 285 ctc tcc cct ctg atc cac gtg ccc ccc ggc tgc agc acg gag ctc aac       973
Leu Ser Pro Leu Ile His Val Pro Pro Gly Cys Ser Thr Glu Leu Asn
            290                 295                 300 cac ctt ggc tac cag ttt gtg cag aga gtg ttt gag aag cac gac cag      1021
His Leu Gly Tyr Gln Phe Val Gln Arg Val Phe Glu Lys His Asp Gln
        305                 310                 315 gac cgc gac ggc gcc ctc tcg ccc gtg gag ctg caa agc ctt ttc agt      1069
Asp Arg Asp Gly Ala Leu Ser Pro Val Glu Leu Gln Ser Leu Phe Ser
320                 325                 330 gtg ttc cca gca gcg ccc tgg ggc ccc gag ctc cca cgc aca gtc cgc      1117
Val Phe Pro Ala Ala Pro Trp Gly Pro Glu Leu Pro Arg Thr Val Arg
335                 340                 345                 350 aca gag gcc ggc cgg ttg ccc ctg cac gga tac ctc tgc cag tgg acc      1165
Thr Glu Ala Gly Arg Leu Pro Leu His Gly Tyr Leu Cys Gln Trp Thr
                355                 360                 365 ctg gtg acc tac ctg gac gtc cgg agc tgc ctt gga cac cta ggc tac      1213
Leu Val Thr Tyr Leu Asp Val Arg Ser Cys Leu Gly His Leu Gly Tyr
            370                 375                 380 ctg ggc tac ccc acc ctc tgt gag cag gac cag gcc cat gcc atc aca      1261
Leu Gly Tyr Pro Thr Leu Cys Glu Gln Asp Gln Ala His Ala Ile Thr
        385                 390                 395 gtc act cgt gag aag agg ctg gac cag gag aag gga cag acg cag cgg      1309
Val Thr Arg Glu Lys Arg Leu Asp Gln Glu Lys Gly Gln Thr Gln Arg
400                 405                 410 agc gtc ctc ctg tgc aag gtg gta ggg gcc cgt gga gtg ggc aag tct      1357
Ser Val Leu Leu Cys Lys Val Val Gly Ala Arg Gly Val Gly Lys Ser
415                 420                 425                 430 gcc ttc ctg cag gct ttt ctc ggc cgc ggc ctg ggg cac cag gac acg      1405
Ala Phe Leu Gln Ala Phe Leu Gly Arg Gly Leu Gly His Gln Asp Thr
                435                 440                 445 agg gag cag cct ccc ggc tac gcc atc gac acg gtg cag gtc aat gga      1453
Arg Glu Gln Pro Pro Gly Tyr Ala Ile Asp Thr Val Gln Val Asn Gly
```

```
Arg Glu Gln Pro Pro Gly Tyr Ala Ile Asp Thr Val Gln Val Asn Gly
            450                 455                 460 cag gag aag tac ttg atc ctc tgt gag gtg ggc aca gat ggt ctg ctg        1501
Gln Glu Lys Tyr Leu Ile Leu Cys Glu Val Gly Thr Asp Gly Leu Leu
            465                 470                 475 gcc aca tcg ctg gac gcc acc tgt gac gtt gcc tgc ttg atg ttt gat        1549
Ala Thr Ser Leu Asp Ala Thr Cys Asp Val Ala Cys Leu Met Phe Asp
        480                 485                 490 ggc agt gac cca aag tcc ttt gca cat tgt gcc agc gtc tac aag cac        1597
Gly Ser Asp Pro Lys Ser Phe Ala His Cys Ala Ser Val Tyr Lys His
495                 500                 505                 510 cat tac atg gac ggg cag acc ccc tgc ctc ttt gtc tcc tcc aag gcc        1645
His Tyr Met Asp Gly Gln Thr Pro Cys Leu Phe Val Ser Ser Lys Ala
                515                 520                 525 gac ctg ccc gaa ggt gtc gcg gtg tct ggc cca tca ccg gcc gag ttt        1693
Asp Leu Pro Glu Gly Val Ala Val Ser Gly Pro Ser Pro Ala Glu Phe
            530                 535                 540 tgc cgc aag cac cgg cta ccc gct ccc gtg ccg ttc tcc tgt gct ggc        1741
Cys Arg Lys His Arg Leu Pro Ala Pro Val Pro Phe Ser Cys Ala Gly
        545                 550                 555 cca gcc gag ccc agc acc acc atc ttc acc cag ctc gcc acc atg gcc        1789
Pro Ala Glu Pro Ser Thr Thr Ile Phe Thr Gln Leu Ala Thr Met Ala
560                 565                 570 gcc ttc cca cat ttg gtc cac gca gag ctg cat ccc tct tcc ttc tgg        1837
Ala Phe Pro His Leu Val His Ala Glu Leu His Pro Ser Ser Phe Trp
575                 580                 585                 590 ctc cgg ggg ctg ctg ggg gtt gtc ggg gcc gcc gtg gcc gca gtc ctc        1885
Leu Arg Gly Leu Leu Gly Val Val Gly Ala Ala Val Ala Ala Val Leu
                595                 600                 605 agc ttc tca ctc tac agg gtc ctg gtg aag agc cag tgaggcccct            1931
Ser Phe Ser Leu Tyr Arg Val Leu Val Lys Ser Gln
            610                 615 ggtacccaag cccctcccc tgacctgggt gtgcctcgct gctggggctc tgcaggggca      1991
gcacagctgg ggtgcaggcc aggctgccac tccgggaacg cctttgcgcc gggacttttt     2051
gtttctgaag gcagtcgatc tgcagcgggg ccttatgctg ccatgcactg ccctggctcc     2111
tgccggaccc ccagggtggg ccgtggcagg tggctgagca ggagctccca agtgccggcc     2171
accgctgtca gggattgccc accctgggc atcatgtgtg tggggccggg agcacaggt       2231 gtgggagctg gtgaccccag acccagaatt ctcagggctc tacccccctt tcctggtcct    2291
aggtggccag tgggtatgag gagggctgga aggcagagct ttgggccaaa agcaggcgtt    2351
ggggggtccc ccctcaagtt tggagccgtt tccgtggttg tagcagagga ccggaggttg    2411
ggttcctgat taaacttcac tgtgtgtttt ctatctcgga tcccagtctc tgaagacaac    2471
ttgctttgat tcaacctaaa aaaaaaaaaa aaaaaaa                             2509

<210> SEQ ID NO 40
<211> LENGTH: 618
<212> TYPE: PRT
<213> ORGANISM: Homo sapiens
<220> FEATURE:
<223> OTHER INFORMATION: RHOT2

<400> SEQUENCE: 40

Met Arg Arg Asp Val Arg Ile Leu Leu Leu Gly Glu Ala Gln Val Gly
1               5                   10                  15

Lys Thr Ser Leu Ile Leu Ser Leu Val Gly Glu Glu Phe Pro Glu Glu
            20                  25                  30
```

-continued

Val Pro Pro Arg Ala Glu Glu Ile Thr Ile Pro Ala Asp Val Thr Pro
        35                  40                  45

Glu Lys Val Pro Thr His Ile Val Asp Tyr Ser Glu Ala Glu Gln Thr
 50                  55                  60

Asp Glu Glu Leu Arg Glu Ile His Lys Ala Asn Val Val Cys Val
 65                  70                  75                  80

Val Tyr Asp Val Ser Glu Glu Ala Thr Ile Glu Lys Ile Arg Thr Lys
                    85                  90                  95

Trp Ile Pro Leu Val Asn Gly Gly Thr Thr Gln Gly Pro Arg Val Pro
                100                 105                 110

Ile Ile Leu Val Gly Asn Lys Ser Asp Leu Arg Ser Gly Ser Ser Met
            115                 120                 125

Glu Ala Val Leu Pro Ile Met Ser Gln Phe Pro Glu Ile Glu Thr Cys
130                 135                 140

Val Glu Cys Ser Ala Lys Asn Leu Arg Asn Ile Ser Glu Leu Phe Tyr
145                 150                 155                 160

Tyr Ala Gln Lys Ala Val Leu His Pro Thr Ala Pro Leu Tyr Asp Pro
                165                 170                 175

Glu Ala Lys Gln Leu Arg Pro Ala Cys Ala Gln Ala Leu Thr Arg Ile
                180                 185                 190

Phe Arg Leu Ser Asp Gln Asp Leu Asp Gln Ala Leu Ser Asp Glu Glu
        195                 200                 205

Leu Asn Ala Phe Gln Lys Ser Cys Phe Gly His Pro Leu Ala Pro Gln
210                 215                 220

Ala Leu Glu Asp Val Lys Thr Val Val Cys Arg Asn Val Ala Gly Gly
225                 230                 235                 240

Val Arg Glu Asp Arg Leu Thr Leu Asp Gly Phe Leu Phe Leu Asn Thr
                245                 250                 255

Leu Phe Ile Gln Arg Gly Arg His Glu Thr Thr Trp Thr Ile Leu Arg
                260                 265                 270

Arg Phe Gly Tyr Ser Asp Ala Leu Glu Leu Thr Ala Asp Tyr Leu Ser
            275                 280                 285

Pro Leu Ile His Val Pro Pro Gly Cys Ser Thr Glu Leu Asn His Leu
290                 295                 300

Gly Tyr Gln Phe Val Gln Arg Val Phe Glu Lys His Asp Gln Asp Arg
305                 310                 315                 320

Asp Gly Ala Leu Ser Pro Val Glu Leu Gln Ser Leu Phe Ser Val Phe
                325                 330                 335

Pro Ala Ala Pro Trp Gly Pro Glu Leu Pro Arg Thr Val Arg Thr Glu
                340                 345                 350

Ala Gly Arg Leu Pro Leu His Gly Tyr Leu Cys Gln Trp Thr Leu Val
            355                 360                 365

Thr Tyr Leu Asp Val Arg Ser Cys Leu Gly His Leu Gly Tyr Leu Gly
370                 375                 380

Tyr Pro Thr Leu Cys Glu Gln Asp Gln Ala His Ala Ile Thr Val Thr
385                 390                 395                 400

Arg Glu Lys Arg Leu Asp Gln Glu Lys Gly Gln Thr Gln Arg Ser Val
                405                 410                 415

Leu Leu Cys Lys Val Val Gly Ala Arg Gly Val Gly Lys Ser Ala Phe
                420                 425                 430

Leu Gln Ala Phe Leu Gly Arg Gly Leu Gly His Gln Asp Thr Arg Glu
        435                 440                 445

Gln Pro Pro Gly Tyr Ala Ile Asp Thr Val Gln Val Asn Gly Gln Glu

Lys Tyr Leu Ile Leu Cys Glu Val Gly Thr Asp Gly Leu Leu Ala Thr
465             470                 475                 480

Ser Leu Asp Ala Thr Cys Asp Val Ala Cys Leu Met Phe Asp Gly Ser
                485                 490                 495

Asp Pro Lys Ser Phe Ala His Cys Ala Ser Val Tyr Lys His His Tyr
            500                 505                 510

Met Asp Gly Gln Thr Pro Cys Leu Phe Val Ser Ser Lys Ala Asp Leu
        515                 520                 525

Pro Glu Gly Val Ala Val Ser Gly Pro Ser Pro Ala Glu Phe Cys Arg
    530                 535                 540

Lys His Arg Leu Pro Ala Pro Val Pro Phe Ser Cys Ala Gly Pro Ala
545                 550                 555                 560

Glu Pro Ser Thr Thr Ile Phe Thr Gln Leu Ala Thr Met Ala Ala Phe
                565                 570                 575

Pro His Leu Val His Ala Glu Leu His Pro Ser Ser Phe Trp Leu Arg
            580                 585                 590

Gly Leu Leu Gly Val Val Gly Ala Ala Val Ala Val Leu Ser Phe
        595                 600                 605

Ser Leu Tyr Arg Val Leu Val Lys Ser Gln
    610                 615

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      AFP forward primer (5'-3')

<400> SEQUENCE: 41
aactattggc ctgtggcgag                                                   20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      AFP reverse primer (5'-3')

<400> SEQUENCE: 42
tcatccacca ccaagctgc                                                    19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      ALDH2 forward primer (5'-3')

<400> SEQUENCE: 43
gtttggagcc cagtcaccct                                                   20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      ALDH2 reverse primer (5'-3')

-continued

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
    APCS forward primer (5'-3')

<400> SEQUENCE: 45
ggccaggaat atgaacaagc c                                        21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
    APCS reverse primer (5'-3')

<400> SEQUENCE: 46
cttctccagc ggtgtgatca                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
    APOC4 forward primer (5'-3')

<400> SEQUENCE: 47
ggagctgctg gagacagtgg                                          20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
    APOC4 reverse primer (5'-3')

<400> SEQUENCE: 48
tttggattcg aggaaccagg                                          20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
    AQP9 forward primer (5'-3')

<400> SEQUENCE: 49
gcttcctccc tgggactga                                           19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
    AQP9 reverse primer (5'-3')

<400> SEQUENCE: 50
caaccaaagg gcccactaca                                               20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      BUB1 forward primer (5'-3')

<400> SEQUENCE: 51
acccctgaaa aagtgatgcc t                                             21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      BUB1 reverse primer (5'-3')

<400> SEQUENCE: 52
tcatcctgtt ccaaaaatcc g                                             21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      C1S forward primer (5'-3')

<400> SEQUENCE: 53
ttgtttggtt ctgtcatccg c                                             21

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      C1S reverse primer (5'-3')

<400> SEQUENCE: 54
tggaacacat ttcggcagc                                                19

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      CYP2E1 forward primer (5'-3')

<400> SEQUENCE: 55
caaccaagaa tttcctgatc cag                                           23

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      CYP2E1 reverse primer (5'-3')

<400> SEQUENCE: 56
aagaaacaac tccatgcgag c                                            21

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      DLG7 forward primer (5'-3')

<400> SEQUENCE: 57
gcaggaagaa tgtgctgaaa ca                                           22

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      DLG7 reverse primer (5'-3')

<400> SEQUENCE: 58
tccaagtctt tgagaagggc c                                            21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      DUSP9 forward primer (5'-3')

<400> SEQUENCE: 59
cggaggccat tgagttcatt                                              20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      DUSP9 reverse primer (5'-3')

<400> SEQUENCE: 60
accaggtcat aggcatcgtt g                                            21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      E2F5 forward primer (5'-3')

<400> SEQUENCE: 61
ccattcaggc accttctggt                                              20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      E2F5 reverse primer (5'-3')

<400> SEQUENCE: 62
acgggcttag atgaactcga ct                                             22

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      GHR forward primer (5'-3')

<400> SEQUENCE: 63
cttggcactg gcaggatca                                                 19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      GHR reverse primer (5'-3')

<400> SEQUENCE: 64
aggtgaacgg cacttggtg                                                 19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      HPD forward primer (5'-3')

<400> SEQUENCE: 65
atcttcacca aaccggtgca                                                20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      HPD reverse primer (5'-3')

<400> SEQUENCE: 66
ccatgttggt gaggttaccc c                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      IGSF1 forward primer (5'-3')

<400> SEQUENCE: 67
cactcacact gaaaaacgcc c                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      IGSF1 reverse primer (5'-3')

<400> SEQUENCE: 68
gggtggagca attgaaagtc a                                              21

```
<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      NLE1 forward primer (5'-3')

<400> SEQUENCE: 69
atgtgaaggc ccagaagctg                                              20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      NLE1 reverse primer (5'-3')

<400> SEQUENCE: 70
gagaacttcg ggccgtctc                                               19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      RPL10A forward primer (5'-3')

<400> SEQUENCE: 71
tatcccccac atggacatcg                                              20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      RPL10A reverse primer (5'-3')

<400> SEQUENCE: 72
tgccttattt aaacctgggc c                                            21

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      ACTG1 forward primer (5'-3')

<400> SEQUENCE: 73
gatggccagg tcatcaccat                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      ACTG1 reverse primer (5'-3')

<400> SEQUENCE: 74
acaggtcttt gcggatgtcc                                              20
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      EFF1A1 forward primer (5'-3')

<400> SEQUENCE: 75
tcacccgtaa ggatggcaat                                                20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      EFF1A1 reverse primer (5'-3')

<400> SEQUENCE: 76
cggccaacag gaacagtacc                                                20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      PNN forward primer (5'-3')

<400> SEQUENCE: 77
cctttctggt cctggtggag                                                20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      PNN reverse primer (5'-3')

<400> SEQUENCE: 78
tgattctctt ctggtccgac g                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      RHOT2 forward primer (5'-3')

<400> SEQUENCE: 79
ctgcggacta tctctcccct c                                              21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      RHOT2 reverse primer (5'-3')

<400> SEQUENCE: 80
aaaaggcttt gcagctccac                                                20

-continued

```
<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      AFP forward primer

<400> SEQUENCE: 81
gccagtgctg cacttcttca                                              20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      AFP reverse primer

<400> SEQUENCE: 82
tgtttcatcc accaccaagc t                                            21

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      AFP probe

<400> SEQUENCE: 83
atgccaacag gaggccatgc ttca                                         24

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      ALDH2 forward primer

<400> SEQUENCE: 84
tgcaggatgg catgaccat                                               19

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      ALDH2 reverse primer

<400> SEQUENCE: 85
tcttgaactt caggatctgc atca                                         24

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      ALDH2 probe

<400> SEQUENCE: 86
ccaaggagga gatcttcggg cca                                          23

<210> SEQ ID NO 87
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      APCS forward primer

<400> SEQUENCE: 87
agctgggagt cctcatcagg ta                                             22

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      APCS reverse primer

<400> SEQUENCE: 88
cgcagaccct ttttcaccaa                                                20

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
      APCS probe

<400> SEQUENCE: 89
tgctgaattt tggatcaatg ggacacc                                        27

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      APOC4 forward primer

<400> SEQUENCE: 90
tgaaggagct gctggagaca                                                20

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      APOC4 reverse primer

<400> SEQUENCE: 91
cgggctccag aaccattg                                                  18

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      APOC4 probe

<400> SEQUENCE: 92
tggtgaacag gaccagagac gggtg                                          25

<210> SEQ ID NO 93
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      AQP9 forward primer

<400> SEQUENCE: 93
gccatcggcc tcctgatta                                                        19

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      AQP9 reverse primer

<400> SEQUENCE: 94
gttcatggca cagccactgt                                                       20

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      AQP9 probe

<400> SEQUENCE: 95
tgtcattgct tcctccctgg gactg                                                 25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      BUB1 forward primer

<400> SEQUENCE: 96
acatctggtt ttcagtgtgt tgaga                                                 25

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      BUB1 reverse primer

<400> SEQUENCE: 97
gttgcagcaa ccccaaagta a                                                     21

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      BUB1 probe

<400> SEQUENCE: 98
tcagcaacaa accatggaac taccagatcg                                            30

<210> SEQ ID NO 99
<211> LENGTH: 23
<212> TYPE: DNA
```

<213> ORGANISM: Artificial Sequence
<220> FEATURE:
<223> OTHER INFORMATION: Description of Artificial Sequence: Synthetic
      C1S forward primer

<400> SEQUENCE: 99
tcccaatgac aagaccaaat tct                                          23

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      C1S reverse primer

<400> SEQUENCE: 100
agagcccata ggtcccacac t                                            21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      C1S probe

<400> SEQUENCE: 101
cgcagctggc ctggtgtcct g                                            21

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      CYP2E1 forward primer

<400> SEQUENCE: 102
catgagattc agcggttcat ca                                           22

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      CYP2E1 reverse primer

<400> SEQUENCE: 103
ggtgtctcgg gttgcttca                                               19

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      CYP2E1 probe

<400> SEQUENCE: 104
cctcgtgccc tccaacctgc c                                            21

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
DLG7 forward primer

<400> SEQUENCE: 105
gctggagagg agacatcaag aac                                              23

<210> SEQ ID NO 106
<211> LENGTH: 27
<212> TYPE: DNA
<213> ORGANISM: Artificial Sequence
<220> FEATURE:
<223> OTHER INFORMATION: Description of Artificial Sequence: Synthetic
DLG7 reverse primer

<400> SEQUENCE: 106
cctggttgta gaggtgaaaa agtaatc                                          27

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
DLG7 probe

<400> SEQUENCE: 107
tgccagacac atttcttttg gtggtaacc                                        29

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
DUSP9 forward primer

<400> SEQUENCE: 108
ggcctacctc atgcagaagc t                                                21

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
DUSP9 reverse primer

<400> SEQUENCE: 109
gggagatgtt agacttcttc ctcttg                                           26

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
DUSP9 probe

<400> SEQUENCE: 110
cacctctctc tcaacgatgc ctatgacctg                                       30

<210> SEQ ID NO 111
<211> LENGTH: 19
<212> TYPE: DNA
<213> ORGANISM: Artificial Sequence
<220> FEATURE:

```
<223> OTHER INFORMATION: Description of Artificial Sequence: Synthetic
      E2F5 forward primer

<400> SEQUENCE: 111
cctgttcccc cacctgatg                                                      19

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      E2F5 reverse primer

<400> SEQUENCE: 112
tttctgtgga gtcactggag tca                                                 23

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      E2F5 probe

<400> SEQUENCE: 113
cctcacacag ccttcctccc agtcc                                               25

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      GHR forward primer

<400> SEQUENCE: 114
cccaggtgag cgacattaca                                                     20

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      GHR reverse primer

<400> SEQUENCE: 115
catccctgcc ttattctttt gg                                                  22

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      GHR probe

<400> SEQUENCE: 116
cagcaggtag tgtggtcctt tccccg                                              26

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
```

HPD forward primer

<400> SEQUENCE: 117
cccacgctct tcctggaa                                              18

<210> SEQ ID NO 118
<211> LENGTH: 17
<212> TYPE: DNA
<213> ORGANISM: Artificial Sequence
<220> FEATURE:
<223> OTHER INFORMATION: Description of Artificial Sequence: Synthetic
      HPD reverse primer

<400> SEQUENCE: 118
ttgccggctc caaaacc                                               17

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      HPD probe

<400> SEQUENCE: 119
tcatccagcg ccacaaccac ca                                         22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      IGSF1 forward primer

<400> SEQUENCE: 120
gaccattgcc cttgaagagt gt                                         22

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      IGSF1 reverse primer

<400> SEQUENCE: 121
gagaggttga tgaaggagaa ttgg                                       24

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      IGSF1 probe

<400> SEQUENCE: 122
accaagaagg agaaccaggc acccc                                      25

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      NLE1 forward primer

```
<400> SEQUENCE: 123
tgcctccttt gacaagtcca t                                              21

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      NLE1 reverse primer

<400> SEQUENCE: 124
cgcgtaggga agccaggta                                                 19

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      NLE1 probe

<400> SEQUENCE: 125
tgggatggca ggacgggca                                                 19

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      RPL10A forward primer

<400> SEQUENCE: 126
tcggcccagg tttaaataag g                                              21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      RPL10A reverse primer

<400> SEQUENCE: 127
ccactttggc caccatgttt                                                20

<210> SEQ ID NO 128
<211> LENGTH: 27
<212> TYPE: DNA
<213> ORGANISM: Artificial Sequence
<220> FEATURE:
<223> OTHER INFORMATION: Description of Artificial Sequence: Synthetic
      RPL10A probe

<400> SEQUENCE: 128
agttcccttc cctgctcaca cacaacg                                        27

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      ACTG1 forward primer
```

```
<400> SEQUENCE: 129
ggcgcccagc accat                                                    15

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      ACTG1 reverse primer

<400> SEQUENCE: 130
ccgatccaca ccgagtactt g                                             21

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      ACTG1 probe

<400> SEQUENCE: 131
atcaagatca tcgcaccccc agagc                                         25

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      EFF1A1 forward primer

<400> SEQUENCE: 132
gcggtgggtg tcatcaaag                                                19

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      EFF1A1 reverse primer

<400> SEQUENCE: 133
tgggcagact tggtgacctt                                               20

<210> SEQ ID NO 134
<211> LENGTH: 26
<212> TYPE: DNA
<213> ORGANISM: Artificial Sequence
<220> FEATURE:
<223> OTHER INFORMATION: Description of Artificial Sequence: Synthetic
      EFF1A1 probe

<400> SEQUENCE: 134
agtggacaag aaggctgctg gagctg                                        26

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      PNN forward primer

<400> SEQUENCE: 135
```

```
gaattcccgg tccgacaga                                                    19

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      PNN reverse primer

<400> SEQUENCE: 136
tttcggtctc tttcacttct tgaa                                              24

<210> SEQ ID NO 137
<211> LENGTH: 38
<212> TYPE: DNA
<213> ORGANISM: Artificial Sequence
<220> FEATURE:
<223> OTHER INFORMATION: Description of Artificial Sequence: Synthetic
      PNN probe

<400> SEQUENCE: 137
agaggtctat atcagagagt agtcgatcag gcaaaaga                               38

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      RHOT2 forward Primer

<400> SEQUENCE: 138
cccagcacca ccatcttcac                                                   20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      RHOT2 reverse primer

<400> SEQUENCE: 139
ccagaaggaa gagggatgca                                                   20

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      RHOT2 probe

<400> SEQUENCE: 140
cagctcgcca ccatggccg                                                    19
```

MOLECULAR SIGNATURE OF LIVER TUMOR GRADE AND USE TO EVALUATE PROGNOSIS AND THERAPEUTIC REGIMEN

SEQUENCE LISTING

The instant application contains a Sequence Listing which has been submitted in ASCII format via EFS-Web and is hereby incorporated by reference in its entirety. Said ASCII copy, created on Dec. 4, 2012, is named 09837601.txt and is 302,498 bytes in size.

The present invention relates to a method to in vitro determine the grade of a liver tumor in a sample previously obtained from a patient, using a molecular signature based on the expression of a set of genes comprising at least 2, especially has or consist of 2 to 16 genes, preferably a set of 16 genes. In a particular embodiment, the method focuses on hepatoblastoma (HB) or hepatocellular carcinoma (HCC), in adults or in children. The invention is also directed to sets of primers, sets of probes, compositions, kits or arrays, comprising primers or probes specific for a set of genes comprising at least 2 genes, especially has or consists of 2 to 16 genes, preferably exactly 16 genes. Said sets, kits and arrays are tools suitable to determine the grade of a liver tumor in a patient.

The liver is a common site of metastases from a variety of organs such as lung, breast, colon and rectum. However, liver is also a site of different kinds of cancerous tumors that start in the liver (primary liver cancers). The most frequent is the Hepatocellular Carcinoma (HCC) (about 3 out of 4 primary liver cancers are this type) and is mainly diagnosed in adults. In the United States approximately 10,000 new patients are diagnosed with hepatocellular carcinoma each year. Less frequent liver tumours are cholangiocarcinoma (CC) in adults and hepatoblastoma (HB) in children.

The prognosis and treatment options associated with these different kinds of cancers is difficult to predict, and is dependent in particular on the stage of the cancer (such as the size of the tumor, whether it affects part or all of the liver, has spread to other places in the body or its aggressiveness). Therefore, it is important for clinicians and physicians to establish a classification of primary liver cancers (HCC or HB) to propose the most appropriate treatment and adopt the most appropriate surgery strategy. Some factors are currently used (degree of local invasion, histological types of cancer with specific grading, tumour markers and general status of the patient) but have been found to not be accurate and sufficient enough to ensure a correct classification.

As far as the HB is concerned, the PRETEXT (pre-treatment extent of disease) system designed by the International Childhood Liver Tumor Strategy Group (SIOPEL) is a non invasive technique commonly used by clinicians, to assess the extent of liver cancer, to determine the time of surgery and to adapt the treatment protocol. This system is based on the division of the liver in four parts and the determination of the number of liver sections that are free of tumor (Aronson et al. 2005; Journal of Clinical Oncology; 23(6): 1245-1252). A revised staging system taking into account other criteria, such as caudate lobe involvement, extrahepatic abdominal disease, tumor focality, tumor rupture or intraperitoneal haemorrhage, distant metastases, lymph node metastases, portal vein involvement and involvement of the IVC (inferior vena cava) and/or hepatic veins, has been recently proposed (Roebuck; 2007; Pediatr Radiol; 37: 123-132). However, the PRETEXT system, even if reproducible and providing good prognostic value, is based on imaging and clinical symptoms, making this system dependent upon the technicians and clinicians.

There is thus a need for a system, complementary to the PRETEXT system, based on genetic and molecular features of the liver tumors.

The present invention concerns a method or process of profiling gene expression for a set of genes, in a sample previously obtained from a patient diagnosed for a liver tumor. In a particular embodiment said method is designed to determine the grade of a liver tumor in a patient.

By "liver tumor" or "hepatic tumor", it is meant a tumor originating from the liver of a patient, which is a malignant tumor (comprising cancerous cells), as opposed to a benign tumor (non cancerous) which is explicitly excluded. Malignant liver tumors encompass two main kinds of tumors: hepatoblastoma (HB) or hepatocellular carcinoma (HCC). These two tumor types can be assayed for the presently reported molecular signature. However, the present method may also be used to assay malignant liver tumors which are classified as unspecified (non-HB, non-HCC).

The present method may be used to determine the grade of a liver tumor or several liver tumors of the same patient, depending on the extent of the liver cancer. For convenience, the expression "a liver tumor" will be used throughout the specification to possibly apply to "one or several liver tumor(s)". The term "neoplasm" may also be used as a synonymous of "tumor".

In a particular embodiment, the tumor whose grade has to be determined is located in the liver. The presence of the tumor(s) in the liver may be diagnosed by ultrasound scan, x-rays, blood test, CT scans (computerised tomography) and/or MRI scans (magnetic resonance imaging).

In a particular embodiment, the tumor, although originating from the liver, has extended to other tissues or has given rise to metastasis.

In a particular embodiment, the patient is a child i.e., a human host who is under 20 years of age according to the present application. Therefore, in a particular embodiment, the liver tumor is a paediatric HB or a paediatric HCC. In another embodiment, the liver tumor is an adult HCC.

A grade is defined as a subclass of the liver tumor, corresponding to prognostic factors, such as tumor status, liver function and general health status. The present method of the invention allows or at least contributes to differentiating liver tumors having a good prognosis from tumors with a bad prognosis, in terms of evolution of the patient's disease. A good prognosis tumor is defined as a tumor with good survival probability for the patient (more than 80% survival at two years for HB and more than 50% survival at two years for HCC), low probability of metastases and good response to treatment for the patient. In contrast, a bad prognosis tumor is defined as a tumor with an advanced stage, such as one having vascular invasion or/and extrahepatic metastasis, and associated with a low survival probability for the patient (less than 50% survival in two years).

The method of the invention is carried out on a sample isolated from the patient who has previously been diagnosed for the tumor(s) and who, optionally, may have been treated by surgery. In a preferred embodiment, the sample is the liver tumor (tumoral tissue) or of one of the liver tumors identified by diagnosis imaging and obtained by surgery or a biopsy of this tumor. The tumor located in the liver tumor is called the primary tumor.

In another embodiment, the sample is not the liver tumor, but is representative of this tumor. By "representative", it is meant that the sample is regarded as having the same features as the primary tumors, when considering the gene expression profile assayed in the present invention. Therefore, the sample may also consist of metastatic cells (secondary tumors spread into different part(s) of the body) or of a biological fluid containing cancerous cells (such as blood).

The sample may be fixed, for example in formalin (formalin fixed). In addition or alternatively, the sample may be embedded in paraffin (paraffin-embedded) or equivalent products. In particular, the tested sample is a formalin-fixed, paraffin-embedded (FFPE) sample.

One advantage of the method of the present invention is that, despite the possible heterogeneity of some liver tumors (comprising epithelial tumor cells at different stages of liver differentiation within the same tumor), the assay has proved to be reproducible and efficient on liver tumor biopsies obtained from any part of the whole tumor. Therefore, there is no requirement for the isolation of cells presenting particular features except from the fact that they are obtained from a liver tumor or are representative thereof, to carry out the gene expression profile assay.

In a particular embodiment, the tumor originates from a patient having a Caucasian origin, in particular European, North American, Australian, New-Zealander or Afrikaners.

In a first step, the method or process of the invention comprises assaying the expression level of a set of genes in a sample, in order to get an expression profile thereof.

By "expression of a set of genes" (or "gene expression"), it is meant assaying, in particular detecting, the product or several products resulting from the expression of a gene, this product being in the form of a nucleic acid, especially RNA, mRNA, cDNA, polypeptide, protein or any other formats. In a particular embodiment, the assay of the gene expression profile comprises detecting a set of nucleotide targets, each nucleotide target corresponding to the expression product of a gene encompassed in the set.

The expression "nucleotide target" means a nucleic acid molecule whose expression must be measured, preferably quantitatively measured. By "expression measured", it is meant that the expression product(s), in particular the transcription product(s) of a gene, are measured. By "quantitative" it is meant that the method is used to determine the quantity or the number of copies of the expression products, in particular the transcription products or nucleotide targets, originally present in the sample. This must be opposed to the qualitative measurement, whose aim is to determine the presence or absence of said expression product(s) only.

A nucleotide target is in particular a RNA, and most particularly a total RNA. In a preferred embodiment, the nucleotide target is mRNA or transcripts. According to the methods used to measure the gene expression level, the mRNA initially present in the sample may be used to obtain cDNA or cRNA, which is then detected and possibly measured.

In an embodiment, the expression of the gene is assayed directly on the sample, in particular in the tumor. In an alternative embodiment, the expression products or the nucleotide targets are prepared from the sample, in particular are isolated or even purified. When the nucleotide targets are mRNA, a further step comprising or consisting in the retro-transcription of said mRNA into cDNA (complementary DNA) may also be performed prior to the step of detecting expression. Optionally, the cDNA may also be transcribed in vitro to provide cRNA.

During the step of preparation, and before assaying the expression, the expression product(s) or the nucleotide target(s) may be labelled, with isotopic (such as radioactive) or non isotopic (such as fluorescent, coloured, luminescent, affinity, enzymatic, magnetic, thermal or electrical) markers or labels.

It is noteworthy that steps carried out for assaying the gene expression must not alter the qualitative or the quantitative expression (number of copies) of the expression product(s) or of the nucleotide target(s), or must not interfere with the subsequent step comprising assaying the qualitative or the quantitative expression of said expression product(s) or nucleotide target(s).

The step of profiling gene expression comprises determining the expression of a set of genes. Such a set is defined as a group of genes that must be assayed for one test, and especially performed at the same time, on the same patient's sample. A set comprises at least 2 and has especially from 2 to 16 genes, said 2 to 16 genes being chosen from the 16 following genes: alpha-fetoprotein (AFP), aldehyde dehydrogenase 2 (ALDH2), amyloid P component serum (APCS), apolipoprotein C-IV (APOC4), aquaporin 9 (AQP9), budding uninhibited by benzimidazoles 1 (BUB1), complement component 1 (C1S), cytochrome p450 2E1 (CYP2E1), discs large homolog 7 (DLG7), dual specificity phosphatase 9 (DUSP9), E2F5 transcription factor (E2F5), growth hormone receptor (GHR), 4-hydroxyphenylpyruvase dioxygenase (HPD), immunoglogulin superfamily member 1 (IGSF1), Notchless homolog 1 (NLE1) and the ribosomal protein L10a (RPL10A) genes.

A complete description of these 16 genes is given in Table 1. This table lists, from left to right, the symbol of the gene, the complete name of the gene, the number of the SEQ ID provided in the sequence listing, the Accession Number from the NCBI database on June 2008, the human chromosomal location and the reported function (when known).

A set of genes comprises at least 2 out the 16 genes of Table 1, and particularly at least or exactly 2, 3, 4, 5, 6, 7, 8, 9, 10, 11, 12, 13, 14 or 15 out of the 16 genes of Table 1. In a particular embodiment, the set comprises or consists of the 16 genes of Table 1 i.e., the set of genes comprises or consists of AFP, ALDH2, APCS, APOC4, AQP9, BUB1, C1S, CYP2E1, DLG7, DUSP9, E2F5, GHR, HPD, IGSF1, NLE1 and RPL10A genes. Accordingly, unless otherwise stated when reference is made in the present application to a set of 2 to 16 genes of Table 1, it should be understood as similarly applying to any number of genes within said 2 to 16 range.

In other particular embodiments, the set of genes comprises or consists of one of the following sets: (a) the E2F5 and HPD genes, (b) the APCS, BUB1, E2F5, GHR and HPD genes, (c) the ALDH2, APCS, APOC4, BUB1, C1S, CYP2E1, E2F5, GHR and HPD genes, (d) the ALDH2, APCS, APOC4, AQP9, BUB1, C1S, DUSP9, E2F5 and RPL10A genes, or (e) the ALDH2, APCS, APOC4, AQP9, C1S, CYP2E1, E2F5, GHR, IGSF1 and RPL10A genes.

As indicated by the expression "comprises from 2 to 16 genes of Table 1", the set may, besides the specific genes of Table 1, contain additional genes not listed in Table 1. This means that the set must comprises from 2 to 16 genes of Table 1, i.e. 2 to 16 genes of Table 1 (in particular 2, 3, 4, 5, 6, 7, 8, 9, 10, 11, 12, 13, 14, 15, or 16 genes), and optionally comprises one or more additional genes. Said set may also be restricted to said 2 to 16 genes of Table 1.

Additional genes may be selected for the difference of expression observed between the various grades of liver cancer, in particular between a tumor of good prognosis and a tumor of poor prognosis.

TABLE 1

| symbol | Gene name | mRNA SEQ ID | Accession No | Location | Function | Protein SEQ ID |
|---|---|---|---|---|---|---|
| AFP | alpha-fetoprotein | 1 | NM_001134 | 4q11-q13 | plasma protein synthesized by the fetal liver | 2 |
| ALDH2 | aldehyde dehydrogenase 2 family (mitochondrial) | 3 | NM_000690 | 12q24.2 | liver enzyme involved in alcohol metabolism | 4 |
| APCS | amyloid P component, serum | 5 | NM_001639 | 1q21-q23 | secreted glycoprotein | 6 |
| APOC4 | apolipoprotein C-IV | 7 | NM_001646 | 19q13.2 | secreted liver protein | 8 |
| AQP9 | aquaporin 9 | 9 | NM_020980 | 15q22.1-22.2 | water-selective membrane channel | 10 |
| BUB1 | BUB1 budding uninhibited by benzimidazoles 1 homolog (yeast) | 11 | AF043294 | 2q14 | kinase involved in spindle checkpoint | 12 |
| C1S | complement component 1, s subcomponent | 13 | M18767 | 12p13 | component of the cleavage and polyadenylation specificity factor complex | 14 |
| CYP2E1 | cytochrome P450, family 2, subfamily E, polypeptide 1 | 15 | AF182276 | 10q24.3-qter | cytochrome P450 family member involved in drug metabolism | 16 |
| DLG7 | discs, large homolog7 (*Drosophila*) (DLGAP5) | 17 | NM_014750 | 14q22.3 | cell cycle regulator involved in kinetocore formation | 18 |
| DUSP9 | dual specificity phosphatase 9 | 19 | NM_001395 | Xq28 | phosphatase involved in regulation of MAP Kinases | 20 |
| E2F5 | E2F transcription factor 5, p130-binding | 21 | U15642 | 8q21.2 | transcription factor involved in cell cycle regulation | 22 |
| GHR | Growth hormone receptor | 23 | NM_000163 | 5p13-p12 | transmembrane receptor for growth hormone | 24 |
| HPD | 4-hydroxyphenylpyruvate dioxygenase | 25 | NM_002150 | 12q24-qter | enzyme involved in amino-acid degradation | 26 |
| IGSF1 | immunoglobulin superfamily, member 1 | 27 | NM_001555 | Xq25 | cell recognition and regulation of cell behavior | 28 |
| NLE1 | notchless homolog 1 (*Drosophila*) | 29 | NM_018096 | 17q12 | unknown | 30 |
| RPL10A | ribosomal protein L10a | 31 | NM_007104 | 6p21.3-p21.2 | ribosomal protein of 60S subunit | 32 |

The invention also relates to a set of genes comprising or consisting of the 16 genes of Table 1 (i.e., AFP, ALDH2, APCS, APOC4, AQP9, BUB1, C1S, CYP2E1, DLG7, DUSP9, E2F5, GHR, HPD, IGSF1, NLE1 and RPL10A genes), in which 1, 2, 3, 4 or 5 genes out of the 16 genes are substituted by a gene presenting the same features in terms of difference of expression between a tumor of a good prognosis and a tumor of poor prognosis.

In a particular embodiment, the number of genes of the set does not exceed 100, particularly 50, 30, 20, more particularly 16 and even more particularly is maximum 5, 6, 7, 8, 9 or 10.

When considering adding or substituting a gene or several genes to the disclosed set, the person skilled in the art will consider one or several of the following features:

(a) the added gene(s) and/or the substituted gene(s) of Table 1 must present the same features in terms of difference of expression between a tumor of a good prognosis and a tumor of poor prognosis as the genes of Table 1 when taken as a whole. Thus, the expression of the added gene or of the substituted gene in a tumor of a good prognosis is either overexpressed or underexpressed of a factor of at least 2, preferably of at least 5, and more preferably of at least 10, as compared to its expression in a tumor of poor prognosis.

(b) besides presenting the feature in a), the added gene and/or the substituted gene may also provide, in combination with the other genes of the set, discriminant results with respect to the grade of the liver tumors; this discrimination is reflected by the homogeneity of expression profile of this gene in the tumors of a good prognosis on the one hand, and the tumors of poor prognosis in the other hand; and (c) finally, besides features of a) and/or b), the added gene and/or the substituted gene is optionally chosen among genes that are involved in liver differentiation, in particular having a specific expression in fetal liver, or genes that are involved in proliferation, for example in mitosis or associated with ribosomes.

Examples of genes which can be added or may replace genes of the set may be identified in following Table 2.

TABLE 2 list of genes according to p value.

| Gene symbol | mean rC1 | mean rC2 | ratio rC2/rC1 | Parametric p-value | FDR | Description |
|---|---|---|---|---|---|---|
| IPO4 | 123.7 | 248.3 | 2.0 | 2.00E−07 | 0.00036 | importin 4 |
| CPSF1 | 467.8 | 1010.7 | 2.2 | 2.00E−07 | 0.00036 | cleavage and polyadenylation specific factor 1, 160 kDa |
| MCM4 | 25.8 | 90.7 | 3.5 | 1.10E−06 | 0.00115 | MCM4 minichromosome maintenance deficient 4 (*S. cerevisiae*) |
| EIF3S3 | 1319 | 2601.2 | 2.0 | 1.20E−06 | 0.00119 | eukaryotic translation initiation factor 3, subunit 3 gamma, 40 kDa |
| NCL | 1319 | 2655.6 | 2.0 | 1.30E−06 | 0.00122 | nucleolin |
| CDC25C | 35.7 | 99.3 | 2.8 | 1.40E−06 | 0.00124 | cell division cycle 25C |
| CENPA | 28.2 | 78.4 | 2.8 | 1.50E−06 | 0.00124 | centromere protein A, 17 kDa |
| KIF14 | 24.7 | 54.2 | 2.2 | 1.50E−06 | 0.00124 | kinesin family member 14 |
| IPW | 145.7 | 397.6 | 2.7 | 1.90E−06 | 0.0015 | imprinted in Prader-Willi syndrome |
| KNTC2 | 26.8 | 65.1 | 2.4 | 2.20E−06 | 0.00157 | kinetochore associated 2 |
| TMEM48 | 26.4 | 71.7 | 2.7 | 2.30E−06 | 0.00157 | transmembrane protein 48 |
| BOP1 | 87.2 | 270.9 | 3.1 | 2.30E−06 | 0.00157 | block of proliferation 1 |

TABLE 2-continued list of genes according to p value.

| Gene symbol | mean rC1 | mean rC2 | ratio rC2/rC1 | Parametric p-value | FDR | Description |
|---|---|---|---|---|---|---|
| EIF3S9 | 170 | 372.4 | 2.2 | 2.30E−06 | 0.00157 | eukaryotic translation initiation factor 3, subunit 9 eta, 116 kDa |
| PH-4 | 340.9 | 168.2 | 0.5 | 2.40E−06 | 0.00158 | hypoxia-inducible factor prolyl 4-hydroxylase |
| SMC4L1 | 151.5 | 359.3 | 2.4 | 2.50E−06 | 0.0016 | SMC4 structural maintenance of chromosomes 4-like 1 (yeast) |
| TTK | 23.7 | 74.2 | 3.1 | 2.60E−06 | 0.00161 | TTK protein kinase |
| LAMA3 | 696 | 136.3 | 0.2 | 2.80E−06 | 0.00168 | laminin, alpha 3 |
| C10orf72 | 192.6 | 67.7 | 0.4 | 2.90E−06 | 0.00169 | Chromosome 10 open reading frame 72 |
| TPX2 | 73.4 | 401.5 | 5.5 | 3.10E−06 | 0.00171 | TPX2, microtubule-associated, homolog (*Xenopus laevis*) |
| MSH2 | 75.5 | 212.1 | 2.8 | 3.20E−06 | 0.00171 | mutS homolog 2, colon cancer, nonpolyposis type 1 (*E. coli*) |
| DKC1 | 358.1 | 833.5 | 2.3 | 3.20E−06 | 0.00171 | dyskeratosis congenita 1, dyskerin |
| STK6 | 86.4 | 395.3 | 4.6 | 3.30E−06 | 0.00172 | serine/threonine kinase 6 |
| CCT6A | 200.5 | 526.6 | 2.6 | 3.50E−06 | 0.00173 | chaperonin containing TCP1, subunit 6A (zeta 1) |
| SULT1C1 | 67.5 | 314.8 | 4.7 | 3.50E−06 | 0.00173 | sulfotransferase family, cytosolic, 1C, member 1 |
| ILF3 | 142.3 | 294.5 | 2.1 | 3.70E−06 | 0.00174 | interleukin enhancer binding factor 3, 90 kDa |
| IMPDH2 | 916.9 | 2385.6 | 2.6 | 3.70E−06 | 0.00174 | IMP (inosine monophosphate) dehydrogenase 2 |
| HIC2 | 63.4 | 208.8 | 3.3 | 3.90E−06 | 0.00179 | hypermethylated in cancer 2 |
| AFM | 1310.3 | 237.4 | 0.2 | 4.10E−06 | 0.00184 | afamin |
| MCM7 | 187.3 | 465.3 | 2.5 | 4.30E−06 | 0.00189 | MCM7 minichromosome maintenance deficient 7 (*S. cerevisiae*) |
| CNAP1 | 70.2 | 177.5 | 2.5 | 4.40E−06 | 0.00189 | chromosome condensation-related SMC-associated protein 1 |
| CBARA1 | 958 | 475 | 0.5 | 4.60E−06 | 0.00194 | calcium binding atopy-related autoantigen 1 |
| PLA2G4C | 123.3 | 51.2 | 0.4 | 4.90E−06 | 0.00194 | phospholipase A2, group IVC (cytosolic, calcium-independent) |
| CPSF1 | 301.9 | 616 | 2.0 | 5.00E−06 | 0.00194 | cleavage and polyadenylation specific factor 1, 160 kDa |
| SNRPN | 30.9 | 100.6 | 3.3 | 5.00E−06 | 0.00194 | Small nuclear ribonucleoprotein polypeptide N |
| RPL5 | 2754.8 | 4961 | 1.8 | 5.20E−06 | 0.00194 | ribosomal protein L5 |
| C1R | 1446.5 | 366.4 | 0.3 | 5.30E−06 | 0.00194 | complement component 1, r subcomponent |
| C16orf34 | 630.4 | 1109.6 | 1.8 | 5.30E−06 | 0.00194 | chromosome 16 open reading frame 34 |
| PHB | 309.3 | 915.1 | 3.0 | 5.30E−06 | 0.00194 | prohibitin |
| BZW2 | 387.4 | 946.4 | 2.4 | 5.40E−06 | 0.00194 | basic leucine zipper and W2 domains 2 |
| ALAS1 | 1075.8 | 466.5 | 0.4 | 5.50E−06 | 0.00194 | aminolevulinate, delta-, synthase 1 |
| FLJ20364 | 48.6 | 112.4 | 2.3 | 5.70E−06 | 0.00198 | hypothetical protein FLJ20364 |
| RANBP1 | 593.7 | 1168.1 | 2.0 | 5.90E−06 | 0.00201 | RAN binding protein 1 |
| SKB1 | 354.7 | 687.4 | 1.9 | 6.20E−06 | 0.00208 | SKB1 homolog (*S. pombe*) |
| ABHD6 | 402.2 | 196.9 | 0.5 | 6.50E−06 | 0.00213 | abhydrolase domain containing 6 |
| CCNB1 | 60.4 | 330 | 5.5 | 6.60E−06 | 0.00213 | cyclin B1 |
| NOL5A | 246.9 | 716.2 | 2.9 | 7.00E−06 | 0.00213 | nucleolar protein 5A (56 kDa with KKE/D repeat) |
| RPL8 | 3805.7 | 7390.5 | 1.9 | 7.00E−06 | 0.00213 | ribosomal protein L8 |
| BLNK | 211.1 | 39.8 | 0.2 | 7.10E−06 | 0.00213 | B-cell linker |
| BYSL | 167.3 | 269.7 | 1.6 | 7.10E−06 | 0.00213 | bystin-like |
| UBE1L | 247.6 | 142.3 | 0.6 | 7.20E−06 | 0.00213 | ubiquitin-activating enzyme E1-like |
| CHD7 | 118.6 | 312 | 2.6 | 7.40E−06 | 0.00215 | chromodomain helicase DNA binding protein 7 |
| DKFZp762E1312 | 70.2 | 219.4 | 3.1 | 7.60E−06 | 0.00218 | hypothetical protein DKFZp762E1312 (HJURP) |
| NUP210 | 178.4 | 284.9 | 1.6 | 7.70E−06 | 0.00218 | nucleoporin 210 kDa |
| PLK1 | 72.8 | 185.2 | 2.5 | 7.90E−06 | 0.0022 | polo-like kinase 1 (*Drosophila*) |
| ENPEP | 116.2 | 29.4 | 0.3 | 8.00E−06 | 0.0022 | glutamyl aminopeptidase (aminopeptidase A) |
| HCAP-G | 17.7 | 57.8 | 3.3 | 8.40E−06 | 0.00228 | chromosome condensation protein G |
| UGT2B4 | 1117.8 | 246.7 | 0.2 | 9.20E−06 | 0.00245 | UDP glucuronosyltransferase 2 family, polypeptide B4 |
| C20orf27 | 129.7 | 245.3 | 1.9 | 9.30E−06 | 0.00245 | chromosome 20 open reading frame 27 |

TABLE 2-continued list of genes according to p value.

| Gene symbol | mean rC1 | mean rC2 | ratio rC2/rC1 | Parametric p-value | FDR | Description |
|---|---|---|---|---|---|---|
| C6orf149 | 178.7 | 491.1 | 2.7 | 9.40E−06 | 0.00245 | chromosome 6 open reading frame 149 (LYRM4) |

The Accession Numbers of the genes of Table 2, as found in NCBI database in June 2008, are the following: IPO4 (BC136759), CPSF1 (NM_013291), MCM4 (NM_005914.2; NM_182746.1; two accession numbers for the same gene correspond to 2 different isoforms of the gene), EIF3S3 (NM_003756.2), NCL (NM_005381.2), CDC25C (NM_001790.3), CENPA (NM_001809.3; NM_001042426.1), KIF14 (BC113742), IPW (U12897), KNTC2 (AK313184), TMEM48 (NM_018087), BOP1 (NM_015201), EIF3S9 (NM_003751; NM_001037283), PH-4 (NM_177939), SMC4L1 (NM_005496; NM_001002800), TTK (AK315696), LAMA3 (NM_198129), C10orf72 (NM_001031746; NM_144984), TPX2 (NM_012112), MSH2 (NM_000251), DKC1 (NM_001363), STK6 (AY892410), CCT6A (NM_001762; NM_001009186), SULT1C1 (AK313193), ILF3 (NM_012218; NM_004516), IMPDH2 (NM_000884), HIC2 (NM_015094), AFM (NM_001133), MCM7 (NM_005916; NM_182776), CNAP1(AK128354), CBARA1 (AK225695), PLA2G4C (NM_003706), CPSF1(NM_013291), SNRPN (BC000611), RPL5 (AK314720), C1R (NM_001733), C16orf34 (CH471112), PHB (AK312649), BZW2 (BC017794), ALAS1(AK312566), FLJ20364 (NM_017785), RANBP1 (NM_002882), SKB1 (AF015913), ABHD6 (NM_020676), CCNB1 (NM_031966), NOL5A (NM_006392), RPL8 (NM_000973; NM_033301), BLNK (NM_013314; NM_001114094), BYSL (NM_004053), UBE1L(AY889910), CHD7 (NM_017780), DKFZp762E1312 (NM_018410), NUP210 (NM_024923), PLK1(NM_005030), ENPEP(NM_001977), HCAP-G(NM_022346), UGT2B4 (NM_021139), C20orf27 (NM_001039140) and C6orf149 (NM_020408).

In a particular embodiment of the invention, the set of genes of the invention is designed to determine the grade of hepatoblastoma, in particular paediatric hepatoblastoma. In another embodiment, the set of genes is designed to determine the grade of hepatocellular carcinoma, in particular paediatric HCC or adult HCC.

The expression of the genes of the set may be assayed by any conventional methods, in particular any conventional methods known to measure the quantitative expression of RNA, preferably mRNA.

The expression may be measured after carrying out an amplification process, such as by PCR, quantitative PCR (qPCR) or real-time PCR. Kits designed for measuring expression after an amplification step are disclosed below.

The expression may be measured using hybridization method, especially with a step of hybridizing on a solid support, especially an array, a macroarray or a microarray or in other conditions especially in solution. Arrays and kits of the invention, designed for measuring expression by hybridization method are disclosed below.

The expression of a gene may be assayed in two manners:
to determine absolute gene expression that corresponds to the number of copies of the product of expression of a gene, in particular the number of copies of a nucleotide target, in the sample; and
to determine the relative expression that corresponds to the number of copies of the product of expression of a gene, in particular the number of copies of a nucleotide target, in the sample over the number of copies of the expression product or the number of copies of a nucleotide target of a different gene (calculation also known as normalisation). This different gene is not one of the genes contained in the set to be assayed. This different gene is assayed on the same sample and at the same time as the genes of the set to be assayed, and is called an invariant gene or a normalizer. The invariant gene is generally selected for the fact that its expression is steady whatever the sample to be tested. The expression "steady whatever the sample" means that the expression of an invariant gene does not vary significantly between a normal liver cell and the corresponding tumor cell in a same patient and/or between different liver tumor samples in a same patient. In the present specification, a gene is defined as invariant when its absolute expression does not vary in function of the grade of the liver tumors, in particular does not vary in function of the grade of the HB or HCC tumor, and/or does not vary between liver tumor and normal liver cells.

In the present invention, the expression which is assayed is preferably the relative expression of each gene, calculated with reference to at least one (preferably 1, 2, 3 or 4) invariant gene(s). Invariant genes, suitable to perform the invention, are genes whose expression is constant whatever the grade of the liver tumors, such as for example ACTG1, EFF1A1, PNN and RHOT2 genes, whose features are summarized in Table 3. In a particular embodiment preferred, the relative expression is calculated with respect to at least the RHOT2 gene or with respect to the RHOT2 gene.

In another advantageous embodiment, the relative expression is calculated with respect to at least the PNN gene or with respect to the PNN gene. It may be calculated with respect to the RHOT2 and PNN genes.

The calculation of the absolute expression or of the relative expression of each gene of the set and of each invariant gene being assayed with the same method from the same sample, preferably at the same time, enables to determine for each sample a gene expression profile.

TABLE 3

Features of invariant genes. ACTG1, EEF1A1, PNN and RHOT2 proteins are defined in SEQ ID NOs: 34, 36, 38 and 40 respectively.

| symbol | Gene name | SEQ ID* | Accession No | Location | Function |
|---|---|---|---|---|---|
| ACTG1 | actin, gamma 1 | 33 | NM_001614 | 17q25 | cytoplasmic actin cytoskeleton in nonmuscle cells |
| EEF1A1 | eukaryotic translation elongation factor 1 alpha 1 | 35 | NM_001402 | 6q14.1 | enzymatic delivery of aminoacyl tRNAs to the ribosome |
| PNN | pinin, desmosome associated protein | 37 | NM_002687 | 14q21.1 | transcriptional corepressor, RNA splicing regulator |

TABLE 3-continued

Features of invariant genes. ACTG1, EEF1A1, PNN and RHOT2 proteins are defined in SEQ ID NOs: 34, 36, 38 and 40 respectively.

| symbol | Gene name | SEQ ID* | Accession No | Location | Function |
|---|---|---|---|---|---|
| RHOT2 | ras homolog gene family, member T2 | 39 | NM_138769 | 16p13.3 | Signaling by Rho GTPases, mitochondrial protein |

An additional step of the method or process comprises the determination of the grade of said liver tumor, referring to the gene expression profile that has been assayed. In a particular embodiment of the invention, the method is designed to determine the grade of hepatoblastoma, in particular paediatric hepatoblastoma. In another embodiment, the method is designed to determine the grade of hepatocellular carcinoma, in particular paediatric HCC or adult HCC.

According to a particular embodiment of the invention, in the step of the method which is performed to determine the grade of the liver tumor, a gene expression profile or a signature (preferably obtained after normalization), which is thus specific for each sample, is compared to the gene expression profile of a reference sample or to the gene expression profiles of each sample of a collection of reference samples (individually tested) whose grade is known, so as to determine the grade of said liver tumor. This comparison step is carried out with at least one prediction algorithm. In a particular embodiment, the comparison step is carried out with 1, 2, 3, 4, 5 or 6 prediction algorithms chosen in the following prediction algorithms: Compound Covariate Predictor (CCP), Linear Discriminator Analysis (LDA), One Nearest Neighbor (1NN), Three Nearest Neighbor (3NN), Nearest Centroid (NC) and Support Vector Machine (SVM). These six algorithms are part of the "Biometric Research Branch (BRB) Tools" developed by the National Cancer Institut (NCI) and are available on http://linus.nci.nih.gov/BRB-ArrayTools.html. Equivalent algorithms may be used instead of or in addition to the above ones. Each algorithm classifies tumors within either of the two groups, defined as tumors with good prognosis (such as C1) or tumors with bad prognosis (such as C2); each group comprises the respective reference samples used for comparison, and one of these two groups also comprises the tumor to be classified.

Therefore, when 6 algorithms are used, the grade of a tumor sample may be assigned with certainty to the class of good prognosis or to the class of bad prognosis, when 5 or 6 of the above algorithms classified the tumor sample in the same group. In contrast, when less than 5 of the above algorithms classify a tumor sample in the same group, it provides an indication of the grade rather than a definite classification.

Reference samples which can be used for comparison with the gene expression profile of a tumor to be tested are one or several sample(s) representative for tumor with poor prognosis (such as C2), one or several sample(s) representative of tumor with good prognosis (such as C1), one or several sample(s) of a normal adult liver and/or one or several sample(s) of a fetal liver.

Table 4 lists the level of expression of each gene of Table 1 depending upon the status of the reference sample i.e., robust tumor with poor prognostic and robust tumor with good prognostic. Examples of methods to identify such robust tumors are provided in the examples. The present invention provides a new classification method in this respect, which is based on discretization of continuous values.

TABLE 4

Level of expression of the genes of Table 1, with respect to the status of the robust tumors

| Nucleotide target | Expression status in robust tumor | |
|---|---|---|
| | with poor prognosis | with good prognosis |
| AFP | overexpressed | underexpressed |
| ALDH2 | underexpressed | overexpressed |
| APCS | underexpressed | overexpressed |
| APOC4 | underexpressed | overexpressed |
| AQP9 | underexpressed | overexpressed |
| BUB1 | overexpressed | underexpressed |
| C1S | underexpressed | overexpressed |
| CYP2E1 | underexpressed | overexpressed |
| DLG7 | overexpressed | underexpressed |
| DUSP9 | overexpressed | underexpressed |
| E2F5 | overexpressed | underexpressed |
| GHR | underexpressed | overexpressed |
| HPD | underexpressed | overexpressed |
| IGSF1 | overexpressed | underexpressed |
| NLE1 | overexpressed | underexpressed |
| RPL10A | overexpressed | underexpressed |

Reference samples usually correspond to so-called "robust tumor" for which all the marker genes providing the signature are expressed (either under expressed or overexpressed) as expected i.e., in accordance with the results disclosed in Table 5, when tested in similar conditions, as disclosed in the examples hereafter.

A robust tumor having an overexpression of one or several gene(s) selected among ALDH2, APCS, APOC4, AQP9, C1S, CYP2E1, GHR and HPD genes (these genes belong to the so-called group of differentiation-related genes), and/or an underexpression of one or several gene(s) selected among AFP, BUB1, DLG7, DUSP9, E2F5, IGSF1, NLE1 and RPL10A genes (these genes belong to the so-called group of proliferation-related genes), is an indicator of a robust liver tumor, in particular of a hepatoblastoma, with a good prognosis. A robust tumor having an overexpression of one or several gene(s) selected among AFP, BUB1, DLG7, DUSP9, E2F5, IGSF1, NLE1 and RPL10A genes, and/or an underexpression of one or several gene(s) among ALDH2, APCS, APOC4, AQP9, C1S, CYP2E1, GHR and HPD genes, is an indicator of a robust liver tumor, in particular of a hepatoblastoma, with a poor prognosis. In the present application, a gene is said "underexpressed" when its expression is lower than the expression of the same gene in the other tumor grade, and a gene is said "overexpressed" when its expression is higher than the expression of the same gene in the other tumor grade.

In a particular embodiment, Table 5 provides the gene expression profiles of the 16 genes of Table 1 in 13 samples of hepatoblastoma (HB) including 8 samples that have been previously identified as rC1 subtype and 5 samples that have been previously identified as rC2 subtype. This Table can therefore be used for comparison, to determine the gene expression profile of a HB tumor to be classified, with the robust tumors disclosed (constituting reference samples), for a set of genes as defined in the present application. Said comparison involves using the classification algorithms which are disclosed herein, for both the selected reference samples and the assayed sample.

proliferation-related genes or the group of downregulated differentiation-related gene) is used to perform the method.

The invention thus relates to a method enabling the determination of the tumor grade on a patient's sample, which

TABLE 5

Normalized qPCR data of 16 genes in 13 HB samples including 8 samples of the rC1 subtype and 5 samples of the rC2 subtype (in grey). The qPCR values have been obtained by measuring the expression of 16 genes in 8 samples of the rC1 subtype and 5 samples of the rC2 subtype by the SYBR green method using the primers as disclosed in Table 6 below and in the conidtions reported in the examples, and normalized by the ROTH2 gene (primers in Table 7).

| HB | grade | AFP | ALDH2 | APCS | APOC4 | AQP9 | BUB1 | C1S | CYP2E1 | DLG7 | DUSP9 | E2F5 | GHR | HPD | IGSF1 | NLE | RPL10A |
|---|---|---|---|---|---|---|---|---|---|---|---|---|---|---|---|---|---|
| HB5 | rC1 | 0.22 | 1.32 | 1.04 | 1.23 | 1.4 | -0.11 | 1.46 | 0.99 | -0.22 | 0.76 | 0.37 | 1.29 | 1.72 | 0.04 | -0.12 | 0.78 |
| HB49 | rC1 | -0.82 | 1.2 | 0.6 | 1.72 | 0.78 | -1.09 | 0.77 | 0.89 | -1.17 | -1.15 | -1.21 | 0.89 | 1.31 | -1.27 | -2.06 | -0.8 |
| HB59 | rC1 | -0.57 | 0.71 | 0.9 | 1.09 | 0.8 | 0.48 | 0.32 | 0.62 | 0.31 | -0.7 | -1.28 | 0.44 | 0.67 | -1.26 | -0.73 | 0.03 |
| HB69 | rC1 | -1.3 | 0.42 | 0.66 | 0.79 | 0.48 | -1.35 | 0.23 | 1.1 | -1.1 | -1.62 | -0.96 | 0.9 | 0.53 | -1.88 | -1.33 | -0.26 |
| HB72 | rC2 | 1.19 | -2.01 | -1.47 | -1.05 | -1.01 | 1.22 | -1.13 | -1.15 | 1.01 | 0.8 | 0.94 | -0.71 | -1.38 | 0.64 | 0.45 | 0.53 |
| HB73 | rC2 | 0.88 | 0.34 | -0.49 | -0.92 | -1.23 | 1.09 | -0.43 | -0.27 | 1.17 | 0.96 | 0.89 | -1.28 | -0.19 | 0.77 | 0.99 | 0.72 |
| HB74e | rC1 | 0.52 | 0.18 | -0.58 | -0.75 | -0.28 | -0.06 | -0.95 | -0.79 | 0.46 | 0.62 | 0.75 | -0.65 | -0.86 | 0.63 | 0.93 | 0.5 |
| HB74f | rC2 | 1.11 | 1.21 | 0.29 | 1.37 | 0.81 | 1.36 | 0.29 | 0.92 | -1.35 | 0.78 | 1.89 | 0.68 | 0.07 | -1.74 | -0.88 | -0.05 |
| HB75 | rC1 | -0.38 | 0.45 | -0.3 | 0.62 | 0.96 | -0.74 | 0.05 | 0.91 | -0.59 | 0.15 | 0.4 | 0.32 | 0.79 | -0.3 | -0.35 | -0.5 |
| HB80 | rC2 | 1.63 | -0.4 | -0.26 | 0.06 | -0.99 | 1.31 | -1.26 | -0.34 | 1.37 | 0.95 | 0.81 | 0.64 | -0.87 | 1.61 | 1.23 | 1.11 |
| HB81 | rC1 | -0.56 | 0.66 | 1.1 | 0.88 | 0.84 | -0.66 | 1.16 | 1.32 | -0.69 | -0.14 | -0.1 | 1.11 | 1.29 | 0.06 | 0.06 | 0.44 |
| HB83 | rC1 | -0.73 | 0.5 | 0.78 | 1.04 | 1.2 | -0.24 | 1.11 | -0.21 | -0.84 | -0.64 | -1.41 | 0.63 | 0.61 | -0.22 | -1.09 | -1.92 |
| HB86 | rC2 | 1.08 | -0.09 | -1.29 | -0.43 | -0.3 | 1.21 | -1.12 | -0.25 | 1.13 | 1.26 | 0.88 | -0.52 | -0.98 | 1.08 | 0.46 | 1.56 |

The method of the present invention is also suitable to classify new tumor samples, and to use them as new reference samples. Therefore, the gene expression values of these new reference samples may be used in combination or in place of some of the values reported in Table 5.

In another embodiment of the invention, the step of determining the tumor grade comprises performing a method of discretization of continuous values of gene expression obtained on the set of genes the tested patients' samples. Discretization is generally defined as the process of transforming a continuous-valued variable into a discrete one by creating a set of contiguous intervals (or equivalently a set of cutpoints) that spans the range of the variable's values. Discretization has been disclosed for use in classification performance in Lustgarten J. L. et al, 2008.

The inventors have observed that discretization can be effective in determining liver tumor grade, especially for those tumors described in the present application, including Hepatoblastoma (HB) or Hepatocellular carcinoma (HCC).

The discretization method is especially disclosed in the examples where it is illustrated by using data obtained on tumor samples wherein these data are those obtained from profiling the 16 genes providing the large set of genes for expression profiling according to the invention. It is pointed out that the discretization method may however be carried out on a reduced number of profiled genes within this group of 16 genes, starting from a set consisting of 2 genes (or more genes) including one (or more) overexpressed proliferation-related genes chosen among AFP, BUB1, DLG7, DUSP9, E2F5, IGSF1, NLE1 and RPL10A and one downregulated differentiation-related gene chosen among ALDH2, APCS, APOC4, AQP9, C1S, CYP2E1, GHR, HPD, said genes being thus classified as a result of gene profiles observed on robust tumors with poor prognosis (according to the classification in Table 4 above). In particular embodiments of the discretization method, the number of assayed gene for expression profiling is 2, 4, 6, 8, 10, 12, 14 or 16 and the same number of genes in each category (either the group of overexpressed proliferation-related genes or the group of downregulated differentiation-related gene) is used to perform the method.

The invention thus relates to a method enabling the determination of the tumor grade on a patient's sample, which comprises a classification of the tumor through discretization according to the following steps:

measuring the expression and especially the relative (normalized) expression of each gene in a set of genes defined as the signature of the tumor, for example by quantitative PCR thereby obtaining data as Ct or preferably Delta Ct, wherein said set of genes is divided in two groups, a first group consisting of the proliferation-related genes and a second group consisting of the differentiation-related genes (as disclosed above), comparing the values measured for each gene, to a cut-off value determined for each gene of the set of genes, and assigning a discretized value to each of said measured values with respect to said cut-off value, said discretized value being advantageously a "1" or a "2" value assigned with respect to the cut-off value of the gene and optionally, if two cut-offs values are used for one gene, a further discretized value such as a "1.5" or another value between "1" or "2" may be assigned for the measured values which are intermediate between the cut-offs values, determining the average of the discretized values for the genes, in each group of the set of genes, determining the ratio of the average for the discretized values for the proliferation-related genes on the average for the discretized values for the differentiation-related genes, thereby obtaining a score for the sample, comparing the obtained score for the sample with one or more sample cut-off(s), wherein each cut-off has been assessed for a selected percentile, determining the tumor grade as C1 or C2, as a result of the classification of the sample with respect to said sample cut-off.

The above defined ratio of average values may be alternatively calculated as the ratio of the average for the discresized values for the differentiation-related genes on the average for the discretized values for the proliferation-related genes, to obtain a score. If this calculation made is adopted the cut-offs values are inversed, i.e., are calculated as 1/xxx.

In order to carry out the discretization method of the invention, the data obtained on the assayed genes for profiling a patient's sample are preferably normalized with respect to one or more invariant gene(s) of the present invention, in order to prevent detrimental impact on the results that may arise from possible inaccuracy in the quantification of initial nucleic acid, especially RNA, in the sample.

Normalization with respect to one invariant gene only, especially when said invariant gene is RHOT2 gene has proved to be relevant in the results obtained by the inventors. Similarly normalization with respect to PNN gene would be an advantageous possibility because the gene does also not vary in expression.

In order to design a discretization method for the determination of tumor grade of an individual sample of a patient, according to the invention, cut-offs values have to be determined to allow the determination of the tumor grade. The cut-offs values can be determined experimentally by carrying out the following steps on expression profiling results obtained on a determined number of tumor samples:

defining a cut-off (threshold value) for each gene in the set of genes designed for the signature, said cut-off corresponding to the value of the absolute or preferably relative (i.e. normalized) expression of said gene at a selected percentile and said percentile being selected for each of two groups of genes defined in the set of genes. In order to do so, the set of profiled genes comprises the same number of genes within each of the 2 groups of genes consisting of the group of overexpressed proliferation-related genes encompassing AFP, BUB1, DLG7, DUSP9, E2F5, IGSF1, NLE1 and RPL10A and the group of downregulated differentiation-related gene encompassing ALDH2, APCS, APOC4, AQP9, C15, CYP2E1, GHR, HPD (said groups being defined based on gene profiles on robust tumors with poor prognosis), in each tumor sample assigning to each expression value (especially normalized expression value) obtained for each expression profiled gene in the sample, a discretized value which is codified with respect to the cut-off value determined for the same gene and in line with the defined contiguous intervals of continuous values, e.g. a discretized value of "1" or "2" if two intervals (categories) are defined or a discretized value of "1", "1.5" (or another values between 1 and 2) or "2" if three intervals are defined, said assignment of discretized value being advantageously such that the "1" is assigned for expression values falling below the cut-off found for the differentiation-related genes and for expression values falling below the cut-off found for the proliferation-related genes, the "2" is assigned for expression values falling above the cut-off found for the differentiation-related genes and for expression values falling above the cut-off found for the proliferation-related genes, and optionally if a "1.5" is used it is assigned to values found between the cut-offs;

on each tumor sample, determining in each group (proliferation-related genes group or differentiation-related genes group) the average value of said assigned discretized values of profiled genes of the set of profiled genes;

determining a score for each sample, as the ratio between the average expression values of said genes in said two groups of genes in the set of profiled genes;

determining on the basis of the obtained scores for all the tumor samples, one or more cut-off value(s) for the sample, corresponding to the respective value(s) at one or more (especially 2 or 3) percentile(s), wherein said percentile(s) is (are) either identical or different from the percentiles(s) selected for the genes.

When the cut-offs values for each gene of the set of genes for profiling have been obtained for a sufficient number of relevant samples and the cut-off value for the sample is determined on the basis of the same samples, these cut-offs can be adopted as reference cut-offs for the user who will be carrying out the analysis of any further patient's tumor sample, especially for the purpose of determining the tumor grade in a patient's sample, if the analysis is performed in identical or similar conditions as the conditions which led to the establishment of the cut-offs values.

Therefore the invention provides cut-offs values as reference cut-offs, in order to carry out the determination of tumor grade in particular testing conditions as those disclosed below and in the examples.

In a particular embodiment of the method of discretization, the cut-off for each gene is the value corresponding to a determined percentile, which can be different for each of the considered two groups of genes (proliferation-related genes on the one hand and differentiation-related genes on the other hand). The selected percentile (or quantile) is determined with respect to the fraction of tumors (such as 1/3 or more) harbouring some chosen features such as overexpression of proliferation-related genes and/or downregulation of differentiation-related genes, in the two groups of genes of the set of genes. Especially, when one intends to assign more weight to tumors displaying strong overexpression of proliferation-related genes and/or strong downregulation of differentiation-related genes, the cut-off corresponds to a high quantile (above the $50^{th}$, preferably the $60^{th}$, or even above the $65^{th}$, such as the $67^{th}$ and for example within the range of $55^{th}$ and $70^{th}$) for said proliferation-related genes and the cut-off corresponds to a low quantile (below the $50^{th}$, preferably equal to or below the $40^{th}$ for example the $33^{rd}$, and for example within the range of between $20^{th}$ and $40^{th}$) of the differentiation-related genes. The cut-off for each group of genes and the cut-off for the sample may be determined with respect to the same percentile(s) or may be determined with respect to different percentile.

According to a particular embodiment of the invention, for HB tumors, the percentile which is chosen for the overexpressed proliferation-related genes is the $67^{th}$ and the percentile which is chosen for the downregulated differentiation-related genes is the $33^{rd}$. According to a particular embodiment of the invention, for HC tumors, the percentile which is chosen for the overexpressed proliferation-related genes is the $60^{th}$ and the percentile which is chosen for the downregulated differentiation-related genes is the $40^{rd}$.

Each percentile (or cut-off value corresponding to the percentile) defines a cutpoint and the discretized values for each gene are either "1" or "2" below or above said percentile. The values "1" and "2" are distributed with respect to the percentiles so as to create the highest difference in the values of the calculated ratio for the most different tumor grades. This is illustrated in the examples for the selected percentiles.

It has been observed that in a preferred embodiment of the invention, the relative values of the profiled genes are determined by real-time PCR (qPCR).

Conditions to carry out the real-time PCR are disclosed herein, especially in the examples, as conditions applicable to analyzed samples.

PCR primers and probes suitable for the performance of RT-PCR are those disclosed herein for the various genes.

In a particular embodiment of the invention, the analysed tumor is a hepatoblastoma and its grade is determined by discretization as disclosed above and illustrated in the examples, taking into account that:

the set of assayed genes for profiling is constituted of the 16 genes disclosed;

the invariant gene (of reference) is RHOT2;

the cut-offs value for each gene based on −dCt (minus delta Ct) measures) are:

AFP: 3.96139596; ALDH2: 4.3590482; APCS: 4.4691582; APOC4: 2.03068712; AQP9: 3.38391456; BUB1: −1.41294708; C1S: 4.24839464; CYP2E1: 6.70659644; DLG7: −3.3912188; DUSP9: 2.07022648; E2F5: −0.72728656; GHR: −0.1505569200; HPD: 2.27655628; IGSF1: 0.1075015200; NLE: −0.02343571999; RPL10A: 6.19723876.

the cut-off value for the sample is 0.91 (for the 67$^{th}$) and optionally a further the cut-off value for the sample is 0.615 (for the 33$^{rd}$). In such a case, a sample with a score above 0.91 is classified into the C2 class and a sample with a score below 0.91 is classified into the C1 class. The reference to the cut-off at 0.615 may be used to refine the results for values between both cut-offs.

In another embodiment of the invention, the tumor is an hepatocellular carcinoma and its grade is determined by discretization as disclosed above and illustrated in the examples, taking into account that:

the set of assayed genes for profiling is constituted of the 16 genes disclosed;

the invariant gene (of reference) is RHOT2;

the cut-offs value for each gene based on −dCt (minus delta Ct) measures) are:

| Gene name | Cut-off for Taqman | Cut-off for SybrGreen |
|---|---|---|
| AFP | −1.2634010 | −2.3753035 |
| ALDH2 | 4.014143 | 5.314302 |
| APCS | 5.6142907 | 6.399079 |
| APOC4 | −0.7963158 | 4.656336 |
| AQP9 | 4.2836011 | 5.446966 |
| BUB1 | −1.2736579 | −3.634476 |
| C1S | 6.3514679 | 6.240002 |
| CYP2E1 | 6.9562419 | 5.829384 |
| DLG7 | −2.335694 | −4.614352 |
| DUSP9 | −7.979559 | −1.8626715 |
| E2F5 | −0.4400218 | −1.367846 |
| GHR | 1.0832632 | 1.169362 |
| HPD | 6.7480328 | 6.736329 |
| IGSF1 | −4.8417785 | 7.6653982 |
| NLE | −1.6167268 | −1.82226 |
| RPL10A | 6.2483056 | 5.731897 | the cut-off value for the score of a sample based on the ration between the average of the discretized values of the "proliferation-related genes" on the "differentiation-related genes" are 0.66 determined as the 30$^{th}$ percentile of the score) and 0.925 (determined as the 67$^{th}$ percentile of the score) In such a case, a sample with a score above 0.925 is classified into the C2 class and a sample with a score below 0.66 is classified into the C1 class. The sample with a score (initial score) between 0.66 and 0.925 can be assigned to an intermediate class. It can alternatively be classified as C1 or C2 using a modified score corresponding to the average of the discretized values of the "proliferation-related genes". A new cut-off value is determined for said genes, which is the cut-off value for the modified score (in the present case it is 1.3). This cut-off can be determined via a percentile (here the 60$^{th}$) of the distribution of the modified scores, using the samples of the intermediate class. A sample (initially classified in the intermediate class) with a modified score below 1.3 can be re-classified into the C1 class, and a sample with a modified score above 1.3 can be re-classified into the C2 class.

It is observed that the refinement of the results which are between the cut-offs of the samples is advantageous for hepatocellular carcinoma in order to increase the relevancy of the information on the tumor grade.

Generally said refinement of the classification of the intermediate results in the HCC is obtained by performing the following steps:

a modified score is determined which corresponds to the average of the discretized values of the "proliferation-related genes" only for the sample. A new cut-off value is determined for said genes, which is the cut-off value for the modified score (in the present case it is 1.3). This cut-off can be determined via a percentile (here the 60$^{th}$) of the distribution of the modified scores, using the samples of the intermediate class. A sample (initially classified in the intermediate class) with a modified score below the "proliferation cut-off" (for example 1.3) can be re-classified into the C1 class, and a sample with a modified score above the "proliferation cut-off" (for example 1.3) can be re-classified into the C2 class.

From the 16 genes expressed in liver cells listed in Table 1, a set comprising from 2 to 16 genes (or more generally a set as defined herein) may be used to assay the grade of tumor cells in a tumor originating from the liver. The results obtained, after determining the expression of each of the genes of the set, are then treated for classification according to the steps disclosed herein. The invention relates to each and any combination of genes disclosed in Table 1, to provide a set comprising from 2 to 16 of these genes, in particular a set comprising or consisting of 2, 3, 4, 5, 6, 7, 8, 9, 10, 11, 12, 13, 14, 15 or 16 of these genes. In the designed set, one or many genes of Table 1 may be modified by substitution or by addition of one or several genes as explained above, which also enable to determine the grade of the liver tumor, when assayed in combination with the other genes.

In a preferred embodiment, the liver tumor is a paediatric HB, and the method or process of the invention enables to distinguish a first class, called C1, qualifying as a good prognosis tumor and a second class, called C2, qualifying as a poor prognosis tumor. The C1 grade is predominantly composed of fetal histotype cells (i.e., well differentiated and non proliferative cells). In contrast, the C2 grade presents cells other than the fetal histotype such as embryonic, atypic (crowded fetal), small cell undifferiantiated (SCUD) and/or macrotrabecular cells.

The present invention also relates to a kit suitable to determine the grade of a liver tumor from the sample obtained from a patient. This kit is appropriate to carry out the method or process described in the present application.

In a particular embodiment, the kit comprises a plurality of pairs of primers specific for a set of genes to be assayed, said set comprising from 2 to 16 genes, said 2 to 16 genes being chosen in the group consisting of AFP, ALDH2, APCS, APOC4, AQP9, BUB1, C1S, CYP2E1, DLG7, DUSP9, E2F5, GHR, HPD, IGSF1, NLE1 and RPL10A genes.

By "plurality", it is mean that the kit comprises at least as many pairs of primers as genes to enable assaying each selected gene, and in particular the nucleotide target of this gene. Accordingly, each gene and in particular its nucleotide target is specifically targeted by a least one of these pairs of primers. In a particular embodiment, the kit comprises the same number of pairs of primers as the number of genes to assay and each primer pair specifically targets one of the genes, and in particular the nucleotide targets of one of these genes, and does not hybridize with the other genes of the set.

The kits of the invention are defined to amplify the nucleotide targets of the sets of genes as described in the present invention. Therefore, the kit of the invention comprises from 2 to 16 pairs of primers which, when taken as a whole, are specific for said from 2 to 16 genes out of the 16 genes of Table 1. In particular, the kit comprises or consists of 2, 3, 4, 5, 6, 7, 8, 9, 10, 11, 12, 13, 14 or 15 pairs of primers specific for 2, 3, 4, 5, 6, 7, 8, 9, 10, 11, 12, 13, 14 or 15 out of the 16 genes of Table 1. In a particular embodiment, the kit comprises or consists of 16 pairs of primers specific for the 16 genes of Table 1 i.e., a primer pair specific for each of the following genes: AFP, ALDH2, APCS, APOC4, AQP9, BUB1, C1S, CYP2E1, DLG7, DUSP9, E2F5, GHR, HPD, IGSF1, NLE1 and RPL10A genes.

When the set of genes has been modified by the addition or substitution of at least one gene as described above, the kit is adapted to contain a pair of primers specific for each added or substituted gene(s). As indicated by the term "comprises", the kit may, besides the pairs of primers specific for the genes of Table 1, contain additional pair(s) of primers.

In a particular embodiment, the kit comprises at least one pair of primers (preferably one) for at least one invariant gene (preferably one or two) to be assayed for the determination of the expression profile of the genes, by comparison with the expression profile of the invariant gene.

The number of pairs of primers of the kit usually does not exceed 100, particularly 50, 30, 20, more particularly 16, and even more particularly is maximum 5, 6, 7, 8, 9 or 10.

In the kits of the invention, it is understood that, for each gene, at least one pair of primers and preferably exactly one pair, enabling to amplify the nucleotide targets of this gene, is present. When the kits provide several pairs of primers for the same gene, the gene expression level is measured by amplification with only one pair of primers. It is excluded that amplification may be performed using simultaneously several pairs of primers for the same gene.

As defined herein, a pair of primers consists of a forward polynucleotide and a backward polynucleotide, having the capacity to match its nucleotide target and to amplify, when appropriate conditions and reagents are brought, a nucleotide sequence framed by their complementary sequence, in the sequence of their nucleotide target.

The pairs of primers present in the kits of the invention are specific for a gene i.e., each pair of primers amplifies the nucleotide targets of one and only one gene among the set. Therefore, it is excluded that a pair of primers specific for a gene amplifies, in a exponential or even in a linear way, the nucleotide targets of another gene and/or other nucleic acids contained in sample. In this way, the sequence of a primer (whose pair is specific for a gene) is selected to be not found in a sequence found in another gene, is not complementary to a sequence found in this another gene and/or is not able to hybridize in amplification conditions as defined in the present application with the sequence of the nucleotide targets of this another gene.

In a particular embodiment, the forward and/or backward primer(s) may be labelled, either by isotopic (such as radioactive) or non isotopic (such as fluorescent, biotin, fluorochrome) methods. The label of the primer(s) leads to the labelling of the amplicon (product of amplification), since the primers are incorporated in the final product.

The design of a pair of primers is well known in the art and in particular may be carried out by reference to Sambrook et al. (Molecular Cloning, A laboratory Manual, Third Edition; chapter 8 and in particular pages 8.13 to 8.16). Various softwares are available to design pairs of primers, such as Oligo™ or Primer3.

Therefore, each primer of the pair (forward and backward) has, independently from each other, the following features:
their size is from 10 and 50 bp, preferably 15 to 30 bp; and
they have the capacity to hybridize with the sequence of the nucleotide targets of a gene.

In a particular embodiment, when the pairs of primers are used in a simultaneous amplification reaction carried out on the sample, the various primers have the capacity to hybridize with their respective nucleotide targets at the same temperature and in the same conditions.

Conventional conditions for PCR amplification are well known in the art and in particular in Sambrook et al. An example of common conditions for amplification by PCR is dNTP (200 mM), $MgCl_2$ (0.5-3 mM) and primers (100-200 nM).

In a particular embodiment, the sequence of the primer is 100% identical to one of the strands of the sequence of the nucleotide target to which it must hybridize with, i.e. is 100% complementary to the sequence of the nucleotide target to which it must hybridize. In another embodiment, the identity or complementarity is not 100%, but the similarity is at least 80%, at least 85%, at least 90% or at least 95% with its complementary sequence in the nucleotide target. In a particular embodiment, the primer differs from its counterpart in the sequence of the sequence of the nucleotide target by 1, 2, 3, 4 or 5 mutation(s) (deletion, insertion and/or substitution), preferably by 1, 2, 3, 4 or 5 nucleotide substitutions. In a particular embodiment, the mutations are not located in the last 5 nucleotides of the 3' end of the primer.

In a particular embodiment, the primer, which is not 100% identical or complementary, keeps the capacity to hybridize with the sequence of the nucleotide target, similarly to the primer that is 100% identical or 100% complementary with the sequence of the nucleotide target (in the hybridization conditions defined herein). In order to be specific, at least one of the primers (having at least 80% similarity as defined above) of the pair specific for a gene can not hybridize with the sequence found in the nucleotide targets of another gene of the set and of another gene of the sample.

In a particular embodiment, the pairs of primers used for amplifying a particular set of genes are designed, besides some or all of the features explained herein, in order that the amplification products (or amplicons) of each gene have approximately the same size. By "approximately" is meant that the difference of size between the longest amplicon and the shortest amplicon of the set is less than 30% (of the size of the longest amplicon), preferably less than 20%, more preferably less than 10%. As particular embodiments, the size of the amplicon is between 100 and 300 bp, such as about 100, 150, 200, 250 or 300 bp.

The nucleotide sequences of the 16 genes of Table 1 are provided in the Figures, and may be used to design specific pairs of primers for amplification, in view of the explanations above.

Examples of primers that may be used to measure the expression of the genes of Table 1, in particular to amplify the nucleotide targets of the genes of Table 1, are the primers having the sequence provided in Table 6 or variant primers having at least 80% similarity (or more as defined above) with the sequences defined in Table 6.

TABLE 6

Sequence of forward and backward primers of the 16 genes defined in Table 1. These primers may be used in any real-time PCR, in particular the SYBR green technique, except for the Taqman ® protocol.

| Target | Product size (bp) | Forward primer (5'-3') | Reverse primer (5'-3') |
|---|---|---|---|
| AFP | 151 | AACTATTGGCCTGTGGCGAG | TCATCCACCACCAAGCTGC |
| ALDH2 | 151 | GTTTGGAGCCCAGTCACCCT | GGGAGGAAGCTTGCATGATTC |
| APCS | 151 | GGCCAGGAATATGAACAAGCC | CTTCTCCAGCGGTGTGATCA |
| APOC4 | 151 | GGAGCTGCTGGAGACAGTGG | TTTGGATTCGAGGAACCAGG |
| AQP9 | 151 | GCTTCCTCCCTGGGACTGA | CAACCAAAGGGCCCACTACA |
| BUB1 | 152 | ACCCCTGAAAAGTGATGCCT | TCATCCTGTTCCAAAAATCCG |
| C1S | 141 | TTGTTTGGTTCTGTCATCCGC | TGGAACACATTTCGGCAGC |
| CYP2E1 | 151 | CAACCAAGAATTTCCTGATCCAG | AAGAAACAACTCCATGCGAGC |
| DLG7 | 151 | GCAGGAAGAATGTGCTGAAACA | TCCAAGTCTTTGAGAAGGGCC |
| DUSP9 | 151 | CGGAGGCCATTGAGTTCATT | ACCAGGTCATAGGCATCGTTG |
| E2F5 | 151 | CCATTCAGGCACCTTCTGGT | ACGGGCTTAGATGAACTCGACT |
| GHR | 151 | CTTGGCACTGGCAGGATCA | AGGTGAACGGCACTTGGTG |
| HPD | 151 | ATCTTCACCAAACCGGTGCA | CCATGTTGGTGAGGTTACCCC |
| IGSF1 | 152 | CACTCACACTGAAAAACGCCC | GGGTGGAGCAATTGAAAGTCA |
| NLE1 | 151 | ATGTGAAGGCCCAGAAGCTG | GAGAACTTCGGGCCGTCTC |
| RPL10A | 151 | TATCCCCCACATGGACATCG | TGCCTTATTTAAACCTGGGCC |

The kit of the invention may further comprise one or many pairs of primers specific for one or many invariant genes, in particular specific for ACTG1, EFF1A1, PNN and/or RHOT2 genes. The pair of primers specific for invariant gene(s) may be designed and selected as explained above for the pair of primers specific for the genes of the set of the invention. In a particular embodiment, the pairs of primers of the invariant genes are designed in order that their amplification product (or amplicon) has approximately the same size as the amplicon of the genes of the set to be assayed (the term approximately being defined as above, with respect to the longest amplicon of the set of genes). Examples of primers that may be used to amplify the particular invariant genes are primers having the sequence provided in Table 7 or primers having at least 80% similarity (or more as defined above) with the sequences defined in Table 7.

The kits of the invention may also further comprise, in association with or independently of the pairs of primers specific for the invariant gene(s), reagents necessary for the amplification of the nucleotide targets of the sets of the invention and if any, of the nucleotide targets of the invariant genes.

The kits of the invention may also comprise probes as disclosed herein in the context of sets of probes, compositions and arrays. In particular, the kits also comprise the four dNTPs (nucleotides), amplification buffer, a polymerase (in particular a DNA polymerase, and more particularly a thermostable DNA polymerase) and/or salts necessary for the activity of the polymerase (such as $Mg^{2+}$).

Finally, the kits may also comprise one or several control sample(s) i.e., at least one sample(s) representative of tumor with bad (i.e., poor) prognosis (in particular a HB C2 grade), at least one sample(s) representative of tumor with good

TABLE 7

Sequence of forward and backward primers specific for the invariant genes defined in Table 3. These primers may be used in real-time PCR, in particular the SYBR green technique, except for the Taqman ® protocol.

| Target | Product size (bp) | Forward primer (5'-3') | Reverse primer (5'-3') |
|---|---|---|---|
| ACTG1 | 151 | GATGGCCAGGTCATCACCAT | ACAGGTCTTTGCGGATGTCC |
| EFF1A1 | 151 | TCACCCGTAAGGATGGCAAT | CGGCCAACAGGAACAGTACC |
| PNN | 151 | CCTTTCTGGTCCTGGTGGAG | TGATTCTCTTCTGGTCCGACG |
| RHOT2 | 151 | CTGCGGACTATCTCTCCCCTC | AAAAGGCTTTGCAGCTCCAC | prognosis (in particular a HB C1 grade), at least one sample of a normal adult liver and/or at least one sample of a fetal liver.

The kits may also comprise instructions to carry out the amplification step or the various steps of the method of the invention.

The invention is also directed to a set of probes suitable to determine the grade of a liver tumor from the sample obtained from a patient. This set of probes is appropriate to carry out the method or process described in the present invention. It may also be part of the kit.

This set of probes comprises a plurality of probes in particular from 2 to 16 probes, these 2 to 16 probes being specific for genes chosen in the group consisting of AFP, ALDH2, APCS, APOC4, AQP9, BUB1, C1S, CYP2E1, DLG7, DUSP9, E2F5, GHR, HPD, IGSF1, NLE1 and RPL10A genes.

By "plurality", it is mean that the set of probes comprises at least as many probes as genes to assay. In a particular embodiment, the array comprises the same number of probes as the number of genes to assay.

The probes of the sets of the invention are selected for their capacity to hybridize to the nucleotide targets of the sets of genes as described in the present invention. Therefore, the set of probes of the invention comprise from 2 to 16 probes specific for 2 to 16 genes out of the 16 genes of Table 1. In particular, the sets of probes comprise or consist of 2, 3, 4, 5, 6, 7, 8, 9, 10, 11, 12, 13, 14 or 15 probes specific of 2, 3, 4, 5, 6, 7, 8, 9, 10, 11, 12, 13, 14 or 15 out of the 16 genes of Table 1. In a particular embodiment, the sets of probes comprise or consist of 16 probes specific for the 16 genes of Table 1 i.e., a probe specific of each of the following genes: AFP, ALDH2, APCS, APOC4, AQP9, BUB1, C1S, CYP2E1, DLG7, DUSP9, E2F5, GHR, HPD, IGSF1, NLE1 and RPL10A genes.

The specificity of the probes is defined according to the same parameters as those applying to define specific primers.

When the set of genes has been modified by the addition or substitution of at least one gene as described above, the set of probes is adapted to contain a probe specific for the added or substituted gene(s). As indicated by the term "comprises", the set of probes may, besides the probes specific for the genes of Table 1, contain additional probe(s).

The number of probes of the set does usually not exceed 100, particularly 50, 30, 20, more particularly 16, and even more particularly is maximum 5, 6, 7, 8, 9 or 10.

In the set of probes of the invention, it is understood that for each gene corresponds at least one probe to which the nucleotide target of this gene hybridize to. The set of probes may comprise several probes for the same gene, either probes having the same sequence or probes having different sequences.

As defined herein, a probe is a polynucleotide, especially DNA, having the capacity to hybridize to the nucleotide target of a gene. Hybridization is usually carried out at a temperature ranging from 40 to 60° C. in hybridization buffer (see example of buffers below). These probes may be oligonucleotides, PCR products or cDNA vectors or purified inserts. The size of each probe is independently to each other from 15 and 1000 bp, preferably 100 to 500 bp or 15 to 500 bp, more preferably 50 to 200 bp or 15 to 100 bp. The design of probes is well known in the art and in particular may be carried out by reference to Sambrook et al. (Molecular Cloning, A laboratory Manual, Third Edition; chapters 9 and 10 and in particular pages 10.1 to 10.10).

The probes may be optionally labelled, either by isotopic (radioactive) or non isotopic (biotin, flurorochrome) methods. Methods to label probes are disclosed in Sambrook et al. (Molecular Cloning, A laboratory Manual, Third Edition; chapter 8 and in particular page 9.3.) In a particular embodiment, the probes are modified to confer them different physicochemical properties (such as by methylation, ethylation). In another particular embodiment, the probes may be modified to add a functional group (such as a thiol group), and optionally immobilized on bead (preferably glass beads).

In a particular embodiment, the sequence of the probe is 100% identical to a part of one strand of the sequence of the nucleotide target to which it must hybridize, i.e. is 100% complementary to a part of the sequence of the nucleotide target to which it must hybridize. In another embodiment, the identity or complementarity is not 100% and the similarity is at least 80%, at least 85%, at least 90% or at least 95% with a part of the sequence of the nucleotide target. In a particular embodiment, the probe differs from a part of one strand of the sequence of the nucleotide target by 1 to 10 mutation(s) (deletion, insertion and/or substitution), preferably by 1 to 10 nucleotide substitutions. By "a part of", it is meant consecutive nucleotides of the nucleotide target, which correspond to the sequence of the probe.

In a particular embodiment, the probe, which is not 100% identical or complementary, keeps the capacity to hybridize, in particular to specifically hybridize, to the sequence of the nucleotide target, similarly to the probe which is 100% identical or 100% complementary with the sequence of the nucleotide target (in the hybridization conditions defined herein).

In a particular embodiment, the size of the probes used to assay a set of genes is approximately the same for all the probes. By "approximately" is meant that the difference of size between the longest probe and the shortest probe of the set is less than 30% (of the size of the longest probe), preferably less than 20%, more preferably less than 10%.

The set of probes of the invention may further comprise at least one (preferably one) probe specific for at least one invariant gene (preferably one or two), in particular specific for ACTG1, EFF1A1, PNN and/or RHOT2 genes. The probes specific for invariant gene(s) may be designed and selected as explained above for the probes specific for genes of the sets of the invention. In a particular embodiment, the probes specific of the invariant genes have approximately the same size as the probes specific of the genes of the set of be assayed (the term approximately being defined as above, with respect to the longest probes of the set of genes).

The invention is also directed to an array suitable to determine the grade of a liver tumor from the sample obtained from a patient. This array is appropriate to carry out the method or process described in the present application.

An array is defined as a solid support on which probes as defined above, are spotted or immobilized. The solid support may be porous or non-porous, and is usually glass slides, silica, nitrocellulose, acrylamide or nylon membranes or filters.

The arrays of the invention comprise a plurality of probes specific for a set of genes to be assayed. In particular, the array comprises, spotted on it, a set of probes as defined above.

The invention also relates to a composition comprising a set of probes as defined above in solution.

In a first embodiment, the probes (as defined above in the set of probes) may be modified to confer them different physicochemical properties (such as methylation, ethylation). The nucleotide targets (as defined herein and prepared from the sample) are linked to particles, preferably magnetic particles, for example covered with ITO (indium tin oxide) or polyimide. The solution of probes is then put in contact with the target nucleotides linked to the particles. The probe/target complexes are then detected, for example by mass spectrometry.

Alternatively, probes may be modified to add a functional group (such as a thiol group) and immobilized on beads (preferably glass beads). These probes immobilized on beads are put in contact with a sample comprising the nucleotide targets, and the probe/target complexes are detected, for example by capillary reaction.

The invention is also directed to kits comprising the sets of probes, the compositions or the arrays of the invention and preferably the primer pairs disclosed herein. These kits may also further comprise reagents necessary for the hybridization of the nucleotide targets of the sets of genes and/or of the invariant genes, to the probes (as such, in the compositions or on the arrays) and the washing of the array to remove unbound nucleotides targets.

In a particular embodiment, the kits also comprise reagents necessary for the hybridization, such as prehybridization buffer (for example containing 5×SSC, 0.1% SDS and 1% bovine serum albumin), hybridization buffer (for example containing 50% formamide, 10×SSC, and 0.2% SDS), low-stringency wash buffer (for example containing 1×SSC and 0.2% SDS) and/or high-stringency wash buffer (for example containing 0.1×SSC and 0.2% SDS).

The kits may also comprise one or several control sample(s) i.e., at least one sample(s) representative for tumor with poor prognosis, at least one sample(s) representative of tumor with good prognosis, at least one sample of a normal adult liver and/or at least one sample of a fetal liver. Alternatively, it may comprise the representation of a gene expression profile of such tumors.

Finally, the invention provides a kit as described above further comprising instructions to carry out the method or process of the invention.

The arrays and/or kits (either comprising pairs of primers or probes or arrays or compositions of the invention or all the components) according to the invention may be used in various aspects, in particular to determine the grade of a liver tumor from a patient, especially by the method disclosed in the present application.

The arrays and/or kits according to the invention are also useful to determine, depending upon the grade of the liver tumor, the risk for a patient to develop metastasis. Indeed, the classification of a liver tumor in the class with poor prognosis is highly associated with the risk of developing metastasis.

In another embodiment, the arrays and/or kits according to the invention are also useful to define, depending upon the grade of the liver tumor, the therapeutic regimen to apply to the patient.

The invention also relates to a support comprising the data identifying the gene expression profile obtained when carrying out the method of the invention.

BRIEF DESCRIPTION OF THE DRAWINGS

The colour version of the drawings as filed is available upon request to the European Patent Office.

(A) Schematic overview of the approach used to identify robust clusters of samples, including two tumor clusters (rC1 and rC2) and one non-tumor cluster (NL) (B) Expression profiles of 982 probe sets (824 genes) that discriminate rC1 and rC2 samples (p<0.001, two-sample t test). Data are plotted as a heatmap where red and green correspond to high and low expression in $\log_2$-transformed scale. (C) Molecular classification of 25 HB samples and status of CTNNB1 gene and β-catenin protein. C1 and C2 classification was based on rC1 and rC2 gene signature by using six different statistical predictive methods (CCP, LDA, 1NN, 3NN, NC and SVM) and the leave-one-out cross-validation. Black and gray squares indicate mutations of the CTNNB1 and AXIN1 genes. Immunohistochemical analysis of β-catenin in representative C1 and C2 cases is shown. (D) Expression of representative Wnt-related and β-catenin target genes (p<0.005, two-sample t test) in HB subclasses and non-tumor livers (NL). (E) Classification of hepatoblastoma by expression profile of a 16-gene signature. (F) Classification of normal human livers of children with HB (from 3 months to 6 years of age) (NT) or fetal livers at 17 to 35 weeks of gestation (FL) by expression profile of a 16-gene signature.

Figure 2:
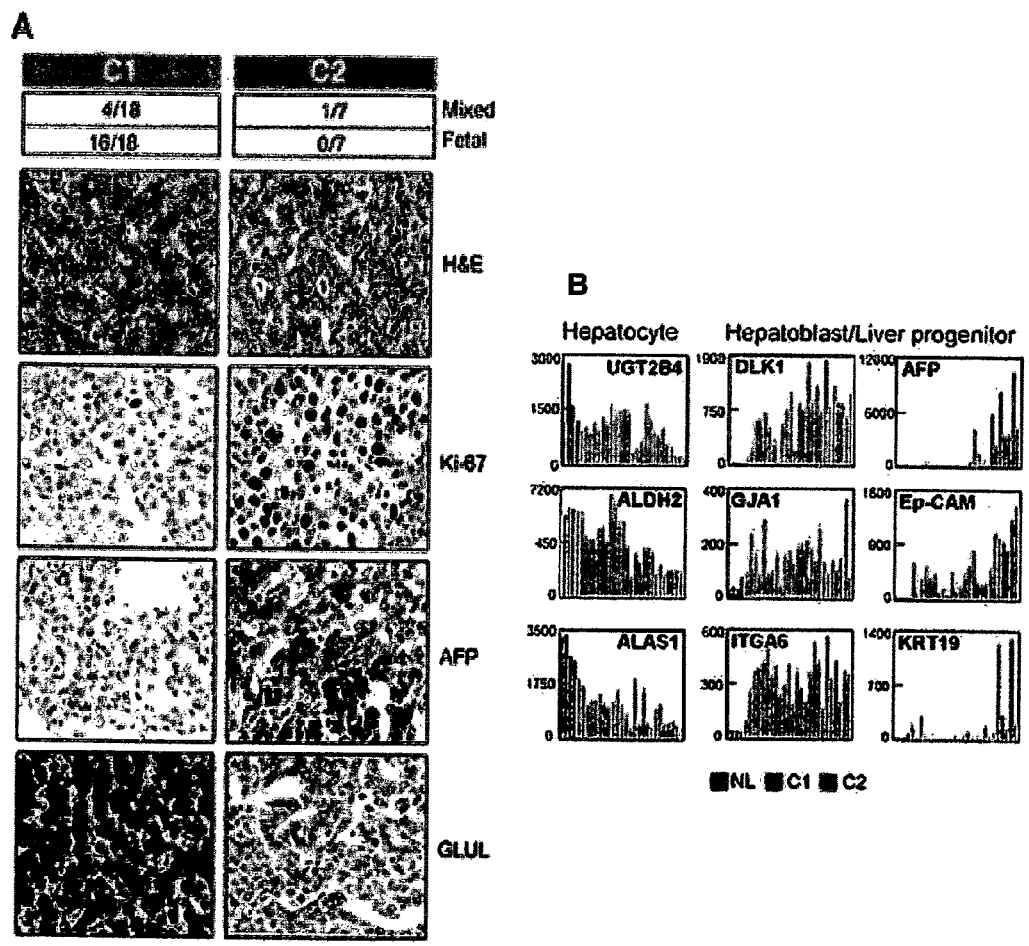

FIG. 2: Molecular HB subclasses are related to liver development stages. (A) Distinctive histologic and immunostaining patterns of HB subclasses C1 and C2. From top to bottom: numbers indicate the ratio of mixed epithelial-mesenchymal tumors and of tumors with predominant fetal histotype in C1 and C2 subtypes; hematoxylin and eosin (H&E) and immunostaining of Ki-67, AFP and GLUL in representative samples. Magnification, ×400. (B) Expression of selected markers of mature hepatocytes and hepatoblast/liver progenitors in HB subclasses and non-tumor livers.

Figure 3:
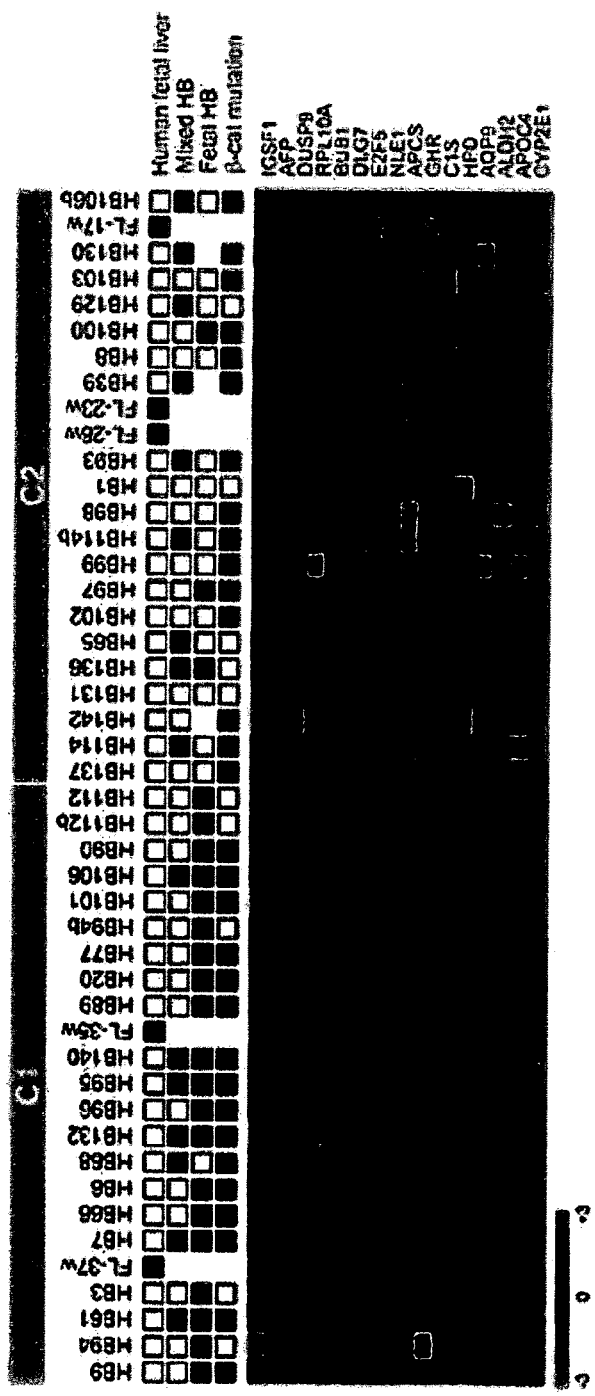

FIG. 3: Validation of the 16-gene signature by qPCR in an independent set of 41 HBs. Expression profiles of the 16 genes forming the HB classifier are shown as a heatmap that indicates high (red) and low (green) expression according to $\log_2$-transformed scale. HB tumors, HB biopsies (b) and human fetal livers (FL) at different weeks (w) of gestation were assigned to class 1 or 2 by using the 16-gene expression profile, six different statistical predictive methods (CCP, LDA, 1NN, 3NN, NC and SVM) and leave-one-out cross-validation. Black boxes in the rows indicate from top to bottom: human fetal liver, mixed epithelial-mesenchymal histology, predominant fetal histotype, and β-catenin mutation.

Figure 4:
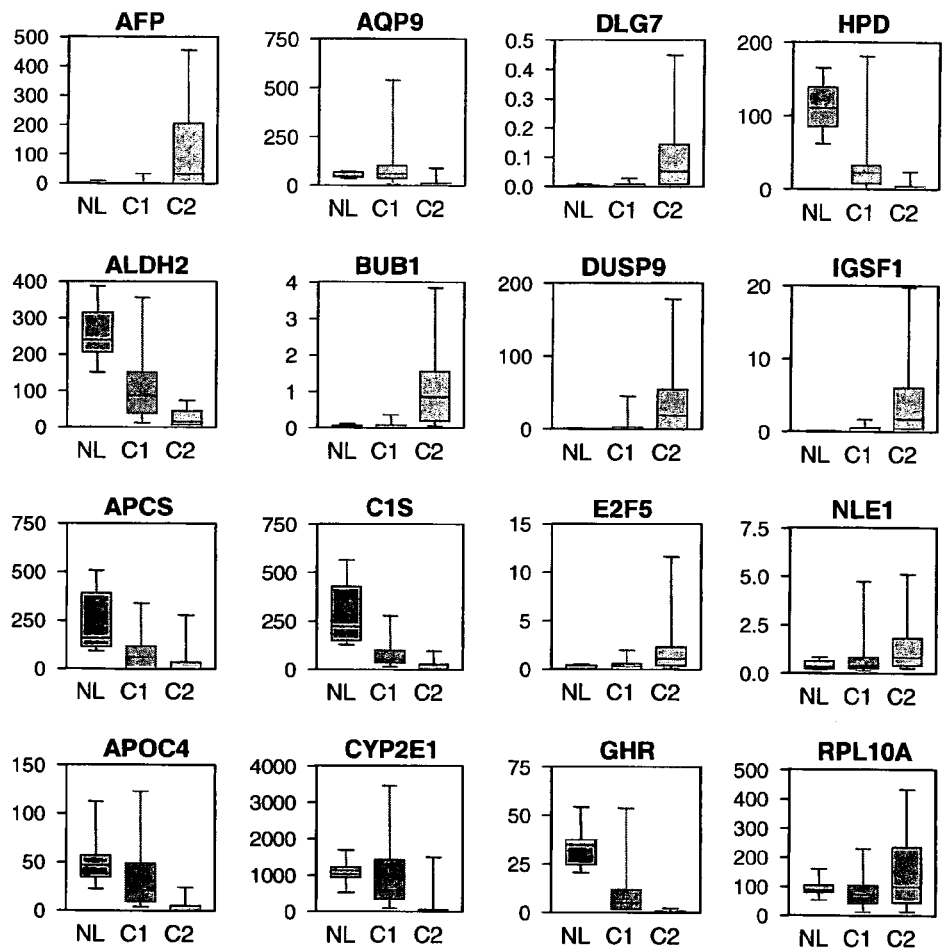

FIG. 4: Gene expression of the 16 genes of the prognostic liver cancer signature assessed by qPCR is presented as box-plot. The boxes represent the 25-75 percentile range, the lines the 10-90 percentile range, and the horizontal bars the median values.

FIG. 5: Expression level of the 16 liver prognostic signature genes shown case by case in 46 hepatoblastomas and 8 normal livers. C1 tumors (green), C2 tumors (red) and normal liver (white).

FIG. 6. Correlation between molecular HB subtypes and clinical outcome in 61 patients. (A) Association of clinical and pathological data with HB classification in the complete set of 61 patients. Only significant correlations (Chi-square test) are shown. PRETEXT IV stage indicates tumorous involvement of all liver sections. (B) Kaplan-Meier plots of overall survival for 48 patients that received preoperative chemotherapy. Profiling via the 16-gene expression signature was used to define C1 and C2 subclasses in tumors resected after chemotherapy, and differences between survival curves were assessed with the log-rank test. (C) Overall survival of 17 HB patients for which pretreatment biopsies or primary surgery specimens were available. The signature was applied exclusively to tumor samples without prior therapy. (D) Multivariate analysis including 3 variables associated to patient's survival. The predominant histotype is defined as either fetal or other (including embryonal, crowed-fetal, macrotrabecular or SCUD types). Tumor stage is defined by PRETEXT stage (Perilongo et al., 2000) and/or distant metastasis at diagnosis and/or vascular invasion. HR, Hazard Ratio; CI, Confidence Interval.

FIG. 7: Clinical, pathological and genetic characteristics of 61 HB cases. SR: standard risk; HR: high risk according to SIOPEL criteria; NA: not available; PRETEXT: pre-treatment extent of disease according to SIOPEL; DOD: dead of disease; *: Vascular invasion was defined by radiological analysis; **: The predominant epithelial histotype variable categorized as "others" included embryonal, crowded fetal, macrotrabecular, and undifferentiated histotypes.

FIG. 8: Clinical, pathological and genetic characteristics of 66 HB samples; Tumor ID number indicates patient number. When more than one sample from the same patient was analyzed, the representative sample used for statistical analysis of clinical correlations is marked by an asterisk; b: biopsy. HB74F: fetal component of HB74; HB74e: embryonal component of HB74. Gender: M, male; F, female; Y, yes; N, no; NA, not available. Multifocality: S, solitary nodules; M, multiple nodules. Histology: E, epithelial; M, mixed; CF, crowded fetal; F, fetal; E, embryonal; M, macrotrabecular; PF, pure fetal; S, SCUD. PRETEXT β-catenin status: wt, wild-type; Δex3, in-frame deletion of part or all exon 3 sequence; FAP, familial polyposis kindred; AXIN1, Axin 1 nonsense mutation (R533stop, $\underline{C}$GA to $\underline{T}$GA). stage: I to IV according to SIOPEL (Aronson et al., 2005). Treatment protocol: S, standard risk; H, high risk according to SIOPEL. Outcome: A, alive free of disease; DOD, dead of disease; D, death unrelated to cancer; R, alive with recurrence of disease.

FIG. 9: Correlation between molecular HB subtypes and clinical outcome in 86 patients. (A) Association of clinical and pathological data with HB classification in the complete set of 86 patients. Only significant correlations (Chi-square test) are shown. PRETEXT IV stage indicates tumorous involvement of all liver sections. (B) Kaplan-Meier plots of overall survival for 73 patients that received preoperative chemotherapy. Profiling via the 16-gene expression signature was used to define C1 and C2 subclasses in tumors resected after chemotherapy, and differences between survival curves were assessed with the log-rank test. (C) Overall survival of 29 HB patients for which pretreatment biopsies or primary surgery specimens were available. The signature was applied exclusively to tumor samples without prior therapy. (D) Multivariate analysis including 3 variables associated to patient's survival. The predominant histotype is defined as either fetal or other (including embryonal, crowed-fetal, macrotrabecular or SCUD types). Tumor stage is defined by PRETEXT stage (Perilongo et al., 2000) and/or distant metastasis at diagnosis and/or vascular invasion. HR, Hazard Ratio; CI, Confidence Interval.

Figure 10:
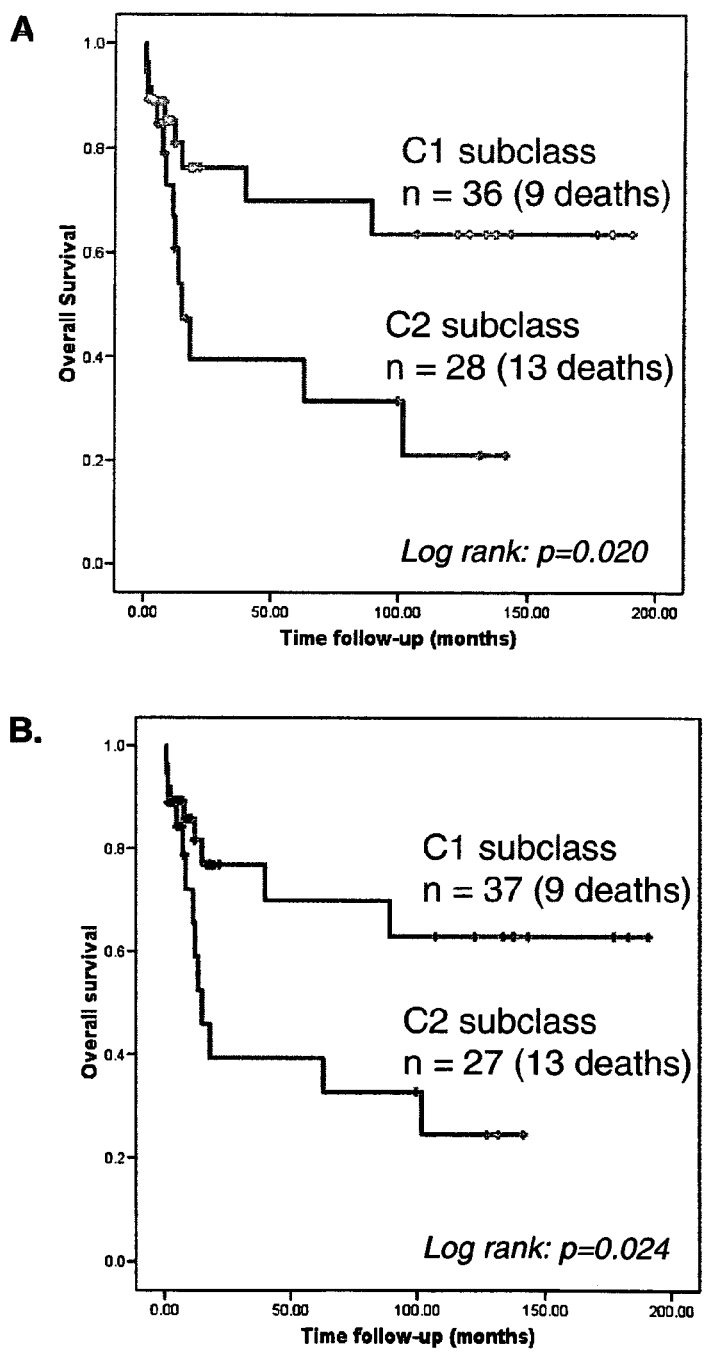

FIG. 10: Correlation between molecular HCC subtypes and clinical outcome in 64 patients. Kaplan-Meier estimates of overall survival in 64 HCC patients using molecular classification with 16 genes, with the unsupervised clustering (centroid) (A) or unsupervised clustering (average) (B).

Figure 11:
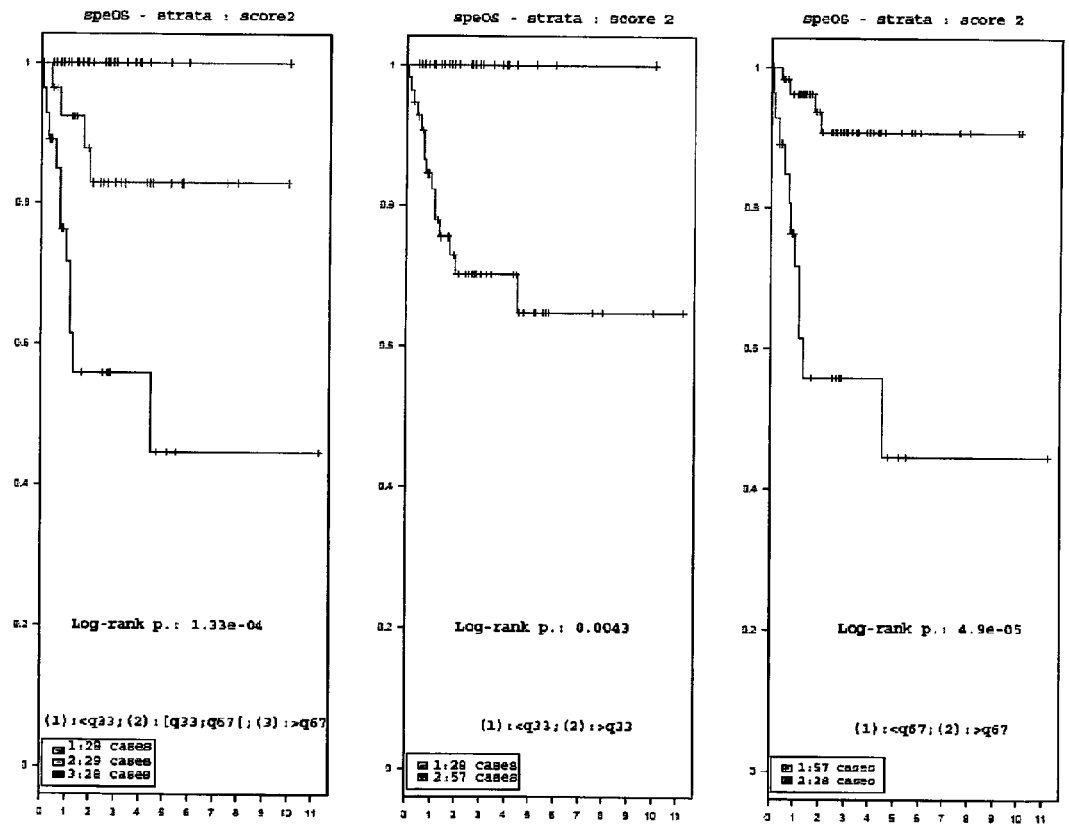

FIG. 11: Analysis of the probability of overall survival (OS) of 85 hepatoblastoma patients using Kaplan-Meier estimates. Left pannel: cases were classified by the discretization method into 3 classes using as cut-offs the $33^{rd}$ percentile and the $67^{th}$ percentile. Middle pannel: cases were classified into 2 classes using the $33^{rd}$ percentile. Right pannel: cases were classified into 2 classes using the $67^{th}$ percentile.

Figure 12:
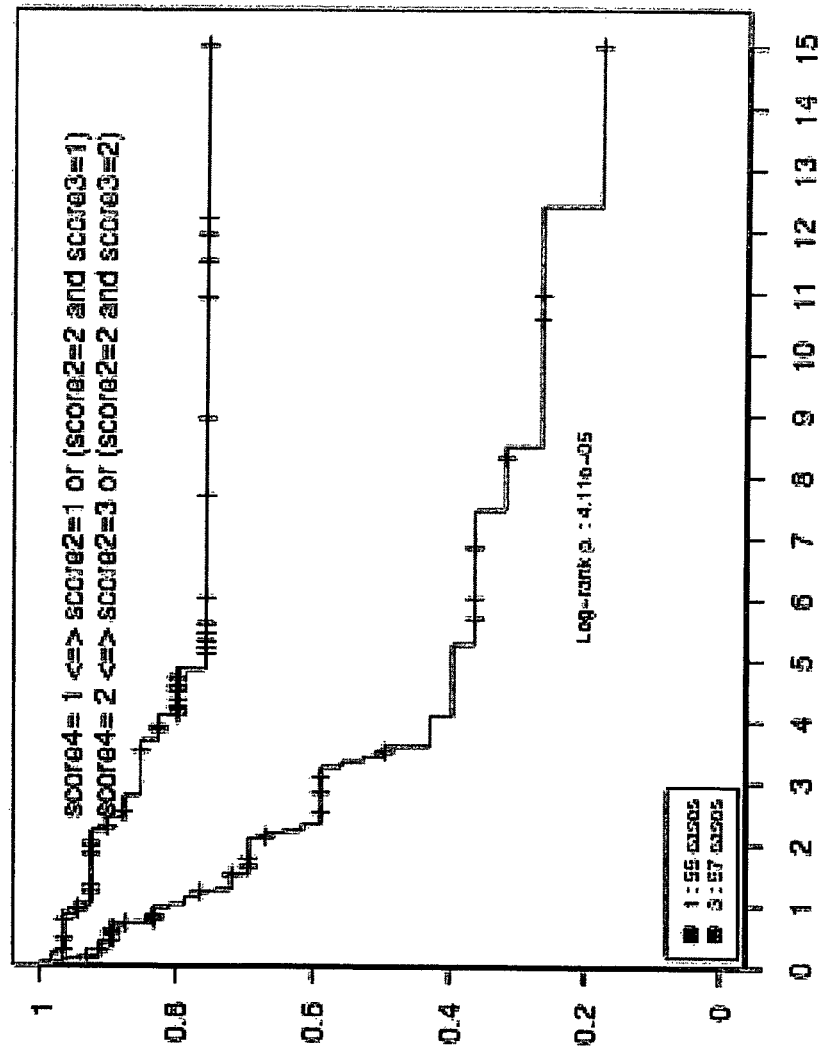
Figure 12H:
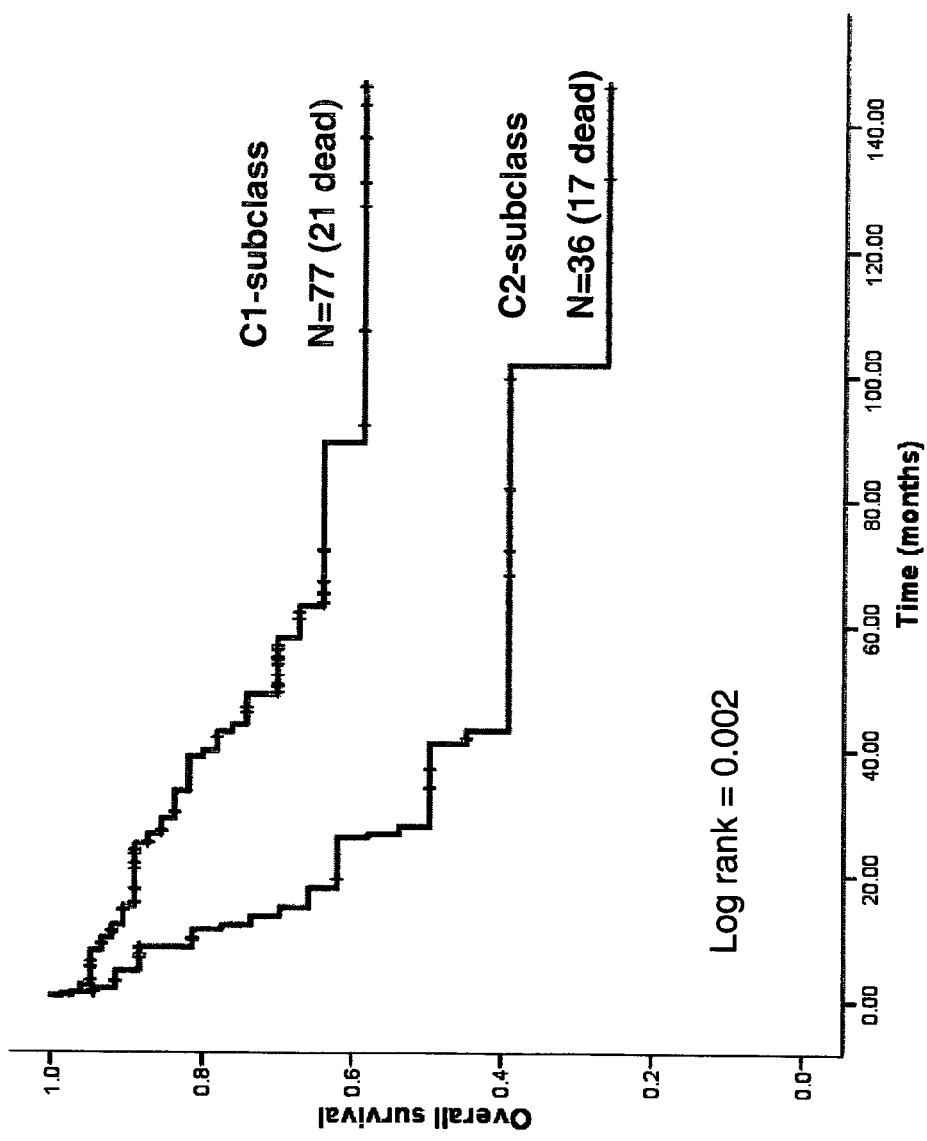
Figure 12I:
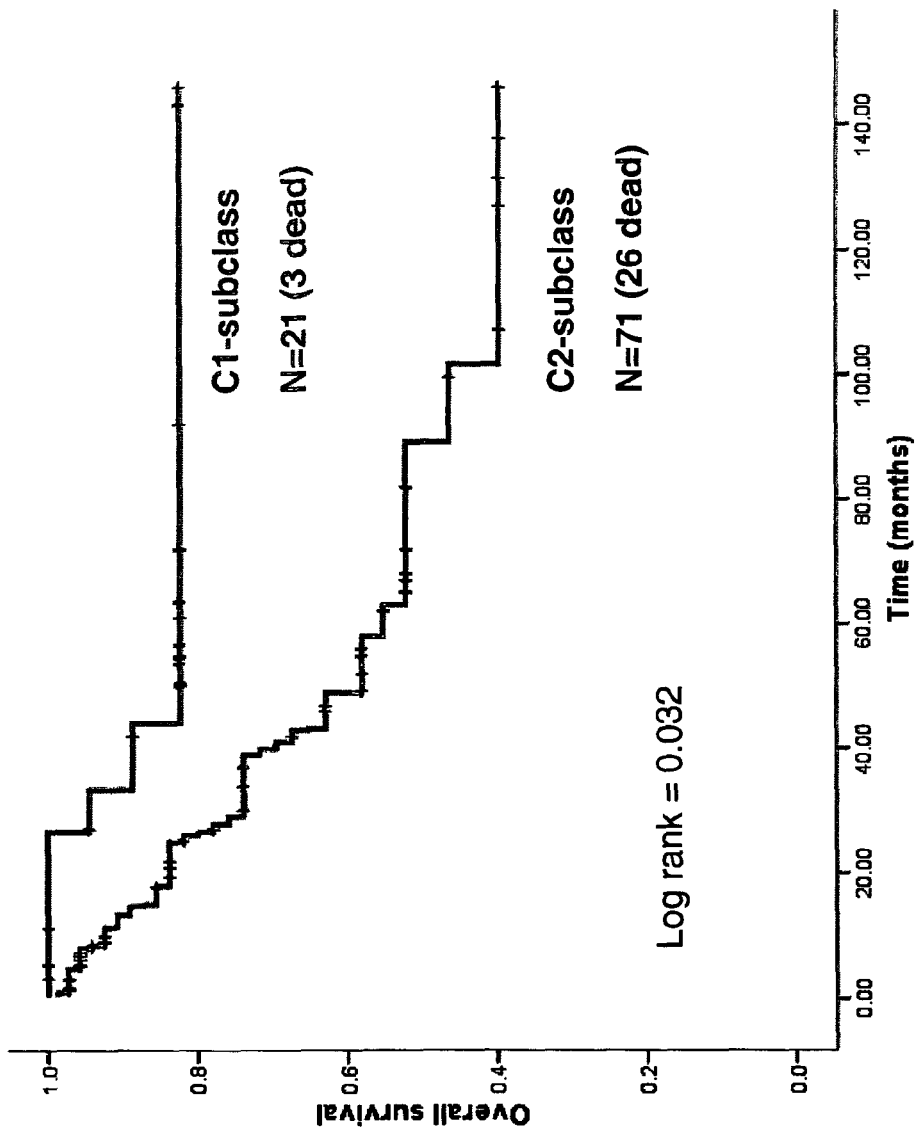
Figure 12K:
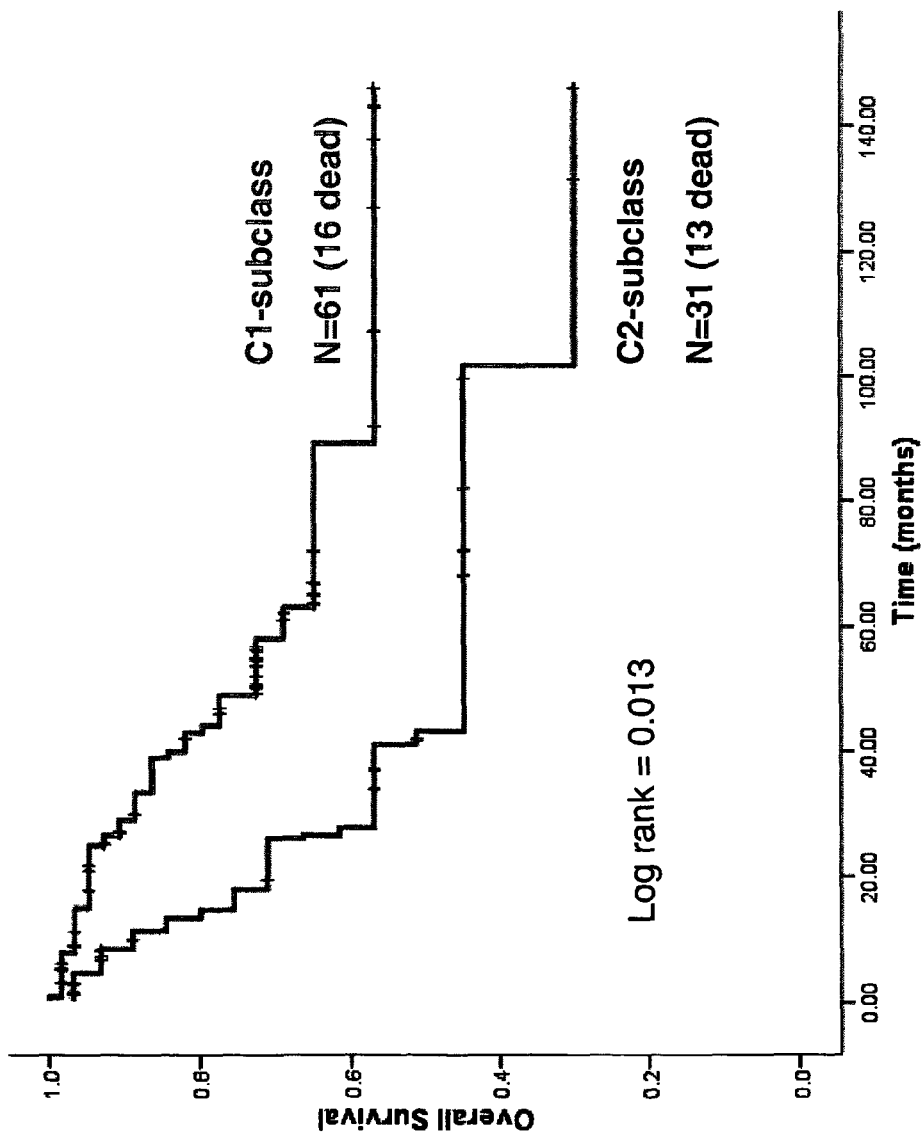

FIG. 12: Analysis of the probability of overall survival (OS) or disease-free survival (DFS) of 113* HCC patients using Kaplan-Meier estimates and log-rank test.
* Among the total series of 114 patients, survival data were not available for one case.

Patients were treated either by partial hepatectomy (PH) or by orthotopic liver transplantation (OLT). Unless specified, the follow-up was closed at 146 months.

A: HCC cases were classified into 3 classes by the discretization method using as cut-offs the $33^{rd}$ and the $67^{th}$ percentiles.

B: 47 HCC cases previously classified into the intermediate class (33<p<67, see pannel A) were subdivided into 2 new subclasses using the $60^{th}$ percentile of proliferation-related genes.

C: 92 HCC cases treated by partial hepatectomy (PH) were classified into 3 classes as in pannel A.

D: 21 HCC cases treated by orthotopic liver transplantation (OLT) were classified into 2 classes using as cut-off the $67^{th}$ percentile.

E: HCC cases were classified into 2 classes using different combinations of scores as described in Table F.

F: HCC cases were classified into 2 classes using as cut-off the $33^{rd}$ percentile.

G: HCC cases were classified into 2 classes using as cut-off the $50^{th}$ percentile.

H: HCC cases were classified into 2 classes using as cut-off the $67^{th}$ percentile.

I: 92 HCC cases treated by partial hepatectomy (PH) were classified into 2 classes using as cut-off the $33^{rd}$ percentile.

J: 92 HCC cases treated by partial hepatectomy (PH) were classified into 2 classes using as cut-off the $50^{th}$ percentile.

K: 92 HCC cases treated by partial hepatectomy (PH) were classified into 2 classes using as cut-off the $67^{th}$ percentile.

L: Disease-free survival of 113 HCC cases after classification into 2 classes using as cut-off the $67^{th}$ percentile. Follow-up was closed at 48 months. Data were not significant when the follow-up was closed at 146 months.

M: Disease-free survival of 92 HCC cases treated by PH, after classification into 2 classes as cut-off the $67^{th}$ percentile. Follow-up was closed at 48 months. Data were not significant when the follow-up was closed at 146 months.

Figure 13:
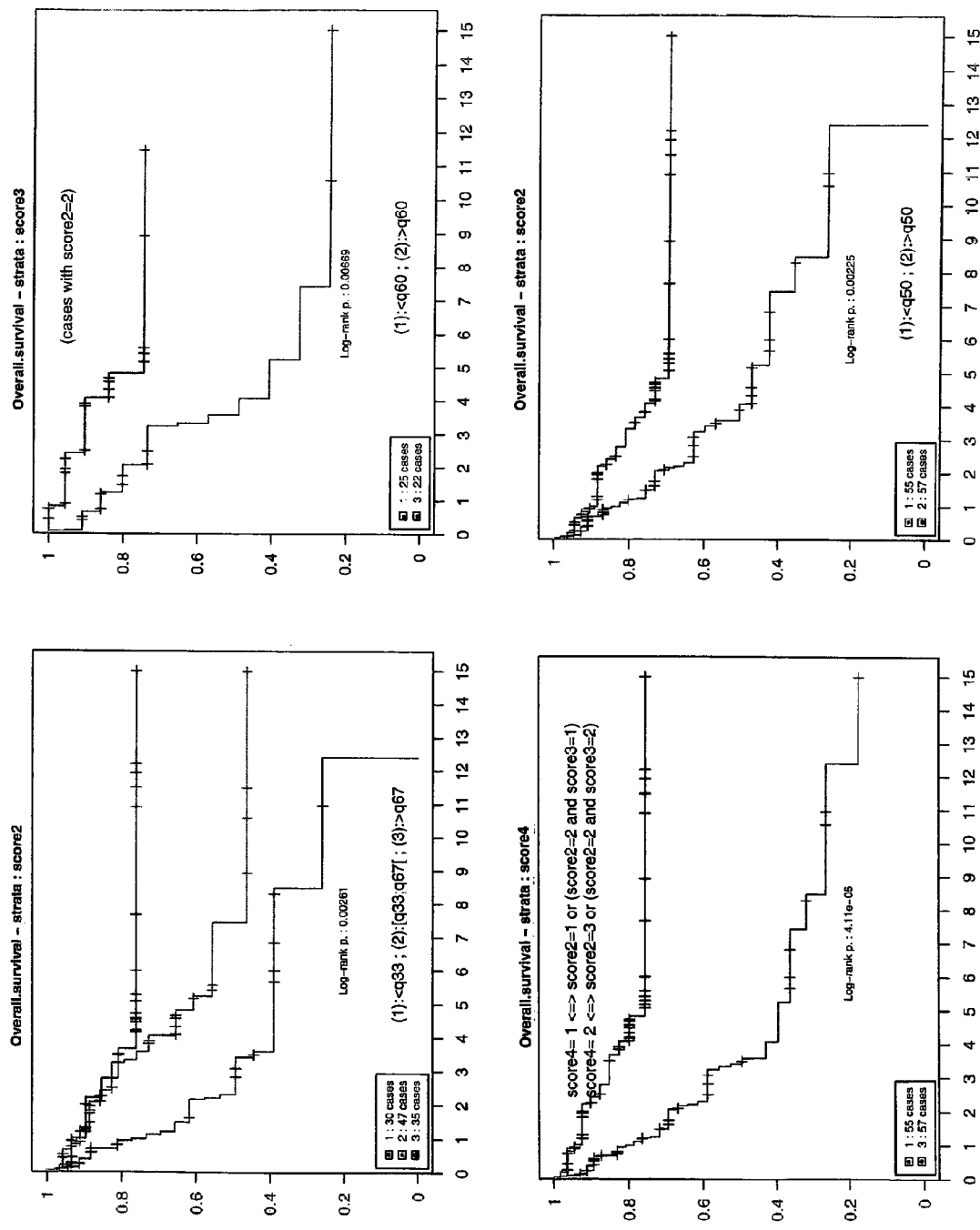

FIG. 13: Analysis of the probability of overall survival (OS) or disease-free survival (DFS) HCC patients using Kaplan-Meier estimates and log-rank test.

EXAMPLES

Experimental Procedures

A. Patients and Tissue Samples.

Sixty-six tumor specimens and biopsies from 61 patients with hepatoblastoma were collected from different hospitals in France (52 cases), Italy (6 cases), United Kingdom (1 case), Switzerland (1 case) and Slovakia (1 case). Forty-eight patients received chemotherapy treatment prior to surgery, most being enrolled in clinical trials of the International Childhood Liver Tumour Strategy Group (SIOPEL) (Perilongo et al., 2000). Samples from fresh tumors avoiding fibrotic and necrotic areas and from adjacent non tumor livers were snap frozen at the time of surgery and stored at −80° C. FIG. 7 describes patient characteristics and clinicopathological parameters.

Patients were children with median age of 2 years, and male:female ratio of 1.5. The median follow-up was 32 months; during this period, 15 patients died from disease. The histology of all tumor specimens was centrally reviewed by expert pathologist according to previously described criteria (Finegold et al., 2007; Zimmermann, 2005). Twenty-five tumors were analyzed on oligonucleotide microarrays and 24 of them, for which DNA was available, were subjected to aCGH analysis, while a second set of 41 tumors was analyzed by qPCR (FIG. 8). No difference was observed in significant clinical and pathological data as well as in the percentage of cases carrying β-catenin mutation between the two sets. This study has been approved by the Ethics Committee of Institut Pasteur, and informed consent of the families was obtained at each Medical Center, in accordance with European Guidelines for biomedical research and with national laws in each country.

B. Oligonucleotide Microarrays and Gene Expression Data Analysis

Twenty-five HB samples and 4 non-tumor samples including a pool of livers from 3 males and a second from 3 females were analyzed using Affymetrix HG-U133A oligonucleotide arrays. Total RNA was prepared using FastPrep® system (Qbiogene, Strasbourg, France) and RNeasy mini Kit (Qiagen, Courtaboeuf, France). RNA quality was checked with the Agilent 2100 Bioanalyzer (Agilent Technologies, Palo Alto, Calif.). Microarray experiments were performed according to the manufacturer's instructions. Affymetrix microarray data were normalized using RMA method (Irizarry et al., 2003). Class discovery was done as described elsewhere (Lamant et al., 2007). Pathway and Gene Ontology enrichment analyses were performed using GSEA method (Subramanian et al., 2005) and hypergeometric tests. For supervised tests and class prediction, we used Biometric Research Branch (BRB) ArrayTools v3.2.2 software, developed by R. Simon and A. Peng. Permutations of the measurements are then used to estimate the FDR (the percentage of genes identified by chance). Additionally, mouse fetal livers at E18.5 and postnatal livers at 8 days of birth were profiled on Affymetrix MG-U74A, B v2 arrays. Data were processed and analyzed as aforementioned.

Except when indicated, transcriptome analysis was carried out using either an assortment of R system software packages (http://www.R-project.org, v2.3.0) including those of Bioconductor v1.8 (Gentleman et al., 2004) or original R code.

B.1. Normalization

Raw data from Affymetrix HG-U133A 2.0 GeneChip™ microarrays were normalized in batch using robust multi-array average method (R package affy, v1.10.0) (Irizarry et al., 2003). Probe sets corresponding to control genes or having a "_x_" annotation were masked yielding a total of 19,787 probe sets available for further analyses.

B.2. Class Discovery

Step 1

Variance Test

The variance of each probe set across samples was tested and compared to the median variance of all the probe sets, using the model: $((n-1) \times Var_{probe\ set})/Var_{med}$, where n refers to the number of samples. By using the same filtering tool of BRB ArrayTools software, the P-value for each probe set was obtained by comparison of this model to a percentile of Chi-square distribution with $(n-1)$ degrees of freedom.

Robust Coefficient of Variation (rCV)

The rCV was calculated for each probe set as follows. After ordering the intensity values of n samples from min to max, we eliminated the min and max values and we calculated the coefficient of variation (CV) for the remaining values.

Unsupervised Probe Sets Selection

Unsupervised selection of probe set lists was based on the two following criteria:
(i) variance test at P<0.01,
(ii) rCV less than 10 and superior to a given rCV percentile. We used eight rCV percentile thresholds (60%; 70%; 80%; 90%; 95%; 97.5%; 99%; 99.5%), which yielded 8 probe set lists.

Step 2: Generation of a Series of 24 Dendrograms

Hierarchical clustering was performed by using the 8 rCV-ranked probe sets lists, 3 different linkage methods (average, complete and Ward's), and 1-Pearson correlation as a distance metric (package cluster v1.9.3). This analysis generated 24 dendrograms.

Step 3:

Stability Assessment

The intrinsic stability of each of the 24 dendrograms was assessed by comparing each dendrogram to the dendrograms obtained after data "perturbation" or "resampling" (100 iterations). Perturbation stands for the addition of random gaussian noise ($\mu=0$, $\sigma=1.5 \times$median variance calculated from the data set) to the data matrix, and resampling for the random substitution of 5% of the samples by virtual sample's profiles, generated randomly. The comparison between dendrograms across all iterations yielded a mean 'similarity score' (see below). The overall stability was assessed by calculating a mean similarity score, using all pairs of the 24 dendrograms.

Similarity Score

To compare two dendrograms, we compared the two partitions in k clusters (k=2 to 8) obtained from these two dendrograms. To compare a pair of partitions, we used a similarity measure, which corresponds to the symmetric difference distance (Robinson and Foulds, 1981).

Step 4: Identification of Robust Clusters

We identified groups in which any pair of samples was co-classified in at least 22 of the 24 partitions, and considered only groups made of 4 samples or more. Then, for any pair of these groups, we calculated the mean number of co-classification of any sample in the first group with any sample in the second group. We aggregated the groups for which this score was at least 18 (over the 24 partitions).

B.3. Supervised Tests

We compared gene expression between two classes of samples by using the Student's t test with random variance model option (BRB ArrayTools software, version 3.4.0a, developed by Dr. Richard Simon and Amy Peng Lam, http://linus.nci.nih.gov/BRB-ArrayTools.html). False Discovery Rates were assessed by using 1000 random permutations of labels (Monte Carlo approach).

B.4. Classification

To classify samples according to gene expression profile, we used the Class prediction tool of BRB ArrayTools software using all 6 following algorithms: Compound Covariate Predictor (CCP), Linear Discriminant Analysis (LDA), 1-Nearest Neighbor (1 NN), 3-Nearest Neighbors (3NN), Nearest Centroid (NC) and Support Vector Machines (SVM). Each sample was classified according to the majority of the 6 algorithms. Samples classified as C2 by at least 3 algorithms were classified accordingly.

B.5. Gene Ontology and Pathway Analysis

We used a hypergeometric test to measure the association between a gene (probe set) list and a gene ontology term (GO term), as in GO stats R package (R. Gentleman). To this end, we mapped the gene list and the GO terms to non-redundant Entrez Gene identifiers by using the annotation file HG-U133_Plus_2.annot.csv (http://www.affymetrix.com, Dec. 14, 2006). GO terms and their relationships (parent/child) were downloaded from http://www.geneontology.org (version Dec. 31, 2006). The list of proteins associated to GO terms (table gene_association.goa_human) and mapping the Entrez Gene ids (table human.xrefs) were downloaded from ftp://ftp.ebi.ac.uk/pub/databases/GO/goa.

KEGG pathway annotation was done by Onto-tools software (http://vortex.cs.wayne.edu/ontoexpress/servlet/UserInfo). We designated a significance threshold of each hypergeometric test at P<0.001, and the condition that a GO term or pathway be represented by at least 3 Entrez Gene identifiers.

B.6. Gene Set Enrichment Analysis (GSEA)

GSEA (Subramanian et al., 2005) was used to evaluate the correlation of a specific gene list with two different sample groups (phenotypes). Briefly, this method calculates an enrichment score after ranking all genes in the dataset based on their correlation with a chosen phenotype and identifying the rank positions of all the members of a defined gene set. We used the signal2noise ratio as a statistic to compare specific and random phenotypes in order to evaluate statistical differences.

C. Array-Based Comparative Genomic Hybridization (aCGH)

Genomic DNA from 24 HBs and 3 non-tumor liver samples was analyzed using aCGH chips designed by the CIT-CGH consortium. This array contains 3400 sequence-verified PAC/BAC clones spaced at approximately 1 Mb intervals, spotted in triplicate on Ultra Gaps slides (Corning Inc, Corning, N.Y.).

The aCGH chip was designed by CIT-CGH consortium (Olivier Delattre laboratory, Curie Institute, Paris; Charles Theillet laboratory, CRLC Val d'Aurelle, Montpellier; Stanislas du Manoir laboratory, IGBMC, Strasbourg and the company IntegraGen™). DNAs were labeled by the random priming method (Bioprime DNA labelling system; Invitrogen, Cergy-Pontoise, France) with cyanine-5 (Perkin-Elmer, Wellesley, Mass.). Using the same procedure, we labeled control DNAs with cyanine-3. After ethanol-precipitation with 210 µg of Human Cot-1 DNA (Invitrogen), resuspension in hybridization buffer (50% formamide), denaturation at 95° C. for 10 minutes and prehybridization at 37° C. for 90 minutes, probes were cohybridized on aCGH. The aCGH slides were previously preblocked with a buffer containing 2.6 mg succinic anhydride/118 ml N-methyl-2-pyrrolidinone/32 ml sodium tetraborate decahydrate, pH 8.0 (Sigma-Aldrich, Lyon, France). After washing, arrays were scanned using a 4000B scan (Axon, Union City, Calif.). Image analysis was performed with Genepix 5.1 software (Axon) and ratios of Cy5/Cy3 signals were determined. The aCGH data were normalized using lowess per block method (Dudoit et al., 2002). Comparison between groups was done using chi-square test or Fisher's exact test, as appropriate.

Status assignment (Gain/Loss) was performed using R package GLAD v1.6.0. Computation of recurrent minimal genomic alterations was done using slight modification of a previously described method (Rouveirol et al., 2006). For comparison between groups, we used the Fischer exact test. Complete aCGH data will be published elsewhere.

D. Mouse Microarray Analysis

Murine Genome Affymetrix U74v2 A and B arrays were used to investigate liver expression at embryonic day 18.5 (E18.5) and at 8 days after birth (PN8). Each time point consisted of a pool of livers from 3-5 animals analyzed in triplicate. Microarray experiments were performed according to the manufacturer's instructions.

Publicly available Affymetrix Mouse Genome (MG) 430 2.0 array liver expression data at embryonic time points E11.5, E12.5, E13.5, E14.5, and E16.5 days of gestation (Otu et al., 2007), were downloaded from the Gene Expression Omnibus (GEO) database (http://www.ncbi.nlm.nih.gov/geo/query/acc.cgi?acc=GSE6998).

MG-U74v2, MG-430 2.0 and HG-133A 2.0 array intra- and cross-species probeset comparison was achieved by using the Affymetrix NetAffx analysis center and by choosing "Good Match" degree of specificity. Unification of sample replicates, multiple array data standardization and Heatmap visualization was done by using dCHIP v1.6 software. Comparison of fetal liver stages by supervised analysis was performed using BRB ArrayTools software as previously described, by classing E11.5 and E12.5 as "Early" and E14.5 and E16.5 as "Late" fetal liver stage. Supervised signature was applied to HB array data, and intensity cut-off=60 was chosen in order to remove probesets that did not reach such intensity level in at least one sample.

E. Quantitative PCR Analysis (qPCR)

For qPCR analysis, we used RNA from 52 tumor samples (including 11 samples analyzed on microarrays, see FIG. 8), and from 8 non-tumor livers and 5 human fetal livers (RNAs purchased from BioChain Institute, Hayward, Calif.).

RNA was extracted by using either Trizol, RNeasy kit (QIAGEN) or miRvana kit (Ambion), then quantified and quality-checked by Agilent technology. For each cDNA preparation, 1 µg of RNA was diluted at the final concentration of 100 ng/µl, and reverse transcribed with the Superscript RT kit (Invitrogen, Carlsbad, Calif.) following the manufacturer's protocol. Random primers (Promega, Charbonniéres-les-Bains, France) were added at the final concentration of 30 ng/µl and the final volume was 20 µl.

The cDNA was diluted 1:25, and 5 µl were used for each qPCR reaction. We added 5 µl of 2×Sybr Green Master mix (Applied Biosystems) and 0.3 µl of each specific primer (final concentration 300 nM). Each reaction was performed in triplicate. qPCR reactions were run on the Applied Biosystems 7900HT Fast Real-Time PCR System with a 384-well thermo-block, in the following conditions: 2 min at 50° C. to activate Uracil-N-glycosylase (UNG)-mediated erase of aspecific reaction; 10 min at 95° C. to activate the polymerase and inactivate the UNG; 40 cycles (15 sec at 95° C. denaturation step and 1 min at 60° C. annealing and extension); and final dissociation step to verify amplicon specificity.

The lists of primers used for qPCR are provided in Table 6 and Table 7 above.

F. Immunohistochemistry (IHC)

IHC was carried out as reported previously (Wei et al., 2000). For antigen retrieval at 95° C., we used 1 mM EDTA (pH 8) for β-catenin and Ki-67 IHC, and 10 mM citrate buffer (pH 6) for AFP and GLUL IHC. We used monoclonal antibodies against β-catenin and GLUL (Cat. Nos. 610154 and 610517; BD Biosciences, Le Pont de Claix, France) and Ki-67 (M7240, Dako, Trappes, France) and polyclonal antibody against AFP (N1501, Dako). Reactions were visualized using the ChemMate Dako Envision Detection kit (Dako) and diaminobenzidine. Subcellular distribution and quantitative evaluation of immunostaining in the different histotypes were assessed by examining at least ten random high-power fields.

G. Clinical Data Analysis

We used the Chi-square test for comparisons between groups. Survival curves were calculated according to the Kaplan-Meier method, using the log-rank test to assess differences between curves. Variables independently related to survival were determined by stepwise forward Cox regression analysis. Follow-up was closed at February 2007 or at time of death. Statistical analysis was done with SPSS software v10.0 (SPSS Inc., Chicago, Ill.).

H. Examples of Other Pairs of Primers and Probes for the 16 Genes of Table 1 and the 4 Invariant Genes (Table 3) that can be Used in the Taqman® Method.

AFP forward primer:
GCCAGTGCTGCACTTCTTCA
AFP reverse primer:
TGTTTCATCCACCACCAAGCT
AFP probe:
ATGCCAACAGGAGGCCATGCTTCA
(for each polynucleotide, the sequence is given from 5' to 3')

Figure 1A:
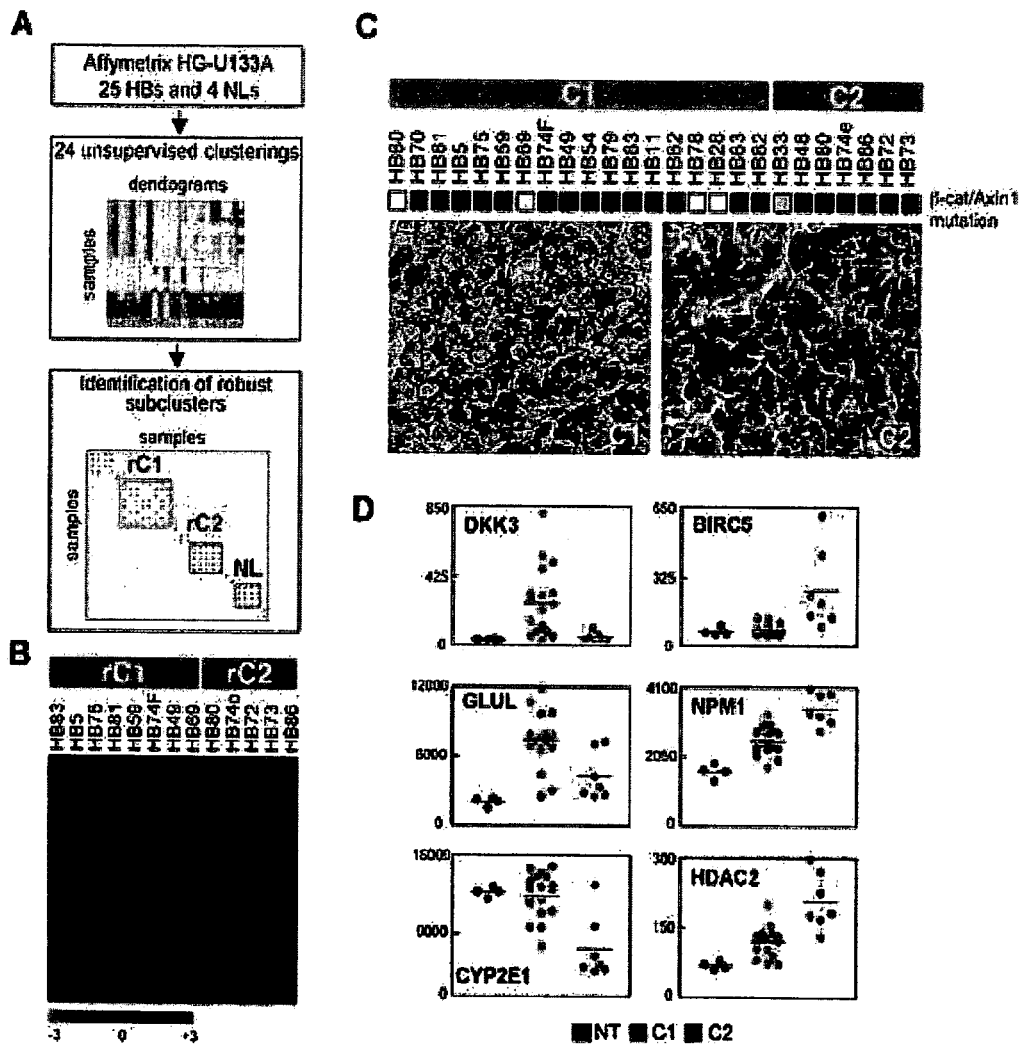
FIG. 1. Identification of two HB subclasses by expression profiling.
Figure 1B:
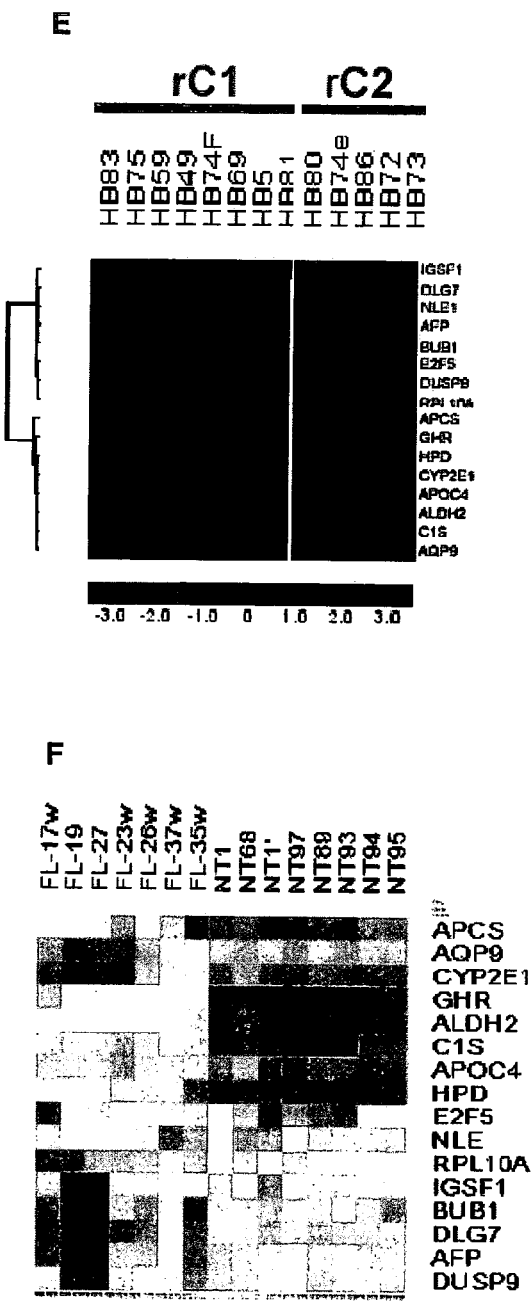

ALDH2 forward primer:
TGCAGGATGGCATGACCAT
ALDH2 reverse primer:
TCTTGAACTTCAGGATCTGCATCA
ALDH2 probe:
CCAAGGAGGAGATCTTCGGGCCA APCS forward primer:
AGCTGGGAGTCCTCATCAGGTA
APCS reverse primer:
CGCAGACCCTTTTTCACCAA
APCS probe:
TGCTGAATTTTGGATCAATGGGACACC APOC4 forward primer:
TGAAGGAGCTGCTGGAGACA
APOC4 reverse primer:
CGGGCTCCAGAACCATTG
APOC4 probe:
TGGTGAACAGGACCAGAGACGGGTG AQP9 forward primer:
GCCATCGGCCTCCTGATTA
AQP9 reverse primer:
GTTCATGGCACAGCCACTGT
AQP9 probe:
TGTCATTGCTTCCTCCCTGGGACTG BUB1 forward primer:
ACATCTGGTTTTCAGTGTGTTGAGA
BUB1 reverse primer:
GTTGCAGCAACCCCAAAGTAA
BUB1 probe:
TCAGCAACAAACCATGGAACTACCAGATCG C1S forward primer:
TCCCAATGACAAGACCAAATTCT
C1S reverse primer:
AGAGCCCATAGGTCCCACACT
C1S probe:
CGCAGCTGGCCTGGTGTCCTG CYP2E1 forward primer:
CATGAGATTCAGCGGTTCATCA
CYP2E1 reverse primer:
GGTGTCTCGGGTTGCTTCA
CYP2E1 probe:
CCTCGTGCCCTCCAACCTGCC DLG7 forward primer:
GCTGGAGAGGAGACATCAAGAAC
DLG7 reverse primer:
CCTGGTTGTAGAGGTGAAAAAGTAATC
DLG7 probe:
TGCCAGACACATTTCTTTTGGTGGTAACC DUSP9 forward primer:
GGCCTACCTCATGCAGAAGCT
DUSP9 reverse primer:
GGGAGATGTTAGACTTCTTCCTCTTG
DUSP9 probe:
CACCTCTCTCTCAACGATGCCTATGACCTG E2F5 forward primer:
CCTGTTCCCCCACCTGATG
E2F5 reverse primer:
TTTCTGTGGAGTCACTGGAGTCA
E2F5 probe:
CCTCACACAGCCTTCCTCCCAGTCC GHR forward primer:
CCCAGGTGAGCGACATTACA
GHR reverse primer:
CATCCCTGCCTTATTCTTTTGG
GHR probe:
CAGCAGGTAGTGTGGTCCTTTCCCCG HPD forward primer:
CCCACGCTCTTCCTGGAA
HPD reverse primer:
TTGCCGGCTCCAAAACC
HPD probe:
TCATCCAGCGCCACAACCACCA IGSF1 forward primer:
GACCATTGCCCTTGAAGAGTGT
IGSF1 reverse primer:
GAGAGGTTGATGAAGGAGAATTGG
IGSF1 probe:
ACCAAGAAGGAGAACCAGGCACCCC NLE1 forward primer:
TGCCTCCTTTGACAAGTCCAT
NLE1 reverse primer:
CGCGTAGGGAAGCCAGGTA
NLE1 probe:
TGGGATGGCAGGACGGGCA RPL10A forward primer
TCGGCCCAGGTTTAAATAAGG
RPL10A reverse primer
CCACTTTGGCCACCATGTTT
RPL10A Taqman probe
AGTTCCCTTCCCTGCTCACACACAACG ACTG1 forward primer:
GGCGCCCAGCACCAT
ACTG1 reverse primer:
CCGATCCACACCGAGTACTTG
ACTG1 probe:
ATCAAGATCATCGCACCCCCAGAGC EEF1A1 forward primer:
GCGGTGGGTGTCATCAAAG
EEF1A11 reverse primer:
TGGGCAGACTTGGTGACCTT
EEF1A11 probe:
AGTGGACAAGAAGGCTGCTGGAGCTG PNN forward primer:
GAATTCCCGGTCCGACAGA
PNN reverse primer:
TTTCGGTCTCTTTCACTTCTTGAA
PNN probe:
AGAGGTCTATATCAGAGAGTAGTCGATCAGGCAAAAGA RHOT2 forward primer:
CCCAGCACCACCATCTTCAC
RHOT2 reverse primer:
CCAGAAGGAAGAGGGATGCA
RHOT2 Taqman probe:
CAGCTCGCCACCATGGCCG Results Identification of Two HB Subclasses by Gene Expression Profiling For robust unsupervised classification, we generated and screened a series of 24 dendrograms to identify samples that co-clustered whatever the method and the gene list. We obtained two robust subgroups of tumors named robust Cluster 1 (rC1, n=8) and robust Cluster 2 (rC2, n=5) (FIG. 1A). Comparison of rC1 and rC2 expression profiles identified 824 genes (p<0.001, false discovery rate (FDR)=0.02) (FIG. 1B). KEGG pathway analysis pinpointed a strong enrichment of cell cycle related genes (p<$10^{-11}$), most being up-regulated in rC2 tumors. These genes were mainly assigned to GO categories including mitosis regulation, spindle checkpoint, nucleotide biosynthesis, RNA helicase activity, ribosome biogenesis, and translational regulation. Evidence that rC2 tumors were faster proliferating than rC1 tumors was further confirmed by Ki-67 immunostaining (see FIG. 2A).

The remaining tumors were classified into C1 (rC1-related) and C2 (rC2-related) subclasses by applying a predictive approach based on the rC1/rC2 gene signature and using robust samples as training set (FIG. 1C). Both groups exhibited similar, high rates of β-catenin mutations, and accordingly, immunohistochemistry (IHC) of β-catenin showed cytoplasmic and nuclear staining of the protein in the majority of HBs. However, β-catenin localization was predominantly membranous and cytoplasmic in C1 tumors, whereas it showed frequent loss of membrane anchoring and intense nuclear accumulation in C2 tumors (FIG. 1C).

We observed differential expression of a number of Wnt members and targets between subclasses. C2 tumors showed increased expression of MYCN, BIRC5 that encodes the anti-apoptotic factor Survivin, NPM1 (encoding nucleophosmin) and HDAC2. By contrast, most C1 tumors prominently expressed the Wnt antagonist DKK3, BMP4, and genes previously found to be activated in liver tumors carrying mutant β-catenin (Boyault et al., 2007; Renard et al., 2007; Stahl et al., 2005). Remarkably, most genes related to liver functions are expressed in the perivenous area of adult livers, such as GLUL, RHBG, and two members of the cytochrome p450 family: CYP2E1 and CYP1A1 (Benhamouche et al., 2006; Braeuning et al., 2006) (FIG. 1D).

Further evidence that the rC1 subclass was enriched in genes assigned to the hepatic perivenous program was provided by Gene Set Enrichment Analysis (GSEA), a computational method for assessing enrichment of a predefined gene list in one class as compared with another (Subramanian et al., 2005). Thus, Wnt/β-catenin signaling appears to activate different transcriptional programs in HB subtypes, likely reflecting different cellular contexts.

HB Subclasses Evoke Distinct Phases of Liver Development

Next, we sought to determine whether HB subclasses were associated with specific histological phenotypes. Mixed epithelial-mesenchymal tumors that represented 20% of cases were not significantly associated with C1 and C2 subclasses. By contrast, a tight association was found with the main epithelial component, which defines the cell type occupying more than 50% of tumor cross-sectional areas. Sixteen out of 18 C1 tumors displayed a predominant fetal phenotype, including 4 'pure fetal' cases, whereas all C2 tumors showed a more immature pattern, with prevailing embryonal or crowded-fetal histotypes associated with high proliferation (Finegold, 1994) ($p<0.0001$) (FIG. 2A). Further relationship between molecular subclasses and hepatic developmental stages was provided by the finding that a number of mature hepatocyte markers were markedly downregulated in C2 compared to C1 tumors (Tables 1 and 2). Conversely, C2 tumors showed strong overexpression (35-fold) of the oncofetal AFP gene associated to high protein levels in tumor cells by IHC (FIG. 2A) and in patients' sera ($r=0.79$, $p<0.0001$). C2 tumors also abundantly expressed hepatic progenitor markers such as KRT19 (encoding cytokeratin 19) and TACSTD1, also known as Ep-CAM (FIG. 2B).

To better define the relationships between HB subclasses and phases of hepatic differentiation, we first generated a liver development-related gene signature by making use of publicly available mouse fetal and adult liver data sets (Otu et al., 2007). When applied to HB samples, this signature was able to distinguish by hierarchical clustering two HB groups closely matching the C1/C2 classification. Next, we integrated HB gene expression data with the orthologous genes expressed in mouse livers at embryonic days (E) 11.5 to 18.5, and at 8 days of birth. In unsupervised clustering, most C2 tumors co-clustered with mouse livers at early stages of embryonic development (E11.5 and E12.5), whereas C1 tumors gathered with mouse livers at late fetal and postnatal stages. Together, these data comfort the notion that tumor cells in C2 and C1 subtypes are arrested at different points of the hepatic differentiation program.

Identification of a 16-Gene Signature as HB Classifier

To investigate the relevance of molecular HB classification in an independent set of tumors, we defined a HB classifier signature derived from the top list of genes differentially expressed between rC1 and rC2 clusters. After qPCR assessment, a list of 16 top genes at $p \leq 10^{-7}$ was selected to form a class predictor (Table 1). Most of these genes show drastic variations in expression level during liver development, and among them, BUB1 and DLG7 have been repeatedly identified as hESC markers (Assou et al., 2007). The 16-gene expression profile was first investigated in rC1 and rC2 samples used as training set, and it predicted classification with 100% of accuracy in these samples, using either microarray or qPCR data. The robustness of this signature was confirmed by correct classification into C1 and C2 subclasses of all 13 remaining tumors analyzed by microarray (FIG. 1E). Expression profiles of fetal livers and normal liver for these 16-gene signature were also assayed (FIG. 1F). This signature was therefore employed to classify a new, independent set of 41 HB samples by qPCR (FIGS. 4 and 5 and Table 8), resulting in 21 tumors categorized as C1 and 20 tumors as C2 subtype (FIG. 3).

Extending our previous observation, C1/C2 classification in this new set of tumors was unrelated to CTNNB1 mutation rate. Using qPCR, we also confirmed enhanced expression in C2 tumors of liver progenitor markers such as AFP, Ep-CAM, and KRT19, as well as MYCN (FIG. 3). Moreover, while a similar percentage of C1 and C2 tumors displayed mesenchymal components, a predominant fetal histotype was found in 95% of tumors of the C1 subtype, whereas in 82% of C2 tumors, the major component displayed less differentiated patterns such as embryonal, crowded-fetal, macrotrabecular and SCUD types ($p<0.0001$) (FIG. 3). To further assess the association of HB subclasses with liver development, 5 human fetal livers at different weeks of gestation were included in the qPCR studies. In unsupervised clustering, fetal livers at late (>35 weeks) and earlier (17 to 26 weeks) developmental stages were classified as C1 and C2 respectively, further supporting that HB subclasses reflect maturation arrest at different developmental phases.

TABLE 8

Gene expression of the prognostic signature for liver cancer by quantitative RT-PCR.

| | C1 | | | C2 | | | NL | | | Fold-change | | | |
|---|---|---|---|---|---|---|---|---|---|---|---|---|---|
| | median | min | max | median | min | max | median | min | max | C1/NL | C2/NL | C2/C1 | C1/C2 |
| AFP | 0.4 | 0.0 | 33.3 | 30.7 | 0.0 | 456.1 | 0.2 | 0.0 | 8.8 | 2.3 | 38.1 | 16.5 | 0.1 |
| ALDH2 | 87.1 | 13.2 | 356.7 | 15.0 | 2.2 | 74.4 | 240.4 | 151.6 | 387.6 | 0.3 | 0.1 | 0.2 | 5.2 |
| APCS | 61.6 | 1.1 | 338.9 | 1.9 | 0.0 | 276.2 | 158.6 | 92.7 | 509.5 | 0.2 | 0.0 | 0.1 | 19.8 |

TABLE 8-continued

Gene expression of the prognostic signature for liver cancer by quantitative RT-PCR.

| | C1 | | | C2 | | | NL | | | Fold-change | | | |
|---|---|---|---|---|---|---|---|---|---|---|---|---|---|
| | median | min | max | median | min | max | median | min | max | C1/NL | C2/NL | C2/C1 | C1/C2 |
| APOC4 | 21.3 | 4.3 | 122.8 | 1.6 | 0.1 | 24.2 | 47.0 | 22.3 | 112.4 | 0.5 | 0.0 | 0.1 | 16.1 |
| AQP9 | 60.6 | 8.0 | 540.6 | 2.5 | 0.1 | 90.1 | 46.6 | 38.0 | 72.7 | 1.3 | 0.1 | 0.1 | 18.9 |
| BUB1 | 0.0 | 0.0 | 0.4 | 0.9 | 0.1 | 3.9 | 0.0 | 0.0 | 0.1 | 1.2 | 16.1 | 13.4 | 0.1 |
| C1S | 51.1 | 14.9 | 277.2 | 7.5 | 1.3 | 96.0 | 223.4 | 129.3 | 565.3 | 0.2 | 0.0 | 0.2 | 5.7 |
| CYP2E1 | 583.2 | 97.7 | 3463.0 | 19.7 | 0.4 | 1504.0 | 1128.6 | 527.6 | 1697.0 | 0.7 | 0.0 | 0.0 | 51.6 |
| DLG7 | 0.0 | 0.0 | 0.0 | 0.1 | 0.0 | 0.5 | 0.0 | 0.0 | 0.0 | 1.7 | 12.4 | 7.3 | 0.1 |
| DUSP9 | 1.5 | 0.4 | 45.7 | 19.1 | 0.0 | 179.0 | 0.6 | 0.2 | 1.3 | 4.0 | 18.3 | 4.6 | 0.2 |
| E2F5 | 0.2 | 0.0 | 2.0 | 1.1 | 0.1 | 11.7 | 0.1 | 0.0 | 0.5 | 1.8 | 6.5 | 3.5 | 0.3 |
| GHR | 5.2 | 0.0 | 54.0 | 0.5 | 0.0 | 2.4 | 35.2 | 20.8 | 54.5 | 0.1 | 0.0 | 0.1 | 8.6 |
| HPD | 22.9 | 0.9 | 182.0 | 1.2 | 0.1 | 23.8 | 111.5 | 62.6 | 165.7 | 0.2 | 0.0 | 0.1 | 14.0 |
| IGSF1 | 0.1 | 0.0 | 1.7 | 1.7 | 0.0 | 19.8 | 0.1 | 0.0 | 0.1 | 2.2 | 22.4 | 10.2 | 0.1 |
| NLE | 0.4 | 0.1 | 4.8 | 0.8 | 0.3 | 5.1 | 0.4 | 0.2 | 0.8 | 1.2 | 2.2 | 1.8 | 0.5 |
| RPL10A | 73.3 | 12.0 | 230.4 | 98.2 | 11.9 | 432.8 | 86.9 | 54.1 | 159.9 | 0.8 | 1.1 | 1.5 | 0.7 |

NL, non-tumor liver; C1, good prognosis hepatoblastomas; C2, bad prognosis hepatoblastomas. Shown are the median values of 46 hepatoblastomas from 41 patients, the minimal and maximal values in each class, and the fold changes between classes. Data are presented in arbitrary units after normalization of the raw quantitative PCR values with genes (ACTG1, EFF1A1, PNN and RHOT2) that presents highly similar values in all samples. Gene expression of the 16 genes are presented on FIGS. 4 and 5.

The 16-Gene Signature as a Strong Independent Prognostic Factor

In a First Set of 61 Patients

The clinical impact of HB molecular classification was addressed in a first set of 61 patients (FIGS. 7 and 8), comprising 37 (61%) C1 and 24 (39%) C2 cases. Besides strong association with predominant immature histotypes, HBs of the C2 subclass were tightly associated with features of advanced tumor stage, such as vascular invasion and extrahepatic metastasis (FIG. 6A). Accordingly, overall survival of these patients was markedly impaired. Kaplan-Meier estimates of overall survival probability at 2-years were 50% for patients with C2 tumors and 90% for patients with C1 tumors (p=0.0001, log rank test), and similar trends were seen for disease-free survival probabilities (data not shown). Next, we examined whether pre-operative chemotherapy treatment given to 48 patients could affect tumor classification. These cases were evenly distributed among HB subclasses, with no significant association with molecular classification. Of note, available pretreatment biopsies were assigned to the same subclass as matched resected tumors in 3 out of 4 cases (see FIG. 3; HB112 and HB112b have been both classified as C1 grade, and HB114 and HB114b have been both classified as C2 grade). We examined the performance of the 16-gene signature on the 48 tumors resected after chemotherapy, and found significant difference in outcome between patients with C1 and C2 type HBs (p=0.0021, log rank test) (FIG. 6B). Remarkably, Kaplan-Meier analysis confirmed C2 subclass as a poor prognostic group in 17 cases for which pre-treatment biopsies or primary surgery specimens were available (p=0.0318, log rank test) (FIG. 6C).

We further assessed the prognostic validity of the 16-gene signature for all patients in multivariate analysis, using a Cox proportional hazards model with pathological and clinical variables associated to patients' survival. This analysis identified the signature as an independent prognostic factor, with better performance than tumor stage defined by PRETEXT stage, vascular invasion and extrahepatic metastases (FIG. 6D). Thus, this signature demonstrated strong prognostic relevance when compared to current clinical criteria.

In a Second Set of 86 Patients

Figure 9A:
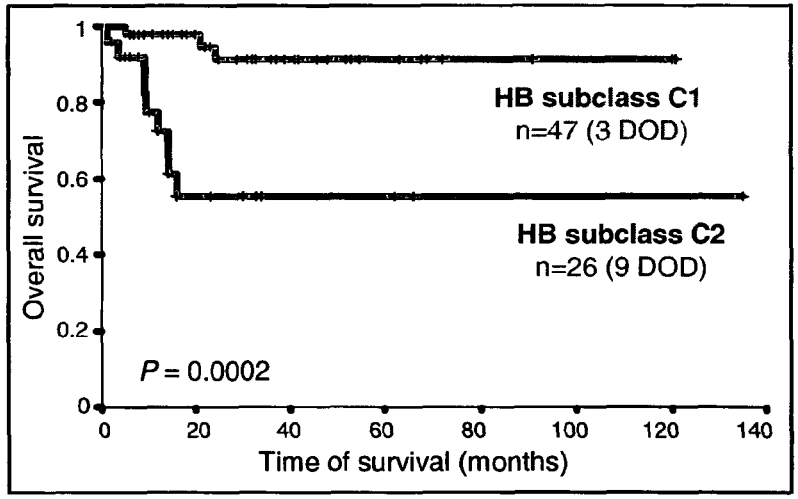

The clinical impact of HB molecular classification was addressed in a second set of patients (comprising the sample of the first set), comprising 53 (61%) C1 and 33 (39%) C2 cases. Besides strong association with predominant immature histotypes, HBs of the C2 subclass were tightly associated with features of advanced tumor stage, such as vascular invasion and extrahepatic metastasis (FIG. 9A). Accordingly, overall survival of these patients was markedly impaired. Kaplan-Meier estimates of overall survival probability at 2-years were 60% for patients with C2 tumors and 94% for patients with C1 tumors (p=0.00001, log rank test), and similar trends were seen for disease-free survival probabilities (Table 9).

TABLE 9

Survival analysis (Kaplan Meier, log rank test); DFS: disease-free survival; Others: dead or alive with recurrent disease.

| N. of patients | 61 C1 + 25 C2 = 86 | P value |
|---|---|---|
| Survival (all patients) | Alive/Dead | |
| C1 | 50/3 | <0.00001 |
| C2 | 20/13 | |
| DFS (all patients) | DFS/others | |
| C1 | 48/5 | <0.00001 |
| C2 | 18/15 | |
| Survival (non-treated patients) | Alive/Dead | |
| C1 | 12/0 | 0.0164 |
| C2 | 11/6 | |
| DFS (non-treated patients) | DFS/others | |
| C1 | 12/0 | 0.0213 |
| C2 | 12/6 | |

Figure 9B:
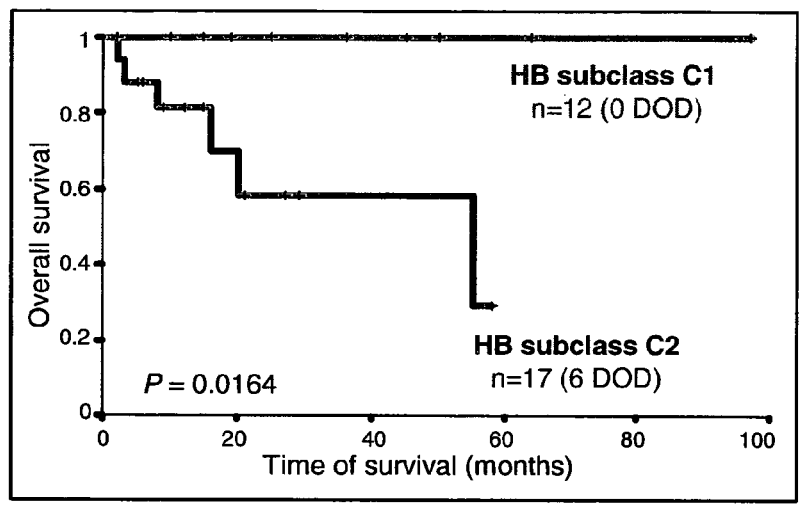

Next, we examined whether pre-operative chemotherapy treatment given to 73 patients could affect tumor classification. These cases were evenly distributed among HB subclasses, with no significant association with molecular classification. We examined the performance of the 16-gene signature on the 73 tumors resected after chemotherapy, and found significant difference in outcome between patients with C1 and C2 type HBs (p=0.0002, log rank test) (FIG. 9B). Remarkably, Kaplan-Meier analysis confirmed C2 subclass as a poor prognostic group in 29 cases for which pre-treatment biopsies or primary surgery specimens were available (p=0.0164, log rank test) (FIG. 9C).

We further assessed the prognostic validity of the 16-gene signature for all patients in multivariate analysis, using a Cox proportional hazards model with pathological and clinical variables associated to patients' survival. This analysis identified the signature as an independent prognostic factor, with better performance than tumor stage defined by PRETEXT stage, vascular invasion and extrahepatic metastases (FIG. 9D).

Finally, various clinical elements of 103 HB samples from 86 patients were compared with respect to their classification as C1 or C2 grade using the 16-gene signature (Table 10).

TABLE 10

Clinical correlations.

| N. of patients | 61 + 25 = 86 | p-value (chi-square) |
|---|---|---|
| Gender | ns | |
| Chemotherapy treatment | Yes/No | |
| C1 | 47/6 | ns |
| C2 | 26/7 | |
| Chemotherapy protocol | STD/High | |
| C1 | 30/13 | 0.007 |
| C2 | 9/16 | |
| TUMOR STAGE | Early/Advanced | |
| C1 | 32/20 | 0.005 |
| C2 | 10/23 | |
| Metastasis | No/Yes | |
| C1 | 43/10 | 0.004 |
| C2 | 17/16 | |
| Vascular Invasion | No/Yes | |
| C1 | 36/15 | 0.005 |
| C2 | 13/20 | |
| Advanced Pretext stage (IV) | No/Yes | |
| C1 | 42/9 | ns |
| C2 | 24/7 | |
| Multifocality | No/Yes | |
| C1 | 36/17 | ns |
| C2 | 18/14 | |
| Histology | Ep/Mixed | |
| C1 | 31/21 | ns |
| C2 | 20/13 | |
| Main Epith Comp | Fetal/NonFetal | |
| C1 | 48/4 | <0.0001 |
| C2 | 6/22 | |

STD: standard risks (cisplatine)
High: high risk (cisplatine/doxorubicine, intensified treatment);
Tumor stage (defined as Vasc. Inv and/or metastasis and/or PRETEXT stage IV);
metastasis: extrahepatic metastasis (mainly lung);
vascular invasion is determined by imagery;
Pretext IV (involved an intrahepatic extent of the tumor to all hepatic sections);
multifocality (more than 2 tumor nodules);
Ep: pure epithelial form
Mixed: mesenchymatous and epithelial mixed form;
Fetal: well differentiated;
non fetal: embryonic, atypic, SCUD and/or macrotrabecular cells.

The above results carried out on a first set of 61 patients, and on a second completed set of 86 patients, demonstrate that the 16-gene signature, identified in the present application, is a strong prognostic relevance when compared to current clinical criteria.

Discussion

The present application demonstrates that, using integrated molecular and genetic studies, hepatoblastoma encompass two major molecular subclasses of tumors that evoke early and late phases of prenatal liver development. Aberrant activation of the canonical Wnt pathway represented a seminal event in both tumor types, with cumulated mutation rates of β-catenin, APC and AXIN over 80%. However, depending on tumor differentiation stage, Wnt signaling activated distinct transcriptional programs involved in tumor growth and invasiveness or in liver metabolism. Further comparisons of immature, embryonal-type HBs with the bulk of more differentiated, fetal-type tumors revealed a tight correlation between stage of hepatic maturation arrest and clinical behavior, notably vascular invasion and metastatic spread, and patients' survival.

Molecular HB Subclasses are Determined by Liver Differentiation Stages

In this study, expression-based classification of HB was achieved through a highly reliable statistical method combining different unsupervised hierarchical clustering approaches. This method led to the selection of two robust tumor subgroups, and this robustness was confirmed using a new, independent set of samples and 16 relevant genes discriminating these tumor subgroups. These results demonstrated that the most significant differences between HB subclasses can be ascribed to distinct hepatic differentiation stages, as defined by comparison with expression profiles of mouse livers at early (E11.5-E12.5) and late (E14.5-E18.5) embryonic stages. These studies also provide biological relevance to early histologic classification that distinguished fetal and embryonal cells as major HB components (Weinberg and Finegold, 1983). The C1 subclass recapitulates liver features at the latest stage of intrauterine life, both by expression profile and by mostly fetal morphologic patterns, while in the C2 subclass, transcriptional program and predominant embryonal histotype resemble earlier stages of liver development. Thus, despite frequent morphological heterogeneity in HB, these expression-based subclasses closely matched the histologic types found to be prevailing after microscopic examination of the entire tumor mass.

These results, showing that childhood liver tumors recapitulate programs of their developing counterpart, are in line with recent studies using cross-species comparisons. It has been demonstrated that clinically distinct medulloblastoma subtypes can be identified by their similarity with precise stages of murine cerebellar development (Kho et al., 2004). Evidence for conserved mechanisms between development and tumorigenesis was also obtained in Wilms' tumor, the embryonic kidney malignancy, which shares expression of sternness and imprinted genes with murine metanephric blastema (Dekel et al., 2006). It was noticed that HBs, like Wilms' tumors, exhibit robust overexpression of a number of paternally expressed genes like DLK1, IGF2, PEG3, and PEG10 that are involved in growth induction processes and downregulated with differentiation during development.

Previous studies using stem cell markers and markers of hepatocytic and biliary lineages have described differential patterns among HB components that reflect sequential stages of liver development (Schnater et al., 2003). The present data extent these observations, and indicate that immature C2-type tumor cells evoke hepatic cancer progenitor cells, with distinctive overexpression of highly relevant markers such as cytokeratin 19 and Ep-CAM (Roskams, 2006). Recently, embryonic stem/progenitor cells have been isolated from human fetal livers, either by enrichment of blast-like cells in primary hepatoblast cultures or by immunoselection of Ep-CAM-positive epithelial cells (Dan et al., 2006; Schmelzer et al., 2007). These cell lines have self-renewal capacity and can differentiate into mature hepatocytes and cholangiocytes, and one of them also gives rise to various mesenchymal lineages (Dan et al., 2006). Whether HBs arise from transformation of these cell types is presently unknown. As malignant mesenchymal derivatives are frequently admixed with epithelial tissues in HB, it is tempting to speculate that this tumor occurs from a multipotent progenitor harboring characteristics of mesenchymal-epithelial transitional cells. Moreover, since no significant differences in gene expression profiles was noted here between pure epithelial and mixed epithelial-mesenchymal HBs, tumor cells likely kept intrinsic capacities to undergo epithelial-mesenchymal transition.

A salient feature of immature HBs is the characteristic interplay of sternness and proliferation found in aggressive tumors (Glinsky et al., 2005). The C2-type expression profile was significantly enriched in hESC markers, including the mitotic cell cycle and spindle assembly checkpoint regulators cyclin B1, BUB1, BUB1B, and Aurora kinases. These mitotic kinases are centrosomal proteins that ensure proper spindle assembly and faithful chromosome segregation in mitosis. Overexpression of these kinases or other components of the spindle checkpoint induces centrosome amplification and defects in chromosome segregation leading to chromosome number instability and aneuploidy (Marumoto et al., 2005; Zhou et al., 1998). Non-disjunctional events are involved in developmental syndromes (Hassold and Hunt, 2001), and might be responsible for increased rate of chromosomal imbalances evidenced here in C2-type HBs.

Context-Dependent Transcriptional Programs Driven by Wnt Signalling

Mutational activation of β-catenin is a hallmark of HB, and accordingly, we found intracellular accumulation and nuclear localization of the protein in virtually all tumors, albeit with variable frequencies and intensities. Both immature and differentiated tumors overexpressed AXIN2 and DKK1, reflecting an attempt to activate a negative feedback loop aimed at limiting the Wnt signal. However, the two HB subtypes showed significant differences in β-catenin immunoexpression, illustrated by concomitant nuclear accumulation and decreased membranous localization of the protein in poorly differentiated, highly proliferative HBs. Heterogeneous distribution of nuclear β-catenin within colorectal tumors has been linked to different levels of Wnt signaling activity, resulting from differential combinations of autocrine and paracrine factors (Fodde and Brabletz, 2007). Similarly, nuclear β-catenin might be related to the absence of membranous E-cadherin in immature HBs, as we reported previously (Wei et al., 2000), and to cross-talks with growth-stimulating pathways in less differentiated cells. In this context, increased dosage of Wnt signaling might induce migratory and invasive phenotype.

Major differences between the two HB subtypes were found here in expression levels of Wnt targets involved in liver functions. Recent studies have demonstrated that Wnt/β-catenin signaling governs liver metabolic zonation by controlling positively the perivenous gene expression program and negatively the periportal program (Benhamouche et al., 2006). In our study, overexpression of hepatic perivenous markers such as GLUL was prominent in differentiated HBs, while genes encoding periportal functions like GLS2 were downregulated. This profile is highly similar to those of human and murine HCCs expressing mutant β-catenin (Boyault et al., 2007; Stahl et al., 2005), and corresponds to an hepatic signature of Wnt target genes. Accordingly, the zonation-related profile was lessened in poorly differentiated HBs, and mutant β-catenin was found to activate a different, muscle-related expression program in the pediatric Wilms' tumor (Zirn et al., 2006).

Clinical Implications

The clinical behavior of many human solid tumors has been related to their differentiation status and proliferative rate. We show that HB does not depart from this rule, with strong correlation of molecular subclasses linked to hepatic differentiation with clinical tumor stage and patient's outcome. This correlation was mainly determined by differences in invasive and metastatic phenotypes between the two subclasses, but not by differences in tumor localization or tumor extension across liver sections, which defines the preoperative staging (PRETEXT) utilized to evaluate tumor resectability (Perilongo et al., 2000). Major differences in expression profiles of the two molecular HB subtypes led us to elucidate a 16-gene signature that proved highly efficient in stratification of HBs as well as normal livers according to hepatic developmental stage. Most importantly, this classifier also discriminated aggressive tumors, exhibited powerful survival predictor capacities in pre-treatment biopsies and surgical specimens, and demonstrated strong prognostic relevance when confronted to current clinical criteria in multivariate analysis. Although immature HBs have been associated to worse clinical outcome as opposed to differentiated HBs (Weinberg and Finegold, 1983), frequent cellular heterogeneity has hampered the use of histopathologic criteria for defining risk groups, excepted for a minority of cases showing 'pure fetal' or SCUD types. The expression signature afforded here enables direct appraisal of the global degree of tumor cell maturation, allowing to bypass these difficulties. Thus, it can improve the outcome prediction and clinical management of hepatoblastoma, by identifying cases with increased risk of developing metastasis, or conversely, by avoiding unnecessary over-treatment.

In conclusion, the present application identifies a 16-gene signature that distinguishes two HB subclasses and that is able to discriminate invasive and metastatic hepatoblastomas, and predicts prognosis with high accuracy. The identification of this expression signature with dual capacities may be used in recognizing liver developmental stage and in predicting disease outcome. This signature can be applied to improve clinical management of pediatric liver cancer and develop novel therapeutic strategies, and is therefore relevant for therapeutic targeting of tumor progenitor populations in liver cancer.

Analysis of 64 Hepatocellular Carcinoma (HCC) from 64 Patients

Real time RT-PCR (Taqman methodology) was performed on 67 HCC samples, as disclosed for HB samples above. The clinical characteristics of the 67 patients diagnosed with HCC as well as the features of the HCC samples are disclosed in Tables 11 and 12 below.

Amplification was carried out with primers of the 16-gene signature disclosed in Table 6. Data were normalized to the expression of the ROTH2 gene (primers disclosed in Table 7) and analyzed by the ΔCt method. Quantitative PCR data are disclosed in Table 13.

TABLE 11 features of the HCC samples obtained from 67 patients (pages 60 to 62)

| Tumor id | follow-up length (years) | tumor grade (Edmonson) | tumor differentiation according to OMS | tumor size | vascular invasion macro | vascular invasion micro | recurrence or metastasis |
|---|---|---|---|---|---|---|---|
| HC1 | 0.07 | 3 | moderately differentiated | 120 | NA | absent | no recurrence |
| HC10 | 0.95 | 4 | moderately/poorly differentiated | 75 | absent | absent | no recurrence |
| HC11 | 11.10 | NA | NA | 15 | absent | absent | no recurrence |
| HC12 | 0.05 | NA | Well differentiated | 60 | NA | NA | no recurrence |
| HC14 | 1.00 | NA | moderately/poorly differentiated | 80 | NA | NA | no recurrence |
| HC15 | 1.22 | 3 | moderately differentiated | 60 | present | present | no recurrence |

TABLE 11-continued features of the HCC samples obtained from 67 patients (pages 60 to 62)

| Tumor id | follow-up length (years) | tumor grade (Edmonson) | tumor differentiation according to OMS | tumor size | vascular invasion macro | vascular invasion micro | recurrence or metastasis |
|---|---|---|---|---|---|---|---|
| HC17 | 10.96 | 2 | Well differentiated | 100 | absent | absent | no recurrence |
| HC18 | 0.39 | 3 | moderately differentiated | 140 | present | present | NA |
| HC20 | 15.40 | NA | Well differentiated | 40 | NA | NA | no recurrence |
| HC21 | 0.70 | NA | NA | 100 | NA | NA | NA |
| HC22 | 11.50 | NA | Well differentiated | 45 | absent | absent | no recurrence |
| HC23 | 11.93 | 2 | Well differentiated | 50 | absent | absent | no recurrence |
| HC25 | 15.87 | 2 | Well differentiated | 140 | absent | absent | NA |
| HC27 | 0.10 | NA | Well differentiated | 15 | absent | absent | no recurrence |
| HC28 | 0.10 | NA | moderately differentiated | 120 | NA | present | no recurrence |
| HC3 | 3.33 | 2 | Well differentiated | 60 | absent | absent | recurrence |
| HC30 | 11.78 | 3 | moderately differentiated | 16 | NA | NA | no recurrence |
| HC32 | 0.66 | 2 | Well differentiated | 60 | absent | NA | no recurrence |
| HC34 | 14.72 | 2 | Well differentiated | 140 | absent | absent | recurrence |
| HC37 | 0.20 | NA | moderately differentiated | 35 | present | present | non |
| HC38 | 1.12 | NA | NA | 50 | absent | NA | recurrence |
| HC4 | 11.48 | 2 | Well differentiated | 100 | absent | absent | no recurrence |
| HC41 | 7.44 | 2 | Well differentiated | 30 | NA | absent | recurrence |
| HC42 | 10.58 | 3 | moderately differentiated | 130 | possible; non certain | present | no recurrence |
| HC43 | 10.20 | NA | moderately differentiated | 15 | NA | NA | no recurrence |
| HC52 | 0.25 | 3 | moderately differentiated | 110 | absent | absent | no recurrence |
| HC58 | 8.30 | 2 | moderately differentiated | 100 | absent | absent | no recurrence |
| HC6 | 1.25 | 2 | Well differentiated | 90 | absent | present | recurrence |
| HC64 | 5.25 | 3 | moderately differentiated | 40 | absent | absent | recurrence |
| HC66 | 8.93 | 2-3 | Well to moderately differentiated | 75 | absent | absent | no recurrence |
| HC7 | 1.50 | 2-3 | Well differentiated | 100 | present | present | recurrence |
| HC8 | 8.48 | 3 | moderately differentiated | 30 | absent | absent | no recurrence |
| HC9 | 0.02 | 3-4 | moderately/poorly differentiated | 100 | present | present | no recurrence |
| HC101 | 1.00 | 2-3 | Well to moderately differentiated | 35 | present | present | no recurrence |
| HC102 | 0.10 | NA | Poorly differentiated | 200 | present | present | no recurrence |
| HC103 | 1.82 | 2-3 | Well to moderately differentiated | 55 | absent | present | recurrence |
| HC104 | 0.17 | 2-3 | Well to moderately differentiated | 160 | Possible; non certain | present | no recurrence |
| HC105 | 0.56 | 3 | moderately differentiated | 40 | present | present | recurrence |
| HC106 | 1.70 | 3 | moderately differentiated | 80 | present | present | no recurrence |
| HC107 | 1.75 | 2 | Well differentiated | 60 | absent | absent | no recurrence |
| HC108 | 1.62 | 3 | moderately differentiated | 26 | absent | present | no recurrence |
| HC109 | 1.00 | 1-2 | Well to very well differentiated | 30 | absent | absent | no recurrence |
| HC110 | 1.00 | 3 | moderately differentiated | 30 | present | present | no recurrence |
| HC111 | 0.60 | 3 | moderately differentiated | 40 | present | present | no recurrence |
| HC112 | 1.48 | 2-3 | Well to moderately differentiated | 18 | absent | absent | no recurrence |
| HC113 | 1.00 | 2-3 | Well to moderately differentiated | 50 | present | present | no recurrence |
| HC114 | 0.44 | 2 | Well differentiated | 36 | absent | absent | no recurrence |
| HC119 | 0.75 | 1 | Well differentiated | 90 | absent | absent | no recurrence |
| HC120 | 0.69 | 3 | moderately differentiated | 140 | absent | absent | no recurrence |
| HC121 | 1.00 | 2-3 | Well to moderately differentiated | 28 | absent | absent | no recurrence |
| HC122 | 0.93 | 1 | Very well differentiated | 40 | absent | absent | no recurrence |
| HC123 | 0.90 | 3 | moderately differentiated | 26 | absent | present | no recurrence |
| HC124 | 0.82 | 2-3 | Well to moderately differentiated | 20 | absent | present | no recurrence |
| HC125 | 0.60 | 3 | moderately differentiated | 150 | Possible; non certain | present | no recurrence |
| HC126 | 0.75 | 2 | Well differentiated | 20 | present | present | recurrence |
| HC127 | 0.40 | 3 | moderately differentiated | 43 | probable | probable | no recurrence |
| HC128 | 0.52 | 3 | moderately differentiated | 62 | absent | absent | no recurrence |
| HC129 | 0.30 | 3 | moderately differentiated | 25 | absent | present | no recurrence |
| HC131 | 0.42 | 1-2 | Well differentiated | 130 | present | present | recurrence |
| HC132 | 0.25 | 2-3 | Well to moderately differentiated | 115 | present | present | recurrence |
| HC133 | 0.44 | 2 | Well to moderately differentiated | 110 | absent | present | no recurrence |
| HC134 | 0.10 | 3 | moderately differentiated | 30 | absent | present | no recurrence |
| HC135 | 0.14 | 3 | moderately differentiated | 38 | absent | Possible; non certain | no recurrence |
| HC136 | 0.26 | 2-3 | Well to moderately differentiated | 120 | absent | present | no recurrence |

N.A: non available; macro: macrovacular invasion; micro: microvacular invasion

TABLE 12 features of the HCC samples obtained from 67 patients, and features of patients (pages 63 and 64)

| Tumor ID | Score METAVIR Activity | Score METAVIR Fibrosis | Chronic viral hepatitis | Viral etiology HBV | Viral etiology HCV | alcohol | Other etiologies |
|---|---|---|---|---|---|---|---|
| HC1 | NA | 4 | no | no | no | yes | |
| HC10 | NA | 4 | yes | yes | no | no | |
| HC11 | NA | NA | yes | yes | yes | no | |
| HC12 | NA | NA | yes | yes | no | no | |
| HC14 | NA | NA | yes | no | yes | yes | |
| HC15 | 3 | 3 | no | no | no | yes | |
| HC17 | NA | 3 | yes | yes | no | no | |
| HC18 | 2 | 4 | no | no | no | yes | |
| HC20 | NA | NA | no | no | no | yes | |
| HC21 | NA | NA | no | no | no | yes | |
| HC22 | NA | NA | no | no | no | yes | |
| HC23 | NA | 0 | no | no | no | no | |
| HC25 | 0 | 0 | no | no | no | no | |
| HC27 | NA | NA | yes | no | yes | no | |
| HC28 | 0 | 0 | no | no | no | no | |
| HC3 | NA | 4 | yes | no | yes | no | |
| HC30 | NA | 4 | no | no | no | yes | |
| HC32 | NA | 4 | yes | no | yes | no | |
| HC34 | NA | 0 | no | no | no | no | |
| HC37 | NA | NA | no | no | no | yes | |
| HC38 | NA | 4 | yes | no | yes | no | |
| HC4 | NA | 1 | no | no | no | no | |
| HC41 | NA | 4 | yes | no | yes | no | |
| HC42 | 2 | 1 | yes | yes | no | no | |
| HC43 | NA | NA | yes | no | no | no | |
| HC52 | NA | 4 | yes | yes | no | no | |
| HC58 | 2 | 3 | yes | no | yes | no | |
| HC6 | NA | 1 | no | no | no | yes | Hemochro |
| HC64 | 2 | 2 | yes | no | yes | no | |
| HC66 | NA | 4 | yes | yes | no | yes | |
| HC7 | 2 | 3 | no | no | no | yes | |
| HC8 | NA | 4 | yes | no | yes | no | |
| HC9 | 1 | 3 | no | no | no | yes | |
| HC101 | 2 | 4 | yes | yes | yes | yes | |
| HC102 | 1 | 1 | yes | yes | yes | no | |
| HC103 | 3 | 4 | yes | yes | no | no | |
| HC104 | 0 | 1 | no | no | no | no | |
| HC105 | 2 | 4 | yes | no | yes | no | |
| HC106 | 1 | 4 | yes | yes | no | no | |
| HC107 | 0 | 0-1 | no | no | no | yes | |
| HC108 | 1 | 1 | yes | no | yes | no | |
| HC109 | 2 | 4 | no | no | no | yes | NASH |
| HC110 | 1 | 4 | yes | no | yes | yes | |
| HC111 | 1 | 4 | no | no | no | yes | |
| HC112 | 2 | 2 | no | no | no | no | NASH |
| HC113 | 1 | 4 | yes | no | yes | no | |
| HC114 | 2 | 3 | no | no | no | yes | |
| HC119 | 2 | 1 | no | no | no | no | NASH |
| HC120 | 2 | 3 | yes | yes | no | no | |
| HC121 | 2 | 4 | yes | no | yes | no | |
| HC122 | 0 | 1 | no | no | no | no | |
| HC123 | 2 | 4 | yes | no | yes | yes | |
| HC124 | 1 | 4 | yes | yes | no | no | |
| HC125 | 2 | 4 | no | no | no | yes | NASH |
| HC126 | 1 | 4 | yes | yes | no | no | |
| HC127 | 2 | 4 | yes | no | yes | no | |
| HC128 | 1 | 1 | no | no | no | no | NASH |
| HC129 | 2 | 4 | no | no | no | yes | |
| HC131 | 0 | 1 | no | no | no | no | |
| HC132 | 1 | 1 | yes | yes | no | no | |
| HC133 | 2 | 2 | no | no | no | yes | |
| HC134 | 2 | 3 | yes | no | yes | no | |
| HC135 | 1 | 2 | yes | yes | no | no | |
| HC136 | 0 | 1 | no | no | no | no | |

N.A: non available; HBV: hepatitis B virus; HCV; hepatitis C virus; hemochro: hemochromatosis; NASH: non alcoholic steatohepatitis.

TABLE 13

Quantitative PCR data of the 16-gene signature normalized to the expression of the ROTH2 gene (pages 65 to 68)

| | HC1 | HC3 | HC4 | HC6 | HC7 | HC8 | HC9 | HC10 | HC11 |
|---|---|---|---|---|---|---|---|---|---|
| AFP | −2.212911 | −3.865709 | −7.6758115 | −7.9469815 | 5.311541 | 2.0890815 | −7.0483095 | 2.3869635 | 0.6488335 |
| ALDH2 | 6.2372335 | 6.230074 | 2.186358 | 5.4231035 | 4.0446765 | 3.9297005 | 3.0017225 | 0.95212 | 5.958108 |
| APOC4 | 0.614689 | 0.95786 | −1.608247 | 0.9614255 | −3.550537 | −0.6776965 | −9.6721075 | NA | 1.076151 |
| APCS | 7.0721355 | 7.52919 | 5.845683 | 7.3704745 | 5.1967915 | 6.567126 | −0.017488 | −1.0272875 | 7.7638255 |
| AQP9 | 6.047695 | 6.7334475 | 3.759528 | 7.006052 | 6.351893 | 3.1082155 | 3.7536735 | 1.3400495 | 6.122144 |
| BUB1 | −3.841505 | −0.147459 | −4.221132 | −0.5252045 | −0.299039 | −1.214781 | 2.980029 | −1.864677 | −2.362454 |
| C1S | 8.163492 | 8.7963405 | 5.8997645 | 8.162856 | 4.062593 | 7.2991535 | 4.830331 | 2.639902 | 8.319293 |
| CYP2E1 | 10.3093235 | 10.428074 | 7.1147515 | 10.1334265 | 11.024027 | 7.7910075 | 0.5825245 | 3.604805 | 9.575619 |
| DLG7 | −5.30317 | −2.057513 | −4.4226465 | −1.6282005 | −1.169221 | −2.80866 | 1.3733475 | NA | −2.8432205 |
| DUSP9 | −11.616567 | −8.8462855 | −9.4268185 | −10.22051 | −6.6521625 | −9.6946695 | −9.5262655 | NA | NA |
| E2F5 | 0.05328 | −1.909804 | −1.7432195 | 0.024339 | −0.2833465 | −0.0193165 | 0.711082 | −1.344368 | −0.736822 |
| GHR | 2.655512 | 2.069524 | −2.0012965 | 1.887805 | −1.7428205 | 2.342442 | −2.3242195 | −0.4900285 | 4.757848 |
| HPD | 9.449416 | 8.549803 | 9.415253 | 8.5958965 | 6.183977 | 5.329776 | −0.011478 | 2.932809 | 9.029214 |
| IGSF1 | −6.46034 | −7.249974 | NA | −7.1580385 | −3.192514 | −2.806768 | −4.026769 | NA | −7.6390015 |
| NLE1 | −1.159417 | −1.5801355 | −3.1459935 | 0.6940375 | −0.3919565 | −1.579419 | −0.80375 | NA | −1.9328755 |
| RPL10A | 6.6225235 | 6.0562915 | 4.4121905 | 6.8637555 | 7.1381125 | 6.2574845 | 6.3016635 | 9.1966395 | 7.379063 |

| | HC12 | HC15 | HC17 | HC18 | HC20 | HC21 | HC22 | HC23 | HC25 |
|---|---|---|---|---|---|---|---|---|---|
| AFP | −6.538312 | 6.14089 | 7.1950405 | −6.856588 | −0.65281 | −4.3070475 | −4.418018 | −5.538438 | −3.90298 |
| ALDH2 | 4.6271565 | 4.5178635 | 2.6522585 | 1.840894 | 6.287083 | 2.175112 | 5.331214 | 5.853486 | 6.162477 |
| APOC4 | −1.221393 | −5.156026 | −2.395651 | −3.84764 | 3.2094885 | −6.2591235 | 0.5455545 | 0.5708905 | 1.834891 |
| APCS | 6.942673 | 3.380102 | 4.5167035 | 4.916924 | 8.2117635 | 5.9159775 | 6.6835035 | 6.9009145 | 8.798759 |
| AQP9 | 4.1878425 | 2.373344 | 2.8711295 | 3.6093495 | 7.354605 | 1.1452535 | 5.7992305 | 6.651868 | 8.758959 |
| BUB1 | −3.293346 | 0.8830545 | 1.0884485 | −0.063545 | −1.4635025 | 0.0802935 | −2.173361 | −2.5475915 | −2.5679685 |
| C1S | 6.850023 | 7.1343975 | 6.035123 | 4.263272 | 8.471663 | 5.7190985 | 7.2514145 | 8.2212235 | 8.5606875 |
| CYP2E1 | 7.284587 | 4.9390935 | 6.037085 | 5.811062 | 10.2536915 | 1.2878015 | 8.0876755 | 9.047509 | 10.814935 |
| DLG7 | −4.7199665 | −0.1414205 | 0.666284 | −1.512286 | −2.1165725 | −0.322455 | −3.3904095 | −3.848364 | −3.34202 |
| DUSP9 | NA | −4.4342765 | −3.163581 | −8.7756845 | −9.6208445 | −7.8162765 | −10.827291 | NA | −7.1111525 |

TABLE 13-continued

Quantitative PCR data of the 16-gene signature normalized to the expression of the ROTH2 gene (pages 65 to 68)

| | | | | | | | | | |
|---|---|---|---|---|---|---|---|---|---|
| E2F5 | −2.4002515 | 1.399564 | 1.206766 | −2.426129 | −1.1944835 | −0.0686475 | −0.7133385 | −1.4330655 | 0.049846 |
| GHR | 2.2402875 | 0.2426 | −2.353691 | −2.9035 | 4.5756335 | 0.71981 | 2.416651 | 3.7226655 | 1.9012935 |
| HPD | 9.656029 | 4.473096 | 0.6808655 | 5.7101575 | 10.6864405 | 4.0108195 | 9.8859985 | 9.583194 | 9.1845675 |
| IGSF1 | −7.466951 | 0.0722075 | −6.0490105 | −2.4248235 | NA | −2.954814 | −5.6986975 | −7.200325 | NA |
| NLE1 | −1.64183 | −0.321593 | −0.386649 | −1.3815525 | −1.118745 | −1.618369 | −1.9449755 | −1.823275 | −1.770127 |
| RPL10A | 5.178571 | 6.8777395 | 7.068098 | 5.9464565 | 7.542193 | 6.309556 | 7.194012 | 5.9526365 | 7.4507165 |

| | HC26 | HC27 | HC28 | HC30 | HC32 | HC34 | HC37 | HC38 | HC41 |
|---|---|---|---|---|---|---|---|---|---|
| AFP | −5.69175 | −0.626755 | NA | 6.4370325 | 0.0037145 | −6.6945705 | −1.3519745 | 4.053435 | −2.7156435 |
| ALDH2 | 5.0135775 | 5.6309605 | 1.913778 | 3.8476295 | 6.802666 | 5.11617 | 5.808058 | 4.596143 | 6.3503265 |
| APOC4 | 0.2581675 | 1.53158 | −6.0251725 | 0.2797975 | 2.574347 | 0.5860455 | −0.0768065 | −0.129322 | 2.281983 |
| APCS | 7.2072275 | 7.2809855 | 1.0475505 | 7.1142435 | 7.500133 | 7.134934 | 6.755895 | 5.045701 | 5.612517 |
| AQP9 | 3.8645965 | 5.4736555 | 0.9613895 | 5.0250435 | 7.530391 | 6.9427395 | 6.3416265 | 6.0302545 | 7.8444565 |
| BUB1 | 0.545363 | −0.8889165 | −5.7426525 | −0.190936 | −5.1317805 | −1.2674215 | −2.4955985 | 0.321483 | −0.587016 |
| C1S | 7.2351705 | 8.172076 | 4.910584 | 7.5279395 | 7.854502 | 7.719763 | 6.921051 | 6.101331 | 6.88808 |
| CYP2E1 | 0.671071 | 8.6350095 | 3.6858305 | 7.5682115 | 9.4408715 | 8.545814 | 10.1686795 | 8.1123675 | 9.5090495 |
| DLG7 | −0.9710395 | −2.3158215 | NA | −0.189092 | −5.7080765 | −2.339621 | −2.6534895 | −1.4386515 | −1.840185 |
| DUSP9 | −8.5287915 | −10.241011 | NA | −9.0027 | −9.73163 | −9.9728495 | NA | −5.2298755 | −8.727439 |
| E2F5 | −1.1845665 | −0.4045835 | −4.334386 | 1.0623035 | −0.054818 | −1.4281575 | −1.2212655 | −0.037887 | 0.466649 |
| GHR | 1.964045 | 2.623084 | −1.9788575 | 2.635437 | 2.0027475 | 1.563203 | 2.9415775 | 0.2025015 | 1.428749 |
| HPD | 7.6403735 | 9.597772 | 3.3142495 | 7.537 | 9.0015185 | 8.3685675 | 10.367265 | 7.547286 | 8.0015745 |
| IGSF1 | −5.4960635 | −5.588995 | NA | −2.651022 | NA | −10.112616 | −7.5570255 | −0.680358 | −7.243464 |
| NLE1 | −1.851733 | −1.851285 | −2.4559905 | −1.2674865 | −1.208576 | −1.934745 | −1.9881245 | −2.1250395 | −0.15624 |
| RPL10A | 5.9670715 | 7.6623025 | 5.521873 | 7.5046195 | 8.8437815 | 6.594006 | 6.901637 | 5.1574215 | 7.7043325 |

| | HC42 | HC43 | HC44 | HC52 | HC58 | HC60 | HC64 | HC66 | HC101 |
|---|---|---|---|---|---|---|---|---|---|
| AFP | −5.216493 | −1.7983435 | −0.564605 | 10.3337105 | 1.891958 | 7.624821 | 5.0266755 | 3.156328 | −6.873135 |
| ALDH2 | 4.4086495 | 5.457548 | 7.1344115 | 2.1920375 | 2.1172735 | 3.6860195 | 4.992107 | 3.8408415 | 4.339036 |
| APOC4 | −0.627239 | −0.7055185 | 0.499817 | −8.124407 | −11.8524 | −0.545509 | 0.7860345 | −0.6773785 | −0.5787185 |
| APCS | 4.1054755 | 7.607914 | 7.567581 | 5.9818015 | −4.1106695 | 8.100997 | 7.4148835 | 8.2106815 | 6.288568 |
| AQP9 | 6.063786 | 4.7175855 | 6.058158 | −0.4848805 | −2.817265 | 6.8503395 | 7.0526325 | 6.2767975 | 4.6233735 |
| BUB1 | −2.224818 | −2.8634735 | −3.5668895 | −1.2986035 | 1.9395175 | −0.576028 | −1.367463 | −1.1272665 | 0.081457 |
| C1S | 6.3060565 | 7.9862115 | 8.547705 | 5.6337865 | 3.691331 | 8.167253 | 7.1364365 | 8.026875 | 7.321092 |
| CYP2E1 | 9.1411555 | 8.760714 | 9.1133175 | 1.7693015 | −4.3317445 | 9.1875325 | 9.682147 | 8.601088 | 5.806032 |
| DLG7 | −3.2531575 | −4.2390495 | −4.814388 | −2.599359 | 0.1957495 | −2.2644225 | −2.386875 | −2.7680135 | −1.3084655 |
| DUSP9 | NA | −10.525647 | NA | −3.8059605 | −3.656912 | −6.618755 | −7.3184655 | −11.5673955 | −8.828389 |
| E2F5 | −0.3673235 | −0.894345 | −1.894272 | 0.4419525 | 0.804087 | −0.432422 | −0.2876185 | −0.968982 | −1.871516 |
| GHR | −1.2545395 | 3.2916395 | 4.5598275 | −1.843696 | −3.7242975 | −1.4079225 | 0.349645 | −1.2501855 | 0.1466275 |
| HPD | 8.2669835 | 8.997825 | 9.158005 | 2.481945 | 1.8257985 | 8.4643875 | 8.6027575 | 8.5231325 | 5.7252795 |
| IGSF1 | −2.899766 | −5.5544715 | −5.769786 | 2.254168 | 1.3471695 | −0.7884805 | −3.3382005 | −9.185554 | −4.1394545 |
| NLE1 | −0.9401045 | −1.8422595 | −2.0303285 | −1.9474305 | −1.209522 | −1.9133155 | −1.817699 | −1.962008 | −1.4546305 |
| RPL10A | 5.577659 | 5.480403 | 5.8488475 | 5.6154705 | 6.0601515 | 5.7041285 | 6.4617635 | 5.415169 | 6.144011 |

| | HC102 | HC103 | HC104 | HC105 | HC106 | HC107 | HC108 | HC109 | HC110 |
|---|---|---|---|---|---|---|---|---|---|
| AFP | −4.119697 | 1.6193685 | 5.5094265 | 2.3444245 | −3.42054 | −4.136209 | −4.500336 | −4.833024 | −3.5240185 |
| ALDH2 | 2.476355 | 3.889904 | 4.936239 | 4.239726 | 6.1642895 | 6.7443095 | 3.6076385 | 5.8617665 | 3.6707715 |
| APOC4 | −5.453696 | −0.54698 | −0.5059805 | −3.577778 | −0.7836775 | 4.4534435 | −2.478085 | 0.729565 | −0.256479 |
| APCS | −2.3952165 | 6.014572 | 5.624234 | 7.703333 | 7.8462545 | 9.2080655 | 7.275462 | 6.222909 | 5.043319 |
| AQP9 | 0.0196725 | 7.151639 | 0.501258 | 4.2748795 | 5.85913 | 8.8878655 | 4.4353395 | 6.4504115 | 4.5999895 |
| BUB1 | −0.5553155 | −2.086008 | −1.311194 | 0.945674 | −4.8909655 | −1.7415115 | −0.3807995 | −2.2918285 | −1.449943 |
| C1S | 5.939374 | 5.965432 | 6.716137 | 7.774455 | 8.060072 | 9.2061165 | 7.1031155 | 7.406001 | 6.9163195 |
| CYP2E1 | −2.8566735 | 8.266311 | 9.0888685 | 5.698899 | 9.9949555 | 9.3234825 | 3.889942 | 8.7101925 | 7.145766 |
| DLG7 | −2.1385165 | −2.957914 | −1.821739 | −0.814912 | −6.2678815 | −1.357756 | −2.2445545 | −3.222524 | −2.333076 |
| DUSP9 | −8.6628475 | −12.521336 | −5.396553 | −5.4214725 | −11.174152 | −6.6136855 | −8.0946735 | −10.4709205 | −11.616244 |
| E2F5 | 0.830934 | −1.8003215 | −2.305498 | 2.0730715 | −2.208171 | 2.78876 | 0.0923905 | −1.9924345 | −2.512512 |
| GHR | 0.947389 | 0.636723 | 1.6860905 | 0.682142 | 5.342392 | 2.935929 | 1.6363755 | 2.9233285 | 1.0803015 |
| HPD | 0.568809 | 6.717282 | 8.46781 | 2.288109 | 9.4440475 | 10.460972 | 2.9674235 | 7.8859205 | 8.1908235 |
| IGSF1 | −2.708733 | −9.802921 | 0.1438735 | −1.422332 | −7.401009 | NA | −7.967922 | −10.0122565 | −8.1469415 |
| NLE1 | −1.1534675 | −2.594702 | −1.610158 | −0.471391 | −1.968983 | −0.000835 | −0.932052 | −2.6102395 | −2.3529485 |
| RPL10A | 5.283399 | 4.423835 | 6.21159 | 6.315756 | 5.769397 | 8.6686655 | 5.818028 | 5.541229 | 5.245476 |

| | HC111 | HC112 | HC113 | HC114 | HC119 | HC120 | HC121 | HC122 | HC123 |
|---|---|---|---|---|---|---|---|---|---|
| AFP | −1.883473 | −2.8803905 | 1.208649 | −5.4433695 | 1.0580855 | −4.0065425 | −4.254961 | −2.3763095 | 0.821555 |
| ALDH2 | 3.8304065 | 4.8726745 | 4.407016 | 4.7113965 | 6.159706 | 4.257398 | 4.556431 | 6.2844515 | 4.220769 |
| APOC4 | −1.130067 | −0.7777655 | −2.366969 | −0.833243 | 1.894453 | −3.5241745 | −2.167313 | 1.279577 | −0.68167 |
| APCS | 5.976754 | 6.764675 | 5.197177 | 6.723142 | 9.375177 | 5.6838965 | 6.2688205 | 6.9942545 | 5.778659 |
| AQP9 | 4.1657805 | 5.2735435 | 2.681192 | 4.445291 | 7.6266135 | 6.8239115 | 4.38702 | 6.8198535 | 6.410177 |
| BUB1 | 0.621548 | 0.3135015 | −3.4825665 | −1.7431855 | −0.797564 | −0.0740105 | −2.4486685 | −6.0183915 | −1.190323 |
| C1S | 6.278164 | 7.455794 | 6.338769 | 7.866014 | 9.1461175 | 8.5708615 | 8.118416 | 7.7653135 | 5.383781 |
| CYP2E1 | 4.46942 | 2.5741475 | 6.443846 | 7.3429245 | 7.095824 | 7.6044515 | 7.765037 | 9.450349 | 8.528543 |
| DLG7 | −0.769283 | −0.9196845 | −4.5602875 | −3.1500875 | −1.712686 | −1.9563135 | −2.852561 | −7.228946 | −2.929576 |
| DUSP9 | −9.137462 | −10.105965 | −7.8299455 | −11.804112 | −9.106547 | −5.8119685 | −9.706684 | −9.9054825 | −11.584458 |
| E2F5 | 1.045678 | 0.0373705 | −2.82243 | −0.0450475 | −0.0248045 | 1.229768 | −0.910943 | −3.5033365 | −0.646839 |
| GHR | 1.1576425 | 2.5391085 | 2.16232 | 2.5053965 | 3.7649595 | 3.196589 | 2.2774645 | 2.400201 | −1.810364 |

TABLE 13-continued

Quantitative PCR data of the 16-gene signature normalized to the expression of the ROTH2 gene (pages 65 to 68)

| HPD | 7.245347 | 7.714358 | 6.685692 | 6.835254 | 9.220498 | 8.5127155 | 7.480725 | 8.7301975 | 4.7774665 |
|---|---|---|---|---|---|---|---|---|---|
| IGSF1 | −1.86965 | −3.4428695 | −2.045068 | −5.1813245 | −5.39017 | −9.404196 | −5.980435 | −8.6480295 | −5.1400615 |
| NLE1 | −1.012752 | −1.119237 | −2.156348 | −1.3170345 | −0.400823 | −1.1096815 | −1.758163 | −2.2430545 | −1.5951645 |
| RPL10A | 5.568205 | 6.1905075 | 5.8884625 | 5.795905 | 7.954231 | 6.4517175 | 6.4042545 | 5.199782 | 4.7323885 |

| | HC124 | HC125 | HC126 | HC127 | HC128 | HC129 | HC131 | HC132 | HC133 |
|---|---|---|---|---|---|---|---|---|---|
| AFP | 3.9525335 | −4.806564 | −5.899437 | −0.0390765 | 5.8636305 | −3.430757 | −1.491189 | 5.4265205 | −5.1621395 |
| ALDH2 | 4.027289 | 4.5451465 | 5.02839 | 2.41699 | 5.085525 | 4.6298475 | 5.425994 | 3.105643 | 4.2462915 |
| APOC4 | −0.0499065 | 2.6326775 | 0.407895 | 0.8680995 | −0.626498 | −1.863955 | 2.4702 | −6.9974515 | 0.63156 |
| APCS | 5.391271 | 6.5321595 | 5.2838365 | 4.846116 | 5.087517 | 4.8448705 | 8.6617295 | −3.2748865 | 7.145861 |
| AQP9 | 4.463488 | 8.370224 | 3.6163545 | 1.8613935 | 4.3184915 | 2.870839 | 7.4772145 | 3.9244375 | 6.05182 |
| BUB1 | −1.592563 | 1.1627945 | −2.6943025 | −2.048769 | −1.3297375 | −2.3688215 | −0.727709 | 0.2895395 | −4.9277675 |
| C1S | 5.151686 | 8.4244055 | 7.1365955 | 6.3641695 | 6.828468 | 7.302922 | 7.525072 | 4.390082 | 7.3188145 |
| CYP2E1 | 9.520436 | 9.426232 | 5.226091 | 6.1813065 | 7.4344035 | 2.692798 | 8.98645 | 7.0455735 | 8.1908895 |
| DLG7 | −2.03781 | 0.3286545 | −3.944339 | −2.96212 | −2.6299155 | −3.6405185 | −1.461713 | −1.5572645 | −5.5447335 |
| DUSP9 | −8.81055 | −9.3740615 | −8.7174575 | −8.672372 | −8.499355 | −7.0627455 | −8.415907 | −3.3843145 | −8.022457 |
| E2F5 | 0.574165 | −0.028878 | −3.271927 | −2.162602 | −4.393094 | −0.470421 | 0.154573 | 1.9018925 | −2.6341825 |
| GHR | 2.2369305 | 0.697866 | 1.824385 | 0.129431 | 1.9716885 | 2.332961 | 4.009655 | 1.7710325 | 2.2298335 |
| HPD | 7.832169 | 5.7813 | 1.865621 | 3.4481965 | 5.7052855 | 5.502918 | 8.960383 | 2.3653865 | 6.1281315 |
| IGSF1 | −1.4450915 | −10.2234745 | −7.659377 | −3.1503205 | −2.72995 | −5.692623 | −7.5832005 | −1.947055 | NA |
| NLE1 | −0.1499775 | −0.405397 | −2.033278 | −2.205965 | −1.949352 | −1.683808 | −1.5313675 | 0.2035885 | −1.4173895 |
| RPL10A | 6.691521 | 7.1196575 | 5.389272 | 4.3385115 | 6.6181545 | 4.8697295 | 6.775249 | 6.7796075 | 5.762015 |

| | HC134 | HC135 | HC136 |
|---|---|---|---|
| AFP | | | |
| ALDH2 | 2.8738695 | −0.909107 | −0.4105125 |
| APOC4 | 4.061101 | 2.7442165 | 6.0408575 |
| APCS | −0.1134065 | −0.7630605 | 0.7390785 |
| AQP9 | 7.5103485 | 0.959726 | 7.150737 |
| BUB1 | 5.550642 | 4.0595615 | 5.996196 |
| C1S | 1.7425995 | −1.2018365 | −4.288554 |
| CYP2E1 | 8.4609335 | 4.667223 | 8.243333 |
| DLG7 | 7.859701 | 4.30592 | 9.042865 |
| DUSP9 | 0.8148735 | −2.250305 | −5.5267715 |
| E2F5 | −4.96739 | −5.794605 | −10.9307725 |
| GHR | 3.1030595 | 0.986165 | −2.4040865 |
| HPD | 1.3138565 | −0.6955465 | 4.013948 |
| IGSF1 | 7.231144 | 6.7262275 | 8.223611 |
| NLE1 | −0.3848995 | −4.394354 | −7.4962365 |
| RPL10A | 0.794433 | −0.9780515 | −2.426321 |
| AFP | 7.7140665 | 6.689595 | 5.5069335 |

NA: non available

Data were then analyzed by unsupervised clustering (dCHIP software) using 2 methods: average and centroid. Tumors were clustered into 2 groups, C1 and C2. Most of the samples have been attributed the same classification using the 2 methods, except for 6 samples (9%) that have been attributed a different classification (Table 15).

Clinical Parameters Associated to the C1 and C2 Molecular Subclasses

The clinico-pathological parameters of patients and tumors were compared between the two groups C1 and C2, using student's t test and Kaplan-Meier estimates. Since some data are not available for 3 patients, the following statistical studies were performed on 64 tumors.

Survival Analysis

There is a strong correlation of the molecular classification into C1 and C2 with patient's survival by using both classifications (Log rank: Centroid p=0.020 and Average p=0.024) (FIG. 10). In this figure, censored cases indicate the end of the follow-up (the last visit) for individual cases. Probability of survival at two years is 78% for C1 subclass and 39% for C2 subclass (the follow-up may be less than 2 years for some patients).

Association of HCC Classification with Clinical Variables

Table 14 shows the correlation between some clinical variable and the classification of the tumors.

TABLE 14

| Variable | C1 | C2 | p-value |
|---|---|---|---|
| Tumor grade >2 (Edmonson) | 13/29 | 21/23 | <0.0001 |
| Moderately-poorly differentiated (OMS) | 17/36 | 23/25 | <0.0001 |
| Macrovascular Invasion | 6/30 | 9/21 | 0.074 |
| Microvascular Invasion | 13/32 | 15/22 | 0.043 |
| Recurrence | 7/36 | 5/25 | ns |

(ns: non-significant)

TABLE 15

Classification of samples by unsupervised clustering (dCHIP software): average and centroid methods.

| Tumor ID | average | centroid | comparison |
|---|---|---|---|
| HC1 | C1 | C1 | Same |
| HC10 | C2 | C2 | Same |
| HC11 | C1 | C1 | Same |
| HC12 | C1 | C1 | Same |
| HC14 | C1 | C1 | Same |
| HC15 | C2 | C2 | Same |
| HC17 | C2 | C2 | Same |
| HC18 | C2 | C2 | Same |
| HC20 | C1 | C1 | Same |
| HC21 | C2 | C2 | Same |
| HC22 | C1 | C1 | Same |

TABLE 15-continued

Classification of samples by unsupervised clustering (dCHIP software): average and centroid methods.

| Tumor ID | average | centroid | comparison |
|---|---|---|---|
| HC23 | C1 | C1 | Same |
| HC25 | C1 | C1 | Same |
| HC26 | C1 | C2 | Different |
| HC27 | C1 | C1 | Same |
| HC28 | C2 | C2 | Same |
| HC3 | C1 | C1 | Same |
| HC30 | C2 | C2 | Same |
| HC32 | C1 | C1 | Same |
| HC34 | C1 | C1 | Same |
| HC37 | C1 | C1 | Same |
| HC38 | C2 | C2 | Same |
| HC4 | C1 | C1 | Same |
| HC41 | C1 | C1 | Same |
| HC42 | C2 | C1 | Different |
| HC43 | C1 | C1 | Same |
| HC44 | C1 | C1 | Same |
| HC52 | C2 | C2 | Same |
| HC58 | C2 | C2 | Same |
| HC6 | C1 | C1 | Same |
| HC60 | C2 | C2 | Same |
| HC64 | C2 | C2 | Same |
| HC66 | C1 | C1 | Same |
| HC7 | C2 | C2 | Same |
| HC8 | C2 | C2 | Same |
| HC9 | C2 | C2 | Same |
| HC101 | C1 | C2 | Different |
| HC102 | C2 | C2 | Same |
| HC103 | C1 | C1 | Same |
| HC104 | C2 | C2 | Same |
| HC105 | C2 | C2 | Same |
| HC106 | C1 | C1 | Same |
| HC107 | C1 | C1 | Same |
| HC108 | C1 | C1 | Same |
| HC109 | C1 | C1 | Same |
| HC110 | C1 | C1 | Same |
| HC111 | C2 | C2 | Same |
| HC112 | C1 | C2 | Different |
| HC113 | C2 | C2 | Same |
| HC114 | C1 | C1 | Same |
| HC119 | C1 | C1 | Same |
| HC120 | C1 | C1 | Same |
| HC121 | C1 | C1 | Same |
| HC122 | C1 | C1 | Same |
| HC123 | C2 | C1 | Different |
| HC124 | C2 | C2 | Same |
| HC125 | C1 | C1 | Same |
| HC126 | C1 | C1 | Same |
| HC127 | C2 | C2 | Same |
| HC128 | C2 | C2 | Same |
| HC129 | C1 | C2 | Different |
| HC131 | C1 | C1 | Same |
| HC132 | C2 | C2 | Same |
| HC133 | C1 | C1 | Same |
| HC134 | C2 | C2 | Same |
| HC135 | C2 | C2 | Same |
| HC136 | C1 | C1 | Same |

In a second analysis, the global set of 64 tumors was analyzed independently of the C1/C2 classification, for parameters associated to survival. Results are presented in Table 16.

TABLE 16

| Variable | Log rank |
|---|---|
| Tumor grade >2 | 0.108 |
| Mod-poor Diff. Degree | 0.400 |
| Macrovasc. Inv. | 0.004 |
| Microvasc. Inv. | 0.026 |
| recurrence | ns |
| Tumor size 2 cm | 0.397 |
| Score METAVIR Activity | ns |
| Score METAVIR Fibrosis <2 vs. ≧2 (variable 3) | 0.038 |
| Chronic hepatitis | 0.948 |
| HBV | 0.093 |
| HCV | 0.352 |
| Alcohol | 0.225 |

(ns: non-significant)

These results demonstrate that the methods and the signatures of the invention are able to determine the grade not only of HB tumors but also of HCC tumors. The inventors have shown that hierarchical clustering is an efficient method for classification of tumor grade especially for HB. For HCC, this method may be less sufficient (less robust) when the amplitude of variation of expression results of the genes is less important than for HB.

Classification of Hepatoblastomas and Hepatocellular Carcinomas Using the Method of Discretization of Continuous Values.

85 hepatoblastomas (HBs) and 114 hepatocellular carcinomas (HCCs) including to the samples used in the above examples have been analyzed by quantitative PCR using the 16-gene signature and have been classified by the method of discretization of continuous values in order to determine their tumor grade.

Description of the Methodology for Classification

The inventors have designed a methodology for classification based on the principle of discretization of continuous values which refers to the process of converting continuous variables to "discretized" or nominal sets of values.

The major advantage of the discretization method relies on the definition of a cut-off for codification of each qPCR value (either by the Taqman or by the SybrGreen method), which provides an intrinsic score to directly classify an individual sample. There is hence no requirement to compare a sample to a large series of samples. In contrast, in other classification methods, the assigned subclass (such as C1 or C2 disclosed herein) is relative to the values obtained in a large number of cases. Moreover, the use of the average discretized values allows to tolerate missing values when analyzing the qPCR results (i.e. missed amplification of one of the genes for technical reasons).

Using the qPCR data of the 16 genes normalized to the reference RHOT2 gene (−deltaCt values), a cut-off (or threshold) has been defined for each gene. The −deltaCt values are converted into discrete values "1" or "2" depending on an assigned cut-off. In order to privilege the identification of samples that display strong overexpression of proliferation-related genes and/or strong downregulation of differentiation-related genes, the cut-offs have been defined as follows:

for the 8 proliferation-related genes (AFP, BUB1, DLG7, DUSP9, E2F5, IGSF1, NLE1, RPL10A), all −DeltaCts with a value above the $67^{th}$ percentile have been assigned discretized value "2", otherwise the assigned value was "1".

for the 8 differentiation-related genes (ALDH2, APCS, APOC4, AQP9, C1S, CYP2E1, GHR, HPD), all −deltaCts with a value below the $33^{rd}$ percentile have been assigned discretized value "1", otherwise the assigned value was "2".

Classification of 85 Hepatoblastomas (HB)
RNA Preparation and Quantitative PCR

RNA was extracted by using either Trizol, RNeasy kit (QIAGEN) or miRvana kit (Ambion), then quantified and quality-checked by Agilent technology.

For quantitative PCR analysis, the Sybr Green approach was used as described in point E. above. For each cDNA preparation, 1 μg of RNA was diluted at the final concentration of 100 ng/μl, and reverse transcribed with the Superscript RT kit (Invitrogen) following the manufacturer's protocol. Random primers were added at the final concentration of 30 ng/μl and the final volume was 20 μl. The cDNA was diluted 1:25, and 5 μl were used for each qPCR reaction. We added 5 μl of 2×Sybr Green Master mix (Applied Biosystems) and 0.3 μl of each specific primer (disclosed in point H. above) (final concentration 300 nM). Each reaction was performed in triplicate. qPCR reactions were run on the Applied Biosystems 7900HT Fast Real-Time PCR System with a 384-well thermo-block, and the conditions were the following:

2 min at 50° C. to activate Uracil-N-glycosylase (UNG)-mediated erase of a specific reaction 10 min at 95° C. to activate the polymerase and inactivate the UNG 40 cycles:

15 sec at 95° C. denaturation step 1 min at 60° C. annealing and extension

Final dissociation step to verify amplicon specificity.

The normalized qPCR (deltaCt) values of the 85 HB samples are given in Table A.

Analysis of qPCR Data.

Assignment of a discretized value for the 8 proliferation-related genes ("AFP" "BUB1" "DLG7" "DUSP9" "E2F5" "IGSF1" "NLE" "RPL10A") was based on the $67^{th}$ quantile (i.e. percentile), given that around ⅓ of HB cases overexpress proliferation genes, which is correlated with tumor aggressiveness and poor outcome. Assignment of a discretized value for the 8 differentiation-related genes ("ALDH2" "APCS" "APOC4" "AQP9" "C1S" "CYP2E1" "GHR" "HPD") was based on the $33^{rd}$ quantile, given that around ⅓ of HB cases underexpress differentiation genes, which is correlated with tumor aggressiveness and poor outcome.

The cut-offs (or thresholds) selected for the –deltaCT value of each gene were determined after considering said chosen percentiles for each group of genes are as follows:
AFP: 3.96139596; ALDH2: 4.3590482; APCS: 4.4691582; APOC4: 2.03068712; AQP9: 3.38391456; BUB1: −1.41294708; C1S: 4.24839464; CYP2E1: 6.70659644; DLG7: −3.3912188; DUSP9: 2.07022648; E2F5: −0.72728656; GHR: −0.1505569200; HPD: 2.27655628; IGSF1: 0.1075015200; NLE: −0.02343571999; RPL10A: 6.19723876

For the sample, the relative expression value is determined for each gene of the set of profiled genes. Each value is compared to the cut-off for the corresponding gene and is then discretized as a result of its position with respect to said cut-off.

The next step consisted in assigning a discretized score to each sample as follows:

1—the average of the "discretized" values of the 8 proliferation-related genes was determined. The 8 proliferation-related genes are the following: AFP, BUB1, DLG7, DUSP9, E2F5, IGSF1, NLE, and RPL10A.

2—the average of the "discretized" values of the 8 differentiation-related genes was determined. The 8 differentiation-related genes are the following: ALDH2, APCS, APOC4, AQP9, C1S, CYP2E1, GHR, and HPD.

3—The score for each sample was determined as the ratio between the average of proliferation-related genes and the average of differentiation-related genes.

According to this calculation, a score of 2 is the maximal score for highly proliferating and poorly differentiated tumors, whereas well differentiated and slowly proliferating tumors will have a minimal score of 0.5.

Based on the scores assigned to the 85 HB samples analyzed, cut-offs were identified to separate the samples into relevant subclasses. Two different cut-offs that correspond to the 33rd (0.615), and 67th percentile (0.91) have been assessed, leading to the definition of either 2 or 3 subclasses. These data together with the clinical data of 85 HB cases are given in the Table B.

Statistical Analysis of Clinical Correlations

All statistical correlations were analyzed using the discrete classification into 2 subclasses with the $67^{th}$ percentile (see $3^{rd}$ column of the table given in Table B).

| Characteristics | Samples with score <$67^{th}$ percentile | Samples with score >$67^{th}$ percentile | p-values (chi-square test) |
|---|---|---|---|
| Previous C1/C2 classification | 52/5 | 2/26 | 1.0739e−14 |
| Gender Male/Female | 28/29 | 7/21 | 0.03368 |
| PRETEXT.stage I-II/III-IV | 30/25 | 11/15 | 0.30367 |
| Distant Metastasis No/Yes | 45/12 | 15/13 | 0.015808 |
| Vascular invasion No/Yes | 38/17 | 11/17 | 0.0090345 |
| Multifocality No/Yes | 38/18 | 15/13 | 0.20088 |
| Histology Epithelial/Mesenchymal | 34/22 | 16/22 | 0.75303 |
| β-catenin mutation No/Yes | 8/45 | 8/16 | 0.067697 |
| Main epithelial component Fetal/Other* | 49/7 | 5/21 | 2.33206e−9 |

*Other = embryonal, macrotrabecular, crowded fetal

The best correlation of the discrete classification was observed with the previous classification into C1 and C2 classes, followed by the main epithelial histological component. The correlation with patients' survival is also excellent, as shown by using the Kaplan-Meier estimates and the log-rank test. Illustrative Kaplan-Meier curves are given in FIG. 11 for specific cancer-related survival, using different percentiles to classify the tumors.

In conclusion, this study shows that the discretization method allows to classify hepatoblastoma as efficiently as the previously described method.

A similar approach was therefore applied to the analysis of hepatocellular carcinoma.

Analysis of 114 Hepatocellular Carcinomas (HC)
RNA Preparation

RNA was extracted by using either Trizol, RNeasy kit (QIAGEN) or miRvana kit (Ambion), then quantified and quality-checked by Agilent technology.

For each cDNA preparation, 1 μg of RNA was diluted at the final concentration of 100 ng/μl, and reverse transcribed with the Superscript RT kit (Invitrogen) following the manufacturer's protocol. Random primers were added at the final concentration of 30 ng/μl and the final volume was 20 μl. The cDNA was diluted 1:25, and 5 μl were used for each qPCR reaction. We added 5 μl of 2×Sybr Green Master mix or the Taqman Master mix (Applied Biosystems) and specific primers (and probes when using Taqman chemistry) at the concentration indicated by the manufacturer. Each reaction was performed in triplicate. qPCR reactions were run on the Applied Biosystems 7900HT Fast Real-Time PCR System with a 384-well thermo-block, and the conditions were the following:
- 2 min at 50° C. to activate Uracil-N-glycosylase (UNG)-mediated erase of aspecific reaction (omit if using the Taqman approach)
- 10 min at 95° C. to activate the polymerase and inactivate the UNG
- 40 cycles:
  - 15 sec at 95° C. denaturation step
  - 1 min at 60° C. annealing and extension
- Final dissociation step to verify amplicon specificity (omit if using the Taqman approach)

Quantitative PCR

Real time RT-PCR was performed for 16 genes on 114 HCC samples using two different technologies:
- Sybr Green as described above for hepatoblastoma (26 samples).
- Taqman methodology (88 samples) using primers and probes designed and publicly released by Applied Biosystems company.

Examples

| | |
|---|---|
| AFP forward primer: | GCCAGTGCTGCACTTCTTCA |
| AFP reverse primer: | TGTTTCATCCACCACCAAGCT |
| AFP Taqman probe: | ATGCCAACAGGAGGCCATGCTTCA |
| RHOT2 forward primer: | CCCAGCACCACCATCTTCAC |
| RHOT2 reverse primer: | CCAGAAGGAAGAGGGATGCA |
| RHOT2 Taqman probe: | CAGCTCGCCACCATGGCCG |

Each reaction was performed in triplicate for Sybr Green protocol and in duplicate for the taqman protocol. qPCR reactions were run on the Applied Biosystems 7900HT Fast Real-Time PCR System with a 384-well thermo-block. Raw data for each gene were normalized to the expression of the ROTH2 gene, providing the deltaCt values that were then used for tumor classification into subclasses using the discretization method.

The normalized qPCR values (deltaCt) of the 16 genes in 26 HCC samples analyzed by the Sybr Green approach is given in Table C. The deltaCt values for 88 HCCs analyzed by the Taqman approach are given in Table D.

Analysis of qPCR Data.

The −deltaCt values for each gene in each sample was used. The cut-offs (or thresholds) selected for each gene using the Taqman method or the SybrGreen method are as follows:

TABLE E of cut-offs for discretization values

| Gene name | Cut-off for Taqman | Cut-off for SybrGreen |
|---|---|---|
| AFP | −1.2634010 | −2.3753035 |
| ALDH2 | 4.014143 | 5.314302 |
| APCS | 5.6142907 | 6.399079 |
| APOC4 | −0.7963158 | 4.656336 |
| AQP9 | 4.2836011 | 5.446966 |
| BUB1 | −1.2736579 | −3.634476 |
| C1S | 6.3514679 | 6.240002 |
| CYP2E1 | 6.9562419 | 5.829384 |
| DLG7 | −2.335694 | −4.614352 |
| DUSP9 | −7.979559 | −1.8626715 |
| E2F5 | −0.4400218 | −1.367846 |
| GHR | 1.0832632 | 1.169362 |
| HPD | 6.7480328 | 6.736329 |
| IGSF1 | −4.8417785 | 7.6653982 |
| NLE | −1.6167268 | −1.82226 |
| RPL10A | 6.2483056 | 5.731897 |

For the sample, the relative expression value is determined for each gene of the set of profiled genes. Each value is compared to the cut-off for the corresponding gene and is then discretized as a result of its position with respect to said cut-off.

The next step consisted in assigning a score to each sample as follows:

1—the average of the "discretized" values of the 8 proliferation-related genes was determined. The 8 proliferation-related genes are the following: AFP, BUB1, DLG7, DUSP9, E2F5, IGSF1, NLE, and RPL10A.

2—the average of the "discretized" values of the 8 differentiation-related genes was determined. The 8 differentiation-related genes are the following: ALDH2, APCS, APOC4, AQP9, C1S, CYP2E1, GHR, and HPD.

3—The score for each sample was determined as the ratio between the average of proliferation-related genes and the average of differentiation-related genes.

According to this calculation, a score of 2 is the theoretical maximal score for highly proliferating and poorly differentiated tumors, whereas well differentiated and slowly proliferating tumors will have a theoretical minimal score of 0.5.

Based on the scores assigned to the 114 samples analyzed, cut-offs are identified to separate the samples into relevant subclasses. Three different cut-offs that correspond to the 30rd (0.66), 50th (0.8125) and 67th percentile (0.925) have been assessed, leading to 4 different classification methods.

Table F of discretized values for 114 HCCs using 3 different thresholds and 4 combinations

| Sample | score | Method 1 3-class: (1): <q30 (2): q30 q67; (3): >q67 | Method 2 2-class: (1): <q30 (2): >q30 | Method 3 2-class: (1): <q67 (2): >q67 | Method 4 2-class: (1): <q50; (2): >q50 | Overall. survival | Follow-up (years) |
|---|---|---|---|---|---|---|---|
| HC 001 | 0.6875 | 2 | 2 | 1 | 1 | 1 | 0.07 |
| HC 003 | 0.6875 | 2 | 2 | 1 | 1 | 1 | 3.33 |
| HC 004 | 0.7272727 | 2 | 2 | 1 | 1 | 0 | 11.48 |
| HC 006 | 0.8125 | 2 | 2 | 1 | 2 | 1 | 1.25 |
| HC 007 | 1.4545455 | 3 | 2 | 2 | 2 | 1 | 1.5 |
| HC 008 | 1.0769231 | 3 | 2 | 2 | 2 | 1 | 8.48 |

Table F of discretized values for 114 HCCs using 3 different thresholds and 4 combinations

| Sample | score | Method 1 3-class: (1): <q30 (2): q30 q67; (3): >q67 | Method 2 2-class: (1): <q30 (2): >q30 | Method 3 2-class: (1): <q67 (2): >q67 | Method 4 2-class: (1): <q50; (2): >q50 | Overall. survival | Follow-up (years) |
|---|---|---|---|---|---|---|---|
| HC 009 | 1.75 | 3 | 2 | 2 | 2 | 1 | 0.02 |
| HC 010 | 1.5 | 3 | 2 | 2 | 2 | 1 | 0.95 |
| HC 011 | 0.6428571 | 1 | 1 | 1 | 1 | 0 | 12.2 |
| HC 012 | 0.5714286 | 1 | 1 | 1 | 1 | 1 | 0.05 |
| HC 014 | 0.625 | 1 | 1 | 1 | 1 | 1 | 1 |
| HC 015 | 1.6 | 3 | 2 | 2 | 2 | 1 | 1.22 |
| HC 017 | 1.875 | 3 | 2 | 2 | 2 | 0 | 10.96 |
| HC 018 | 1.5 | 3 | 2 | 2 | 2 | 1 | 0.39 |
| HC 020 | 0.7857143 | 2 | 2 | 1 | 1 | 0 | 15.4 |
| HC 021 | 1.5555556 | 3 | 2 | 2 | 2 | 1 | 0.7 |
| HC 022 | 0.5625 | 1 | 1 | 1 | 1 | 0 | 11.5 |
| HC 023 | 0.5 | 1 | 1 | 1 | 1 | 0 | 11.93 |
| HC 025 | 0.7142857 | 2 | 2 | 1 | 1 | 1 | 15.87 |
| HC 026 | 0.7142857 | 2 | 2 | 1 | 1 | 1 | 0.83 |
| HC 027 | 0.8125 | 2 | 2 | 1 | 2 | 1 | 0.1 |
| HC 028 | 1 | 3 | 2 | 2 | 2 | 1 | 0.1 |
| HC 030 | 1 | 3 | 2 | 2 | 2 | 1 | 12.4 |
| HC 032 | 0.7857143 | 2 | 2 | 1 | 1 | 1 | 0.66 |
| HC 034 | 0.625 | 1 | 1 | 1 | 1 | 0 | 15.7 |
| HC 037 | 0.5714286 | 1 | 1 | 1 | 1 | 1 | 0.2 |
| HC 038 | 1.0769231 | 3 | 2 | 2 | 2 | 1 | 1.12 |
| HC 041 | 0.8666667 | 2 | 2 | 1 | 2 | 1 | 7.44 |
| HC 042 | 0.8791209 | 2 | 2 | 1 | 2 | 0 | 10.58 |
| HC 043 | 0.5 | 1 | 1 | 1 | 1 | 0 | 10.9 |
| HC 052 | 1.3333333 | 3 | 2 | 2 | 2 | NA | 0.25 |
| HC 058 | 1.875 | 3 | 2 | 2 | 2 | 0 | 8.3 |
| HC 060 | 1 | 3 | 2 | 2 | 2 | NA | NA |
| HC 064 | 0.8666667 | 2 | 2 | 1 | 2 | 1 | 5.25 |
| HC 066 | 0.7142857 | 2 | 2 | 1 | 1 | 0 | 8.93 |
| HC 101 | 0.9230769 | 2 | 2 | 1 | 2 | 0 | 2.5 |
| HC 102 | 1.625 | 3 | 2 | 2 | 2 | 0 | 0.1 |
| HC 103 | 0.75 | 2 | 2 | 1 | 1 | 0 | 1.82 |
| HC 104 | 0.8666667 | 2 | 2 | 1 | 2 | 0 | 2.1 |
| HC 105 | 1.4545455 | 3 | 2 | 2 | 2 | 0 | 0.56 |
| HC 106 | 0.5 | 1 | 1 | 1 | 1 | 0 | 2 |
| HC 107 | 0.8571429 | 2 | 2 | 1 | 2 | 0 | 1.75 |
| HC 108 | 1 | 3 | 2 | 2 | 2 | 0 | 1.62 |
| HC 109 | 0.5 | 1 | 1 | 1 | 1 | 0 | 1.3 |
| HC 110 | 0.6923077 | 2 | 2 | 1 | 1 | 0 | 1.95 |
| HC 111 | 1.1818182 | 3 | 2 | 2 | 2 | 1 | 0.7 |
| HC 112 | 0.8666667 | 2 | 2 | 1 | 2 | 0 | 1.48 |
| HC 113 | 1.1 | 3 | 2 | 2 | 2 | 1 | 1 |
| HC 114 | 0.6666667 | 2 | 2 | 1 | 1 | 0 | 0.44 |
| HC 115 | 0.875 | 2 | 2 | 1 | 2 | 0 | 0.75 |
| HC 116 | 0.9333333 | 3 | 2 | 2 | 2 | 0 | 0.69 |
| HC 117 | 0.6 | 1 | 1 | 1 | 1 | 0 | 1.2 |
| HC 118 | 0.5 | 1 | 1 | 1 | 1 | 0 | 0.93 |
| HC 119 | 0.8461538 | 2 | 2 | 1 | 2 | 0 | 1.2 |
| HC 120 | 1 | 3 | 2 | 2 | 2 | 0 | 0.82 |
| HC 121 | 0.9285714 | 3 | 2 | 2 | 2 | 0 | 0.6 |
| HC 122 | 0.6666667 | 2 | 2 | 1 | 1 | 0 | 0.75 |
| HC 123 | 1 | 3 | 2 | 2 | 2 | 0 | 0.8 |
| HC 124 | 0.7857143 | 2 | 2 | 1 | 1 | 0 | 0.52 |
| HC 125 | 0.8181818 | 2 | 2 | 1 | 2 | 0 | 0.9 |
| HC 126 | 0.8125 | 2 | 2 | 1 | 2 | 0 | 0.42 |
| HC 127 | 1.6 | 3 | 2 | 2 | 2 | 0 | 0.25 |
| HC 128 | 0.6095238 | 1 | 1 | 1 | 1 | 0 | 0.44 |
| HC 129 | 1 | 3 | 2 | 2 | 2 | 1 | 0.15 |
| HC 130 | 1.7777778 | 3 | 2 | 2 | 2 | 0 | 0.14 |
| HC 131 | 0.5625 | 1 | 1 | 1 | 1 | 0 | 0.26 |
| HC 137 | 1.2222222 | 3 | 2 | 2 | 2 | 0 | 5.67 |
| HC 138 | 0.75 | 2 | 2 | 1 | 1 | 0 | 5.58 |
| HC 139 | 1.3333333 | 3 | 2 | 2 | 2 | 0 | 6 |
| HC 140 | 0.5714286 | 1 | 1 | 1 | 1 | 0 | 4.17 |
| HC 141 | 0.6153846 | 1 | 1 | 1 | 1 | 0 | 5.08 |
| HC 142 | 0.8888889 | 2 | 2 | 1 | 2 | 1 | 4.08 |
| HC 143 | 1.375 | 3 | 2 | 2 | 2 | 0 | 2.83 |
| HC 144 | 0.6153846 | 1 | 1 | 1 | 1 | 0 | 6 |
| HC 145 | 0.8 | 2 | 2 | 1 | 1 | 0 | 5.58 |

Table F of discretized values for 114 HCCs using 3 different thresholds and 4 combinations

| Sample | score | Method 1 3-class: (1): <q30 (2): q30 q67; (3): >q67 | Method 2 2-class: (1): <q30 (2): >q30 | Method 3 2-class: (1): <q67 (2): >q67 | Method 4 2-class: (1): <q50 (2): >q50 | Overall. survival | Follow-up (years) |
|---|---|---|---|---|---|---|---|
| HC 146 | 0.9 | 2 | 2 | 1 | 2 | 0 | 4.33 |
| HC 147 | 0.6666667 | 2 | 2 | 1 | 1 | 0 | 3.83 |
| HC 148 | 1.1 | 3 | 2 | 2 | 2 | 0 | 3.08 |
| HC 149 | 1.2222222 | 3 | 2 | 2 | 2 | 1 | 3.42 |
| HC 150 | 0.6666667 | 2 | 2 | 1 | 1 | 0 | 5.42 |
| HC 151 | 0.6153846 | 1 | 1 | 1 | 1 | 0 | 2.25 |
| HC 152 | 0.6428571 | 1 | 1 | 1 | 1 | 1 | 3.67 |
| HC 153 | 0.6923077 | 2 | 2 | 1 | 1 | 1 | 4.83 |
| HC 154 | 1.375 | 3 | 2 | 2 | 2 | 1 | 2.21 |
| HC 155 | 0.8181818 | 2 | 2 | 1 | 2 | 0 | 4.1 |
| HC 156 | 1.4 | 3 | 2 | 2 | 2 | 1 | 2.31 |
| HC 157 | 1 | 3 | 2 | 2 | 2 | 1 | 3.59 |
| HC 159 | 0.7272727 | 2 | 2 | 1 | 1 | 1 | 2.42 |
| HC 161 | 0.6 | 1 | 1 | 1 | 1 | 0 | 4.47 |
| HC 162 | 1.1111111 | 3 | 2 | 2 | 2 | 0 | 3.49 |
| HC 163 | 0.6 | 1 | 1 | 1 | 1 | 1 | 2.21 |
| HC 164 | 0.6428571 | 1 | 1 | 1 | 1 | 0 | 4.54 |
| HC 165 | 0.6428571 | 1 | 1 | 1 | 1 | 0 | 4.72 |
| HC 168 | 0.6 | 1 | 1 | 1 | 1 | 0 | 6 |
| HC 169 | 0.6 | 1 | 1 | 1 | 1 | 1 | 2.78 |
| HC 170 | 0.5625 | 1 | 1 | 1 | 1 | 0 | 5.29 |
| HC 171 | 0.8181818 | 2 | 2 | 1 | 2 | 0 | 4.57 |
| HC 172 | 0.8333333 | 2 | 2 | 1 | 2 | 0 | 3.9 |
| HC 173 | 0.6428571 | 1 | 1 | 1 | 1 | 0 | 4.21 |
| HC 176 | 0.6428571 | 1 | 1 | 1 | 1 | 0 | 4.57 |
| HC 177 | 0.6666667 | 2 | 2 | 1 | 1 | 0 | 5.42 |
| HC 178 | 0.7142857 | 2 | 2 | 1 | 1 | 0 | 2.5 |
| HC 179 | 0.8181818 | 2 | 2 | 1 | 2 | 0 | 5.17 |
| HC 180 | 0.8571429 | 2 | 2 | 1 | 2 | 1 | 3.58 |
| HC 181 | 1 | 3 | 2 | 2 | 2 | 0 | 6.83 |
| HC 182 | 0.5625 | 1 | 1 | 1 | 1 | 0 | 3.5 |
| HC 183 | 0.7333333 | 2 | 2 | 1 | 1 | 1 | 4.08 |
| HC 184 | 0.9230769 | 2 | 2 | 1 | 2 | 1 | 2.08 |
| HC 185 | 0.7692308 | 2 | 2 | 1 | 1 | 0 | 2.25 |
| HC 186 | 0.9285714 | 3 | 2 | 2 | 2 | 1 | 2.17 |
| HC 187 | 0.6428571 | 1 | 1 | 1 | 1 | 0 | 7.67 |
| HC 188 | 0.7142857 | 2 | 2 | 1 | 1 | 0 | 4.67 |
| HC 189 | 0.8666667 | 2 | 2 | 1 | 2 | 1 | 3.25 |
| HC 190 | 0.7619048 | 2 | 2 | 1 | 1 | 0 | 5.58 |

Samples were separated into the corresponding subgroups, and subsequent analysis was carried out using the 4 classification methods. Survival for each group was determined using the Kaplan-Meier estimates and the log-rank test.

Statistical Analysis of Clinical Correlations with the Subclasses for 114 HCCs

A complete table with all clinical and pathological data collected for 114 HCC patients is given in Table G. The different parameters are represented as follows:

TABLE H

| Clinical and pathological parameters and molecular classification of 114 HB cases. Characteristics | |
|---|---|
| Etiology[†*] | |
| Alcohol | 40 (36%) |
| HCV | 26 (23%) |
| HBV | 23 (20%) |
| Hemochromatosis | 6 (5%) |
| NASH | 6 (5%) |
| Unknown | 23 (20%) |
| Treatment (SR, OLT) | 93/21 |
| Chronic viral hepatitis[†] | 46 (41%) |
| Liver cirrhosis[†] | 44 (48%) |
| Tumor characteristics | |
| Macrovascular invasion[†] | 20 (25%) |
| Microvascular invasion[†] | 47 (50%) |
| Mean tumor size, cm (range)[†] | 7.9 (1.5-22) |
| Multifocality | 46 (48%) |
| Histology: | |
| Edmonson Tumor grade[†] (1/2/3/4) | 7/35/47/5 |
| OMS Tumor differentiation (W/M/P) | 51/55/6 |

TABLE H-continued

Clinical and pathological parameters and molecular classification of 114 HB cases.
Characteristics Classification with 16-genes by discretization

| | |
|---|---|
| 40th Percentile (C1/C2) | 30/84 |
| 50th Percentile (C1/C2) | 55/59 |
| 67th Percentile (C1/C2) | 77/37 |
| Mean follow-up, months (range) | 43.6 (0.26-146) |
| Tumor recurrence† | 43 (40%) |
| Alive/DOD† | 75/38 |

Abbreviations:
HCV, hepatitis C virus;
HBV, hepatitis B virus;
NASH, Nonalcoholic steatohepatitis;
SR, surgical resection;
OLT, orthotopic liver transplantation;
W, well differentiated;
M, moderately differentiated;
P, poorly differentiated;
NA, not available;
DOD, dead of cancer.
*12 cases have more than one etiological agent and data were not available for 2 cases.
†Data were not available for all cases. Percentages were deduced from available data.

In a second step, the intrinsic parameters of the tumors correlated with patients' survival were analyzed. In this series of tumors, only tumor grade (Edmonson) and vascular invasion were significantly correlated with survival.

TABLE I

Summary of the clinical variables associated to overall survival (Kaplan-Meier curves and log-rank test). This Table does not take into account the molecular classification.

| Variable | N. patients | Log rank | N. patients With PH | Log rank |
|---|---|---|---|---|
| Edmonson Tumor grade (1-2/3-4) | 94 | 0.028 | 73 | 0.032 |
| Tumor diff. OMS (Well/Moderate-poorly diff.) | 111 | 0.406 | 90 | 0.647 |
| High proliferation: >10 Mitosis in 10 fields 40x (N/Y) | 45 | 0.054 | 34 | 0.402 |
| Macrovascular Invasion (N/Y) | 79 | 0.001 | 59 | 0.010 |
| Microvascular Invasion (N/Y) | 92 | 0.007 | 72 | 0.050 |
| Tumor size ≥10 cm | 113 | 0.298 | 92 | 0.314 |

Classification by Discretization of Continuous Values

The clinico-pathological parameters were compared between the tumor groups using student's t test and chi-square test. Survival was analyzed by using Kaplan-Meier curves and log rank test. A special attention was given to the classification with the 67th percentile. Follow-up was closed at 146 months for overall survival (OS) and at 48 months for disease-free survival (DFS).

TABLE J

Association of 16-gene classification by discretization with clinical and pathological data (chi-square test).
Abbreviations: P33, 33rd percentile, P50, 50th percentile and P67, 67th percentile.

| | p-value | | | P67 | | |
|---|---|---|---|---|---|---|
| Variable | P33 | P50 | P67 | C1 | C2 | comments |
| Edmonson Tumor grade: grade 1 and 2 (well differentiated) vs. 3 and 4 (moderately and poorly diff.) | 0.006 | <0.001 | <0.001 | 38/27 | 4/25 | 20 cases with missing values |
| Tumor differentiation OMS (Well/Moderate- versus poorly differentiated) | 0.006 | 0.001 | <0.001 | 45/32 | 6/29 | 2 cases with missing values |
| High proliferation: >10 mitosis in 10 fields 40x (N/Y) | 0.021 | 0.001 | 0.001 | 22/7 | 4/12 | |
| Macrovascular Invasion (N/Y) | 0.097 | 0.033 | 0.008 | 44/8 | 16/12 | The cases defined as possible are considered negative. |
| Microvascular Invasion (N/Y) | 0.071 | 0.001 | 0.009 | 37/26 | 9/21 | The cases defined as possible are considered negative. |
| Tumor size </≥10 cm | ns | ns | 0.015 | 57/20 | 19/18 | Different cut-offs assessed: 2, 3, 5 and 10 cm |
| Multifocality (N/Y) | ns | ns | ns | 35/30 | 15/16 | |
| Macronodules of regeneration | ns | ns | ns | 24/9 | 12/4 | |
| Norm Liver A0F0-A0F1 | ns | ns | ns | 48/17 | 27/7 | |
| Cirrhosis AXF4 (N/Y) | ns | ns | ns | 31/29 | 17/15 | |
| Score METAVIR Activity > 0 (N/Y) | 0.053 | 0.044 | ns | 19/32 | 5/20 | |
| Score METAVIR Activity > 1 (N/Y) | ns | 0.20 | ns | 31/20 | 15/10 | |
| Score METAVIR Fibrosis > 0 (N/Y) | 0.041 | ns | ns | 5/48 | 2/27 | |
| Score METAVIR Fibrosis > 1 (N/Y) | ns | ns | ns | 19/35 | 7/22 | |
| Score METAVIR Fibrosis > 2 (N/Y) | ns | ns | ns | 24/30 | 8/21 | |

TABLE J-continued

Association of 16-gene classification by discretization with clinical
and pathological data (chi-square test).
Abbreviations: P33, 33$^{rd}$ percentile, P50, 50$^{th}$ percentile and P67, 67$^{th}$ percentile.

| | p-value | | | P67 | | |
|---|---|---|---|---|---|---|
| Variable | P33 | P50 | P67 | C1 | C2 | comments |
| Score METAVIR Fibrosis > 3 (N/Y) | ns | ns | ns | 26/28 | 15/14 | |
| Chronic viral hepatitis (N/Y) | 0.047 | ns | ns | 48/29 | 18/17 | |
| HBV (N/Y) | 0.075 | ns | ns | 62/15 | 27/8 | |
| HCV (N/Y) | ns | ns | ns | 61/16 | 25/10 | |
| Alcohol (N/Y) | ns | ns | ns | 47/30 | 25/10 | |
| Recurrence (N/Y) | ns | ns | ns | 41/32 | 24/11 | HCC034 and HCC030 censored |
| Survival (N/Y) | 0.050 | 0.023 | 0.031 | 56/21 | 19/17 | HCC025 and HCC030 censored |
| DFS (N/Y) | ns | ns | ns | 35/42 | 15/21 | HCC025 and HCC030 censored |

In conclusion, these data show significant correlations between molecular classification using the 3 methods and the following parameters: Tumor grade (Edmonson), tumor differentiation (OMS), proliferation rate, vascular invasion and survival. In contrast, the classifications were not correlated with etiological factors (viral hepatitis, alcohol, etc. . . . ), with the state of the disease in adjacent, non tumoral livers or with tumor recurrence.

The data suggest that classification using the 67$^{th}$ percentile seems to be the most adequate and is strongly recommended to classify HCCs.

Multivariate Analysis

To further determine the efficiency of the molecular classification using the 67$^{th}$ percentile, we performed multivariate analysis with the Cox regression test on two sets of patients for which all data were available:

91 patients that received either surgical resection or orthoptic liver transplantation (OLT)
  71 patients that received surgical resection.

Different variables associated to survival in the clinical settings have been included in the multivariate analysis: 1) Edmonson grade, 2) microvascular invasion and 3) Molecular classification using the 67th percentile.

TABLE K

Multivariate test (Cox regression).

| N patients | variable | HR | 95% CI | p-value |
|---|---|---|---|---|
| 91 (surgical resections and OLT) | Molec classsif (p67) | 2.534 | (1.214-5.289) | 0.016 |
| | Edmonson Tumor grade (1-2/3-4) | 1.690 | (0.747-3.823) | 0.205 |
| | Microvascular Invasion (N/Y) | 2.451 | (1.105-5.435) | 0.024 |
| 71 (only surgical resections) | Molec classsif (p67) | 2.646 | (1.1156.278) | 0.032 |
| | Edmonson Tumor grade (1-2/3-4) | 2.697 | (1.103-6.592) | 0.026 |
| | Microvascular Invasion (N/Y) | 1.681 | (0.648-4.359) | 0.282 |

Correlation of the Molecular Classifications with Survival

For overall survival (OS) and disease-free survival (DFS), we compared the efficiency of the 3 methods of discretization that separate the samples into 2 subclasses. Independent studies were made for patients that received surgical resection and for patients that received orthoptic liver transplantation (OLT). The ability of the 16-gene signature to discriminate between recurrent and non-recurrent tumors was also assessed.

TABLE L

Summary of survival analysis using Kaplan-Meier curves and log-rank test

| Analysis | N. patients | Classif. method | Log rank |
|---|---|---|---|
| OS | 113 | P33 | 0.037 |
| | 113 | P50 | 0.005 |
| | 113 | P67 | 0.002 |
| DFS | 113 | P33 | 0.078 |
| | 113 | P50 | 0.019 |
| | 113 | P67 | 0.072 |
| recurrence | 108 | P33* | 0.134* |
| | 108 | P50* | 0.115* |
| | 108 | P67 | 1.000 |
| Analysis of 92 cases that received surgical resection | | | |
| OS | 92 | P33 | 0.032 |
| | 92 | P50 | 0.009 |
| | 92 | P67 | 0.013 |
| DFS | 92 | P40 | ns |
| | 92 | P50 | ns |
| | 92 | P67 | ns |
| recurrence | 88 | P33 | ns |
| | 88 | P50 | ns |
| | 88 | P67 | ns |

Abbreviations:
OS, overall survival;
DFS, disease free survival
*There is a trend but it is not significant and it is lost in the P60 analysis The different analyses are illustrated in the Kaplan-Meier plots shown in FIG. 12. The discretization method of classification showed the same efficiency in the analysis of tumors obtained either from surgical resection (also called partial hepatectomy, PH) or from orthotopic liver transplantation (OLT), showing that the clinical management of the tumor had no impact on the classification.

In conclusion, the method described herein is able to classify HCC cases according to tumor grade and patient's survival, and represents a powerful tool at diagnosis to stratify the tumors according to the prognosis, and for further clinical management of HCC. In particular, it may be an excellent tool for the decision of orthotopic liver transplantation, since the criteria used currently are limited and often poorly informative of the outcome.

Protocol for Applying the Method to a New Sample

The following protocol is designed according to the invention:

1—extract total RNA from the tumor specimen using well established technologies.
2—synthesize cDNA synthesis (suggested conditions: 1 μg RNA and 300 ng of random hexamers for a 20 μl-reaction)
3—amplify the selected genes said genes being in equal number of each of the groups defined as overexpressed proliferation-related genes group and downregulated differentiation-related genes group (profiled genes within the group of 2 to 16 genes) and the reference gene (invariant gene) such as for example the RHOT2 gene 1:5 cDNA dilution, using either Taqman or SybrGreen qPCR technology.
4—determine the Delta Ct (DCt) value for each gene
5—compare the value with the threshold of reference (for HB or for HC) in order to assign a discretized value of "1" or "2".
5—determine the average of discretized values in each group, i.e., for the selected proliferation-related genes (up to 8) separately for and the selected differentiation-related genes (up to 8) and determine the ratio of these 2 average values which is the score of the sample.
6—compare the result with the reference scores corresponding to the following cut-offs:
C1
  |30rd=0.6667
  |50th=0.8125
  |67th=0.925
C2

Example

For patient X having an HC tumor a Taqman qPCR is performed.

Step one: assignment of discretized values to each selected gene among proliferation-related genes and differentiation-related genes. Example: the DCt of AFP is −4.0523 The cut-off for AFP for qPCR using Taqman technology is −1.2634010 Given that −4.0523 is lower than the cut-off, the assigned discretized value is 2.

Step two: Determination of the average of discretized values for the 2 sets of 8 genes:
AFP=2; BUB1=1; DLG7=2; DUSP9=2; E2F5=2; IGSF1=1; NLE=2; RPL10A=1;
AVERAGE OF PROLIFERATION-RELATED GENES: (2+1+2+2+2+1+2+1)/8=1.625
ALDH2=1; APCS=1; APOC4=1; AQP9=1; C1S=2; CYP2E1=2; GHR=1; HPD=2;
AVERAGE OF DIFFERENTIATION-RELATED GENES: (1+1+1+1+2+2+1+2)/8=1.375

Step Three: calculate the ratio proliferation/differentiation score.
In this example: 1.625/1.375=1.18182

Step 4: compare the result with the reference scores:
C1
  |30$^{rd}$ percentile=0.6667
  |50$^{th}$ percentile=0.8125
  |67$^{th}$ percentile=0.925
C2

Classification based on the value of the ratio=1.18182.
As the value is above the 67$^{th}$ percentile, the assigned class is C2.

TABLE A

| id | AFP | ALDH2 | APCS | APOC4 | AQP9 | BUB1 | C1S | CYP2E1 |
|---|---|---|---|---|---|---|---|---|
| HB1 | −7.684892 | −4.592702 | −0.660189 | −2.651319 | −4.194894 | −1.068025 | −1.394659 | −3.334692 |
| HB100 | −7.682724 | −3.849128 | −0.372566 | 0.297278 | −0.305738 | 0.65983 | −2.572264 | −7.352142 |
| HB101 | 1.801478 | −7.157316 | −1.166513 | −4.924476 | −8.067838 | 6.222865 | −5.284734 | −11.757699 |
| HB102 | −7.761115 | −5.696697 | −1.044129 | −2.374592 | −3.447046 | 2.724363 | −3.657616 | −5.769417 |
| HB103 | 2.908026 | −2.580629 | −2.748625 | −2.55635 | 1.480624 | 3.891875 | −2.819372 | 0.454623 |
| HB106 | 0.294848 | −7.534485 | −1.424535 | −5.377043 | −7.886612 | 4.855797 | −6.80698 | −11.496242 |
| HB107 | 0.719866 | −6.546079 | −9.18522 | −3.425075 | −6.189664 | 3.901806 | −5.609115 | −10.6711555 |
| HB11 | 1.492805 | −3.560021 | −5.094387 | −1.031623 | −8.42849 | 2.086834 | −6.166353 | −9.043371 |
| HB112 | 4.155252 | −6.486961 | −0.154814 | −4.48155 | −5.634596 | 3.762347 | −7.88579 | −8.960815 |
| HB114 | 6.2971 | −3.966456 | 5.02266 | 0.604275 | 3.037682 | 4.23408 | −5.29691 | −0.313326 |
| HB118 | 0.318307 | −4.311795 | −5.146409 | −3.787568 | −5.428442 | 2.329959 | −5.284827 | −7.342423 |
| HB121 | −0.971033 | −6.879043 | −8.355819 | −4.679393 | −6.361435 | 2.329708 | −6.559457 | −8.87105 |
| HB122 | 2.188721 | −6.220957 | −7.7399 | −3.410743 | −5.745306 | 3.309004 | −6.327656 | −8.906339 |
| HB125 | 2.929931 | −4.053616 | −4.882212 | −2.32494 | −3.352398 | 5.067815 | −4.255762 | −7.887455 |
| HB126 | 2.458273 | −5.577951 | −6.518289 | −3.182407 | −5.243351 | 5.270089 | −5.814672 | −8.188307 |
| HB129 | −4.930877 | −2.124281 | −0.744262 | 1.154663 | −0.846572 | 0.421372 | −2.925458 | −4.708874 |
| HB130 | −4.86199 | −1.139837 | −1.398588 | 0.115559 | −1.313951 | 1.669543 | −2.37235 | 0.175598 |
| HB131 | 5.545406 | −1.714367 | −1.045683 | 2.628822 | 1.903853 | 1.972112 | −2.306818 | 0.069456 |
| HB132 | 2.654369 | −3.71955 | −6.543987 | −3.876868 | −4.7099 | 4.043489 | −4.801651 | −7.725089 |
| HB136 | 5.005516 | −3.234557 | −4.827283 | 2.471208 | −0.502385 | −1.945351 | −4.324749 | −4.844765 |
| HB140 | 2.835457 | −7.041546 | −6.88604 | −5.561912 | −5.089682 | 4.140594 | −6.023758 | −10.477228 |
| HB142 | 5.200474 | −4.919616 | 2.416807 | 2.058522 | −3.396171 | 1.380591 | −5.965126 | 1.196438 |
| HB145 | 3.58286 | −5.186236 | −5.18731 | NA | −5.118895 | 5.58416 | −5.786933 | −7.880334 |
| HB146 | −1.290056 | −5.422341 | −5.973879 | −3.869993 | −5.908024 | 0.982626 | −4.124487 | −8.751883 |
| HB147 | −9.442257 | −3.655303 | −0.362122 | 1.179633 | −2.349782 | −1.51351 | −2.756099 | 0.30832 |
| HB148 | −3.566401 | −5.382548 | −6.721533 | −2.380348 | −6.951359 | 1.183916 | −4.188648 | −7.101147 |
| HB150 | 2.356994 | −5.56181 | −5.496186 | −4.45536 | −5.603247 | 5.136577 | −5.435261 | −8.522001 |
| HB153 | −2.086302 | −4.364035 | −4.049735 | −1.1908 | −4.342186 | 2.437297 | −6.055092 | −7.522683 |
| HB155 | −1.951256 | −5.140738 | −7.17357 | −0.801318 | 4.538929 | 4.038538 | −5.939438 | 3.058475 |
| HB156 | −6.523604 | −4.658012 | −5.112322 | −1.499462 | −1.13031 | 1.970226 | −4.763811 | −8.138508 |
| HB157 | −8.747252 | −3.193287 | −0.914651 | 0.563787 | −0.139273 | 0.648195 | −3.089302 | −2.404646 |
| H6160 | 4.40621 | −0.878277 | −2.381785 | −1.9527 | 0.770799 | 4.516203 | −2.89522 | 1.197611 |
| HB162 | −1.127062 | −5.142195 | −6.564426 | −2.432348 | −5.179601 | 3.27157 | −4.959578 | −9.351464 |
| HB165 | −1.015428 | −1.578048 | −1.612095 | −1.677494 | 1.921123 | −0.416058 | −4.579384 | −0.458984 |
| HB167 | −7.323435 | −5.692388 | −6.461153 | −2.470512 | −4.912208 | −0.369976 | −4.949694 | −10.583324 |
| HB170 | −0.980072 | −5.786627 | −7.265156 | −3.690367 | −5.952908 | 1.548967 | −6.61768 | −8.574004 |
| HB171 | 2.310988 | −5.687635 | −7.127181 | −3.794631 | −5.898635 | 2.05689 | −6.420469 | −8.856566 |

TABLE A-continued

| | | | | | | | | |
|---|---|---|---|---|---|---|---|---|
| HB172 | 4.547243 | −0.385469 | −1.804453 | −1.833478 | 2.11442 | 4.373205 | −3.929151 | 1.277285 |
| HB173 | 1.889759 | −5.184791 | −4.471618 | −2.235657 | −5.743057 | 2.116789 | −4.966413 | −7.319851 |
| HB175 | −2.0436 | −6.05152 | −8.152949 | −2.996302 | −3.829205 | 3.036838 | −5.151913 | −9.108766 |
| HB184 | −6.561121 | −2.895788 | −5.35813 | −1.653786 | 0.293844 | −0.082754 | −3.084271 | −3.362889 |
| HB20 | 4.752153 | −4.811256 | −5.712608 | −2.133951 | −5.361771 | 5.572378 | −4.283688 | −8.390209 |
| HB28 | −4.001793 | −4.719296 | −7.514733 | −2.385516 | −3.869707 | 0.599685 | −5.187286 | −9.373678 |
| HB3 | 0.027392 | −4.565046 | −4.462833 | −2.255273 | −4.14636 | 4.676108 | −5.373064 | −6.610781 |
| HB33 | −7.497741 | −3.066759 | −5.881217 | 0.250334 | 0.950966 | 0.500246 | −3.829096 | −6.510759 |
| HB39 | −8.613403 | −3.166427 | 3.421734 | 1.699859 | −0.944463 | −0.146929 | −1.480822 | −0.727464 |
| HB48 | −4.768603 | −3.632136 | −4.882397 | −2.170561 | −4.965403 | 1.366439 | −3.944489 | −9.061667 |
| HB49 | 1.818606 | −5.933777 | −5.948111 | −4.936781 | −5.434931 | 4.576628 | −5.318794 | −9.381172 |
| HB5 | −2.282703 | −6.147963 | −7.059143 | −4.107155 | −7.593099 | 2.501017 | −6.573836 | −9.813634 |
| HB54 | 1.132255 | −4.844075 | −5.655802 | −2.937193 | −4.595442 | 3.040468 | −4.999207 | −8.199672 |
| HB59 | 1.334928 | −6.792009 | −7.221196 | −5.590302 | −6.300828 | 1.42553 | −5.648808 | −9.279234 |
| HB6 | −1.610623 | −7.099329 | −7.979286 | −5.729452 | −5.2647225 | 2.920021 | −5.482511 | −10.151809 |
| HB60 | −0.594337 | −5.206398 | −6.67766 | −1.663871 | −2.889326 | 3.97632 | −5.504179 | −6.743858 |
| HB61 | −5.058775 | −6.113525 | −5.991888 | −3.527984 | −5.387419 | 3.269827 | −6.119246 | −8.943929 |
| HB62 | −1.989342 | −4.487171 | −6.502588 | −0.923844 | −4.712471 | 3.449967 | −4.22945 | −7.087853 |
| HB63 | −0.891056 | −4.153057 | −5.680458 | −2.637115 | −5.710062 | 4.49543 | −2.939154 | −9.095241 |
| HB65 | 3.025127 | −4.346225 | −5.338104 | −1.175748 | −1.226393 | −0.613979 | −5.196916 | −4.645702 |
| HB66 | −1.861761 | −4.166485 | −5.897819 | −2.09279 | −3.003258 | 4.774807 | −4.585607 | −6.839392 |
| HB68 | −4.313608 | −6.550704 | −6.762513 | −3.66757 | −5.982654 | 4.060667 | −5.956246 | −8.393607 |
| HB69 | −1.820363 | −9.245314333 | −8.965648 | −7.384871667 | −9.430164667 | −2.026701667 | −8.961309 | −12.31658 |
| HB7 | 1.334084 | −4.488213 | −5.853708 | −2.13753 | −5.142938 | 4.894117 | −4.082335 | −8.118103 |
| HB70 | 2.021391 | −5.678476 | −7.496267 | −1.771 | −4.346458 | 2.174971 | −7.066038 | −8.392057 |
| HB72 | −11.99570467 | 3.978023333 | −1.371737333 | −2.543168667 | −6.278723667 | −5.504070333 | −7.162789667 | −8.103601333 |
| HB73 | −10.69629133 | −8.263771333 | −4.869197667 | −2.900671333 | −5.802080667 | −5.324255333 | −8.090371 | −9.754354333 |
| HB74F | 3.831288 | −7.73216 | −4.940396 | −6.3439 | −6.355995 | 6.130615 | −5.584023 | −10.472842 |
| HB75 | 0.474553 | −6.309674 | −2.777247 | −4.334006 | −6.807299 | 4.545387 | −5.115577 | −10.418948 |
| HB77 | 2.915987 | −5.645872 | −6.698372 | −2.284956 | −5.392377 | 4.544876 | −5.559466 | −8.695429 |
| HB78 | −3.945686 | −2.82555 | −2.986284 | −1.790335 | −0.938738 | 4.523136 | −2.620165 | −5.945013 |
| HB79 | −0.781193 | −5.652768 | −5.454157 | −3.953162 | −5.051444 | 0.254305 | −5.44242 | −9.05667 |
| HB8 | −6.696169 | −3.108913 | 0.498461 | 1.361801 | −3.322642 | 0.055848 | −0.348042 | −1.877119 |
| HB80 | −8.8331005 | −4.713883 | −2.9124615 | −2.810437 | −0.838727 | −0.7226515 | −2.5925445 | −5.408417 |
| HB81 | −4.851198667 | −10.55296467 | −10.55292033 | −7.621321667 | −10.19195633 | −2.962795333 | −10.17992067 | −12.72629433 |
| HB82 | −1.942166 | −5.620028 | −5.739178 | −3.972123 | −6.520482 | 0.934055 | −3.737063 | −8.932744 |
| HB83 | −4.169107 | −9.660034667 | −9.382586667 | −8.05219 | −10.951863 | −3.521245667 | −10.12345167 | −9.850559667 |
| HB86 | −6.283735 | −5.287677 | 0.896011 | −1.494853 | −2.934412 | −0.46896 | −2.879366 | −5.76077 |
| HB89 | 2.996384 | −7.323446 | −7.464817 | −5.120874 | −5.856518 | 4.907738 | −6.676481 | −9.415603 |
| HB9 | −3.679937 | −4.761778 | −6.571455 | −2.775269 | −6.201772 | 2.209541 | −3.895565 | −8.86438 |
| HB90 | 2.024206 | −8.47846 | −1.33932 | −6.745716 | −6.677122 | 5.899195 | −8.114672 | −10.459034 |
| HB93 | −4.610162 | −5.583852 | −5.277197 | −1.990982 | −2.698011 | −1.085743 | −4.488914 | −3.388975 |
| HB94 | 1.79868 | −5.621254 | −7.718202 | −6.940586 | −6.67335 | 3.551727 | −6.54809 | −8.572742 |
| HB95 | −0.444835 | −5.745006 | −8.404602 | −5.637613 | −6.396063 | 6.671045 | −5.701559 | −10.554918 |
| HB96 | −4.775396 | −6.402052 | −6.123253 | −4.340961 | −5.066688 | 3.365736 | −6.521753 | −9.090145 |
| HB97 | −6.841231 | −6.21691 | −6.275051 | −3.638382 | −3.617558 | 2.362203 | −6.58495 | −5.781372 |
| HB98 | −4.911783 | −2.946932 | 6.478933 | 4.211147 | 0.395926 | 2.311268 | −2.827802 | 0.584022 |
| HB99 | −4.551378 | −1.14591 | −5.549696 | −1.796859 | 1.62906 | 2.600714 | −2.483835 | −3.848236 |

Table of the normalized qPCR data (deltaCt values) of 85 hepatoblastomas used for classification by discretization.

| id | DLG7 | DUSP9 | E2F5 | GHR | HPD | IGSF1 | NLE | RPL10A |
|---|---|---|---|---|---|---|---|---|
| HB1 | 4.140368 | −5.212318 | −0.812424 | 1.207583 | 3.840983 | −0.715134 | −0.812792 | −8.675945 |
| HB100 | 4.399124 | −5.749706 | 0.27698 | 1.907294 | −0.113253 | −2.800323 | 0.547899 | −6.153046 |
| HB101 | 7.086329 | −0.641871 | 0.737702 | −3.913751 | −4.340259 | 7.086329 | 0.191689 | −6.757648 |
| HB102 | 7.380694 | −4.303866 | 1.144778 | 0.2784 | −0.284245 | −2.545668 | 0.856607 | −6.803817 |
| HB103 | 5.997143 | 0.880421 | 3.697478 | 1.249386 | −2.713306 | 1.392197 | −0.453035 | −4.535615 |
| HB106 | 6.79755 | −1.540745 | 0.77722 | −4.155098 | −5.747164 | 2.274385 | 0.291903 | −6.637275 |
| HB107 | 5.239962 | −1.184244 | 3.145996 | −1.891404 | −4.433271 | 3.119114 | −0.053334 | −6.319917 |
| HB11 | 3.688558 | −1.412987 | −0.179621 | −0.149048 | −1.897658 | 2.297186 | −0.19686 | −5.623341 |
| HB112 | 6.035002 | −2.179125 | −0.998979 | −3.575994 | −4.671755 | −0.776138 | −2.252113 | −7.8479 |
| HB114 | 6.2971 | 2.615827 | 0.886564 | 0.002487 | 1.919397 | 2.50863 | 1.785623 | −7.055851 |
| HB118 | 3.935101 | 2.405105 | 2.275962 | −0.451819 | −4.812319 | 2.339813 | 0.486307 | −5.904633 |
| HB121 | 3.458157 | −2.1882 | 1.247645 | −1.155575 | −5.938235 | 3.750147 | 1.867907 | −5.131548 |
| HB122 | 3.562777 | 1.229723 | 2.386559 | −1.961029 | −5.590919 | 2.406687 | 1.976893 | −5.368023 |
| HB125 | 5.700252 | 0.274642 | 2.864883 | 0.118717 | −3.155289 | 2.138032 | −0.470879 | −3.478449 |
| HB126 | 6.32602 | 0.274197 | 3.089709 | −1.334371 | −5.227705 | 2.726599 | 0.54385 | −4.787822 |
| HB129 | 4.474485 | −3.829751 | 1.158283 | 3.025728 | 1.984295 | −0.074354 | 1.326073 | −5.682215 |
| HB130 | 5.297728 | −2.554008 | 2.251163 | 3.317556 | 0.885962 | 0.039307 | 1.389742 | −4.829542 |
| HB131 | 5.801168 | 2.269272 | 2.226921 | 1.235598 | 2.035452 | 5.621114 | 1.777334 | −4.96776 |
| HB132 | 8.18041 | 0.433104 | 4.507503 | −0.157093 | −2.441422 | 5.855213 | 2.895208 | −3.579579 |
| HB136 | 1.140686 | 0.10165 | −2.336947 | 0.261203 | 0.124159 | 3.807218 | −0.676358 | −7.113232 |
| HB140 | 9.015818 | −0.401264 | 2.325356 | −3.379102 | −3.148068 | 3.156456 | 0.80129 | −7.308986 |
| HB142 | 6.203192 | 4.554631 | 3.03661 | 2.598877 | 4.150455 | 8.782461 | 1.428955 | −6.630178 |
| HB145 | 6.734264 | 1.908734 | 2.518779 | −1.358174 | −5.181668 | 4.610406 | 1.707345 | −4.6775 |
| HB146 | 0.991164 | −0.681828 | 0.1227 | −0.510651 | −4.471483 | 0.777004 | 0.176935 | −5.992209 |
| HB147 | −1.376061 | −4.733546 | −2.588397 | 1.772494 | −1.944032 | −2.698708 | −0.565682 | −7.527854 |
| HB148 | 1.7033 | −1.806502 | −0.663069 | −1.376372 | −5.121145 | −0.683001 | −0.431826 | −6.201895 |

TABLE A-continued

| | | | | | | | | |
|---|---|---|---|---|---|---|---|---|
| HB150 | 5.800233 | 0.8436 | 2.758596 | −1.181738 | −5.492037 | 2.891937 | 0.439392 | −4.69542 |
| HB153 | 3.096912 | −2.657862 | 0.449197 | −0.480929 | −4.261986 | 3.34336 | 1.423023 | −5.963837 |
| HB155 | 4.360922 | −1.23259 | 0.752365 | −3.062474 | 0.657144 | −1.091013 | 0.911424 | −5.964497 |
| HB156 | 2.483547 | −1.214228 | 0.687246 | −1.107323 | −3.806189 | −1.181305 | 0.159847 | −5.65452 |
| HB157 | 0.181175 | −4.1451 | 0.297747 | 1.940187 | −3.850885 | −1.38623 | 0.041349 | −5.820536 |
| HB160 | 6.224569 | 2.906158 | 4.403545 | 2.633949 | −2.138569 | 3.355814 | −0.100123 | −4.568688 |
| HB162 | 4.25017 | −1.453283 | 1.117439 | −0.163468 | −4.733881 | 1.809885 | −0.022627 | −4.822098 |
| HB165 | −0.010488 | 1.837305 | 0.47467 | −2.953007 | −0.655058 | −1.791164 | −0.933062 | −5.535221 |
| HB167 | 0.509668 | −1.707485 | 0.198742 | 0.269552 | −4.442331 | −1.197651 | −0.240385 | −5.755341 |
| HB170 | 2.567207 | 1.148738 | 1.360144 | −2.397242 | −4.944439 | 2.424619 | −0.463297 | −5.539725 |
| HB171 | 2.278353 | 1.67404 | 2.062277 | −1.193735 | −4.984552 | 2.19098 | 0.230044 | −4.81411 |
| HB172 | 6.060459 | 2.366999 | 3.689341 | 2.93017 | −1.316921 | 2.571025 | −0.153162 | −3.812616 |
| HB173 | 2.779999 | 1.921427 | 3.05205 | −0.20919 | −4.475376 | 0.418818 | 0.678606 | −4.361307 |
| HB175 | 4.414558 | −1.623242 | 1.49 | −0.662783 | −4.684446 | 3.524049 | 1.78088 | −5.173616 |
| HB184 | 1.361379 | −1.542307 | −0.588812 | 1.814793 | −2.048922 | −0.326393 | 0.097971 | −4.663763 |
| HB20 | 9.423325 | −0.34174 | 2.066057 | −0.975735 | −3.695854 | 4.361484 | 1.157495 | −5.27136 |
| HB28 | 1.922989 | −2.304861 | 1.222545 | −0.120436 | −5.154703 | −0.192738 | 1.819854 | −5.824864 |
| HB3 | 7.285685 | 0.65201 | 2.301029 | −0.049158 | 0.117373 | 4.46221 | 1.743745 | −6.911792 |
| HB33 | 1.659659 | −4.338262 | −0.148233 | 1.134133 | −4.625204 | −2.34198 | 1.272614 | −5.63922 |
| HB39 | 2.485354 | −4.927491 | −1.241931 | 1.694781 | −0.33289 | −2.652634 | −0.149609 | −6.579218 |
| HB48 | 1.583391 | −3.620772 | −0.089081 | 1.342382 | −2.330218 | 0.686163 | 1.169838 | −6.508074 |
| HB49 | 5.652893 | 2.41148 | 3.776672 | −1.220476 | −5.746779 | 4.727596 | 2.190021 | −4.286949 |
| HB5 | 3.674234 | −2.082424 | 0.98073 | −1.943451 | −6.561791 | 1.592167 | 0.449005 | −6.230808 |
| HB54 | 3.556268 | 3.982183 | 3.025795 | −0.158057 | −4.638333 | 3.623678 | 1.995039 | −5.061096 |
| HB59 | 5.127336 | 0.250753 | 3.459250 | −2.269072 | −4.727738 | 6.045093 | 1.466312 | −6.48303 |
| HB6 | 6.733353 | −0.246309 | 3.812183 | −2.459856 | −3.728987 | 0.835057 | 2.205872 | −7.208765 |
| HB60 | 5.188517 | 2.869544 | 3.228365 | −0.276338 | −4.031974 | 2.026116 | 2.577353 | −4.502382 |
| HB61 | 5.827933 | −5.51457 | 1.00606 | −3.272672 | −4.816797 | −0.203871 | 0.753758 | −6.140918 |
| HB62 | 4.328277 | 0.708512 | 1.218963 | 1.021692 | −3.265138 | 0.731519 | 2.223877 | −5.334147 |
| HB63 | 5.003075 | −1.082094 | 0.951357 | 1.316553 | 2.000601 | 4.964996 | 1.31674 | −6.741518 |
| HB65 | 2.978487 | −0.087486 | −1.274388 | 0.080222 | −2.417946 | 1.06702 | −1.371523 | −6.195428 |
| HB66 | 8.039274 | −0.423313 | 2.141981 | −1.148424 | −1.349111 | −0.305017 | 1.586659 | −5.393141 |
| HB68 | 7.010986 | −0.530541 | 2.520261 | 0.232431 | −1.779051 | −0.603113 | 2.342104 | −4.959414 |
| HB69 | 3.071106 | −0.626059667 | 3.421015 | −5.118794333 | −6.824055667 | 11.819556 | −0.603036 | −2.847600667 |
| HB7 | 8.076437 | −0.833011 | 1.354912 | −0.884629 | −2.106592 | 2.978739 | 2.384133 | −5.458546 |
| HB70 | 4.083519 | 3.896364 | 2.616204 | −3.614294 | −6.063097 | 2.060379 | 1.506083 | −4.669554 |
| HB72 | −1.688566667 | −8.976227 | −1.809692 | −1.750672 | −3.40203 | −6.090071333 | −2.505424 | −5.054027 |
| HB73 | −2.068555667 | −9.537516 | −1.965151 | −0.544775 | −5.542041333 | −7.013002667 | −3.078154667 | −5.580986333 |
| HB74F | 8.986048 | 0.497828 | 4.585503 | −2.916191 | −3.041943 | 7.759608 | 1.654283 | −6.380865 |
| HB75 | 7.231393 | −2.411839 | 0.378995 | −1.925637 | −5.055106 | 2.61456 | 1.017432 | −5.77539 |
| HB77 | 9.66177 | −0.139299 | 2.727198 | −1.675013 | −4.079932 | 2.793758 | 2.146337 | −4.964228 |
| HB78 | 5.293419 | −0.185629 | 1.735594 | 0.020191 | −3.984125 | −2.010153 | −0.114956 | −3.94071 |
| HB79 | 1.90306 | 1.145681 | 1.319285 | −1.978228 | −5.757335 | 0.01942 | −0.194167 | −5.016158 |
| HB8 | 1.950257 | −4.043236 | −1.814636 | 2.280516 | 1.100353 | 0.314694 | 0.29834 | −7.823095 |
| HB80 | 2.660644 | −4.9166885 | −0.374031 | 0.675995 | −0.4253495 | −4.2048885 | −0.8782055 | −7.919531 |
| HB81 | 2.155925333 | −5.738363 | 0.932455333 | −5.565798 | −8.171378 | −1.999123333 | −2.092100667 | −4.795482 |
| HB82 | 1.47049 | −3.938165 | −0.549544 | −1.023595 | −3.267403 | 8.008069 | 0.067941 | −7.635394 |
| HB83 | 2.492243 | −4.003930333 | 4.737920667 | −4.561133333 | −6.966227667 | −0.028684333 | −0.855054667 | 1.789090833 |
| HB86 | 3.219092 | −5.894534 | −0.496662 | 0.35847 | −0.121981 | −2.31061 | 0.046472 | −8.510995 |
| HB89 | 8.255339 | 1.284916 | 3.638735 | −2.665258 | −5.177704 | 3.273649 | 1.279167 | −5.898171 |
| HB9 | 4.940411 | −1.989636 | 0.700504 | −0.698968 | −3.255601 | 2.609339 | 1.300875 | −6.54224 |
| HB90 | 6.54891 | 1.104162 | 1.408459 | −5.754423 | −7.507485 | 4.45026 | 1.52717 | −6.250036 |
| HB93 | 3.902565 | −7.483471 | −0.488108 | 0.969648 | −1.415501 | −1.818147 | −0.829773 | −7.824402 |
| HB94 | 8.669386 | −1.132305 | 0.490788 | 8.498726 | −6.819645 | 7.800646 | −0.149162 | −5.793072 |
| HB95 | 6.921267 | −1.620869 | 2.726241 | −2.193777 | −5.454765 | 1.364738 | 0.279802 | −5.172451 |
| HB96 | 6.685021 | −0.591271 | 1.973021 | −4.924202 | −4.91283 | 1.722505 | 1.829525 | −5.638435 |
| HB97 | 6.474525 | −5.800537 | 1.05047 | −0.911789 | −4.571465 | −4.308964 | −0.87035 | −6.60257 |
| HB98 | 6.837198 | −2.065483 | 2.482301 | 1.17723 | −0.98407 | −0.701098 | 1.175939 | −5.166874 |
| HB99 | 6.353711 | −4.201828 | 1.467552 | 1.703655 | −0.109186 | −0.822266 | 1.226265 | −3.572067 |

TABLE B

| tumor ID | score (ratio) | 67th percentile-related score (2-classes) | percentile-related score (3-classes) | previous 16 gene based classification | Gender | Age months | AFP at diagnosis ng/mL | Chemo-therapy treatment | Treatment protocol | PRETEXT stage | Distant Metastasis |
|---|---|---|---|---|---|---|---|---|---|---|---|
| HB122 | 0.5 | 1 | 1 | C1 | M | 10 | 88000 | Y | H | I | N |
| HB126 | 0.5 | 1 | 1 | C1 | F | 12 | 153840 | Y | S | II | N |
| HB145 | 0.5 | 1 | 1 | C1 | M | 7 | 56000 | Y | S | II | N |
| HB150 | 0.5 | 1 | 1 | C1 | F | 5 | 82000 | Y | S | III | N |
| HB175 | 0.5 | 1 | 1 | C1 | M | 9 | 220000 | Y | S | II | N |
| HB20 | 0.5 | 1 | 1 | C1 | F | 50 | 880 | Y | S | II | N |
| HB49 | 0.5 | 1 | 1 | C1 | F | 15 | 11000 | Y | S | II | N |
| HB54 | 0.5 | 1 | 1 | C1 | M | 10 | 180 | N | N | I | N |
| HB70 | 0.5 | 1 | 1 | C1 | F | 42 | 812 | Y | S | II | N |

TABLE B-continued

| | | | | | | | | | | | |
|---|---|---|---|---|---|---|---|---|---|---|---|
| HB77 | 0.5 | 1 | 1 | C1 | F | 9 | 204000 | Y | S | II | N |
| HB89 | 0.5 | 1 | 1 | C1 | M | 13 | 448 | Y | S | I | N |
| HB95 | 0.5 | 1 | 1 | C1 | M | 28 | 1000000 | Y | H | IV | Y |
| HB118 | 0.53333333 | 1 | 1 | C1 | M | 17 | 14500 | Y | S | NA | Y |
| HB132 | 0.53333333 | 1 | 1 | C1 | F | 23 | 2078 | Y | NA | III | N |
| HB121 | 0.5625 | 1 | 1 | C1 | F | 14 | 296000 | Y | S | III | N |
| HB140 | 0.5625 | 1 | 1 | C1 | M | 3 | 22758 | Y | S | II | N |
| HB162 | 0.5625 | 1 | 1 | C1 | F | 9 | 960000 | Y | S | III | N |
| HB171 | 0.5625 | 1 | 1 | C1 | F | 17 | 300 | Y | S | II | N |
| HB173 | 0.5625 | 1 | 1 | C1 | F | 27 | 66810 | Y | S | I | N |
| HB59 | 0.5625 | 1 | 1 | C1 | F | 24 | 5643 | Y | S | II | N |
| HB6 | 0.5625 | 1 | 1 | C1 | M | 24 | 320000 | Y | S | II | N |
| HB74F | 0.5625 | 1 | 1 | C1 | M | 96 | 325 | N | N | I | N |
| HB96 | 0.5625 | 1 | 1 | C1 | M | 101 | 2265000 | Y | H | IV | N |
| HB60 | 0.57142857 | 1 | 1 | C1 | F | 30 | 1990800 | Y | H | II | N |
| HB7 | 0.57142857 | 1 | 1 | C1 | M | 33 | 45000 | Y | S | I | N |
| HB101 | 0.6 | 1 | 1 | C1 | M | 42 | 67747 | Y | S | III | N |
| HB106 | 0.6 | 1 | 1 | C1 | F | 11 | 320000 | Y | H | IV | N |
| HB90 | 0.6 | 1 | 1 | C1 | F | 74 | 300 | N | N | II | N |
| HB62 | 0.61538462 | 1 | 2 | C1 | M | 16 | 1708400 | Y | H | IV | N |
| HB107 | 0.625 | 1 | 2 | C1 | M | 30 | 16000 | Y | H | IV | Y |
| HB170 | 0.625 | 1 | 2 | C1 | M | 20 | 123000 | Y | H | III | Y |
| HB5 | 0.625 | 1 | 2 | C1 | M | 84 | 300000 | Y | H | III | Y |
| HB125 | 0.64285714 | 1 | 2 | C1 | F | 15 | 360000 | Y | H | IV | Y |
| HB75 | 0.66666667 | 1 | 2 | C1 | M | 21 | 131000 | Y | S | II | N |
| HB9 | 0.66666667 | 1 | 2 | C1 | F | 16 | 84000 | Y | NA | III | N |
| HB94 | 0.66666667 | 1 | 2 | C1 | M | 29 | 1270 | Y | S | I | N |
| HB61 | 0.6875 | 1 | 2 | C1 | F | 126 | 346000 | Y | NA | IV | Y |
| HB69 | 0.6875 | 1 | 2 | C1 | M | 25 | 1163 | Y | S | I | N |
| HB79 | 0.6875 | 1 | 2 | C1 | M | 144 | 1200 | Y | S | II | N |
| HB3 | 0.69230769 | 1 | 2 | C1 | F | 22 | 3192 | Y | S | I | N |
| HB66 | 0.69230769 | 1 | 2 | C1 | M | 6 | 1000000 | Y | S | III | N |
| HB68 | 0.71428571 | 1 | 2 | C1 | F | 11 | 119320 | Y | S | III | N |
| HB146 | 0.73333333 | 1 | 2 | C1 | F | 11 | NA | N | N | NA | N |
| HB155 | 0.75 | 1 | 2 | C2 | M | 9 | 849500 | Y | S | II | N |
| HB63 | 0.75 | 1 | 2 | C1 | M | 204 | NA | N | N | III | N |
| HB11 | 0.76923077 | 1 | 2 | C1 | F | 18 | 626100 | Y | H | IV | Y |
| HB153 | 0.78571429 | 1 | 2 | C1 | F | 27 | 1000000 | Y | H | IV | Y |
| HB28 | 0.8125 | 1 | 2 | C1 | M | 34 | 172500 | Y | NA | II | N |
| HB83 | 0.8125 | 1 | 2 | C1 | M | 15 | 285 | Y | S | II | N |
| HB156 | 0.85714286 | 1 | 2 | C2 | F | 2 | 468000 | Y | S | III | N |
| HB112 | 0.86666667 | 1 | 2 | C1 | M | 36 | 725 | Y | S | II | N |
| HB82 | 0.86666667 | 1 | 2 | C1 | M | 120 | 179000 | N | N | II | N |
| HB97 | 0.86666667 | 1 | 2 | C1 | F | 42 | 700000 | Y | H | IV | N |
| HB81 | 0.875 | 1 | 2 | C1 | M | 22 | 322197 | Y | H | III | Y |
| HB103 | 0.9 | 1 | 2 | C2 | F | 57 | 750000 | Y | H | IV | Y |
| HB114 | 0.9 | 1 | 2 | C2 | F | 21 | 8783 | Y | S | II | N |
| HB142 | 0.90909091 | 1 | 2 | C2 | F | 48 | 605000 | Y | H | III | Y |
| HB148 | 0.93333333 | 2 | 3 | C1 | M | 17 | 200730 | Y | S | II | N |
| HB167 | 0.93333333 | 2 | 3 | C2 | M | 34 | 1500000 | Y | H | NA | Y |
| HB73 | 0.9375 | 2 | 3 | C2 | F | 24 | 667786 | Y | H | III | Y |
| HB131 | 1 | 2 | 3 | C2 | M | 6 | 7511 | Y | H | II | Y |
| HB65 | 1 | 2 | 3 | C2 | M | 6 | 1740 | N | N | III | N |
| HB78 | 1 | 2 | 3 | C1 | M | 126 | 376000 | Y | S | II | N |
| HB72 | 1.07142857 | 2 | 3 | C2 | F | 16 | 1412000 | Y | S | III | Y |
| HB48 | 1.07692308 | 2 | 3 | C2 | M | 72 | 35558 | Y | H | IV | N |
| HB102 | 1.09090909 | 2 | 3 | C2 | M | 41 | 1331000 | N | N | II | N |
| HB160 | 1.125 | 2 | 3 | C2 | M | 45 | 342000 | Y | H | II | Y |
| HB172 | 1.125 | 2 | 3 | C2 | M | 50 | 64170 | Y | H | II | Y |
| HB99 | 1.22222222 | 2 | 3 | C2 | M | 72 | 277192 | N | N | IV | Y |
| HB130 | 1.25 | 2 | 3 | C2 | F | 19 | 1980000 | Y | H | II | Y |
| HB98 | 1.25 | 2 | 3 | C2 | M | 60 | 1285000 | V | H | III | V |
| HB136 | 1.3 | 2 | 3 | C2 | M | 6 | 31828 | Y | S | III | N |
| HB165 | 1.3 | 2 | 3 | C2 | M | 13 | 18600 | Y | S | II | N |
| HB1 | 1.36363636 | 2 | 3 | C2 | F | 43 | 3000 | Y | H | IV | Y |
| HB93 | 1.36363636 | 2 | 3 | C2 | M | 22 | 107000 | V | S | III | N |
| HB129 | 1.375 | 2 | 3 | C2 | M | 96 | 14000 | N | N | I | N |
| HB33 | 1.4 | 2 | 3 | C2 | M | 12 | 765890 | Y | H | IV | N |
| HB100 | 1.44444444 | 2 | 3 | C2 | M | 48 | 576000 | N | N | III | N |
| HB184 | 1.44444444 | 2 | 3 | C2 | M | 41 | 912500 | Y | H | IV | Y |
| HB157 | 1.55555556 | 2 | 3 | C2 | M | 7 | 356000 | Y | H | NA | Y |
| HB80 | 1.6 | 2 | 3 | C2 | M | 180 | 37000 | Y | H | III | Y |
| HB86 | 1.66666667 | 2 | 3 | C2 | M | 0.08 | 74000 | N | N | III | N |
| HB8 | 1.75 | 2 | 3 | C2 | F | 8 | 44610 | Y | NA | II | N |
| HB147 | 2 | 2 | 3 | C2 | F | 9 | 2355000 | Y | S | II | N |
| HB39 | 2 | 2 | 3 | C2 | F | 11 | 862067 | Y | S | III | N |

TABLE B-continued

| tumor ID | Vascular invasion | Multifocality | Histology | Main Epithelial component | beta-catenin status | Follow-up (months) | Outcome | Surgery Type | speOS | Follow-up (years) |
|---|---|---|---|---|---|---|---|---|---|---|
| HB122 | N | S | Mx | F | mut | 18 | A | R | 0 | 1.5 |
| HB126 | N | S | Mx | F | mut | 17 | A | R | 0 | 1.416666667 |
| HB145 | N | S | Mx | F | mut | 14 | A | R | 0 | 1.166666667 |
| HB150 | N | M | Mx | F | NA | 6 | A | R | 0 | 0.5 |
| HB175 | N | M | Mx | F | mut | 7 | A | R | 0 | 0.583333333 |
| HB20 | N | S | Ep | F | mut | 42 | A | R | 0 | 3.5 |
| HB49 | N | S | Ep | F | mut | 6 | D | R | 0 | 0.5 |
| HB54 | N | S | Ep | PF | mut | 49 | A | R | 0 | 4.083333333 |
| HB70 | N | S | Ep | PF | mut | 53 | R | R | 0 | 4.416666667 |
| HB77 | N | S | Ep | F | mut | 37 | A | R | 0 | 3.083333333 |
| HB89 | N | S | Ep | F | mut | 33 | A | R | 0 | 2.75 |
| HB95 | Y | M | Mx | F | mut | 32 | A | LT | 0 | 2.666666667 |
| HB118 | NA | M | Ep | F | wt (FAP) | 31 | A | R | 0 | 2.583333333 |
| HB132 | N | S | Mx | F | mut | 121 | A | R | 0 | 10.08333333 |
| HB121 | N | M | Mx | F | mut | 18 | A | R | 0 | 1.5 |
| HB140 | N | S | Mx | F | mut | 22 | A | R | 0 | 1.833333333 |
| HB162 | N | S | Mx | F | mut | 13 | A | R | 0 | 1.083333333 |
| HB171 | N | S | Ep | F | mut | 9 | A | R | 0 | 0.75 |
| HB173 | N | S | Ep | F | NA | 11 | A | R | 0 | 0.916666667 |
| HB59 | N | S | Ep | PF | mut | 72 | A | R | 0 | 6 |
| HB6 | Y | S | Ep | F | mut | 48 | A | R | 0 | 4 |
| HB74F | Y | S | Ep | F | mut | 35 | A | R | 0 | 2.916666667 |
| HB96 | Y | M | Ep | F | mut | 23 | R | LT | 0 | 1.916666667 |
| HB60 | Y | S | Ep | F | wt | 63 | A | R | 0 | 5.25 |
| HB7 | Y | S | Mx | F | mut | 46 | A | R | 0 | 3.833333333 |
| HB101 | N | S | Ep | F | mut | 20 | A | R | 0 | 1.666666667 |
| HB106 | N | S | Mx | F | mut | 25 | A | R | 0 | 2.083333333 |
| HB90 | N | S | Ep | F | mut | 35 | A | R | 0 | 2.916666667 |
| HB62 | N | S | Mx | F | mut | 69 | A | R | 0 | 5.75 |
| HB107 | Y | M | Ep | F | mut | 25 | A | LT | 0 | 2.083333333 |
| HB170 | Y | M | Ep | F | wt (FAP) | 15 | A | R | 0 | 1.25 |
| HB5 | Y | M | Ep | F | mut | 24 | DOD | R | 1 | 2 |
| HB125 | N | M | Mx | F | mut | 17 | A | LT | 0 | 1.416666667 |
| HB75 | Y | S | Mx | F | mut | 41 | A | R | 0 | 3.416666667 |
| HB9 | N | S | Ep | PF | mut | 91 | A | R | 0 | 7.583333333 |
| HB94 | N | S | Ep | PF | wt | 29 | A | R | 0 | 2.416666667 |
| HB61 | Y | M | Mx | F | mut | 5 | DOD | R | 1 | 0.416666667 |
| HB69 | N | S | Ep | PF | wt | 55 | A | R | 0 | 4.583333333 |
| HB79 | N | M | Ep | M | mut | 39 | A | LT | 0 | 3.25 |
| HB3 | N | S | Ep | F | wt | 55 | A | R | 0 | 4.583333333 |
| HB66 | N | S | Ep | F | mut | 68 | A | R | 0 | 5.666666667 |
| HB68 | N | S | Mx | E | mut | 52 | A | R | 0 | 4.333333333 |
| HB146 | NA | S | NA | NA | NA | 1 | D | R | 0 | 0.083333333 |
| HB155 | N | S | Mx | CF | mut | 8 | A | R | 0 | 0.666666667 |
| HB63 | Y | M | Mx | F | mut | 96 | A | R | 0 | 8 |
| HB11 | Y | M | Mx | F | mut | 21 | DOD | R | 1 | 1.75 |
| HB153 | N | M | Mx | CF | mut | 8 | A | LT | 0 | 0.666666667 |
| HB28 | N | S | Ep | F | wt | 120 | A | R | 0 | 10 |
| HB83 | N | S | Ep | PF | mut | 53 | A | R | 0 | 4.416666667 |
| HB156 | N | NA | Ep | F | NA | 6 | A | R | 0 | 0.5 |
| HB112 | N | S | Ep | F | wt | 32 | A | R | 0 | 2.666666667 |
| HB82 | N | S | Ep | F | mut | 63 | A | R | 0 | 5.25 |
| HB97 | Y | M | Ep | F | mut | 30 | A | R | 0 | 2.5 |
| HB81 | Y | M | Ep | F | mut | 36 | A | R | 0 | 3 |
| HB103 | Y | M | Ep | M | mut | 9 | DOD | M | 1 | 0.75 |
| HB114 | N | S | Mx | E | mut | 23 | A | R | 0 | 1.916666667 |
| HB142 | Y | S | Ep | NA | mut | 16 | A | R | 0 | 1.333333333 |
| HB148 | N | S | Mx | F | mut | 11 | A | R | 0 | 0.916666667 |
| HB167 | Y | M | Ep | F | mut | 2 | A | R | 0 | 0.166666667 |
| HB73 | Y | S | Ep | E | mut | 16 | DOD | R | 1 | 1.333333333 |
| HB131 | N | S | Ep | E | wt | 1 | DOD | R | 1 | 0.083333333 |
| HB65 | N | M | Mx | E | wt | 2 | DOD | R | 1 | 0.166666667 |
| HB78 | Y | M | Ep | CF | wt | 32 | A | R | 0 | 2.666666667 |
| HB72 | Y | M | Mx | E | mut | 9.5 | DOD | R | 1 | 0.791666667 |
| HB48 | Y | M | Ep | CF | mut | 9 | DOD | R | 1 | 0.75 |
| HB102 | N | S | Ep | CF | mut | 4 | D | B | 0 | 0.333333333 |
| HB160 | Y | S | Mx | E | NA | 14 | R | R | 0 | 1.166666667 |
| HB172 | Y | M | Mx | F/E | NA | 10 | A | R | 0 | 0.833333333 |
| HB99 | Y | M | Ep | E | mut | 7 | DOD | B | 1 | 0.583333333 |
| HB130 | N | S | Mx | NA | mut | 62 | A | R | 0 | 5.166666667 |
| HB98 | Y | S | Ep | M | wt (FAP) | 30 | A | M | 0 | 2.5 |
| HB136 | N | S | Mx | F | wt | 34 | A | R | 0 | 2.833333333 |
| HB165 | N | M | Mx | F/E | mut | 4 | A | R | 0 | 0.333333333 |
| HB1 | Y | M | Ep | E | wt (FAP) | 12 | DOD | R | 1 | 1 |
| HB93 | Y | M | Mx | E | mut | 33 | A | LT | 0 | 2.75 |
| HB129 | N | S | Mx | E | wt (FAP) | 54 | DOD | R | 1 | 4.5 |
| HB33 | Y | M | Ep | CF | wt (AXIN1) | 3.5 | DOD | R | 1 | 0.291666667 |

TABLE B-continued

| HB100 | N | S | Ep | F | mut | 20 | A | B | 0 | 1.666666667 |
|---|---|---|---|---|---|---|---|---|---|---|
| HB184 | Y | M | Ep | E | NA | 14 | DOD | LT | 1 | 1.166666667 |
| HB157 | N | M | Ep | CF | mut | 5 | R | LT | 0 | 0.416666667 |
| HB80 | Y | S | Ep | CF | mut | 14 | DOD | R | 1 | 1.166666667 |
| HB86 | Y | S | Ep | E | mut | 57 | A | R | 0 | 4.75 |
| HB8 | Y | S | Ep | E | mut | 135 | A | R | 0 | 11.25 |
| HB147 | N | S | Mx | F | NA | 12 | A | R | 0 | 1 |
| HB39 | Y | S | Mx | NA | mut | 66 | A | R | 0 | 5.5 |

TABLE C

| Gene Name | AFP | ALDH2 | APCS | APOC4 | AQP9 | BUB1 | C1S | CYP2E1 |
|---|---|---|---|---|---|---|---|---|
| HC161 | 2.079447 | −5.920384 | −6.086912 | −7.366206 | −7.320175 | 4.176845 | −6.502865 | −9.12672475 |
| HC162 | 4.056751 | −3.64102 | −4.586098 | −5.663246 | −4.233021 | 3.559124 | −4.64283 | −4.136919 |
| HC163 | 3.323238 | −6.086663 | −6.399079 | −4.052853 | −6.010302 | 4.772507 | −6.776158 | −8.515956 |
| HC164 | 3.075226 | −6.146711 | −7.241796 | −3.371322 | −5.446966 | 3.634476 | −7.462807 | −5.829384 |
| HC165 | 2.685177 | 7.0470725 | −6.294538 | −7.242275 | −6.94561 | 4.029514 | −5.926596 | −3.033642 |
| HC168 | 1.501031 | −6.016314 | −6.696324 | −5.130347 | −5.64774 | 3.305894 | −6.883263 | −4.411302 |
| HC169 | 2.880925 | −6.024682 | −6.87168 | −4.19185 | −6.058572 | 4.09117 | −6.767215 | −8.63753 |
| HC170 | 2.3753035 | 6.6226955 | 8.3702955 | 5.4072375 | 5.6954625 | 5.5639145 | 8.0538815 | −9.7948605 |
| HC171 | 3.001804 | −2.573977 | −4.213123 | −4.040673 | −4.992701 | 3.583809 | −5.226561 | 1.25382 |
| HC172 | 1.164528 | −5.314302 | −6.094652 | −4.127298 | −3.890072 | 3.991173 | −6.240002 | 2.279678 |
| HC173 | 4.694127 | −6.373823 | −5.51865 | −6.056863 | −6.314031 | 4.30288 | −4.863168 | −8.649852 |
| HC176 | 4.066485 | −5.552505 | −5.444218 | −5.551191 | −5.815727 | 6.073568 | −5.850428 | −9.402043 |
| HC177 | 2.692613 | −5.43842 | −3.091896 | −4.656336 | −5.907612 | 3.452047 | −6.412596 | −10.50172 |
| HC178 | 0.554213 | −5.646708 | −7.296414 | −4.588115 | −5.579087 | 3.125179 | −6.556397 | −6.591304 |
| HC179 | 1.910595 | −4.139932 | −8.136252 | −6.036987 | −2.847761 | 3.895205 | −4.943672 | −5.283326 |
| HC180 | 3.212685 | −5.831134 | −7.519348 | −5.962761 | −6.611712 | 1.5179 | −6.130592 | −9.203789 |
| HC181 | 6.030393 | −4.04397 | −2.03808 | −0.956533 | −2.850753 | 5.430677 | −4.712002 | −2.555649 |
| HC182 | 3.376941 | −7.072651 | −7.74873 | −5.2003 | −5.445893 | 6.665657 | −7.899793 | −10.089271 |
| HC183 | 3.149578 | −4.684626 | −7.045155 | −3.800078 | −7.042931 | 2.40337 | −6.412624 | −9.657513 |
| HC184 | −0.093476 | −5.985909 | −7.203484 | −5.482853 | −6.208594 | 1.558788 | −6.347367 | −9.658434 |
| HC185 | 1.405595 | −4.748444 | −5.89589 | −3.780913 | −2.802368 | 4.37289 | −5.800822 | −5.410746 |
| HC186 | 1.666457 | −5.52819 | −7.953401 | −3.287374 | −3.805233 | 1.040678 | −7.309734 | −6.699831 |
| HC187 | 3.652111 | −4.151991 | −7.459358 | −6.247812 | −5.346647 | 4.211928 | −6.33068 | −8.629261 |
| HC188 | 0.355562 | −5.261937 | −7.83848 | −4.759525 | −4.839348 | 5.111208 | −7.787661 | −4.575966 |
| HC189 | 1.239891 | −4.501697 | −8.737075 | −6.152778 | −6.402122 | 5.0291015 | −6.951675 | −5.450079 |
| HC190 | 3.306642 | −4.365515 | −7.399538 | −4.721411 | −6.178224 | 3.016906 | −4.970499 | −5.850237 |

| Gene Name | DLG7 | DUSP9 | E2F5 | GHR | HPD | IGSF1 | NLE | RPL10A |
|---|---|---|---|---|---|---|---|---|
| HC161 | 5.322878 | 3.702615 | 1.025512 | −0.817005 | −7.653863 | 14.149408 | 5.1985405 | −5.81852 |
| HC162 | 5.950173 | 1.738977 | 1.432598 | −0.231753 | −6.700146 | 14.781699 | 1.231146 | −5.9665735 |
| HC163 | 5.551408 | 4.00436 | 1.072797 | −2.746621 | −6.213082 | 8.2477055 | 2.203781 | −5.49725 |
| HC164 | 3.98399 | 4.25604 | 2.567639 | −3.606813 | −6.079645 | 12.649441 | 1.946926 | −5.171041 |
| HC165 | 5.723743 | 1.788757 | 1.157215 | −1.197022 | −7.969042 | 4.270796 | 2.620134 | −6.219366 |
| HC168 | 4.362859 | 5.625335 | 2.2963 | −1.169362 | −7.52548 | 8.041574 | 2.337152 | −5.42627 |
| HC169 | 4.614352 | 3.838008 | 1.60884 | −2.921191 | −6.51064 | 8.136143 | 2.099644 | −5.731897 |
| HC170 | 6.6275145 | 1.8626715 | 1.6955475 | 3.9034625 | 7.4271305 | 7.756398 | 2.6917235 | 5.8132855 |
| HC171 | 3.874142 | 5.349357 | 2.074272 | −1.437519 | −5.297939 | 6.325863 | 3.057537 | −3.95361 |
| HC172 | 5.651484 | 5.592005 | 1.291773 | −0.040049 | −6.989866 | 6.998259 | 3.186024 | −3.946432 |
| HC173 | 5.564261 | 4.718996 | 1.367846 | −2.3934 | −7.781913 | 9.1259525 | 1.82226 | −4.957916 |
| HC176 | 6.051409 | 2.248373 | 2.709599 | −3.2392 | −7.594156 | 7.5288985 | 1.817325 | −5.042318 |
| HC177 | 4.083836 | 0.297108 | 2.149313 | −2.166834 | −7.847734 | 5.8240705 | 1.530536 | −5.640103 |
| HC178 | 4.755443 | 4.943904 | 1.038474 | −1.620902 | −5.659262 | 5.416822 | 1.855914 | −4.954215 |
| HC179 | 5.054346 | 1.464274 | 1.372578 | −0.386778 | −6.31274 | 7.244471 | 1.887378 | −5.218281 |
| HC180 | 2.22658 | 0.161194 | 0.215954 | −0.371454 | −6.978048 | 5.185486 | 1.004282 | −6.187635 |
| HC181 | 5.031845 | 4.322323 | 2.990459 | 2.18165 | −0.651095 | 4.292234 | 4.670446 | −2.978533 |
| HC182 | 7.487442 | 2.395117 | 2.329727 | −4.420263 | −7.357922 | 7.932783 | 2.869667 | −5.574881 |
| HC183 | 3.396236 | 3.7002215 | 0.855641 | 0.078707 | −7.1437231 | 1.999761 | 0.63414 | −6.105039 |
| HC184 | 2.407985 | 2.266351 | 6.244093 | 0.670045 | −6.27671 | 6.935964 | 1.564672 | −6.568913 |
| HC185 | 4.6459 | 1.811225 | 2.225761 | −1.246884 | −7.3447631 | 0.1413645 | 1.39443 | −5.015711 |
| HC186 | 2.197157 | −2.717975 | 1.183123 | −2.657936 | −7.680597 | 8.921477 | 1.289946 | −6.631908 |
| HC187 | 4.520672 | 0.066629 | 2.0378 | 1.078709 | −8.251018 | 7.478678 | 1.655093 | −5.763416 |
| HC188 | 5.635841 | 1.839584 | 0.638515 | −1.989428 | −6.736329 | 12.8628775 | 2.27923 | −4.743699 |
| HC189 | 4.419359 | 6.509026 | −0.7698 | −2.238756 | −8.600128 | 11.305903 | −0.437812 | −7.061492 |
| HC190 | 9.264351 | 0.70722 | 4.181534 | −0.773062 | −4.881306 | | 2.422048 | −5.53509 |

TABLE D

Table of normalized qPCR data (deltaCt values) of 88 HCCs analyzed by the Taqman method

| Gene name | AFP | ALDH2 | APOC4 | APCS | AQP9 | BUB1 | C1S | CYP2E1 |
|---|---|---|---|---|---|---|---|---|
| HC 001 | 2.212911 | −6.2372335 | −0.614689 | −7.0721355 | −6.047695 | 3.841505 | −8.163492 | −10.3093235 |
| HC 003 | 3.865709 | −6.230074 | −0.95786 | −7.52919 | −6.7334475 | 0.147459 | −8.7963405 | −10.428074 |
| HC 004 | 7.6758115 | −2.186358 | 1.608247 | −5.845683 | −3.759528 | 4.221132 | −5.8997645 | −7.1147515 |
| HC 006 | 7.9469815 | −5.4231035 | −0.9614255 | −7.3704745 | −7.006052 | 0.5252045 | −8.162856 | −10.1334265 |
| HC 007 | −5.311541 | −4.0446765 | 3.550537 | −5.1967915 | −6.747103 | 0.299039 | −4.062593 | −11.024027 |
| HC 008 | −2.0890815 | −3.9297005 | 0.6776965 | −6.567126 | −3.1082155 | 1.214781 | −7.2991535 | −7.7910075 |
| HC 009 | 7.0483095 | −3.0017225 | 9.6721075 | 0.017488 | −3.7536735 | −2.980029 | −4.830331 | −0.5825245 |
| HC 010 | −2.3869635 | −0.95212 | 0 | 1.0272875 | −1.3400495 | 1.864677 | −2.639902 | −3.604805 |
| HC 011 | −0.6488335 | −5.958108 | −1.076151 | −7.7638255 | −6.122144 | 2.362454 | −8.319293 | −9.575619 |
| HC 012 | 6.538312 | −4.6271565 | 1.221393 | −6.942673 | −4.1878425 | 3.293346 | −6.850023 | −7.284587 |
| HC 014 | 2.987769 | −5.194577 | −1.3542145 | −6.5396565 | −6.8623455 | 1.363697 | −6.8939375 | −10.7465595 |
| HC 015 | −6.14089 | −4.5178635 | 5.156026 | −3.380102 | −2.373344 | −0.8830545 | −7.1343975 | −4.9390935 |
| HC 017 | −7.1950405 | −2.6522585 | 2.395651 | −4.5167035 | −2.8711295 | −1.0884485 | −6.035123 | −6.037085 |
| HC 018 | 6.856588 | −1.840894 | 3.84764 | −4.916924 | −3.6093495 | 0.063545 | −4.263272 | −5.811062 |
| HC 020 | 0.65281 | −6.287083 | −3.2094885 | −8.2117635 | −7.354605 | 1.4635025 | −8.471663 | −10.2536915 |
| HC 021 | 4.3070475 | −2.175112 | 6.2591235 | −5.9159775 | −1.1452535 | −0.0802935 | −5.7190985 | −1.2878015 |
| HC 022 | 4.418018 | −5.331214 | −0.5455545 | −6.6835035 | −5.7992305 | 2.173361 | −7.2514145 | −8.0876705 |
| HC23 | 5.538438 | −5.853486 | −0.5708905 | −6.9009145 | −6.651868 | 2.5475915 | −8.2212235 | −9.047509 |
| HC 025 | 3.90298 | −6.162477 | −1.834891 | −8.798759 | −8.758959 | 2.5679685 | −8.5606875 | −10.814935 |
| HC 026 | 5.69175 | −5.0135775 | −0.2581675 | −7.2072275 | −3.8645965 | −0.545363 | −7.2351705 | −0.671071 |
| HC 027 | 0.626755 | −5.6309605 | −1.53158 | −7.2809855 | −5.4736555 | 0.8889165 | −8.172076 | −8.6350095 |
| HC 028 | 0 | −1.913778 | 6.0251725 | −1.0475505 | −0.9613895 | 5.7426525 | −4.910584 | −3.6858305 |
| HC 030 | −6.4370325 | −3.8476295 | −0.2797975 | −7.1142435 | −5.0250435 | 0.190936 | −7.5279395 | −7.5682115 |
| HC 032 | −0.0037145 | −6.802666 | −2.574347 | −7.500133 | −7.530391 | 5.1317805 | −7.854502 | −9.4408715 |
| HC 034 | 6.6945705 | −5.11617 | −0.5860455 | −7.134934 | −6.9427375 | 1.2674215 | −7.719763 | −8.545814 |
| HC 037 | 1.3519745 | −5.808058 | 0.0768065 | −6.755895 | −6.3416265 | 2.4955985 | −6.921051 | −10.1686795 |
| HC 038 | −4.053435 | −4.596143 | 0.129322 | −5.045701 | −6.0302545 | −0.321483 | −6.101331 | −8.1123675 |
| HC 041 | 2.7156435 | −6.3503265 | −2.281983 | −5.612517 | −7.8444565 | 0.587016 | −6.88808 | −9.5090495 |
| HC 042 | 5.216493 | −4.4086495 | 0.627239 | −4.1054755 | −6.063786 | 2.224818 | −6.3060565 | −9.1411255 |
| HC 043 | 1.7983435 | −5.457548 | 0.7055185 | −7.607914 | −4.7175855 | 2.8634735 | −7.9862115 | −8.760714 |
| HC 052 | −10.3337105 | −2.1920375 | 8.124407 | −5.9818015 | 0.4848805 | 1.2986035 | −5.6337865 | −1.7693015 |
| HC 058 | −1.891958 | −2.1172735 | 11.8524 | 4.1106695 | 2.817265 | −1.9395175 | −3.691331 | 4.3317445 |
| HC 060 | −7.624821 | −3.6860195 | 0.545509 | −8.100997 | −6.8503235 | 0.576028 | −8.167253 | −9.1875325 |
| HC 064 | −5.0266755 | −4.992107 | −0.7860345 | −7.4148835 | −7.0526325 | 1.367463 | −7.1364365 | −9.682147 |
| HC 066 | −3.156328 | −3.8408415 | 0.6773785 | −8.2106815 | −6.2767975 | 1.1272665 | −8.026875 | −8.601088 |
| HC101 | 6.873135 | −4.339036 | 0.5787185 | −6.288568 | −4.6233735 | −0.081457 | −7.321092 | −5.806032 |
| HC102 | 4.119697 | −2.476355 | 5.453696 | 2.3952165 | −0.0196725 | 0.5553155 | −5.939374 | 2.8566735 |
| HC103 | −1.6193685 | −3.889904 | 0.54698 | −6.014572 | −7.151639 | 2.086009 | −5.965432 | −8.266311 |
| HC104 | −5.5094265 | −4.936239 | 0.5059805 | −5.624234 | −0.501258 | 1.311194 | −6.716137 | −9.0888685 |
| HC105 | −2.3444245 | −4.239726 | 3.577778 | −7.703333 | −4.2748785 | −0.945674 | −7.774455 | −5.698899 |
| HC106 | 3.42054 | −6.1642895 | 0.7836775 | −7.8462545 | −5.85931 | 4.8909655 | −8.060072 | −9.9949555 |
| HC107 | 4.136209 | −6.7443095 | −4.4534435 | −9.2080655 | −8.8878655 | 1.7415115 | −9.2061165 | −9.3234825 |
| HC108 | 4.500336 | −3.6076385 | 2.478085 | −7.275462 | −4.4353395 | 0.3807995 | −7.1031155 | −3.889942 |
| HC109 | 4.833024 | −5.8617665 | −0.729565 | −6.222909 | −6.4504115 | 2.2918285 | −7.406001 | −8.7101925 |
| HC110 | 3.5240185 | −3.6707715 | 0.256479 | −5.043319 | −4.5999895 | 1.449943 | −6.9163195 | −7.145766 |
| HC111 | 1.883473 | −3.8304065 | 1.130067 | −5.976754 | −4.1657805 | −0.621548 | −6.278164 | −4.46942 |
| HC112 | 2.8803905 | −4.8726745 | 0.7777655 | −6.764675 | −5.2735435 | −0.3135015 | −7.455794 | −2.5741475 |
| HC113 | −1.208649 | −4.407016 | 2.366969 | −5.197177 | −2.681192 | 3.4825665 | −6.338901 | −6.443846 |
| HC114 | 5.4433695 | −4.7113965 | 0.833543 | −6.723142 | −4.445291 | 1.7431855 | −7.866014 | −7.3429245 |
| HC119 | −1.0580855 | −6.159706 | −1.894453 | −9.375177 | −7.6226315 | 0.797564 | −9.1461175 | −7.095824 |
| HC120 | 4.0065425 | −4.257398 | 3.5241745 | −5.6838965 | −6.8239115 | 0.0740105 | −8.5708615 | −7.6044515 |
| HC121 | 4.254961 | −4.556431 | 2.167313 | −6.2688205 | −4.38702 | 2.4486685 | −8.118416 | −7.765037 |
| HC122 | 2.3763095 | −6.2844515 | −1.279577 | −6.9942545 | −6.8198535 | 6.0183915 | −7.7653135 | −9.450349 |
| HC123 | −0.821555 | −4.220769 | 0.68167 | −5.778659 | −6.410177 | 1.190323 | −5.383781 | −8.528543 |
| HC124 | −3.9525335 | −4.027289 | 0.0499065 | −5.391271 | −4.463488 | 1.592563 | −5.151686 | −9.520436 |
| HC125 | 4.806564 | −4.5451465 | −2.6326775 | −6.5321595 | −8.370224 | −1.1627945 | −8.4244055 | −9.426232 |
| HC126 | 5.899437 | −5.02839 | −0.407895 | −5.2838365 | −3.6163545 | 2.6943025 | −7.1365955 | −5.226091 |
| HC127 | 0.0390765 | −2.41699 | −0.8680995 | −4.846116 | −1.8613935 | 2.048769 | −6.3641695 | −6.1813065 |
| HC128 | −5.8636305 | −5.085525 | 0.626498 | −5.087517 | −4.3184915 | 1.3297375 | −6.828468 | −7.4344035 |
| HC129 | 3.430757 | −4.6298475 | 1.863955 | −4.8448705 | −2.870839 | 2.3688215 | −7.302922 | −2.692798 |
| HC131 | 1.491189 | −5.425994 | −2.4702 | −8.6617295 | −7.4772145 | 0.727709 | −7.525072 | −8.98645 |
| HC132 | −5.4265205 | −3.105643 | 6.9974515 | 3.2748865 | −3.9244375 | −0.2895395 | −4.390082 | −7.0455735 |
| HC133 | 5.1621395 | −4.2462915 | −0.63156 | −7.145861 | −6.05182 | 4.9277675 | −7.3188145 | −8.1908895 |
| HC134 | −2.8738695 | −4.061101 | 0.1134065 | −7.5103485 | −5.550642 | −1.7425995 | −8.4609335 | −7.859701 |
| HC135 | 0.909107 | −2.7442165 | 0.7630605 | −0.959726 | −4.0595615 | 1.2018365 | −4.667223 | −4.30592 |
| HC136 | 0.4105125 | −6.0408575 | −0.7390785 | −7.150737 | −5.996196 | 4.288554 | −8.243333 | −9.042865 |
| HC 137 | −4.378388 | −3.2913795 | 3.209294 | −4.421328 | −0.5225795 | 4.2185175 | −5.647363 | −5.532515 |
| HC 138 | 2.4762965 | −4.8248625 | 1.154563 | −4.883388 | −3.440722 | 3.408251 | −6.459976 | −7.2458685 |
| HC 139 | 2.7547595 | −2.9782295 | 3.0252085 | −5.3858735 | −5.0157665 | 0.9503045 | −6.0281485 | −1.1920485 |
| HC 140 | 6.3489955 | −4.644452 | −1.006979 | −2.1507335 | −5.3387635 | 4.075603 | −6.7373815 | 6.646618 |
| HC 141 | 2.4010865 | −4.8883915 | 0.787009 | −4.7365085 | −4.1224775 | 4.2728295 | −6.8664705 | −2.6765195 |
| HC 142 | 4.5984525 | −3.7946485 | 2.8271835 | −4.9243665 | −3.1411815 | 4.0713025 | −6.3482925 | 2.654871 |
| HC 143 | −4.0727165 | −2.59764 | 1.855993 | −4.8795135 | −2.222047 | 1.6908025 | −4.948264 | −3.1057735 |
| HC 144 | 4.7344185 | −4.3542505 | −1.002913 | −0.432856 | −5.16696 | 2.510931 | −5.3365195 | −4.456082 |
| HC 145 | 8.5175565 | −3.375805 | 0.8672075 | −5.0765195 | −4.091142 | 3.9700095 | −6.960951 | 0.8009 |
| HC 146 | 5.741507 | −3.5738745 | 1.2439275 | −5.1950135 | −3.4305425 | 2.9843625 | −5.666896 | −0.913546 |

TABLE D-continued

Table of normalized qPCR data (deltaCt values) of 88 HCCs analyzed by the Taqman method

| | | | | | | | | |
|---|---|---|---|---|---|---|---|---|
| HC 147 | 6.0474775 | −3.0470955 | 0.2246755 | −5.6213855 | −5.257189 | 2.7534355 | −5.349428 | −6.933909 |
| HC 148 | −1.306432 | −4.0108565 | 0.267747 | −6.3544915 | −3.1846315 | 1.1995135 | −6.2066555 | −4.1428355 |
| HC 149 | −3.9190605 | −3.3456535 | 2.735403 | −1.9099995 | −1.1810265 | 2.704253 | −5.707004 | −5.9300895 |
| HC 150 | 6.1556695 | −2.9923905 | −1.9485835 | −5.821769 | −6.3127705 | 2.452404 | −4.984573 | −7.3184395 |
| HC 151 | 5.5488065 | −4.234966 | 1.372415 | −5.8812085 | −4.0297925 | 3.4239945 | −7.2861515 | −2.304461 |
| HC 152 | 4.917902 | −3.97386 | −4.005999 | −6.5072455 | −7.124415 | 2.5576145 | −5.752235 | −9.98327 |
| HC 153 | 5.6708455 | −5.004032 | −3.204075 | −3.8195495 | −6.2020215 | 1.9670395 | −5.979251 | −7.7421455 |
| HC 154 | 6.699114 | −2.0392575 | 9.6136985 | 0.885791 | −0.68511 | 1.755108 | −0.7395055 | 2.544628 |
| HC 155 | 6.238831 | −3.802053 | 2.0022335 | −6.3105565 | −2.974712 | 4.2276825 | −7.058571 | −4.1514335 |
| HC 156 | −1.582839 | −3.5688085 | 0.917505 | −3.9333845 | −4.163765 | 1.0763025 | −4.6064345 | −8.4802835 |
| HC 157 | 3.657864 | −4.2315665 | 2.513598 | −7.2096625 | −4.573216 | −0.284071 | −5.856564 | −7.9837885 |
| HC 159 | 3.4650565 | −2.6801805 | 2.2596385 | −4.0834345 | −4.42904 | 3.44645 | −5.923485 | −7.778452 |

| Gene name | DLG7 | DUSP9 | E2F5 | GHR | HPD | IGSF1 | NLE1 | RPL10A |
|---|---|---|---|---|---|---|---|---|
| HC 001 | 5.30317 | 11.616567 | −0.05328 | −2.655512 | −9.449416 | 6.46034 | 1.159417 | −6.6225235 |
| HC 003 | 2.057513 | 8.8462855 | 1.909804 | −2.069524 | −8.549803 | 7.249974 | 1.5801355 | −6.0562915 |
| HC 004 | 4.4226465 | 9.4268185 | 1.7432195 | 2.0012965 | −9.415253 | 0 | 3.1459935 | −4.4121905 |
| HC 006 | 1.6282005 | 10.22051 | −0.024339 | −1.887805 | −8.5958965 | 7.1580385 | −0.6940375 | −6.8637555 |
| HC 007 | 1.169221 | 6.6521625 | 0.2833465 | 1.7428205 | −6.183977 | 3.192514 | 0.3919565 | −7.1381125 |
| HC 008 | 2.80866 | 9.6946695 | 0.0193165 | −2.342442 | −5.329776 | 2.806768 | 1.579419 | −6.2574845 |
| HC 009 | −1.3733475 | 9.5262655 | −0.711082 | 2.3242195 | 0.011478 | 4.026769 | 0.80375 | −6.3016635 |
| HC 010 | 0 | 0 | 1.344368 | 0.4900285 | −2.932809 | 0 | 0 | −9.1966395 |
| HC 011 | 2.8432205 | 0 | 0.736822 | −4.757848 | −9.029214 | 7.6390015 | 1.9328755 | −7.379063 |
| HC 012 | 4.7199665 | 0 | 2.4002515 | −2.2402875 | −9.656029 | 7.466951 | 1.64183 | −5.178571 |
| HC 014 | 3.3543285 | 7.7629895 | 1.5332515 | −1.09511 | −9.5837645 | 8.5836025 | 1.47219 | −5.831244 |
| HC 015 | 0.1414205 | 4.4342765 | −1.399564 | −0.2426 | −4.473206 | −0.0722075 | 0.321593 | −6.8777395 |
| HC 017 | −0.666284 | 3.163581 | −1.206766 | 2.353691 | −0.6808655 | 6.0490105 | 0.386649 | −7.068098 |
| HC 018 | 1.512286 | 8.7756845 | 2.426129 | 2.9035 | −5.7101575 | 2.4248235 | 1.3815525 | −5.9464565 |
| HC 020 | 2.1165725 | 9.6208445 | 1.1944835 | −4.5756335 | −10.6864405 | 0 | 1.118745 | −7.542193 |
| HC 021 | 0.322455 | 7.8162765 | 0.0686475 | −0.71981 | −4.0108195 | 2.954814 | 1.618369 | −6.309556 |
| HC 022 | 3.3904095 | 10.827291 | 0.7133385 | −2.416651 | −9.8859985 | 5.6986975 | 1.9449755 | −7.194012 |
| HC23 | 3.848364 | 0 | 1.4330655 | −3.7226655 | −9.583194 | 7.200325 | 1.823275 | −5.9526365 |
| HC 025 | 3.34202 | 7.1111525 | −0.049846 | −1.9012935 | −9.1845675 | 0 | 1.770127 | −7.4507165 |
| HC 026 | 0.9710395 | 8.5287915 | 1.1845665 | −1.964045 | −7.6403735 | 5.4960635 | 1.851733 | −5.9670715 |
| HC 027 | 2.3158215 | 10.241011 | 0.4045835 | −2.623084 | −9.597772 | 5.588995 | 1.851285 | −7.6623025 |
| HC 028 | 0 | 0 | 4.334386 | 1.9788575 | −3.3142495 | 0 | 2.4559905 | −5.521873 |
| HC 030 | 0.189092 | 9.0027 | −1.0623035 | −2.635437 | −7.537 | 2.651022 | 1.2674865 | −7.5046195 |
| HC 032 | 5.7080765 | 9.73163 | 0.054818 | −2.0027475 | −9.0015185 | 0 | 1.208576 | −8.8437815 |
| HC 034 | 2.339621 | 9.9728495 | 1.4281575 | −1.563203 | −8.3685675 | 10.112616 | 1.934745 | −6.594006 |
| HC 037 | 2.6534895 | 0 | 1.2212655 | −2.9415775 | −10.367265 | 7.5570255 | 1.9881245 | −6.901637 |
| HC 038 | 1.4386515 | 5.2298755 | 0.037887 | −0.2025015 | −7.547286 | 0.680358 | 2.1250395 | −5.1574215 |
| HC 041 | 1.840185 | 8.727439 | −0.466649 | −1.428749 | −8.0015745 | 7.243446 | 0.15624 | −7.7043325 |
| HC 042 | 2.3531575 | 0 | 0.3673235 | 1.2545195 | −8.2669835 | 2.899766 | 0.9401045 | −5.577659 |
| HC 043 | 4.2390495 | 10.525647 | 0.894345 | −3.2916395 | −8.997825 | 5.5544715 | 1.8422595 | −5.480403 |
| HC 052 | 2.599359 | 3.8059605 | −0.4419525 | 1.843696 | −2.481945 | −2.254168 | 1.9474305 | −5.6154705 |
| HC 058 | −0.1957495 | 3.656912 | −0.804087 | 3.7242975 | −1.8257985 | −1.3471695 | 1.209522 | −6.0601515 |
| HC 060 | 2.2644225 | 6.618755 | 0.432422 | 1.4079225 | −8.4643875 | 0.7884805 | 1.9133155 | −5.7041285 |
| HC 064 | 2.386875 | 7.3184655 | 0.2876185 | −0.349645 | −8.6027575 | 3.3382005 | 1.817699 | −6.4617635 |
| HC 066 | 2.7680135 | 11.5673955 | 0.968982 | 1.2501855 | −8.5231325 | 9.185554 | 1.962008 | −5.415169 |
| HC101 | 1.3084655 | 8.828389 | 1.871516 | −0.1466275 | −5.7252795 | 4.1394545 | 1.4546305 | −6.144011 |
| HC102 | 2.1385165 | 8.6628475 | −0.830934 | −0.947389 | −0.568509 | 2.708733 | 1.1534675 | −5.283399 |
| HC103 | 2.957914 | 12.521336 | 1.8003215 | −0.636723 | −6.717282 | 9.802921 | 2.594702 | −4.423835 |
| HC104 | 1.821739 | 5.396553 | 2.305498 | −1.6860905 | −8.46781 | −0.1438735 | 1.610158 | −6.21159 |
| HC105 | 0.814912 | 5.4214725 | −2.0730715 | −0.682142 | −2.288109 | 1.422332 | 0.471391 | −6.315756 |
| HC106 | 6.2678815 | 11.174152 | 2.208171 | −5.342392 | −9.4440415 | 7.401009 | 1.968983 | −5.769397 |
| HC107 | 1.357756 | 6.6136855 | −2.78876 | −2.935929 | −10.460972 | 0 | 0.000835 | −8.6686655 |
| HC108 | 2.2445545 | 8.0946735 | −0.0923905 | −1.6363755 | −2.9674235 | 7.967992 | 0.932052 | −5.818028 |
| HC109 | 3.222524 | 10.4709205 | 1.9924345 | −2.9233285 | −7.8859205 | 10.0122565 | 2.6102395 | −5.541229 |
| HC110 | 2.333076 | 11.616244 | 2.512512 | −1.0803015 | −8.1908235 | 8.1469415 | 2.3529485 | −5.245476 |
| HC111 | 0.769283 | 9.137462 | −1.045678 | −1.1576425 | −7.245347 | 1.86965 | 1.012752 | −5.568205 |
| HC112 | 0.9196845 | 10.105965 | −0.0373705 | −2.5391085 | −7.714358 | 3.4428695 | 1.119237 | −6.1905075 |
| HC113 | 4.5602875 | 7.8299455 | 2.82243 | −2.16232 | −6.685692 | 2.045068 | 2.156348 | −5.8884625 |
| HC114 | 3.1500875 | 11.804112 | 0.0450475 | −2.5053965 | −6.835254 | 5.1813245 | 1.3170345 | −5.795905 |
| HC119 | 1.712686 | 9.106547 | 0.0248045 | −3.7649595 | −9.220498 | 5.39017 | 0.400823 | −7.954231 |
| HC120 | 1.9563135 | 5.8119685 | −1.229768 | −3.196589 | −8.5127155 | 9.404196 | 1.1096815 | −6.4517175 |
| HC121 | 2.852561 | 9.706684 | 0.910943 | −2.2774645 | −7.480725 | 5.980435 | 1.758163 | −6.4042545 |
| HC122 | 7.228946 | 9.9054825 | 3.5033365 | −2.400201 | −8.7301975 | 8.6480295 | 2.2430545 | −5.199782 |
| HC123 | 2.929576 | 11.584458 | 0.646839 | 1.810364 | −4.7774665 | 5.1400615 | 1.5951645 | −4.7323885 |
| HC124 | 2.03781 | 8.81055 | −0.574165 | −2.2369305 | −7.832169 | 1.4450915 | 0.1499775 | −6.691521 |
| HC125 | −0.3286545 | 9.3740615 | 0.028878 | −0.697866 | −5.7813 | 10.2234745 | 0.405397 | −7.1196575 |
| HC126 | 3.944339 | 8.7174575 | 3.271927 | −1.824385 | −1.865621 | 7.659377 | 2.033278 | −5.389272 |
| HC127 | 2.96212 | 8.672372 | 2.162602 | −0.129431 | −3.4481465 | 3.1503205 | 2.205965 | −4.3385115 |
| HC128 | 2.6299155 | 8.499355 | 4.393094 | −1.9716885 | −5.7052855 | 2.72995 | 1.949352 | −6.6181545 |
| HC129 | 3.6405185 | 7.0627455 | 0.470421 | −2.332961 | −5.502918 | 5.692623 | 1.683808 | −4.8697295 |
| HC131 | 1.461713 | 8.415907 | −0.154573 | −4.009655 | −8.960383 | 7.5832005 | 1.5313675 | −6.775249 |
| HC132 | 1.5572645 | 3.3843145 | −1.9018925 | −1.7710325 | −2.3653865 | 1.947055 | −0.2035885 | −6.7796075 |
| HC133 | 5.5447335 | 8.022457 | 2.6341825 | −2.2298335 | −6.1281315 | 0 | 1.4173895 | −5.762015 |

TABLE D-continued

Table of normalized qPCR data (deltaCt values) of 88 HCCs analyzed by the Taqman method

| | | | | | | | | |
|---|---|---|---|---|---|---|---|---|
| HC134 | −0.8148735 | 4.96739 | −3.1030595 | −1.3138565 | −7.231144 | 0.3848995 | −0.794433 | −7.7140665 |
| HC135 | 2.250305 | 5.794605 | −0.986165 | 0.6955465 | −6.7262275 | 4.394354 | 0.9780515 | −6.689595 |
| HC136 | 5.5267715 | 10.9307725 | 2.4040865 | −4.013948 | −8.223611 | 7.4962365 | 2.426321 | −5.5069335 |
| HC 137 | 5.2105355 | 4.767228 | 5.62451 | −1.6355645 | −5.8875425 | 1.0556075 | 3.7311615 | −5.2271275 |
| HC 138 | 5.028429 | 5.576937 | 4.1601375 | −1.738341 | −6.019837 | 7.169314 | 4.19882 | −4.2322595 |
| HC 139 | 2.940447 | 4.3133685 | 0.685194 | 1.632571 | −4.6240035 | 3.333358 | 1.7913325 | −6.6866335 |
| HC 140 | 5.1767035 | 10.874029 | 2.488357 | −3.1717235 | −7.5439415 | 9.276635 | 5.0732625 | −4.266519 |
| HC 141 | 6.1148255 | 7.979559 | 2.66802 | −1.687093 | −7.2596615 | #DIV/0! | 3.5973445 | −4.952551 |
| HC 142 | 5.8031125 | 8.2104255 | 2.0983905 | −1.5934495 | −5.8074755 | 9.442329 | 3.4164995 | −4.6520795 |
| HC 143 | 3.470906 | 3.981805 | 1.474377 | 0.695168 | −2.049901 | 3.754627 | 3.058019 | −4.7443975 |
| HC 144 | 3.844786 | 10.7187705 | 3.540563 | −1.6857605 | −6.869217 | 11.9441575 | 4.417722 | −4.817306 |
| HC 145 | 5.482263 | 9.313039 | 2.112409 | −1.525041 | −6.669204 | 10.0458615 | 3.0082705 | −5.7677005 |
| HC 146 | 5.1824885 | 7.611916 | 2.8802325 | −1.791636 | −6.9831945 | 5.450716 | 3.884913 | −4.427413 |
| HC 147 | 4.5366875 | 9.358894 | 3.2373475 | −2.0156545 | −6.053345 | 8.7065355 | 3.732017 | −4.317148 |
| HC 148 | 2.490156 | 5.4985645 | 8.523611 | −0.773246 | −3.7206575 | 5.663583 | 3.295068 | −6.0532135 |
| HC 149 | 3.4454215 | 6.8563245 | 2.4724295 | −0.9357605 | −7.337568 | −0.063395 | 4.267075 | −5.7767065 |
| HC 150 | 3.585447 | 7.980274 | 3.118546 | 0.5916635 | −5.762837 | 9.1651835 | 2.811495 | −5.7495535 |
| HC 151 | 4.613043 | 8.9062765 | 2.2090065 | −2.8000785 | −7.251033 | 9.44137 | 3.5959505 | −4.6972005 |
| HC 152 | 4.17552 | 10.736246 | 4.56538 | −1.578246 | −8.106859 | 12.118351 | 2.6658355 | −6.944767 |
| HC 153 | 3.133394 | 7.298329 | 3.85894 | −0.616143 | −7.947464 | 11.674272 | 2.670245 | −5.0796695 |
| HC 154 | 3.2541115 | 3.139705 | −0.3936805 | −1.070278 | −4.611328 | 1.5925535 | 2.2396475 | −6.2090535 |
| HC 155 | 5.7341595 | 6.4585135 | 2.4375015 | −0.254649 | −7.297162 | 10.0981895 | 3.3878795 | −5.37231 |
| HC 156 | 2.1302465 | 4.4056075 | 1.070339 | 0.42868 | −6.890963 | 2.0124875 | 2.225275 | −7.037827 |
| HC 157 | 1.3778545 | 2.0950385 | −0.56173 | −0.8411435 | −8.474893 | 7.2842685 | 1.6720135 | −6.6310375 |
| HC 159 | 5.727853 | 8.8523415 | 2.7886015 | −1.0442865 | −7.268645 | 8.8204775 | 2.861685 | −5.4777465 |

TABLE G

| HC 000 tumor identification | Date of surgery or transplantation | (PH) or (OLT) | Date of last visit | Date of death | follow-up (years) | re-currence | Date of 1st recurrence or metastasis | secondary OLT after hepatectomy | date of secondary OLT | tumor grade Edmondson | Tumor differentiation (OMS) | tumor size (mm) | vascular invasion macro | vascular invasion micro |
|---|---|---|---|---|---|---|---|---|---|---|---|---|---|---|
| HC 001 | 12 Dec. 1996 | PH | | 07 Jan. 1997 | 0.07 | N | | | | 3 | moderately differentiated | 120 | N | N |
| HC 003 | 21 Feb. 1997 | PH | 20 Aug. 2008 | 20 Jun. 2000 | 3.33 | Y | 4 Nov. 1998 | N | | 2 | well differentiated | 60 | N | N |
| HC 004 | 28 Feb. 1997 | PH | | 06 Jan. 1998 | 11.48 | N | | | | 2 | well differentiated | 100 | N | N |
| HC 006 | 07 Oct. 1996 | PH | | 31 Dec. 1997 | 1.25 | Y | 28 Nov. 1997 | N | | 2 | well differentiated | 90 | Y | Y |
| HC 007 | 02 Jul. 1996 | PH | | 24 Jan. 2005 | 1.50 | Y | 4 Nov. 1997 | N | | 2-3 | Well differentiated | 100 | N | Y |
| HC 008 | 05 Aug. 1996 | PH | | | 8.48 | N | | | | 3 | moderately differentiated | 30 | N | N |
| HC 009 | 28 Aug. 1996 | PH | | 05 Sep. 1996 | 0.02 | N | | | | 3-4 | Moderately poorly | 100 | Y | Y |
| HC 010 | 10 Oct. 1996 | PH | | 20 Sep. 1997 | 0.95 | N | | | | 4 | moderately-poorly | 75 | N | N |
| HC 011 | 10 Oct. 1996 | OLT | 14 Dec. 2008 | | 12.20 | N | | | | 2 | well differentiated | 15 | N | N |
| HC 012 | 24 Oct. 1995 | OLT | | 14 Nov. 1995 | 0.05 | N | | | | 2 | well differentiated | 60 | N | N |
| HC 014 | 10 Jun. 1995 | OLT | | 27 Jul. 1995 | 1.00 | N | | | | 3-4 | Moderate poor | 80 | Y | Y |
| HC 015 | 21 Jul. 1995 | PH | | 10 Oct. 1996 | 1.22 | Y | 10 Oct. 1996 | | | 3 | moderately differentiated | 60 | Y | Y |
| HC 017 | 05 May 1997 | PH | 16 Apr. 2008 | | 10.96 | N | | | | 2 | well differentiated | 100 | N | N |
| HC 018 | 07 May 1997 | PH | | 28 Sep. 1997 | 0.39 | NA | | | | 3 | moderately differentiated | 140 | Y | Y |
| HC 020 | 13 May 1993 | OLT | 20 Oct. 2008 | | 15.40 | N | | | | 2 | well differentiated | 40 | NA | NA |
| HC 021 | 15 Jan. 1992 | PH | | 28 Sep. 1992 | 0.70 | Y | 15 Jun. 1992 | N | | NA | NA | 100 | NA | NA |
| HC 022 | 15 Mar. 1997 | OLT | 02 Sep. 2008 | | 11.50 | N | | | | 2 | well differentiated | 45 | N | N |
| HC 023 | 20 Jul. 1995 | PH | 20 Jun. 2007 | | 11.93 | N | | | | 2 | well differentiated | 50 | N | N |
| HC 025 | 05 Oct. 1992 | PH | | 13 Aug. 2008 | 15.87 | NA | | | | 2 | well differentiated | 140 | Y | Y |
| HC 026 | 04 Jun. 1993 | OLT | | 18 Apr. 1994 | 0.83 | NA | | | | 2 | well differentiated | 30 | Y | Y |
| HC 027 | 20 Jan. 1993 | OLT | | 15 Feb. 1993 | 0.10 | N | | | | 2 | well differentiated | 15 | N | N |
| HC 028 | 16 Feb. 1996 | OLT | | 13 Mar. 1996 | 0.10 | N | | | | 3 | moderately differentiated | 120 | Y | Y |
| HC 030 | 10 Apr. 1996 | PH | | 07 Sep. 2008 | 12.40 | Y | 15 Oct. 1996 | Y | 17 Dec. 1997 | 3 | moderately differentiated | 16 | NA | NA |
| HC 032 | 17 Feb. 1993 | PH | | 17 Oct. 1993 | 0.66 | N | | | | 2 | well differentiated | 60 | N | N |
| HC 034 | 10 Mar. 1993 | PH | 05 Nov. 2008 | | 15.70 | Y | 15 Nov. 1995 | Y | 20 Jun. 1996 | 2 | well differentiated | 140 | N | N |
| HC 037 | 08 Jun. 1997 | OLT | | 13 Aug. 1997 | 0.20 | N | | | | 3 | moderately differentiated | 35 | Y | Y |
| HC 038 | 16 Jul. 1997 | PH | | 28 Aug. 1998 | 1.12 | Y | 1 Jan. 1998 | N | | 2 | moderately differentiated | 50 | N | N |
| HC 041 | 24 Nov. 1997 | PH | | 01 May 2005 | 7.44 | Y | 29 Jun. 1999 | Y | 9 Mar. 2000 2nd recurrence 15 Jan. 2005 | 2 | well differentiated | 30 | N | N |
| HC 042 | 05 Nov. 1997 | PH | 03 Jun. 2008 | | 10.58 | N | | | | 3 | moderately differentiated | 130 | probable | Y |
| HC 043 | 19 Nov. 1997 | OLT | 22 Oct. 2008 | | 10.90 | N | | | | 3 | moderately differentiated | 15 | N | N |
| HC 052 | 17 Feb. 1999 | PH | 18 May 1999 | PDV | 0.25 | N | | | | 3 | moderately differentiated | 110 | N | Y |
| HC 058 | 14 Oct. 1999 | PH | 30 Jan. 2008 | | 8.30 | N | | | | 2 | moderately differentiated | 100 | N | N |

TABLE G-continued

| | | | | | | | | | | | |
|---|---|---|---|---|---|---|---|---|---|---|---|
| HC 060 | 15 May 1925 | PH | | | 5.25 | NA | | | NA | well differentiated | 55 | N | N |
| HC 064 | 10 Apr. 2000 | PH | | 09 Jul. 2005 | | Y | 15 Oct. 2001 | N | 3 | moderately differentiated | 40 | N | N |
| HC 066 | 15 Sep. 1999 | PH | 18 Aug. 2008 | | 8.93 | N | | | 2-3 | well moderately | 75 | N | N |
| HC 101 | 03 May 2006 | OLT | 27 Oct. 2008 | | 2.50 | N | | | 2-3 | well moderately | 35 | Y | Y |
| HC 102 | 12 Jul. 2006 | PH | 18 Aug. 2006 | | 0.10 | N | | | 4 | Peu differencie | 200 | Y | Y |
| HC 103 | 16 Aug. 2006 | PH | 11 Jun. 2008 | | 1.82 | Y | 15 Jan. 2007 | N | 2-3 | well moderately | 55 | N | Y |
| HC 104 | 20 Sep. 2006 | PH | 05 Nov. 2008 | | 2.10 | N | | | 2-3 | well moderately | 160 | probable | Y |
| HC 105 | 11 Dec. 2006 | PH | 04 Jul. 2007 | | 0.56 | Y | 15 Apr. 2007 | N | 3 | moderately differentiated | 40 | Y | Y |
| HC 106 | 22 Jan. 2007 | OLT | 16 Jan. 2009 | | 2.00 | Y | | | 3 | moderately differentiated | 80 | Y | Y |
| HC 107 | 25 Jan. 2007 | PH | 23 Oct. 2008 | | 1.75 | N | | | 2 | well differentiated | 60 | Y | N |
| HC 108 | 12 Feb. 2007 | PH | 24 Sep. 2008 | | 1.62 | N | | | 3 | moderately differentiated | 26 | N | Y |
| HC 109 | 19 Feb. 2007 | OLT | 26 May 2008 | | 1.30 | N | | | 2-3 | well differentiated | 30 | N | N |
| HC 110 | 26 Feb. 2007 | PH | 04 Feb. 2009 | | 1.95 | N | | | 2-3 | well moderately | 30 | N | Y |
| HC 111 | 07 Mar. 2007 | OLT | 08 Sep. 2008 | 03 Oct. 2007 | 0.70 | N | | | 2-3 | well moderately | 40 | Y | Y |
| HC 112 | 19 Mar. 2007 | PH | | | 1.48 | N | | | 2-3 | well moderately | 18 | N | N |
| HC 113 | 23 Mar. 2007 | OLT | 15 Mar. 2008 | | 1.00 | N | | | 2-3 | well moderately | 50 | Y | Y |
| HC 114 | 03 Apr. 2007 | PH | 11 Sep. 2007 | | 0.44 | N | | | 2 | well differentiated | 36 | N | N |
| HC 115 | 01 Aug. 2007 | PH | 29 Apr. 2008 | | 0.75 | N | | | 1 | well differentiated | 90 | N | N |
| HC 116 | 09 Aug. 2007 | PH | 18 Apr. 2007 | | 0.69 | N | | | 3 | moderately differentiated | 140 | N | N |
| HC 117 | 25 Oct. 2007 | OLT | 23 Dec. 2008 | | 1.20 | N | | | 2-3 | well moderately | 28 | N | N |
| HC 118 | 25 Oct. 2007 | PH | 28 Sep. 2008 | | 0.93 | N | | | 1 | well differentiated | 40 | N | N |
| HC 119 | 03 Dec. 2007 | PH | 08 Jan. 2009 | | 1.20 | N | | | 2-3 | well moderately | 26 | N | Y |
| HC 120 | 18 Dec. 2007 | PH | 14 Oct. 2008 | | 0.82 | Y | 12 May 2008 | Y | 2-3 | well moderately | 20 | Y | Y |
| HC 121 | 02 Jan. 2008 | PH | 08 Aug. 2008 | | 0.60 | N | | | 3 | moderately differentiated | 150 | probeble | probable |
| HC 122 | 16 Jan. 2008 | PH | 17 Oct. 2008 | | 0.75 | Y | 10 Oct. 2008 | N | 2 | moderately differentiated | 20 | Y | Y |
| HC 123 | 11 Feb. 2008 | OLT | 01 Dec. 2008 | | 0.80 | N | | | 3 | moderately differentiated | 43 | probable | probable |
| HC 124 | 20 Feb. 2008 | PH | 26 Aug. 2008 | | 0.52 | N | | | 3 | moderately differentiated | 62 | N | N |
| HC 125 | 22 Feb. 2008 | PH | 08 Jan. 2009 | | 0.90 | N | | | 3 | moderately differentiated | 33 | N | Y |
| HC 126 | 12 Mar. 2008 | PH | 14 Aug. 2008 | | 0.42 | Y | 6 Aug. 2008 | N | 1-2 | well differentiated | 130 | Y | Y |
| HC 127 | 19 Mar. 2008 | PH | 20 Jun. 2008 | | 0.25 | Y | 4 Jun. 2008 | N | 2-3 | well moderately | 115 | Y | Y |
| HC 128 | 20 Mar. 2008 | PH | 29 Aug. 2008 | | 0.44 | N | | | 2 | well moderately | 110 | N | Y |
| HC 129 | 01 Apr. 2008 | OLT | | 31 May 2008 | 0.15 | N | | | 3 | moderately differentiated | 30 | N | Y |
| HC 130 | 07 Apr. 2008 | PH | 27 May 2008 | | 0.14 | N | | | 3 | moderately differentiated | 38 | N | probable |
| HC 131 | 10 Apr. 2008 | PH | 15 Jul. 2008 | | 0.26 | N | 03 Oct. 2003 | | 2-3 | well differentiated | 120 | N | Y |
| HC 137 | 19 Jul. 2002 | PH | 31 Mar. 2008 | — | 5.67 | N | — | | NA | moderately differentiated | 10 | NA | NA |
| HC 138 | 25 Apr. 2003 | PH | 03 Dec. 2008 | — | 5.58 | Y | 30 Jun. 2005 | | NA | well differentiated | 5.5 | NA | NA |
| HC 139 | 15 May 2002 | PH | 09 May 2008 | — | 6.00 | N | December 2005 | | NA | moderately differentiated | 16 | NA | NA |
| HC 140 | 03 Jun. 2004 | PH | 05 Aug. 2008 | | 4.17 | Y | 30 Jun. 2005 | | NA | well differentiated | 15 | NA | NA |
| HC 141 | 06 Feb. 2004 | PH | 12 Mar. 2009 | | 5.08 | Y | December 2005 | | NA | well differentiated | 3.5 | NA | NA |
| HC 142 | 14 May 2002 | PH | 21 Jun. 2006 | 21 Jun. 2006 | 4.08 | Y | 24 Mar. 2006 | | NA | well differentiated | 8 | NA | NA |

TABLE G-continued

| | | | | | | | | | | | | |
|---|---|---|---|---|---|---|---|---|---|---|---|---|
| HC 143 | 04 Mar. 2004 | PH | 26 Jan. 2007 | — | 2.83 | Y | 2005 | | NA | well differentiated | 3 | NA | NA |
| HC 144 | 27 Jun. 2002 | PH | 17 Jun. 2008 | — | 6.00 | Y | 16 Mar. 2004 | | NA | well differentiated | 15 | NA | NA |
| HC 145 | 14 Nov. 2002 | PH | 30 Jul. 2008 | — | 5.58 | Y | 09 Jun. 2005 | | NA | well differentiated | 6 | NA | NA |
| HC 146 | 30 Jul. 2004 | PH | 11Dec. 2008 | — | 4.33 | Y | juin-05 | | NA | well differentiated | 7.5 | NA | NA |
| HC 147 | 23 Nov. 2004 | PH | 22 Sep. 2008 | — | 3.83 | Y | 12 Jun. 2008 | | NA | moderately differentiated | 15 | NA | NA |
| HC 148 | 12 Sep. 2003 | PH | 15 Oct. 2006 | — | 3.08 | N | | | NA | moderately differentiated | 21 | NA | NA |
| HC 149 | 26 Aug. 2003 | PH | 16 Jan. 2007 | 16 Jan. 2007 | 3.42 | N | | | NA | NA | 8 | NA | NA |
| HC 150 | 31 Jan. 2003 | PH | 23 Jun. 2008 | — | 5.42 | N | | | NA | moderately differentiated | 13 | NA | NA |
| HC 151 | 10Dec. 2004 | PH | 15 Mar. 2007 | — | 2.25 | N | mars-09 | | NA | well differentiated | 6.5 | NA | NA |
| HC 152 | 14 May 2003 | PH | 17 Jan. 2007 | 17 Jan. 2007 | 3.67 | Y | 06 May 2005 | | NA | well differentiated | 3.5 | NA | NA |
| HC 153 | 25 Feb. 2003 | PH | 24 Dec. 2007 | 24 Dec. 2007 | 4.83 | Y | 01 Jan. 2005 | | NA | well differentiated | 5 | NA | NA |
| HC 154 | 06 Sep. 2004 | PH | | 23 Nov. 2006 | 2.21 | Y | 18 Oct. 2004 | | 2-3 | well differentiated | 45 | Y | Y |
| HC 155 | 18 Oct. 2004 | PH | 09 Dec. 2008 | | 4.10 | Y | 15 Jun. 2006 | 31 May 2005 | 2 | well differentiated | 24 | N | N |
| HC 156 | 03 Feb. 2005 | PH | | 28 May 2007 | 2.31 | Y | | | 3 | moderately differentiated | 70 | N | Y |
| HC 157 | 24 Mar. 2003 | PH | | 26 Oct. 2006 | 3.59 | Y | 15 Aug. 2004 | | 2 | well differentiated | 140 | Y | Y |
| HC 159 | 16 Oct. 2003 | PH | | 18 Mar. 2005 | 2.42 | Y | 03 May 2004 | | 2 | well differentiated | 35 | N | N |
| HC 161 | 20 Aug. 2003 | PH | 06 Feb. 2008 | | 4.47 | Y | | | 2 | well differentiated | 210 | N | Y |
| HC 162 | 30 Oct. 2003 | PH | 25 Apr. 2007 | | 3.49 | N | | | 3 | moderately differentiated | 130 | Y | Y |
| HC 163 | 20 Sep. 2004 | PH | | 07 Dec. 2006 | 2.21 | Y | 01 Sep. 2006 | | 3 | moderately differentiated | 80 | N | Y |
| HC 164 | 05 Sep. 2002 | PH | 21 Mar. 2007 | | 4.54 | N | | | 1 | well differentiated | 90 | N | N |
| HC 165 | 08 Aug. 2003 | PH | 29 May 2008 | | 4.72 | Y | | | 2 | well differentiated | 30 | N | Y |
| HC 168 | 10 Feb. 2003 | PH | 04 Feb. 2009 | | 6.00 | Y | 15 Jul. 2004 | 18 Feb. 2008 | 2 | well differentiated | 25 | N | N |
| HC 169 | 10 Jun. 2002 | PH | 22 Mar. 2005 | 22 Mar. 2005 | 2.78 | N | 15 Mar. 2003 | | 2 | well differentiated | 35 | N | N |
| HC 170 | 14 Mar. 2002 | PH | 28 Jun. 2007 | | 5.29 | N | | | 2 | well differentiated | 220 | Y | N |
| HC 171 | 25 Mar. 2004 | PH | 17 Oct. 2008 | | 4.57 | N | 15 Nov. 2004 | | 4 | Peu differencie | 70 | Y | Y |
| HC 172 | 10 Jan. 2005 | PH | 25 Nov. 2008 | | 3.90 | Y | 25 Nov. 2005 | | 3 | moderately differentiated | 40 | N | Y |
| HC 173 | 18 Dec. 2003 | PH | 03 Mar. 2008 | | 4.21 | N | | | 1 | well differentiated | 40 | N | N |
| HC 176 | 13 Mar. 2002 | PH | 05 Oct. 2006 | | 4.57 | N | | | 2 | well differentiated | 75 | N | N |
| HC 177 | 29 Oct. 2003 | PH | mars-09 | | 5.42 | Y | January 2009 | | 2 | moderately differentiated | 2.3 | NA | N |
| HC 178 | 19 Mar. 2003 | PH | 19 Sep. 2005 | | 2.50 | N | October 2002 | | 2 | well differentiated | 6.5 | NA | N |
| HC 179 | 27 Oct. 2000 | PH | 06 Dec. 2005 | | 5.17 | N | May 2005 | | 2-3 | well-moderate-poor | 9 | NA | Y |
| HC 180 | 9 Apr. 2002 | PH | 03 Nov. 2005 | 03 Nov. 2005 | 3.58 | Y | | | 3 | moderately differentiated | 15 | NA | Y |
| HC 181 | 27 May 2002 | PH | mars-09 | | 6.83 | Y | April 2008 | | 2 | well moderately | 3.5 | NA | Y |
| HC 182 | 30 Mar. 2004 | PH | October 2007 | | 3.50 | Y | | | 1 | well differentiated | 11 | NA | N |
| HC 183 | 21 Jul. 2003 | PH | 02 Sep. 2007 | 02 Sep. 2007 | 4.08 | Y | July 2007 | | 3 | well differentiated | 8 | NA | N |
| HC 184 | 18 Jan. 2002 | PH | 08 Feb. 2004 | 08 Feb. 2004 | 2.08 | Y | April 2002 | | 2 | well differentiated | 6.5 | NA | N |
| HC 185 | 19 Nov. 2002 | PH | 03 Mar. 2005 | | 2.25 | N | | | 3 | moderately differentiated | 3.5 | NA | N |
| HC 186 | 31 Aug. 2004 | PH | 06 Nov. 2006 | 06 Nov. 2006 | 2.17 | N | March 2003 | | 3 | well moderately | 17 | NA | Y |
| HC 187 | 7 Jun. 2001 | PH | fevr-09 | | 7.67 | Y | | | 1 | well differentiated | 8 | NA | Y |

TABLE G-continued

| HC 000 tumor identification | number max of mitosis per 10 fields x40 | multiple Ndules | MacroNdules of regeneration | Nrrmal liver A0F0 or A0F1 | Cirrhosis AXF4 | Score METAVIR Activity | Score METAVIR Fibrosis | chronic viral hepatitis | Etiology HBV | Etiology HCV | alcool | Hemochromatos | -NASH |
|---|---|---|---|---|---|---|---|---|---|---|---|---|---|
| HC 188 | | | 29 Jul. 2004 | PH | | | | | | well differentiated | | 2 | Y | NA | N |
| HC 189 | | | 30 Apr. 2002 | PH | avr-09 | | | | | well differentiated | | 2 | Y | NA | Y |
| HC 190 | | | 29 Jul. 2003 | | 13 Aug. 2005 mars-09 | 13 Aug. 2005 | | | | moderately differentiated | | 3 | N | NA | N |
| | | | | | | | | 4.67 | Y | | | | 13 | | |
| | | | | | | | | 3.25 | Y | | | | 22 | | |
| | | | | | | | | 5.58 | N | | | | 15 | | |

| HC 000 tumor identification | number max of mitosis per 10 fields x40 | multiple Ndules | MacroNdules of regeneration | Nrrmal liver A0F0 or A0F1 | Cirrhosis AXF4 | Score METAVIR Activity | Score METAVIR Fibrosis | chronic viral hepatitis | Etiology HBV | Etiology HCV | alcool | Hemochromatos | -NASH |
|---|---|---|---|---|---|---|---|---|---|---|---|---|---|
| HC 001 | NA | N | | N | Y | NA | 4 | N | N | N | Y | N | N |
| HC 003 | NA | N | | N | Y | NA | 4 | Y | N | Y | Y | N | N |
| HC 004 | NA | N | | Y | N | 0 | 1 | N | N | N | N | N | N |
| HC 006 | NA | Y | | Y | N | 0 | 1 | N | N | N | Y | Y | N |
| HC 007 | NA | N | | N | Y | 2 | 3 | Y | N | Y | Y | N | N |
| HC 008 | NA | N | | N | Y | NA | 4 | N | N | N | Y | N | N |
| HC 009 | NA | Y | | N | N | 1 | 3 | Y | N | Y | Y | N | N |
| HC 010 | NA | N | | N | Y | NA | 4 | Y | Y | N | N | N | N |
| HC 011 | NA | Y | | N | Y | NA | 4 | Y | Y | N | Y | N | N |
| HC 012 | NA | Y | | N | Y | NA | 4 | Y | N | Y | Y | N | N |
| HC 014 | NA | Y | | N | N | NA | 3 | N | N | N | Y | N | N |
| HC 015 | NA | N | | N | Y | 3 | 4 | Y | N | N | Y | N | N |
| HC 017 | NA | Y | | N | Y | 2 | 3 | Y | N | Y | N | N | N |
| HC 018 | NA | N | | N | Y | NA | 4 | N | N | N | Y | N | N |
| HC 020 | NA | Y | | Y | N | NA | 0 | N | N | N | Y | N | N |
| HC 021 | NA | Y | | Y | N | NA | 0 | N | N | N | Y | N | N |
| HC 022 | NA | Y | | N | Y | NA | 4 | Y | Y | N | N | N | N |
| HC 023 | NA | N | | N | Y | 0 | 4 | Y | Y | N | Y | N | N |
| HC 025 | NA | Y | Y | Y | N | NA | 0 | N | N | N | N | N | N |
| HC 026 | NA | Y | | N | Y | NA | 4 | Y | N | Y | N | N | N |
| HC 027 | NA | N | | N | Y | NA | 4 | N | N | Y | N | N | N |
| HC 028 | NA | Y | | N | Y | NA | 4 | Y | Y | N | Y | N | N |
| HC 030 | NA | N | Y | N | Y | NA | 4 | Y | N | N | Y | N | N |
| HC 032 | NA | Y | | N | Y | NA | 4 | Y | Y | N | Y | N | N |
| HC 034 | NA | Y | | N | Y | NA | 4 | N | N | N | N | N | N |
| HC 037 | NA | N | | N | Y | NA | 0 | N | N | N | N | N | N |
| HC 038 | NA | Y | | N | Y | NA | 4 | Y | Y | Y | N | N | N |
| HC 041 | NA | Y | | N | Y | NA | 4 | Y | N | Y | N | N | N |
| HC 042 | NA | Y | | Y | N | NA | 1 | Y | N | Y | N | N | N |
| HC 043 | NA | N | | N | Y | 2 | 4 | Y | N | N | Y | N | N |
| HC 052 | NA | Y | | Y | N | NA | 0-1 | Y | Y | N | Y | N | N |
| HC 058 | NA | Y | | N | Y | 2 | 4 | Y | N | Y | Y | N | N |
| HC 060 | NA | N | | N | Y | | | | | | | | |
| HC 064 | NA | N | | N | N | 2 | 2 | Y | N | Y | N | N | N |
| HC 066 | NA | Y | | N | Y | NA | 4 | Y | Y | Y | Y | N | N |
| HC 101 | 18 | Y | Y | N | N | 2 | 1 | Y | Y | N | N | N | N |
| HC 102 | 7 | N | N | N | N | 1 | 1 | Y | N | Y | N | N | N |
| HC 103 | 8 | Y | Y | Y | N | 3 | 4 | Y | N | N | Y | N | N |
| HC 104 | 10 | Y | N | N | N | 0 | 1 | N | N | N | Y | N | N |
| HC 105 | 20 | Y | N | N | N | 2 | 4 | Y | N | Y | Y | N | N |
| HC 106 | 32 | Y | N | Y | N | 1 | 4 | Y | N | N | Y | N | N |
| HC 107 | 1 | N | N | Y | N | 0 | 0-1 | N | N | N | Y | N | N |
| HC 108 | 18 | N | N | N | Y | 1 | 1 | Y | Y | Y | Y | N | N |
| HC 109 | <1 | Y | Y | N | Y | 2 | 4 | N | N | N | Y | N | Y |

TABLE G-continued

| ID | Value | C1 | C2 | C3 | N1 | N2 | C4 | C5 | C6 | C7 | C8 | C9 | C10 |
|---|---|---|---|---|---|---|---|---|---|---|---|---|---|
| HC 110 | 1 á 5 | Y | N | Y | 1 | 4 | Y | N | Y | Y | N | N | N |
| HC 111 | 45 | Y | Y | Y | 1 | 4 | Y | N | N | N | N | N | Y |
| HC 112 | 0 | N | N | N | 2 | 2 | N | N | Y | Y | N | N | Y |
| HC 113 | 25 | Y | Y | Y | 1 | 4 | Y | Y | Y | Y | N | N | Y |
| HC 114 | <1 | N | N | N | 2 | 4 | Y | Y | N | Y | N | N | N |
| HC 115 | 0 | N | N | N | 2 | 3 | N | N | N | N | N | N | Y |
| HC 116 | 12 | Y | Y | Y | 2 | 1 | Y | N | Y | N | N | N | N |
| HC 117 | 4 | Y | Y | Y | 2 | 3 | Y | Y | Y | N | N | N | N |
| HC 118 | <1 | Y | N | Y | 0 | 4 | Y | Y | Y | N | N | N | N |
| HC 119 | 15 | Y | Y | Y | 2 | 1 | Y | Y | Y | Y | N | N | Y |
| HC 120 | 3 | Y | Y | Y | 1 | 4 | Y | N | Y | N | N | N | N |
| HC 121 | 8 á 30 | ? | N | Y | 2 | 4 | Y | N | Y | Y | N | N | N |
| HC 122 | 8 | N | Y | Y | 1 | 4 | Y | N | Y | Y | N | N | N |
| HC 123 | 4 | N | Y | Y | 2 | 4 | Y | Y | Y | Y | N | N | N |
| HC 124 | 4 | N | Y | Y | 1 | 1 | N | N | N | N | N | N | N |
| HC 125 | 2 | Y | Y | Y | 2 | 4 | Y | Y | Y | Y | N | N | Y |
| HC 126 | 2 | Y | Y | N | 0 | 1 | N | N | N | N | N | N | N |
| HC 127 | >100 | N | N | Z | 1 | 1 | Y | N | N | N | N | N | N |
| HC 128 | 5 | N | N | Z | 2 | 2 | Y | Y | Y | Y | N | Y | Y |
| HC 129 | 40 | Y | Y | Z | 2 | 3 | Y | N | Y | Y | N | N | Y |
| HC 130 | 12 | N | N | Z | 0 | 2 | N | N | N | N | N | N | N |
| HC 131 | 20 á 25 | N | Y | N | 1 | 1 | N | N | N | N | N | N | N |
| HC 137 | NA | | Y | | — | — | | | | | | | |
| HC 138 | NA | | Y | N | — | — | N | N | N | N | N | N | N |
| HC 139 | NA | | Y | N | 0 | — | N | N | N | N | N | N | N |
| HC 140 | NA | | Y | N | — | — | N | N | N | N | N | Y | N |
| HC 141 | NA | | Y | Y | — | 1 | N | N | N | N | N | N | N |
| HC 142 | NA | | Y | — | 1 | — | Y | Y | Y | Y | N | N | N |
| HC 143 | NA | | Y | N | — | 4 | N | N | N | N | N | N | N |
| HC 144 | NA | | Y | | — | — | N | N | N | N | N | N | N |
| HC 145 | NA | | Y | N | 0 | 3 | N | N | N | N | N | N | N |
| HC 146 | NA | | Y | N | 0 | 2 | Y | Y | Y | Y | Y | Y | Y |
| HC 147 | NA | | Y | Z | 0 | 3 | N | N | N | N | N | N | N |
| HC 148 | NA | | Y | | — | — | N | N | N | N | N | N | N |
| HC 149 | NA | | Y | Y | 0 | 0 | Y | Y | Y | Y | N | N | N |
| HC 150 | NA | | Y | N | 0 | 3 | N | N | N | N | N | Y | N |
| HC 151 | NA | | Y | N | 2 | 4 | N | N | N | N | N | N | N |
| HC 152 | NA | | Y | | 0 | 2 | N | N | N | N | N | N | Y |
| HC 153 | NA | N | Y | Z | 0 | 3 | Y | Y | Y | Y | N | N | N |
| HC 154 | 25 | N | Y | N | 0 | 1 | N | N | N | N | N | N | N |

TABLE G-continued

| ID | C1 | C2 | C3 | C4 | C5 | C6 | C7 | C8 | C9 | C10 | C11 | C12 | C13 |
|---|---|---|---|---|---|---|---|---|---|---|---|---|---|
| HC 155 | 1 | N | N | Y | 2 | | 4 | N | N | N | Y | N | N |
| HC 156 | 16 | Y | Y | Y | 2 | | 4 | Y | N | Y | Y | N | N |
| HC 157 | 2 | N | Y | N | 0 | | 1 | N | N | N | N | N | N |
| HC 159 | NA | N | Y | Y | 2 | | 4 | N | N | Y | N | N | N |
| HC 161 | 2 | N | Y | Y | 1 | | 1 | N | N | N | N | N | N |
| HC 162 | 77 | N | N | N | 0 | | 0 | N | N | N | N | N | N |
| HC 163 | 4 | N | Y | Y | 1 | | 4 | N | N | Y | N | Y | N |
| HC 164 | 1 | Y | N | N | 0 | | 1 | N | N | N | N | N | N |
| HC 165 | 4 | N | N | N | 0 | | 2 | Y | N | N | N | N | N |
| HC 168 | 1 | N | Y | Y | 2 | | 4 | N | N | Y | N | N | N |
| HC 169 | NA | N | N | N | 2 | | 4 | N | N | N | N | N | N |
| HC 170 | 0 | Y | Y | N | 0 | | 0 | N | Y | N | N | N | N |
| HC 171 | 10 | N | N | N | 1 | | 2 | N | N | Y | Y | Y | N |
| HC 172 | 28 | Y | Y | Y | 2 | | 3 | Y | Y | N | Y | Y | N |
| HC 173 | 0 | Y | Y | N | 0 | | 0 | Y | Y | Y | N | N | N |
| HC 176 | NA | Y | Y | N | 0 | | 0 | Y | Y | Y | N | Y | N |
| HC 177 | NA | Y | N | | | A1 | F4 | Y | Y | N | Y | Y | N |
| HC 178 | NA | Y | N | | | A1 | F4 | Y | N | Y | N | N | N |
| HC 179 | NA | Y | N | | | A2 | F1 | Y | Y | Y | N | N | N |
| HC 180 | NA | Y | N | | | A2 | F2 | Y | Y | Y | Y | Y | N |
| HC 181 | NA | Y | N | | | A1 | F4 | Y | Y | Y | Y | Y | N |
| HC 182 | NA | N | N | | | | F1 | Y | N | Y | Y | Y | N |
| HC 183 | NA | N | N | | | | F3 | Y | Y | Y | Y | Y | N |
| HC 184 | NA | N | N | | | A1 | F1 | Y | N | Y | Y | N | N |
| HC 185 | NA | N | N | | | | F4 | NA | NA | NA | NA | NA | NA |
| HC 186 | NA | N | N | | | | F0 | N | N | Y | N | N | N |
| HC 187 | NA | Y | Y | | | A1 | F4 | N | N | Y | N | N | N |
| HC 188 | NA | N | N | | | | F0 | Y | Y | Y | Y | Y | N |
| HC 189 | NA | Y | Y | | | | F1 | Y | N | Y | N | N | N |
| HC 190 | NA | Y | Y | | | | F3 | Y | Y | N | Y | N | N |

REFERENCES

Assou, S., Le Carrour, T., Tondeur, S., Strom, S., Gabelle, A., Marty, S., Nadal, L., Pantesco, V., Reme, T., Hugnot, J. P., et al. (2007). A meta-analysis of human embryonic stem cells transcriptome integrated into a web-based expression atlas. Stem Cells 25, 961-973.

Boyault, S., Rickman, D. S., de Reynies, A., Balabaud, C., Rebouissou, S., Jeannot, E., Herault, A., Saric, J., Belghiti, J., Franco, D., et al. (2007). Transcriptome classification of HCC is related to gene alterations and to new therapeutic targets. Hepatology 45, 42-52.

Finegold, M. J., Lopez-Terrada, D. H., Bowen, J., Washington, M. K., and Qualman, S. J. (2007). Protocol for the examination of specimens from pediatric patients with hepatoblastoma. Arch Pathol Lab Med 131, 520-529.

Fodde, R., and Brabletz, T. (2007). Wnt/beta-catenin signaling in cancer stemness and malignant behavior. Curr Opin Cell Biol 19, 150-158.

Glinsky, G. V., Berezovska, O., and Glinskii, A. B. (2005). Microarray analysis identifies a death-from-cancer signature predicting therapy failure in patients with multiple types of cancer. J Clin Invest 115, 1503-1521.

Hirschman, B. A., Pollock, B. H., and Tomlinson, G. E. (2005). The spectrum of APC mutations in children with hepatoblastoma from familial adenomatous polyposis kindreds. J Pediatr 147, 263-266.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264.

Lee, J. S., Heo, J., Libbrecht, L., Chu, I. S., Kaposi-Novak, P., Calvisi, D. F., Mikaelyan, A., Roberts, L. R., Demetris, A. J., Sun, Z., et al. (2006). A novel prognostic subtype of human hepatocellular carcinoma derived from hepatic progenitor cells. Nat Med 12, 410-416.

McLin, V. A., Rankin, S. A., and Zorn, A. M. (2007). Repression of Wnt/β-catenin signaling in the anterior endoderm is essential for liver and pancreas development. Development 134, 2207-2217.

Perilongo, G., Shafford, E., and Plaschkes, J. (2000). SIOPEL trials using preoperative chemotherapy in hepatoblastoma. Lancet Oncol 1, 94-100.

Rowland, J. M. (2002). Hepatoblastoma: assessment of criteria for histologic classification. Med Pediatr Oncol 39, 478-483.

Schnater, J. M., Kohler, S. E., Lamers, W. H., von Schweinitz, D., and Aronson, D. C. (2003). Where do we stand with hepatoblastoma? A review. Cancer 98, 668-678.

Taniguchi, K., Roberts, L. R., Aderca, I. N., Dong, X., Qian, C., Murphy, L. M., Nagorney, D. M., Burgart, L. J., Roche, P. C., Smith, D. I., et al. (2002). Mutational spectrum of beta-catenin, AXIN1, and AXIN2 in hepatocellular carcinomas and hepatoblastomas. Oncogene 21, 4863-4871.

Wei, Y., Fabre, M., Branchereau, S., Gauthier, F., Perilongo, G., and Buendia, M. A. (2000). Activation of beta-catenin in epithelial and mesenchymal hepatoblastomas. Oncogene 19, 498-504.

Lustgarten, J. L. et al (2008)—Improving classification performance with discretization on biomedical datasets. AMIA 2008 Symposium Proceedings, 445-449

The invention claimed is:
1. A method, comprising:
assaying by real-time RT-PCR the expression of each gene in a set of genes in a biological sample
wherein said set of genes comprises from 10 to 16 genes or consists of 10 to 16 genes, said 10 to 16 genes being selected from the group consisting of the alpha-fetoprotein (AFP), aldehyde dehydrogenase 2 (ALDH2), amyloid P component serum (APCS), apolipoprotein C-IV (APOC4), aquaporin 9 (AQP9), budding uninhibited by benzimidazoles 1 (BUB1), complement component 1 (CIS), cytochrome p450 2E1 (CYP2E1), discs large homolog 7 (DLG7), dual specificity phosphatase 9 (DUSP9), E2F5 transcription factor (E2F5), growth hormone receptor (GHR), 4-hydroxyphenylpyruvase dioxygenase (DHP), immunoglobulin superfamily member 1 (IGSF1), Notchless homolog 1 (NLE1) and the ribosomal protein L10a (RPL10A) genes, wherein the biological sample is a hepatoblastoma (HB) or a hepatocellular carcinoma (HCC) obtained from a patient after surgical resection or orthotopic liver transplantation (OLT).

2. The method according to claim 1, further comprising assaying invariant gene RHOT2, and determining relative expression for each gene in the set of genes by normalizing with respect to the invariant RHOT2 gene.

3. The method according to claim 1, wherein said set comprises from 11 to 16 genes or consists of 11 to 16 genes.

4. The method according to claim 1, wherein said set comprises from 12 to 16 genes or consists of 12 to 16 genes.

5. The method according to claim 1, wherein said set comprises from 13 to 16 genes or consists of 13 to 16 genes.

6. The method according to claim 1, wherein said set comprises from 14 to 16 genes or consists of 14 to 16 genes.

7. The method according to claim 1, wherein said set comprises from 15 to 16 genes or consists of 15 to 16 genes.

8. The method according to claim 1, wherein said set comprises 16 genes or consists of 16 genes.

9. A method, comprising:
   assaying by real-time RT-PCR the expression of a set of genes in a sample of a liver tumor from a patient to determine a gene expression profile of said sample, wherein said sample is a hepatoblastoma (HB) or a hepatocellular carcinoma (HCC) sample obtained from a patient after surgical resection or orthotopic liver transplantation (OLT), and wherein said set comprises from 10 to 16 genes or consists of 10 to 16 genes, said 10 to 16 genes being selected from the group consisting of the alpha-fetoprotein (AFP), aldehyde dehydrogenase 2 (ALDH2), amyloid P component serum (APCS), apolipoprotein C-IV (APOC4), aquaporin 9 (AQP9), budding uninhibited by benzimidazoles 1 (BUB1), complement component 1 (C1S), cytochrome p450 2E1 (CYP2E1), discs large homolog 7 (DLG7), dual specificity phosphatase 9 (DUSP9), E2F5 transcription factor (E2F5), growth hormone receptor (GHR), 4-hydroxyphenylpyruvase dioxygenase (DHP), immunoglobulin superfamily member 1 (IGSF1), Notchless homolog 1 (NLE1) and the ribosomal protein L10a (RPL10A) genes, wherein the assaying comprises quantifying the expression of the set of genes with respect to at least one nucleotide target, wherein the nucleotide target is an expression product of an invariant gene selected from the group consisting of ACTG1, EFF1A1, PNN, and RHOT2 genes.

10. The method according to claim 9, wherein the invariant gene is RHOT2 gene.

11. The method according to claim 9, further comprising the preparation of mRNA from the sample.

12. The method according to claim 9, wherein said set of genes comprises a set selected from the group consisting of:
   (a) E2F5 and HPD genes;
   (b) APCS, BUB1, E2F5, GHR and HPD genes;
   (c) ALDH2, APCS, APOC4, BUB1, C1S, CYP2E1, E2F5, GHR and HPD genes;
   (d) ALDH2, APCS, APOC4, AQP9, BUB1, C1S, DUSP9, E2F5 and RPL10A genes;
   (e) ALDH2, APCS, APOC4, AQP9, C1S, CYP2E1, E2F5, GHR, IGSF1 and RPL10A genes; and
   (f) AFP, ALDH2, APCS, APOC4, AQP9, BUB1, C1S, CYP2E1, DLG7, DUSP9, E2F5, GHR, HPD, IGSF1, NLE1 and RPL10A genes.

* * * * *